United States Patent
Dunn et al.

(10) Patent No.: US 7,189,718 B2
(45) Date of Patent: Mar. 13, 2007

(54) NON-NUCLEOSIDE REVERSE TRANSCRIPTASE INHIBITORS

(75) Inventors: James Patrick Dunn, Los Altos, CA (US); Brian William Dymock, St. Albans (GB); Taraneh Mirzadegan, Los Altos, CA (US); Eric Brian Sjogren, Mountain View, CA (US); Steven Swallow, Los Altos, CA (US); Zachary Kevin Sweeney, Redwood City, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 301 days.

(21) Appl. No.: 10/807,993

(22) Filed: Mar. 23, 2004

(65) Prior Publication Data

US 2004/0198736 A1  Oct. 7, 2004

Related U.S. Application Data

(60) Provisional application No. 60/457,144, filed on Mar. 24, 2003.

(51) Int. Cl.
*C07D 237/14* (2006.01)
*C07D 237/22* (2006.01)
*A61K 31/501* (2006.01)

(52) U.S. Cl. ................... 514/236.5; 514/247; 544/114; 544/239

(58) Field of Classification Search ................ 544/114, 544/239; 514/236.5, 247
See application file for complete search history.

(56) References Cited

U.S. PATENT DOCUMENTS 5,886,178 A  3/1999  Allen et al.

FOREIGN PATENT DOCUMENTS

| WO | WO 96/24343 A1 | 8/1996 |
| WO | WO 96/34851 A1 | 11/1996 |
| WO | WO 97/02023 A1 | 1/1997 |
| WO | WO 97/02024 A1 | 1/1997 |
| WO | WO 01/85670 A1 | 11/2001 |

OTHER PUBLICATIONS

Marcus et al., PubMed Abstract (Intervirology, 45(4-6):260-6), 2002.*

Miles, Medline Abstract (Community Pract. vol. 78, Issue 8, pp. 292-294) Aug. 2005.* van Heeswijk et al., PubMed Abstract (Antivir. Ther. 6(4):201-29) Dec. 2001.*

West, Solid Solutions, Solid State Chemistry and its applications, pp. 358 and 365, 1986.*

Vippagunta et al., Crystalline Solids, Advanced Drug Delivery Reviews, 48, pp. 3-26, 2001.*

Ulrich, Chapter 4: Crystallization, Kirk-Othmer Encyclopedia of Chemical Technology, Aug. 2002.*

De Clercq, Erik, "New Developments in Anti-HIV Chemotherapy," *Current Medicinal Chemistry*, 2001,.pp. 1543-1572, vol. 8 No. 13.

Leeson, Paul D., "Selective Thyromimetics. Cardiac-Sparing Thyroid Hormone Analogues Containing 3'-Arylmethyl Substituents," *J. Med. Chem.*, 1989, pp. 320-336, vol. 32, No. 2.

Buckheit, Jr., Robert W., "Non-nucleoside reverse transcriptase inhibitors: perspectives on novel therapeutic compounds and strategies for the treatment of HIV infection," *Expert Opin. Investig. Drugs*, Ashley Publications Ltd., 2001, pp. 1423-1442, vol. 10, No. 8.

Chintakunta, V.K., et al, "3-O-Substituted benzyl pyridazinone derivatives as COX inhibitors", *Eur. J. Med. Chem.*, 37(4):339-347, 2002.

* cited by examiner

*Primary Examiner*—Deepak Rao
(74) *Attorney, Agent, or Firm*—Brian L. Buckwalter

(57) ABSTRACT

This invention relates to novel pyridazinone derivatives of formula I wherein $R^1$–$R^4$, $R^7$, $R^8$ and $X^1$ are as defined in the summary and pharmaceutically acceptable salts and solvates thereof, methods to inhibit or modulate Human Immunodeficiency Virus (HIV) reverse transcriptase with compounds of formula I, pharmaceutical compositions containing of formula I admixed with at least one solvent, carrier or excipient and processes to prepare compounds of formula I. The compounds are useful for treating disorders in which HIV and genetically related viruses are implicated

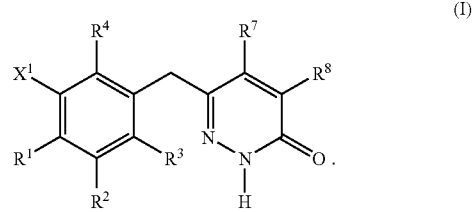

(I)

40 Claims, No Drawings

NON-NUCLEOSIDE REVERSE TRANSCRIPTASE INHIBITORS

CROSS REFERENCE TO PRIOR APPLICATION

This application claims benefit under Title 35 U.S.C. 119(e) of U.S. Provisional Application No. 60/457,144, filed Mar. 24, 2003, which is hereby incorporated by reference in its entirety

FIELD OF THE INVENTION

The invention relates to the field of antiviral therapy and, in particular, to non-nucleoside reverse transcriptase inhibitors for treating Human Immunodeficiency Virus (HIV) mediated diseases. The invention provides novel pyridazinone compounds, pharmaceutical compositions comprising these compounds, methods for treatment or prophylaxis of HIV mediated diseases employing said compounds in monotherapy or in combination therapy.

BACKGROUND OF THE INVENTION

The human immunodeficiency virus HIV is the causative agent of acquired immunodeficiency syndrome (AIDS), a disease characterized by the destruction of the immune system, particularly of the $CD4^+$ T-cell, with attendant susceptibility to opportunistic infections. HIV infection is also associated with a precursor AIDs-related complex (ARC), a syndrome characterized by symptoms such as persistent generalized lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Currently available chemotherapy targets two crucial viral enzymes: HIV protease and HIV reverse transcriptase (J. S. G. Montaner et al. Antiretroviral therapy: 'the state of the art", Biomed & Pharmacother. 1999 53:63–72; R. W. Shafer and D. A. Vuitton, *Highly active retroviral therapy (HAART) for the treatment of infection with human immunodeficiency virus type 1, Biomed. & Pharmacother.* 1999 53:73–86; E. De Clercq, New Developments in Anti-HIV Chemotherap. Curr. Med. Chem. 2001 8:1543–1572). Two general classes of RTI inhibitors have been identified: nucleoside reverse transcriptase inhibitors (NRTI) and non-nucleoside reverse transcriptase inhibitors (NNRTI). NRTIs typically are 2',3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTI are allosteric inhibitors which bind reversibly at a nonsubstrate-binding site on the HIV reverse transcriptase thereby altering the shape of the active site or blocking polymerase activity. (R. W. Buckheit, Jr., *Non-nucleoside reverse transcriptase inhibitors: perspectives for novel therapeutic compounds and strategies for treatment of HIV infection*, Expert Opin. Investig. Drugs 2001 10(8)1423–1442; E. De Clercq *The role of non0-nucleoside reverse transcriptase inhibitors (NNRTIs) in the therapy of HIV-1 infection*, Antiviral Res. 1998 38:153–179; G. Moyle, *The Emerging Roles of Non-Nucleoside Reverse Transcriptase Inhibitors in Antiviral Therapy*, Drugs 2001 61(1):19–26) Although over thirty structural classes of NNRTIs have been identified in the laboratory, only three compounds have been approved for HIV therapy: efavirenz, nevirapine and delavirdine. Although initially viewed as a promising class of compounds, in vitro and in vivo studies quickly revealed the NNRTIs presented a low barrier to the emergence of drug resistant HIV strains and class-specific toxicity. Drug resistance frequently develops with only a single point mutation in the RT.

While combination therapy with NRTIs, PIs and NNRTIs has, in many cases, dramatically lowered viral loads and slowed disease progression, significant therapeutic problems remain. The cocktails are not effective in all patients, potentially severe adverse reactions often occur and the rapidly reproducing HIV virus has proven adroit at creating mutant drug-resistant variants of wild type protease and reverse transcriptase.

There remains a need for safer drugs with activity against wild type and commonly occurring resistant strains of HIV.

Benzyl-pyridazinone compounds have been extensively investigated as thyroxin analogs which can decrease plasma cholesterol without stimulating cardiac activity (A. H. Underwood et al. *A thyromimetic that decreases plasma cholesterol without increasing cardiovascular activity* Nature 1986 324(6096):425–429; P. D. Leeson et al. *Selective thyromimetics. Cardiac-sparing thyroid hormone analogs containing 3'-arylmethyl substituents* J. Med Chem 1989 32(2):320–326; P. D. Leeson et al. EP 0188351). WO9624343 (D. J. Dunnington) discloses oxo-pyridazinylmethyl substituted tyrosines are selective antagonists for the haematopoietic phosphatase SH2 domain which may render them useful to increase erythropoiesis and haematopoiesis. WO 9702023 (D. J. Dunnington) and WO9702024 (D. J. Dunnington) further disclose these compounds are specific inhibitor of the human Stat 6 SH2 domain and may be useful for treating asthma, allergic rhinitis and anemia. WO2001085670 (H. Shiohara et al.) discloses related malonamide derivatives useful for treating circulatory diseases. EP 810218 (D. A. Allen et al.) discloses benzoyl substituted benzyl-pyridazinone compounds which are cyclooxygenase inhibitors and potential antiinflammatory or analgesic compounds. None of the references teaches therapy for HIV infections or inhibition of HIV reverse transcriptase.

SUMMARY OF THE INVENTION

The present invention relates to a compounds according to formula I, methods for treating diseases mediated by human immunodeficieny virus by administration of a compound according to formula I and pharmaceutical compositions for treating diseases mediated by human immunodeficieny virus containing a compound according to formula I,

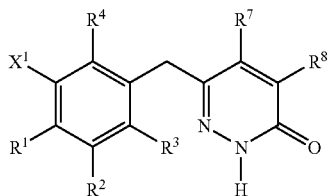

$X^1$ is selected from the group consisting of $R^5O$, $R^5S(O)_n$, $R^5CH_2$, $R^5CH_2O$, $R^5CH_2S(O)_n$, $R^5OCH_2$, $R^5S(O)_nCH_2$, $NR^5R^6$ and $C(=O)R^5$;

$R^1$ and $R^2$ are
(i) each independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, amino, alkylamino, dialkylamino, aminoacyl, nitro and cyano; or,
(ii) taken together are —CH=CH—CH=CH—, or
(iii) taken together along with the carbons to which they are attached form a five- or six-membered heteroaromatic or heterocyclic ring with a one or two heteroatoms independently selected from the group consisting of O, S and NH;

$R^3$ is selected from the group consisting of hydrogen, $C_{1-6}$ alkyl, $C_{1-6}$ haloalkyl, $C_{3-8}$ cycloalkyl, $C_{1-6}$ alkylthio, $C_{1-6}$ haloalkylthio, halogen, amino, alkylamino, dialkylamino, aminoacyl, nitro and cyano;

$R^4$ is selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ haloalkoxy, $C_{1-6}$ haloalkylthio, halogen, amino, alkylamino, dialkylamino, aminoacyl, nitro and cyan $R^5$ is selected from the group consisting of alkyl, haloalkyl, cycloalkyl, phenyl, naphthyl, pyridinyl, pyridine N-oxide, indole, indole N-oxide, quinoline, quinoline N-oxide, pyrimidinyl, pyrazinyl and pyrrolyl; wherein,
said alkyl and said cycloalkyl are optionally substituted with one or two substituents independently selected from the group consisting of alkyl, hydroxy, alkoxy, thiol, alkylthio, halogen, amino, alkylamino, dialkylamino, aminoalkyl, alkylaminoalkyl, and dialkylamino; and,
said phenyl, said naphthyl, said pyridinyl, said pyridine N-oxide, said indole, said indole N-oxide, said quinoline, said quinoline N-oxide, said pyrimidinyl, said pyrazinyl and said pyrrolyl groups are optionally substituted with one to three substituents independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, hydroxy, halogen, amino, $C_{1-6}$ alkylamino, $C_{1-6}$ dialkylamino, aminoacyl, acyl, $C_{1-6}$ alkoxycarbonyl, carbamoyl, $C_{1-6}$ N-alkylcarbamoyl, $C_{1-6}$ N,N-dialkylcarbamoyl, nitro and cyano;

$R^6$ is hydrogen, $C_{1-6}$ alkyl, or acyl;

$R^7$ and $R^8$ (i) taken independently are selected from the group consisting of hydrogen amino, $C_{1-6}$ alkylamino, $C_{1-6}$ dialkylamino, amino-$C_{1-3}$ alkyl, alkylamino-$C_{1-3}$ alkyl, $C_{1-3}$ dialkylamino-$C_{1-3}$ alkyl or $C_{1-6}$ alkyl optionally substituted with one or two substituents independently selected from the group consisting of hydroxy, alkoxy, thiol, alkylthio, $C_{1-6}$ alkylsulfinyl, $C_{1-6}$ sulfonyl, halogen; or, (ii) $R^7$ and $R^8$ taken together are —$(CH_2)_4$—;

n is an integer from 0 to 2; and,
hydrates, solvates, clathrates and acid addition salts thereof.

The invention also relates to a process for preparing a compound according to formula I wherein $X^1$ is $OR^5$ or $SR^5$, $R^5$ is an optionally substituted aryl, alkyl or aralkyl moiety and $R^1$–$R^4$, $R^7$ and $R^8$ are as defined hereinabove

DETAILED DESCRIPTION OF THE INVENTION

In one embodiment of the invention there is provided a compound according to formula I,

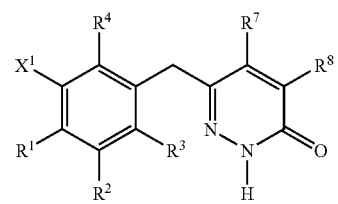

wherein $X^1$ is $R^5O$, $R^5S(O)_n$, $R^5CH_2$, $R^5CH_2O$, $R^5CH_2S(O)_n$, $R^5OCH_2$, $R^5S(O)_nCH_2$ or $NR^5R^6$; and $R^1$, $R^2$, $R^3$, $R^4$, $R^5$, $R^6$, $R^7$ and $R^8$ are as defined hereinabove, and hydrates, solvates, clathrates and acid addition salts thereof.

In another embodiment of the present invention there is provided a compound according to formula I wherein $X^1$ is $R^5O$, $R^5S(O)_n$, $R^5CH_2$, $R^5CH_2O$, $R^5CH_2S(O)_n$, $R^5OCH_2$, $R^5S(O)_nCH_2$ or $NR^5R^6$; $R^5$ is selected from the group consisting of alkyl, haloalkyl, cycloalkyl, phenyl, naphthyl, pyridinyl, pyridine N-oxide, indole, indole N-oxide, quinoline, quinoline N-oxide pyrimidinyl, pyrazinyl and pyrrolyl; wherein, said alkyl and said cycloalkyl are optionally substituted with one or two substituents independently selected from the group consisting of alkyl, hydroxy, alkoxy, thiol, alkylthio, halogen, amino, alkylamino, dialkylamino, aminoalkyl, alkylaminoalkyl, and dialkylamino; and, said phenyl, said naphthyl, said pyridinyl, said pyrimidinyl, said pyrazinyl and said pyrrolyl groups are optionally substituted with one to three substituents independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, alkylamino, dialkylamino, acylamino, acyl and cyano; and, $R^1$, $R^2$, $R^3$, $R^4$, $R^6$, $R^7$ and $R^8$ are as defined hereinabove, and hydrates, solvates, clathrates and acid addition salts thereof.

In another embodiment of the present invention there is provided a compound according to formula I wherein $X^1$ is $OR^5$ or $SR^5$; $R^3$ is hydrogen or fluoro; $R^4$ is hydrogen, chloro, fluoro or methyl; $R^5$ is phenyl optionally substituted with one to three substituents independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, alkylamino, dialkylamino, acylamino, cyano, and acyl; and, $R^7$ and $R^8$ are independently selected from the group consisting of hydrogen, amino, alkylamino, dialkylamino, aminoalkyl, alkylaminoalkyl and dialkylaminoalkyl and $C_{1-6}$ alkyl optionally substituted with hydroxy, alkoxy, thiol, alkylthio or halogen; and $R^1$ and $R^2$ are as defined hereinabove; and hydrates, solvates, clathrates and acid addition salts thereof.

In another embodiment of the present invention there is provided a compound according to formula I wherein $X^1$ is $OR^5$ or $SR^5$; $R^1$ is methyl, ethyl, trifluoromethyl or halogen; $R^3$ is hydrogen or fluoro; $R^4$ is hydrogen, chloro, fluoro or methyl; $R^5$ is phenyl optionally substituted with one to three substituents independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, alkylamino, dialkylamino, acylamino, cyano, and acyl; and, $R^7$ and $R^8$ are independently selected from the group consisting of hydrogen, amino, alkylamino, dialkylamino, aminoalkyl, alkylaminoalkyl and dialkylaminoalkyl and $C_{1-6}$ alkyl optionally substituted with hydroxy, alkoxy, thiol, alkylthio or halogen; and $R^2$ is as defined hereinabove; and hydrates, solvates, clathrates and acid addition salts thereof.

In another embodiment of the present invention there is provided a compound according to formula I wherein $X^1$ is $OR^5$ or $SR^5$; $R^1$ is methyl, ethyl, trifluoromethyl or halogen; $R^3$ is hydrogen or fluoro; $R^4$ is hydrogen, chloro, fluoro or methyl; $R^5$ is phenyl substituted with one substituent selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, alkylamino, dialkylamino, acylamino, cyano, and acyl; and, $R^7$ and $R^8$ are independently selected from the group consisting of hydrogen, amino, alkylamino, dialkylamino, aminoalkyl, alkylaminoalkyl and dialkylaminoalkyl and $C_{1-6}$ alkyl optionally substituted with hydroxy, alkoxy, thiol, alkylthio or halogen; and $R^2$ is as defined hereinabove; and hydrates, solvates, clathrates and acid addition salts thereof.

In another embodiment of the present invention there is provided a compound according to formula I wherein $X^1$ is $OR^5$ or $SR^5$; $R^1$ is methyl, ethyl, trifluoromethyl or halogen; $R^3$ is hydrogen or fluoro; $R^4$ is hydrogen, chloro, fluoro or methyl; $R^5$ is 2,5-disubstituted phenyl which substituents are independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, alkylamino, dialkylamino, acylamino, cyano, and acyl; and, $R^7$ and $R^8$ are independently selected from the group consisting of hydrogen, amino, alkylamino, dialkylamino, aminoalkyl, alkylaminoalkyl and dialkylaminoalkyl and $C_{1-6}$ alkyl optionally substituted with hydroxy, alkoxy, thiol, alkylthio or halogen; and $R^2$ is as defined hereinabove; and hydrates, solvates, clathrates and acid addition salts thereof.

In another embodiment of the present invention there is provided a compound according to formula I wherein $X^1$ is $OR^5$ or $SR^5$; $R^1$ is methyl, ethyl, trifluoromethyl or halogen; $R^3$ is hydrogen or fluoro; $R^4$ is hydrogen, chloro, fluoro or methyl; $R^5$ is 3,5-disubstituted phenyl which substituents are independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, alkylamino, dialkylamino, acylamino, cyano, and acyl; and, $R^7$ and $R^8$ are independently selected from the group consisting of hydrogen, amino, alkylamino, dialkylamino, aminoalkyl, alkylaminoalkyl and dialkylaminoalkyl and $C_{1-6}$ alkyl optionally substituted with hydroxy, alkoxy, thiol, alkylthio or halogen; and $R^2$ is as defined hereinabove; and hydrates, solvates, clathrates and acid addition salts thereof.

In another embodiment of the present invention there is provided a compound according to formula I wherein $X^1$ is $OR^5$ or $SR^5$; $R^1$ is methyl, ethyl, trifluoromethyl or halogen; $R^3$ is hydrogen or fluoro; $R^4$ is hydrogen, chloro, fluoro or methyl; $R^5$ is 2,4-disubstituted phenyl which substituents are independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, alkylamino, dialkylamino, acylamino, cyano, and acyl; and, $R^7$ and $R^8$ are independently selected from the group consisting of hydrogen, amino, alkylamino, dialkylamino, aminoalkyl, alkylaminoalkyl and dialkylaminoalkyl and $C_{1-6}$ alkyl optionally substituted with hydroxy, alkoxy, thiol, alkylthio or halogen; and $R^2$ is as defined hereinabove; and hydrates, solvates, clathrates and acid addition salts thereof.

In another embodiment of the present invention there is provided a compound according to formula I wherein $X^1$ is $OR^5$ or $SR^5$; $R^1$ is methyl, ethyl, trifluoromethyl or halogen; $R^3$ is hydrogen or fluoro; $R^4$ is hydrogen, chloro, fluoro or methyl; $R^5$ is 2,6-disubstituted phenyl which substituents are independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, alkylamino, dialkylamino, acylamino, cyano, and acyl; $R^7$ and $R^8$ are independently selected from the group consisting of hydrogen, amino, alkylamino, dialkylamino, aminoalkyl, alkylaminoalkyl and dialkylaminoalkyl and $C_{1-6}$ alkyl optionally substituted with hydroxy, alkoxy, thiol, alkylthio or halogen; and $R^2$ is as defined hereinabove; and hydrates, solvates, clathrates and acid addition salts thereof.

In another embodiment of the present invention there is provided a compound according to formula I wherein $X^1$ is $OR^5$ or $SR^5$; $R^1$ and $R^2$ are independently selected from the group consisting of hydrogen, $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, amino, alkylamino, dialkylamino, aminoacyl, nitro and cyano; $R^3$ is hydrogen or fluoro; $R^4$, $R^5$, $R^7$ and $R^8$ are as defined hereinabove; and, hydrates, solvates, clathrates and acid addition salts thereof.

In another embodiment of the present invention there is provided a compound according to formula I wherein $X^1$ is $OR^5$; $R^1$ is methyl, ethyl, trifluoromethyl or halogen; $R^2$ and $R^4$ are independently hydrogen, chloro, fluoro, methyl or ethyl; $R^3$ is hydrogen or fluoro; $R^5$ is selected from the group consisting of alkyl, haloalkyl, cycloalkyl, phenyl, naphthyl, pyridinyl, pyridine N-oxide, indole, indole N-oxide, quinoline, quinoline N-oxide pyrimidinyl, pyrazinyl and pyrrolyl; wherein, said alkyl and said cycloalkyl are optionally substituted with one or two substituents independently selected from the group consisting of alkyl, hydroxy, alkoxy, thiol, alkylthio, halogen, amino, alkylamino, dialkylamino, aminoalkyl, alkylaminoalkyl, and dialkylamino; and, said phenyl, said naphthyl, said pyridinyl, said pyrimidinyl, said pyrazinyl and said pyrrolyl groups are optionally substituted with one to three substituents independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, alkylamino, dialkylamino, acylamino, acyl and cyano; $R^7$ is hydrogen, methyl or ethyl; $R^8$ is selected from the group consisting of hydrogen, amino, alkylamino, dialkylamino, aminoalkyl, alkylaminoalkyl, dialkylaminoalkyl and $C_{1-6}$ alkyl optionally substituted with hydroxy, alkoxy, thiol, alkylthio or halogen; and, hydrates, solvates, clathrates and acid addition salts thereof.

In another embodiment of the present invention there is provided a compound according to formula I wherein $X^1$ is OR$^5$; R$^1$ is methyl, ethyl, trifluoromethyl or halogen; R$^2$ and R$^4$ are independently hydrogen, chloro, fluoro, methyl or ethyl; R$^3$ is hydrogen or fluoro; R$^5$ is phenyl substituted with one substituent selected from the group consisting of C$_{1-6}$ alkyl, C$_{1-6}$ alkenyl, C$_{1-6}$ haloalkyl, C$_{3-8}$ cycloalkyl, C$_{1-6}$ alkoxy, C$_{1-6}$ alkylthio, C$_{1-6}$ alkylsulfinyl, C$_{1-6}$ sulfonyl, C$_{1-6}$ haloalkoxy, C$_{1-6}$ haloalkylthio, halogen, alkylamino, dialkylamino, aminoacyl, cyano and acyl substituent; R$^7$ is hydrogen, methyl or ethyl; R$^8$ is selected from the group consisting of hydrogen, amino, alkylamino, dialkylamino, aminoalkyl, alkylaminoalkyl and dialkylaminoalkyl and C$_{1-6}$ alkyl optionally substituted with hydroxy, alkoxy, thiol, alkylthio or halogen; and, hydrates, solvates, clathrates and acid addition salts thereof.

In another embodiment of the present invention there is provided a compound according to formula I wherein X$^1$ is OR$^5$; R$^1$ is methyl, ethyl, trifluoromethyl or halogen; R$^2$ and R$^4$ are independently hydrogen, chloro, fluoro, methyl or ethyl; R$^3$ is hydrogen or fluoro; R$^5$ is phenyl substituted with one substituent selected from the group consisting of halogen, cyano, C$_{1-6}$ alkyl, C$_{1-6}$ alkenyl, C$_{3-8}$ cycloalkyl, C$_{1-6}$ haloalkyl, C$_{1-6}$ alkoxy, C$_{1-6}$ alkylthio and C$_{1-6}$ haloalkoxy; R$^7$ is hydrogen, methyl or ethyl; R$^8$ is selected from the group consisting of hydrogen, amino, alkylamino, dialkylamino, aminoalkyl, alkylaminoalkyl and dialkylaminoalkyl and C$_{1-6}$ alkyl optionally substituted with hydroxy, alkoxy, thiol, alkylthio or halogen; and, hydrates, solvates, clathrates and acid addition salts thereof.

In another embodiment of the present invention there is provided a compound according to formula I wherein X$^1$ is OR$^5$; R$^1$ is halogen, methyl or ethyl; R$^2$ and R$^4$ are independently halogen, chloro, fluoro, methyl or ethyl; R$^3$ and R$^7$ are hydrogen; R$^5$ is a phenyl substituted with one substituent selected from the group consisting of halogen, cyano, C$_{1-6}$ alkyl and C$_{1-6}$ haloalkyl; and, R$^8$ is hydrogen, methyl or ethyl and hydrates, solvates, clathrates and acid addition salts thereof.

In another embodiment of the present invention there is provided a compound according to formula I wherein X$^1$ is OR$^5$; R$^1$ is methyl, ethyl, trifluoromethyl or halogen; R$^2$ and R$^4$ are independently hydrogen, chloro, fluoro, methyl or ethyl; R$^3$ is hydrogen or fluoro; R$^5$ is 2,5-disubstituted phenyl which substituents are independently selected from the group consisting of C$_{1-6}$ alkyl, C$_{1-6}$ alkenyl, C$_{1-6}$ haloalkyl, C$_{3-8}$ cycloalkyl, C$_{1-6}$ alkoxy, C$_{1-6}$ alkylthio, C$_{1-6}$ alkylsulfinyl, C$_{1-6}$ sulfonyl, C$_{1-6}$ haloalkoxy, C$_{1-6}$ haloalkylthio, halogen, alkylamino, dialkylamino, aminoacyl, cyano and acyl substituent; R$^7$ is hydrogen, methyl or ethyl; R$^8$ is selected from the group consisting of hydrogen, amino, alkylamino, dialkylamino, aminoalkyl, alkylaminoalkyl and dialkylaminoalkyl and C$_{1-6}$ alkyl optionally substituted with hydroxy, alkoxy, thiol, alkylthio or halogen; and, hydrates, solvates, clathrates and acid addition salts thereof.

In another embodiment of the present invention there is provided a compound according to formula I wherein X$^1$ is OR$^5$; R$^1$ is methyl, ethyl, trifluoromethyl or halogen; R$^2$ and R$^4$ are independently hydrogen, chloro, fluoro, methyl or ethyl; R$^3$ is hydrogen or fluoro; R$^5$ is 2,5-disubstituted phenyl which substituents are independently selected from the group consisting of halogen, cyano, C$_{1-6}$ alkyl, C$_{1-6}$ alkenyl, C$_{3-8}$ cycloalkyl, C$_{1-6}$ haloalkyl, C$_{1-6}$ alkoxy, C$_{1-6}$ alkylthio and C$_{1-6}$ haloalkoxy; R$^7$ is hydrogen, methyl or ethyl; R$^8$ is selected from the group consisting of hydrogen, amino, alkylamino, dialkylamino, aminoalkyl, alkylaminoalkyl and dialkylaminoalkyl and C$_{1-6}$ alkyl optionally substituted with hydroxy, alkoxy, thiol, alkylthio or halogen; and, hydrates, solvates, clathrates and acid addition salts thereof.

In another embodiment of the present invention there is provided a compound according to formula I wherein X$^1$ is OR$^5$; R$^1$ is halogen, methyl or ethyl; R$^2$ and R$^4$ are independently halogen, chloro, fluoro, methyl or ethyl; R$^3$ and R$^7$ are hydrogen; R$^5$ is a 2,5-disubstituted phenyl which substituents are independently selected from the group consisting of halogen, cyano, C$_{1-6}$ alkyl and C$_{1-6}$ haloalkyl; and, R$^8$ is hydrogen, methyl or ethyl and hydrates, solvates, clathrates and acid addition salts thereof.

In another embodiment of the present invention there is provided a compound according to formula I wherein X$^1$ is OR$^5$; R$^1$ is methyl, ethyl, trifluoromethyl or halogen; R$^2$ and R$^4$ are independently hydrogen, chloro, fluoro, methyl or ethyl; R$^3$ is hydrogen or fluoro; R$^5$ is 3,5-disubstituted phenyl which substituents are independently selected from the group consisting of C$_{1-6}$ alkyl, C$_{1-6}$ alkenyl, C$_{1-6}$ haloalkyl, C$_{3-8}$ cycloalkyl, C$_{1-6}$ alkoxy, C$_{1-6}$ alkylthio, C$_{1-6}$ alkylsulfinyl, C$_{1-6}$ sulfonyl, C$_{1-6}$ haloalkoxy, C$_{1-6}$ haloalkylthio, halogen, alkylamino, dialkylamino, aminoacyl, cyano and acyl substituent; R$^7$ is hydrogen, methyl or ethyl; R$^8$ is selected from the group consisting of hydrogen, amino, alkylamino, dialkylamino, aminoalkyl, alkylaminoalkyl and dialkylaminoalkyl and C$_{1-6}$ alkyl optionally substituted with hydroxy, alkoxy, thiol, alkylthio or halogen; and, hydrates, solvates, clathrates and acid addition salts thereof.

In another embodiment of the present invention there is provided a compound according to formula I wherein X$^1$ is OR$^5$; R$^1$ is methyl, ethyl, trifluoromethyl or halogen; R$^2$ and R$^4$ are independently hydrogen, chloro, fluoro, methyl or ethyl; R$^3$ is hydrogen or fluoro; R$^5$ is 3,5-disubstituted phenyl which substituents are independently selected from the group consisting of halogen, cyano, C$_{1-6}$ alkyl, C$_{1-6}$ alkenyl, C$_{3-8}$ cycloalkyl, C$_{1-6}$ haloalkyl, C$_{1-6}$ alkoxy, C$_{1-6}$ alkylthio and C$_{1-6}$ haloalkoxy; R$^7$ is hydrogen, methyl or ethyl; R$^8$ is selected from the group consisting of hydrogen, amino, alkylamino, dialkylamino, aminoalkyl, alkylaminoalkyl and dialkylaminoalkyl and C$_{1-6}$ alkyl optionally substituted with hydroxy, alkoxy, thiol, alkylthio or halogen; and, hydrates, solvates, clathrates and acid addition salts thereof.

In another embodiment of the present invention there is provided a compound according to formula I wherein X$^1$ is OR$^5$; R$_1$ is halogen, methyl or ethyl; R$^2$ and R$^4$ are independently halogen, chloro, fluoro, methyl or ethyl; R$^3$ and R$^7$ are hydrogen; R$^5$ is a 3,5-disubstituted phenyl which substituents are independently selected from the group consisting of halogen, cyano, C$_{1-6}$ alkyl and C$_{1-6}$ haloalkyl; and, R$^8$ is hydrogen, methyl or ethyl and hydrates, solvates, clathrates and acid addition salts thereof.

In another embodiment of the present invention there is provided a compound according to formula Ia wherein R$^1$ is fluoro, chloro, bromo or methyl; R$^8$ is hydrogen, methyl or ethyl and R$^9$ is C$_{1-6}$ alkyl, C$_{3-8}$ cycloalkyl, C$_{1-6}$ haloalkyl, halogen or cyano.

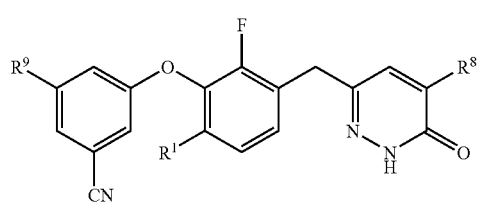

(Ia)

In another embodiment of the present invention there is provided a compound according to formula I wherein $X^1$ is $OR^5$; $R_1$ is methyl, ethyl, trifluoromethyl or halogen; $R^2$ and $R^4$ are independently hydrogen, chloro, fluoro, methyl or ethyl; $R^3$ is hydrogen or fluoro; $R^5$ is 2,4-disubstituted phenyl which substituents are independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, alkylamino, dialkylamino, aminoacyl, cyano and acyl substituent; $R^7$ is hydrogen, methyl or ethyl; $R^8$ is selected from the group consisting of hydrogen, amino, alkylamino, dialkylamino, aminoalkyl, alkylaminoalkyl and dialkylaminoalkyl and $C_{1-6}$ alkyl optionally substituted with hydroxy, alkoxy, thiol, alkylthio or halogen; and, hydrates, solvates, clathrates and acid addition salts thereof.

In another embodiment of the present invention there is provided a compound according to formula I wherein $X^1$ is $OR^5$; $R_1$ is methyl, ethyl, trifluoromethyl or halogen; $R^2$ and $R^4$ are independently hydrogen, chloro, fluoro, methyl or ethyl; $R^3$ is hydrogen or fluoro; $R^5$ is 2,4-disubstituted phenyl which substituents are independently selected from the group consisting of halogen, cyano, $C_{1-6}$ alkyl, $C_{1-6}$ alkenyl, $C_{3-8}$ cycloalkyl, $C_{1-6}$ haloalkyl, $C_{1-6}$ alkoxy, $C_{1-6}$ alkylthio and $C_{1-6}$ haloalkoxy; $R^7$ is hydrogen, methyl or ethyl; $R^8$ is selected from the group consisting of hydrogen, amino, alkylamino, dialkylamino, aminoalkyl, alkylaminoalkyl and dialkylaminoalkyl and $C_{1-6}$ alkyl optionally substituted with hydroxy, alkoxy, thiol, alkylthio or halogen; and, hydrates, solvates, clathrates and acid addition salts thereof.

In another embodiment of the present invention there is provided a compound according to formula I wherein $X^1$ is $OR^5$; $R_1$ is halogen, methyl or ethyl; $R^2$ and $R^4$ are independently halogen, chloro, fluoro, methyl or ethyl; $R^3$ and $R^7$ are hydrogen; $R^5$ is a 2,4-disubstituted phenyl which substituents are independently selected from the group consisting of halogen, cyano, $C_{1-6}$ alkyl and $C_{1-6}$ haloalkyl; and, $R^8$ is hydrogen, methyl or ethyl and hydrates, solvates, clathrates and acid addition salts thereof.

In another embodiment of the present invention there is provided a compound according to formula I wherein $X^1$ is $OR^5$; $R_1$ is methyl, ethyl, trifluoromethyl or halogen; $R^2$ and $R^4$ are independently hydrogen, chloro, fluoro, methyl or ethyl; $R^3$ is hydrogen or fluoro; $R^5$ is 2,6-disubstituted phenyl which substituents are independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, C!4 alkylsulfinyl, $C_{1-6}$ sulfonyl, $C_{1-6}$ haloalkoxy, $C_{1-6}$ haloalkylthio, halogen, alkylamino, dialkylamino, aminoacyl, cyano and acyl substituent; $R^7$ is hydrogen, methyl or ethyl; $R^8$ is selected from the group consisting of hydrogen, amino, alkylamino, dialkylamino, aminoalkyl, alkylaminoalkyl and dialkylaminoalkyl and $C_{1-6}$ alkyl optionally substituted with hydroxy, alkoxy, thiol, alkylthio or halogen; and, hydrates, solvates, clathrates and acid addition salts thereof.

In another embodiment of the present invention there is provided a compound according to formula I wherein $X^1$ is $OR^5$; $R_1$ is methyl, ethyl, trifluoromethyl or halogen; $R^2$ and $R^4$ are independently hydrogen, chloro, fluoro, methyl or ethyl; $R^3$ is hydrogen or fluoro; $R^5$ is 2,6-disubstituted phenyl which substituents are independently selected from the group consisting of halogen, cyano, $C_{1-6}$ alkyl, $C_{1-6}$ alkenyl, $C_{3-8}$ cycloalkyl, $C_{1-6}$ haloalkyl, $C_{1-6}$ alkoxy, $C_{1-6}$ alkylthio and $C_{1-6}$ haloalkoxy; $R^7$ is hydrogen, methyl or ethyl; $R^8$ is selected from the group consisting of hydrogen, amino, alkylamino, dialkylamino, aminoalkyl, alkylaminoalkyl and dialkylaminoalkyl and $C_{1-6}$ alkyl optionally substituted with hydroxy, alkoxy, thiol, alkylthio or halogen; and, hydrates, solvates, clathrates and acid addition salts thereof.

In another embodiment of the present invention there is provided a compound according to formula I wherein $X^1$ is $OR^5$; $R_1$ is halogen, methyl or ethyl; $R^2$ and $R^4$ are independently halogen, chloro, fluoro, methyl or ethyl; $R^3$ and $R_7$ are hydrogen; $R^5$ is a 2,6-disubstituted phenyl which substituents are independently selected from the group consisting of is halogen, cyano, $C_{1-6}$ alkyl and $C_{1-6}$ haloalkyl; and, $R^8$ is hydrogen, methyl or ethyl and hydrates, solvates, clathrates and acid addition salts thereof.

In another embodiment of the present invention there is provided a compound according to formula I wherein $X^1$ is $OR^5$; $R_1$ is halogen, methyl or ethyl; $R^2$ and $R^4$ are independently halogen, chloro, fluoro, methyl or ethyl; $R^3$ and $R^7$ are hydrogen; $R^5$ is a 2,3,5-trisubstituted phenyl which substituents are independently selected from the group consisting of is halogen, cyano, $C_{1-6}$ alkyl and $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, alkylamino, dialkylamino, aminoacyl, cyano, and acyl; and, $R^8$ is hydrogen, methyl or ethyl and hydrates, solvates, clathrates and acid addition salts thereof.

In another embodiment of the present invention there is provided a compound according to formula I wherein $X^1$ is $OR^5$ or $SR^5$; $R^3$ and $R^4$ are hydrogen, chloro, fluoro or methyl; and $R^5$ is an optionally substituted heteroaryl selected from the group consisting of pyridinyl, pyridine N-oxide, indole, indole N-oxide, quinoline, quinoline N-oxide, pyrimidinyl, pyrazinyl and pyrrolyl; and $R^1$, $R^2$, $R^7$ and $R^8$ are as defined hereinabove; and hydrates, solvates, clathrates and acid addition salts thereof.

In another embodiment of the present invention there is provided a compound according to formula I wherein $X^1$ is $R^5O$, $R^5S(O)_n$, $R^5CH_2$, $R^5CH_2O$, $R^5CH_2S(O)_n$, $R^5OCH_2$, $R^5S(O)_nCH_2$ or $NR^5R^6$; $R^1$ and $R^2$ along with the atoms to which they are attached form a fused phenyl, dihydropyran, dihydrofuran or furan ring; and $R^3$, $R^4$, $R^5$, $R^6$, $R^7$ and $R^8$ are as defined hereinabove; and hydrates, solvates, clathrates and acid addition salts thereof.

In another embodiment there is provided a compound according to formula I wherein $X^1$ is $R^5O$ or $R^5S$; $R_1$ and $R^2$ along with the atoms to which they are attached form a fused phenyl, dihydropyran, dihydrofuran or furan ring; $R^3$ and $R^7$ are hydrogen; $R^4$ is hydrogen or fluoro; $R^8$ is hydrogen or methyl; $R^5$ is optionally substituted phenyl; $R^7$ is as defined hereinabove; and hydrates, solvates, clathrates and acid addition salts thereof.

In another embodiment of the present invention there is provided a method for treating an HIV infection, or preventing an HIV infection, or treating AIDS or ARC, comprising administering to a host in need thereof a therapeutically effective amount of a compound of formula I

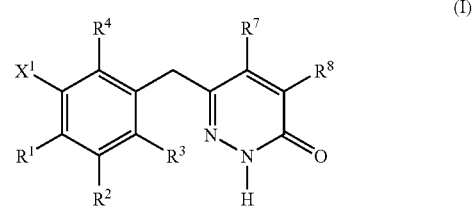

(I)

wherein, $X^1$, $R^1$, $R^2$, $R^3$, $R^4$, $R^5$, $R^6$, $R^7$ and $R^8$ are as defined hereinabove, and hydrates, solvates, clathrates and acid addition salts thereof.

In another embodiment of the present invention there is provided a method for treating an HIV infection, or preventing an HIV infection, or treating AIDS or ARC, comprising administering to a host in need thereof a therapeutically effective amount of a compound of formula I wherein, $X^1$ is $OR^5$, $R^1$ is methyl, ethyl, trifluoromethyl or halogen; $R^2$ and $R^4$ are hydrogen, fluoro, chloro, methyl or ethyl; $R^3$ is hydrogen or fluoro; $R^5$ is optionally substituted phenyl, $R^7$ is hydrogen, methyl or ethyl; and $R^8$ is as defined hereinabove, and hydrates, solvates, clathrates and acid addition salts thereof.

In another embodiment of the present invention there is provided a method for treating an HIV infection, or preventing an HIV infection, or treating AIDS or ARC, comprising administering to a host in need thereof a therapeutically effective amount of a compound of formula Ia wherein $R^1$ is selected from the group consisting of fluoro, chloro, bromo and methyl; $R^8$ is selected from the group consisting of hydrogen, methyl and ethyl; and, $R^9$ is selected from the group consisting of alkyl, cycloalkyl, haloalkyl, halogen and cyano.

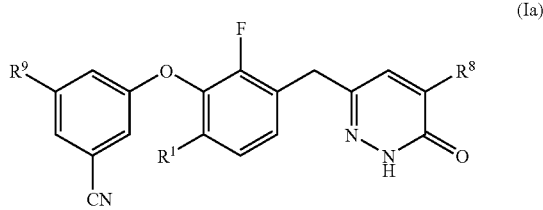

(Ia)

In another embodiment of the present invention there is provided a method for treating an HIV infection, or preventing an HIV infection, or treating AIDS or ARC, comprising co-administering to a host in need thereof a therapeutically effective amount of a compound of formula I wherein, $X^1$ is $OR^5$, $R^1$ is methyl, ethyl, trifluoromethyl or halogen; $R^2$ and $R^4$ are hydrogen, fluoro, chloro, methyl or ethyl; $R^3$ is hydrogen or fluoro; $R^5$ is optionally substituted phenyl, $R^1$ is hydrogen, methyl or ethyl; and $R^8$ is as defined hereinabove, and hydrates, solvates, clathrates and acid addition salts thereof; and, at least one compound selected from the group consisting of HIV protease inhibitors, nucleoside reverse transcriptase inhibitors, non-nucleoside reverse transcriptase inhibitors, CCR5 inhibitors and viral fusion inhibitors.

In another embodiment of the present invention there is provided a method for treating an HIV infection, or preventing an HIV infection, or treating AIDS or ARC, comprising co-administering to a host in need thereof a therapeutically effective amount of a compound of formula I wherein, $X^1$ is $OR^5$, $R^1$ is methyl, ethyl, trifluoromethyl or halogen; $R^2$ and $R^4$ are hydrogen, fluoro, chloro, methyl or ethyl; $R^3$ is hydrogen or fluoro; $R^5$ is optionally substituted phenyl, $R^7$ is hydrogen, methyl or ethyl; and $R^8$ is as defined hereinabove, and hydrates, solvates, clathrates and acid addition salts thereof; and at least one compound selected from the group consisting of saquinavir, ritonavir, nelfinavir, indinavir, amprenavir, lopinavir, and/or reverse transcriptase inhibitors selected from the group consisting of zidovudine, lamivudine, didanosine, zalcitabine, stavudine, rescriptor, sustiva, virmune, efavirenz, nevirapine and delavirdine.

In another embodiment of the present invention there is provided a method for inhibiting a retroviral reverse transcriptase comprising administering to a host in need thereof a therapeutically effective amount of a compound of formula I wherein, $X^1$, $R^1$, $R^2$, $R^3$, $R^4$, $R^5$, $R^6$, $R^7$ and $R^8$ are as defined hereinabove, and hydrates, solvates, clathrates and acid addition salts thereof.

In another embodiment of the present invention there is provided a method for inhibiting a retroviral reverse transcriptase having at least one mutation with respect to the wild type virus comprising administering to a host in need thereof a therapeutically effective amount of a compound of formula I wherein, $X^1$, $R^1$, $R^2$, $R^3$, $R^4$, $R^5$, $R^6$, $R^7$ and $R^8$ are as defined hereinabove, and hydrates, solvates, clathrates and acid addition salts thereof.

In another embodiment of the present invention there is provided a method for treating an HIV infection, or preventing an HIV infection, or treating AIDS or ARC wherein the host is infected with a strain of HIV with reduced susceptibility to efavirenz, nevirapine or delavirdine comprising administering to a host in need thereof a therapeutically effective amount of a compound of formula I wherein, $X^1$, $R^1$, $R^2$, $R^3$, $R^4$, $R^5$, $R^6$, $R^7$ and $R^8$ are as defined hereinabove, and hydrates, solvates, clathrates and acid addition salts thereof.

In another embodiment of the present invention there is provided a pharmaceutical composition comprising a therapeutically effective quantity of a compound of formula I,

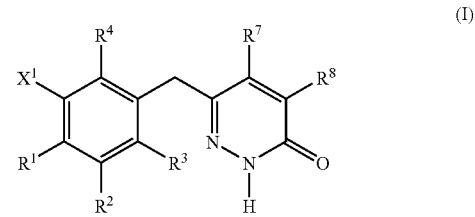

(I)

wherein, $X^1$ is $R^5O$, $R^5S(O)_n$, $R^5CH_2$, $R^5CH_2O$, $R^5CH_2S(O)_n$, $R^5OCH_2$, $R^5S(O)_nCH_2$ or $NR^5R^6$; is hydrogen, $C_{1-6}$ alkyl, $C_{1-6}$ haloalkyl, $C_{3-8}$ cycloalkyl, $C_{1-6}$ alkylthio, $C_{1-6}$ haloalkylthio, halogen, amino, alkylamino, dialkylamino, aminoacyl, nitro and cyano; and $R^1$, $R^2$, $R^3$, $R^4$, $R^5$, $R^6$, $R^7$ and $R^8$ are as defined hereinabove, hydrates, solvates, clathrates and acid addition salts thereof in admixture with at least one pharmaceutically acceptable carrier, excipient or diluent.

In another embodiment of the present invention there is provided a process for preparing a compound of formula I wherein $X^1$ is $OR^5$ or $SR^5$, $R^5$ is an optionally substituted aryl, alkyl or aralkyl moiety and $R^1$–$R^4$, $R^1$ and $R^8$ are as defined hereinabove which process comprises the steps of:
(i) coupling an aryl compound of formula IIa wherein

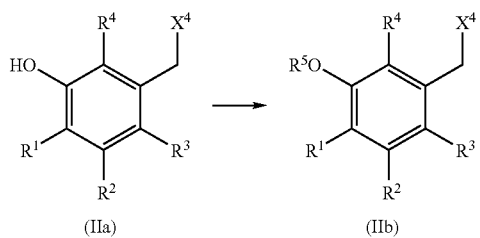

(IIa)   (IIb)

$X^4$ is hydrogen, alkoxycarbonyl or nitrile with (A) an aryl boronic acid or an aryl halide, or (B) an alcohol, alkyl halide or aralkyl halide to produced an ether of formula IIb; (ii) if $X^4$ is hydrogen, (a) brominating the methyl group with NBS and displacing the bromide ($X^4$=Br) with sodium cyanide to produce the corresponding nitrile ($X^4$=CN); (iii) treating a compound of formula IIb with base and condensing the

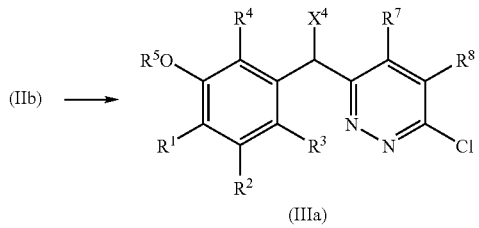

conjugate base with a pyrazine compound to produce a compound of formula IIIa; and (iv) subjecting the alkoxycarbonyl or nitrile to acidic or basic hydrolysis, decarboxylating the resulting carboxylic acid and hydrolysing the chloropyrazine to a pyridazinone of formula I with acetic acid and aqueous hydrochloric acid.

In another embodiment of the present invention there is provided a process as described above for preparing a compound of formula I wherein $X^4$ hydrogen, alkoxycarbonyl or nitrile, $R^5$ is optionally substituted aryl and the ether is prepared by coupling an arylboronic acid and a phenol IIa in the presence of a Cu(II) salt.

In another embodiment of the present invention there is provided a process as described above for preparing a compound of formula I wherein $X^4$ is hydrogen, alkoxycarbonyl or nitrile, $R^5$ is optionally substituted aryl and the ether is prepared by coupling an aryl halide and a phenol IIa in the presence of a Cu(I) salt.

In another embodiment of the present invention there is provided a process as described above for preparing a compound of formula I wherein $X^4$ is hydrogen, alkoxycarbonyl or nitrile, $R^5$ is optionally substituted aryl, alkyl or aralkyl moiety and the ether is prepared by coupling an aryl halide further substituted by electron withdrawing groups, an optionally substituted alkyl halide or an optionally substituted aralkyl halide and a phenol IIa in the presence of a base.

In another embodiment of the present invention there is provided a process as described above for preparing a compound of formula IIIa wherein the base is sodium hydride and the pyrazine compound is a 3,6-dihalopyrazine or a 3-halo-6-alkoxypyrazine.

In another embodiment of the present invention there is provided a process as described above for preparing a compound of formula I wherein the acidic hydrolysis conditions comprise a carboxylic acid and an aqueous hydrohalic acid.

In another embodiment of the present invention there is provided a process as described above for preparing a compound of formula I wherein the acidic hydrolysis conditions comprise acetic acid and aqueous hydrochloric acid.

In another embodiment of the present invention there is provided a process as described above for preparing a compound of formula I wherein the acidic hydrolysis conditions comprise acetic acid, sodium acetate and aqueous hydrochloric acid.

In another embodiment of the present invention there is provided a process as described above for preparing a compound of formula I wherein the alkoxycarbonyl compound is hydrolyzed with base and said chloropyrazine is hydrolyzed with acetic acid and aqueous hydrochloric acid.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition provided in the Summary of the Invention.

The term "optional" or "optionally" as used herein means that a subsequently described event or circumstance may, but need not, occur, and that the description includes instances where the event or circumstance occurs and instances in which it does not. For example, "optionally substituted" means that the moiety may be hydrogen or a substituent.

The term "$C_{1-6}$ alkyl" as used herein denotes an unbranched or branched chain, saturated, monovalent hydrocarbon residue containing 1 to 6 carbon atoms. Examples of alkyl groups include, but are not limited to, lower alkyl groups include methyl, ethyl, propyl, i-propyl, n-butyl, i-butyl, t-butyl or pentyl, isopentyl, neopentyl, hexyl.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "$C_{3-8}$ cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl.

The term "aryl" as used herein means a monocyclic or polycyclic-aromatic group comprising carbon and hydrogen atoms. Examples of suitable aryl groups include, but are not limited to, phenyl, tolyl, indenyl, and 1- or 2-naphthyl, as well as benzo-fused carbocyclic moieties such as 5,6,7,8-tetrahydronaphthyl. An aryl group can be unsubstituted or substituted with one or more suitable substituents which substituents include $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, amino, alkylamino, dialkylamino, aminoacyl, acyl, alkoxycarbonyl, carbamoyl, N-alkylcarbamoyl, N,N-dialkylcarbamoyl, nitro and cyano.

A "heteroaryl group" or "heteroaromatic" as used herein means a monocyclic- or polycyclic aromatic ring comprising up to 15 carbon atoms, hydrogen atoms, and one or more heteroatoms, preferably, 1 to 3 heteroatoms, independently selected from nitrogen, oxygen, and sulfur. As well known to those skilled in the art, heteroaryl rings have less aromatic character than their all-carbon counter parts. Thus, for the purposes of the invention, a heteroaryl group need only have some degree of aromatic character.

Illustrative examples of heteroaryl groups include, but are not limited to, pyridinyl, pyridine N-oxide, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, thienyl, isoxazolyl, indole, indole N-oxide, quinoline, quinoline N-oxide and oxazolyl. A heteroaryl group can be unsubstituted or substituted with one or more suitable substituents selected from hydroxy, oxo, cyano, alkyl, alkoxy, haloalkoxy, alkylthio, halo, haloalkyl, nitro, alkoxycarbonyl, amino, alkylamino, dialkylamino, aminoacyl, alkylsulfonyl, arylsulfinyl, alkoxycarbonyl, carbamoyl, N-alkylcarbamoyl, N,N-dialkylcarbamoyl, acyl unless otherwise indicated.

The term "heterocyclyl" means the monovalent saturated cyclic radical, consisting of one or more rings, preferably one to two rings, of three to eight atoms per ring, incorporating one or more ring heteroatoms (chosen from N,O or $S(O)_{0-2}$), and which can optionally be substituted with one or more, preferably one to three substituents selected from hydroxy, oxo, cyano, alkyl, alkoxy, haloalkoxy, alkylthio, halo, haloalkyl, nitro, alkoxycarbonyl, amino, alkylamino, dialkylamino, aminoacyl, alkylsulfonyl, arylsulfinyl, alkoxycarbonyl, carbamoyl, N-alkylcarbamoyl, N,N-dialkylcarbamoyl, acyl unless otherwise indicated. Examples of heterocyclic radicals include, but are not limited to, furanyl, tetrahydropyranyl, tetrahydrothiophenyl and the like. A nitrogen atom in the heteroaryl ring can optionally be an N-oxide.

The term "alkoxy group" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, heptyloxy including their isomers.

The term "alkylthio group" as used herein means an —S-alkyl group, wherein alkyl is as defined above such as meththio, eththio, n-propylthio, i-propylthio, n-butylthio, i-butylthio, t-butylthio, pentylthio including their isomers.

The term "haloalkoxy group" as used herein means an —O-haloalkyl group, wherein haloalkyl is as defined above. Examples of haloalkoxy groups include, but are not limited to, 2,2,2-trifluoroethoxy, difluoromethoxy and 1,1,1,3,3,3-hexafluoro-iso-propoxy.

The term "haloalkthio group" as used herein means an —S-haloalkyl group, wherein haloalkyl is as defined above. An example of haloalkthio group includes, but are not limited to, 2,2,2-trifluoroeththanthiol.

The term "aryloxy group" as used herein means an O-aryl group wherein aryl is as defined above. An aryloxy group can be unsubstituted or substituted with one or more suitable substituents. Preferably, the aryl ring of an aryloxy group is a monocyclic ring, wherein the ring comprises 6 carbon atoms, referred to herein as "$(C_6)$ aryloxy". The term "optionally substituted aryloxy" means the aryl or group may be substituted with one to three groups selected from the group consisting of $C_{1-6}$ alkyl, $C_{1-6}$ haloalkyl, $C_{3-8}$ cycloalkyl, $C_{1-6}$ alkoxy, $C_{1-6}$ alkylthio, $C_1$ alkylsulfinyl, $C_{1-6}$ sulfonyl, $C_{1-6}$ haloalkoxy, $C_{1-6}$ haloalkylthio, halogen, amino, alkylamino, dialkylamino, aminoacyl, acyl, alkoxycarbonyl, carbamoyl, N-alkylcarbamoyl, N,N-dialkylcarbamoyl, nitro and cyano.

The term "heteroaryloxy group" as used herein means an O-heteroaryl group, wherein heteroaryl is as defined above. The heteroaryl ring of a heteroaryloxy group can be unsubstituted or substituted with one or more suitable substituents. Examples of heteroaryl groups include, but are not limited to, 2-pyridyloxy, 3-pyrrolyloxy, 3-pyrazolyloxy, 2-imidazolyloxy, 3-pyrazinyloxy, and 4-pyrimidyloxy.

The term "acyl" or "alkylcarbonyl" as used herein denotes a radical of formula C(=O)R wherein R is hydrogen, unbranched or branched alkyl containing 1 to 6 carbon atoms or a phenyl group.

The term "alkoxycarbonyl" as used herein denotes a radical of formula C(=O)OR wherein R is, unbranched or branched alkyl as described above.

The term "acylamino" as used herein denotes a radical of formula —NH-(acyl) where acyl is as defined herein.

The term "arylboronic acid" as used herein denotes a radical of formula $ArB(OH)_2$ wherein Ar is an optionally substituted aryl group as described above.

The term "alkylene" as used herein denotes a divalent linear or branched saturated hydrocarbon radical, having from one to six carbons inclusive, unless otherwise indicated. Examples of alkylene radicals include, but are not limited to, methylene, ethylene, propylene, 2-methyl-propylene, butylene, 2-ethylbutylene.

The term "arylalkyl" or "aralkyl" as used herein denotes the radical R'R"—, wherein $R^1$ is an aryl radical as defined herein, and R" is an alkylene radical as defined herein and the arylalkyl group is attached through the alkylene radical. Examples of arylalkyl radicals include, but are not limited to, benzyl, phenylethyl, 3-phenylpropyl.

The term "halogen" as used herein means fluorine, chlorine, bromine, or iodine. Correspondingly, the meaning of the term "halo" encompasses fluoro, chloro, bromo, and iodo. The term "hydrohalic acid" refers to an acid comprised of hydrogen and a halogen.

The term "alkylsulfinyl" as used herein means the radical —S(O)R', wherein R' is alkyl as defined herein. Examples of alkylaminosulfonyl include, but are not limited to methylsulfinyl and iso-propylsulfinyl.

The term "alkylsulfonyl" as used herein means the radical —S(O)$_2$R', wherein R' is alkyl as defined herein. Examples of alkylaminosulfonyl include, but are not limited to methylsulfonyl and iso-propylsulfonyl.

The terms "amino", "alkylamino" and "dialkylamino" as used herein refer to —NH$_2$, —NHR and —NR$_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to NH$_2$(CH$_2$)$_n$—, RHN(CH$_2$)$_n$—, and R$_2$N(CH$_2$)$_n$— respectively wherein n is 1 to 6 and R is alkyl as defined above The prefix "carbamoyl" as used herein means the radical —CONH$_2$. The prefix "N-alkylcabamoyl" and "N,N-dialkylcarbamoyl" means the radical CONHR' or CONR'R" respectively wherein the R' and R" groups are independently alkyl as defined herein.

The term "conjugate base" as used herein means the chemical species produced when an acid (including here a carbon acid) gives up its proton.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C (—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Compounds of formula I which are basic can form pharmaceutically acceptable acid addition salts with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluenesulfonic acid, and the like).

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

The term "clathrate" as used herein means a compound of the invention or a salt thereof in the form of a crystal lattice that contains spaces (e. g., channels) that have a guest molecule (e. g., a solvent or water) trapped within.

The term "wild type" as used herein refers to the HIV virus strain which possesses the dominant genotype which naturally occurs in the normal population which has not been exposed to reverse transcriptase inhibitors. The term "wild type reverse transcriptase" used herein has refers to the reverse transcriptase expressed by the wild type strain which has been sequenced and deposited in the SwissProt database with an accession number P03366.

The term "reduced susceptibility" as used herein refers to about a 10 fold, or greater, change in sensitivity of a particular viral isolate compared to the sensitivity exhibited by the wild type virus in the same experimental system The term "nucleoside and nucleotide reverse transcriptase inhibitors" ("NRTI's) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename; didanosine (ddI) available under the VIDEX tradename.; zalcitabine (ddC) available under the HIVID tradename; stavudine (d4T) available under the ZERIT trademark.; lamivudine (3TC) available under the EPIVIR tradename; abacavir (1592U89) disclosed in WO96/30025 and available under the ZIAGEN trademark; adefovir dipivoxil [bis(POM)-PMEA] available under the PREVON tradename; lobucavir (BMS-180194), a nucleoside reverse transcriptase inhibitor disclosed in EP-0358154 and EP-0736533 and under development by Bristol-Myers Squibb; BCH-10652, a reverse transcriptase inhibitor (in the form of a racemic mixture of BCH-10618 and BCH-10619) under development by Biochem Pharma; emitricitabine [(–)-FTC] licensed from Emory University under U.S. Pat. No. 5,814,639 and under development by Triangle Pharmaceuticals; beta-L-FD4 (also called beta-L-D4C and named beta-L-2', 3'-dicleoxy-5-fluoro-cytidene) licensed by Yale University to Vion Pharmaceuticals; DAPD, the purine nucleoside, (–)-beta-D-2,6,-diamino-purine dioxolane disclosed in EP-0656778 and licensed to Triangle Pharmaceuticals; and lodenosine (FddA), 9-(2,3-dideoxy-2-fluoro-b-D-threo-pentofuranosyl)adenine, an acid stable purine-based reverse transcriptase inhibitor discovered by the NIH and under development by U.S. Bioscience Inc.

The term "non-nucleoside reverse transcriptase inhibitors" ("NNRTI's) as used herein means non-nucleosides that inhibit the activity of HIV-1 reverse transcriptase.

Typical suitable NNRTIs include nevirapine (BI-RG-587) available under the VIRAMUNE tradename; delaviradine (BHAP, U-90152) available under the RESCRIPTOR tradename; efavirenz (DMP-266) a benzoxazin-2-one disclosed in WO94/03440 and available under the SUSTIVA tradename; PNU-142721, a furopyridine-thio-pyrimide; AG-1549 (formerly Shionogi # S-1153); 5-(3,5-dichlorophenyl)-thio-4-isopropyl-1-(4-pyridyl)methyl-1H-imidazol-2-ylmethyl carbonate disclosed in WO 96/10019; MKC-442 (1-(ethoxy-methyl)-5-(1-methylethyl)-6-(phenylmethyl)-(2,4(1H,3H)-pyrimidinedione); and (+)-calanolide A (NSC-675451) and B, coumarin derivatives disclosed in U.S. Pat. No. 5,489,697

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN as well as non-peptide protease inhibitors e.g., VIRACEPT.

Typical suitable PIs include saquinavir available in hard gel capsules under the INVIRASE tradename and as soft gel capsules under the FORTOVASE tradename; ritonavir (ABT-538) available under the NORVIR tradename; indinavir (MK-639) available under the CRIXIVAN tradename; nelfnavir (AG-1343) available under the VIRACEPT; amprenavir (141W94), tradename AGENERASE, a non-peptide protease inhibitor; lasinavir (BMS-234475; originally discovered by Novartis, Basel, Switzerland (CGP-61755); DMP-450, a cyclic urea discovered by Dupont; BMS-2322623, an azapeptide under development by Bristol-Myers Squibb, as a 2nd-generation HIV-1 PI; ABT-378; AG-1549 an orally active imidazole carbamate.

Other antiviral agents include hydroxyurea, ribavirin, IL-2, IL-12, pentafuside and Yissum Project No. 11607. Hydroxyurea (Droxia), a ribonucleoside triphosphate reductase inhibitor, the enzyme involved in the activation of T-cells. Hydroxyurea was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN (aldesleukin) tradename as a lyophilized powder for IV infusion or sc administration upon reconstitution and dilution with water; a dose of about 1 to about 20 million 1 U/day, sc is preferred; a dose of about 15 million 1 U/day, sc is more preferred. IL-12 is disclosed in WO96/25171 and is available as a dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 and available under the FUZEON tradename; pentafuside acts by inhibiting fusion of HIV-1 to target membranes. Pentafuside (3–100 mg/day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV-1 Vif protein. Ribavirin, 1-.beta.-D-ribofuranosyl-1H-1,2,4-triazole-3-carboxamide, is described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include:

(a) triple combination therapies such as two NRTIs and one PI; or (b) two NRTIs and one NNRTI; and (c) quadruple combination therapies such as two NRTIs, one PI and a second PI or one NNRTI. In treatment of naive patients, it is preferred to start anti-HIV-1 treatment with the triple combination therapy; the use of two NRTIs and one PI is preferred unless there is intolerance to PIs. Drug compliance is essential. The CD4.sup.+ and HIV-1-RNA plasma levels should be monitored every 3–6 months. Should viral load plateau, a fourth drug, e.g., one PI or one NNRTI could be added.

Abbreviations

The following abbreviations are used throughout this application and they have the meaning listed below:

| | |
|---|---|
| AIBN | azo-bis-isobutyrylnitrile |
| atm | atmospheres |
| BBN or 9-BBN | 9-borabicyclo[3.3.1]nonane |
| Boc | tert-butoxycarbonyl |
| BOC$_2$O | Di-tert-butyl pyrocarbonate or boc anhydride |
| Bn | benzyl |
| cbz or Z | benzyloxycarbonyl |
| DABCO | diazabicyclooctane |
| DAST | diethylaminosulfur trifluoride |
| DCE | 1,2-dichloroethane |
| DCM | dichloromethane |
| DEAD | diethyl azodicarboxylate |
| DIAD | di-iso-propylazodicarboxylate |
| DIBAL-H | di-iso-butylaluminumhydride |
| DMA | N,N-dimethyl acetamide |
| DMAP | 4-N,N-dimethylaminopyridine |
| DMF | N,N-dimethylformamide |
| dppf | 1,1'-Bis(diphenylphosphino)ferrocene |
| EDCI | 1-(3-dimethylaminopropyl)-3-ethylcarbodiimide hydrochloride |
| EtOAc | ethyl acetate |
| Et$_2$O | diethyl ether |
| Et | ethyl |
| EtOH | ethanol |
| LAH | lithium aluminum hydride |
| LiHMDS | lithium hexamethyl disilazane |
| h | hour(s) |
| HOAc | acetic acid |
| i-Pr | iso-propyl |
| m | minute(s) |
| Me | methyl |
| MeCN | acetonitrile |
| MeOH | methanol |
| MTBE | methyl t-butyl ether |
| NBS | N-bromosuccinimide |
| NMP | N-methylpyrrolidone |
| PCC | pyridinium chlorochromate |
| PDC | pyridinium dichromate |
| psi | pounds per square inch |
| pyr | pyridine |
| rt or RT | room temperature |
| TEA or Et$_3$N | triethylamine |
| Tf | triflate CF$_3$SO$_2$— |
| TFA | trifluoroacetic acid |
| THF | tetrahydrofuran |
| TLC | thin layer chromatography |
| TMHD | 2,2,6,6-tetramethylheptane-2,6-dione |
| TsOH | p-toluenesulfonic acid monohydrate |

EXAMPLES OF COMPOUNDS

Examples of representative compounds within the scope of the invention are provided in the Tables I, II and III. Table I depicts new compounds wherein $X^1$ is $OR^5$ and $R^5$ is optionally substituted aryl or heteroaryl encompassed by the present invention. Table II depicts new compounds wherein $X^1$ is other than $OR^5$ and $R^5$ is optionally substituted aryl or heteroaryl encompassed by the present invention. Table III depicts COX-2 inhibitors wherein X1 is —C(=O)-which have now, unexpectedly, been found to inhibit RT (EP 810218; D. A. Allen et al.). These examples and preparations are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. Table 1 contains representative examples of [3-phenoxybenzyl]pyridazinones. References in the application to compounds in the tables are designated by the table number followed by a dash and the compound number (e.g., I-100)

TABLE I

| cpd # | Structure | Name | [M + H]$^+$ (mw) mp |
|---|---|---|---|
| I-1 | 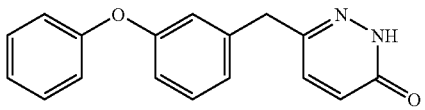 | 6-(3-Phenoxy-benzyl)-2H-pyridazin-3-one | 278$^1$ (278.31) |

TABLE I-continued

| cpd # | Structure | Name | [M + H]+ (mw) mp |
|---|---|---|---|
| I-2 | 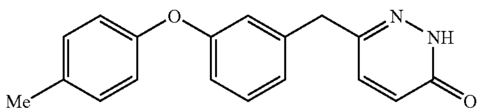 | 6-(3-p-Tolyloxy-benzyl)-2H-pyridazin-3-one | 292[1] (292.33) |
| I-3 | 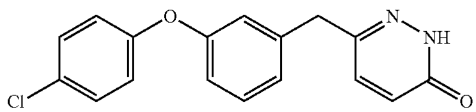 | 6-[3-(4-Chloro-phenoxy)-benzyl]-2H-pyridazin-3-one | 312[1] (312.75) |
| I-4 | 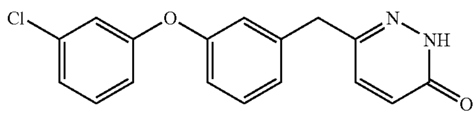 | 6-[3-(3-Chloro-phenoxy)-benzyl]-2H-pyridazin-3-one | 312[1] (312.75) |
| I-5 | 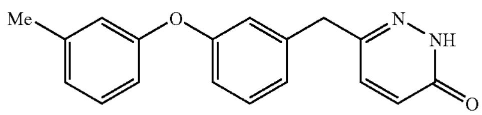 | 6-(3-m-Tolyloxy-benzyl)-2H-pyridazin-3-one | 292[1] (292.33) |
| I-6 | 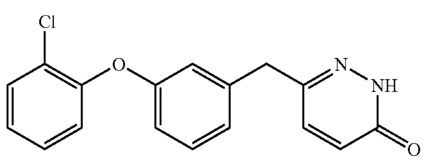 | 6-[3-(2-Chloro-phenoxy)-benzyl]-2H-pyridazin-3-one | 312[1] (312.75) |
| I-7 | 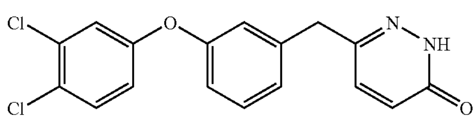 | 6-[3-(3,4-Dichloro-phenoxy)-benzyl]-2H-pyridazin-3-one | 347[1] (347.2) |
| I-8 | 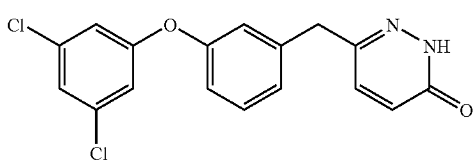 | 6-[3-(3,5-Dichloro-phenoxy)-benzyl]-2H-pyridazin-3-one | 347[1] (347.2) |
| I-9 | 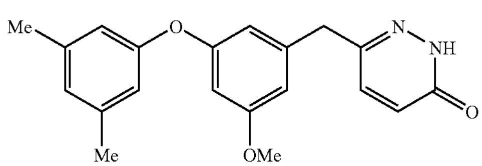 | 6-[3-(3,5-Dimethyl-phenoxy)-5-methoxy-benzyl]-2H-pyridazin-3-one | 336[1] (336.38) |
| I-10 | 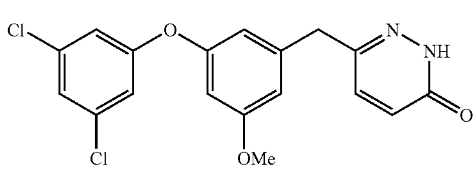 | 6-[3-(3,5-Dichloro-phenoxy)-5-methoxy-benzyl]-2H-pyridazin-3-one | 377[1] (377.22) |
| I-11 | 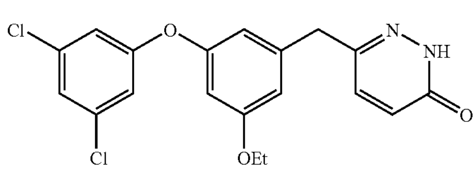 | 6-[3-(3,5-Dichloro-phenoxy)-5-ethoxy-benzyl]-2H-pyridazin-3-one | 391[1] (391.25) |

TABLE I-continued

| cpd # | Structure | Name | [M + H]+ (mw) mp |
|---|---|---|---|
| I-12 | 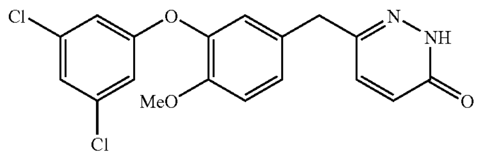 | 6-[3-(3,5-Dichloro-phenoxy)-4-methoxy-benzyl]-2H-pyridazin-3 one | 377 (377.22) |
| I-13 | 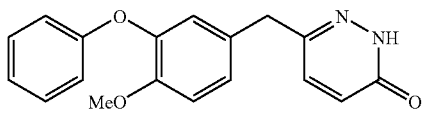 | 6-(4-Methoxy-3-phenoxy-benzyl)-2H-pyridazin-3-one | 308[1] (308.33) |
| I-14 | 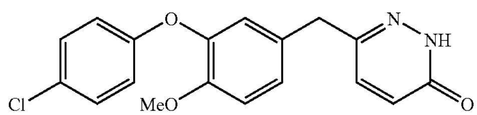 | 6-[3-(4-Chloro-phenoxy)-4-methoxy-benzyl]-2H-pyridazin-3-one | 342[1] (342.78) |
| I-15 | 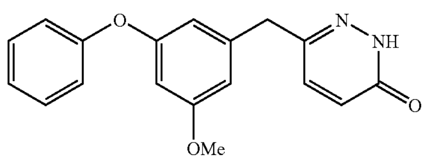 | 6-(5-Methoxy-3-phenoxy-benzyl)-2H-pyridazin-3-one | 308[1] (308.33) |
| I-16 | 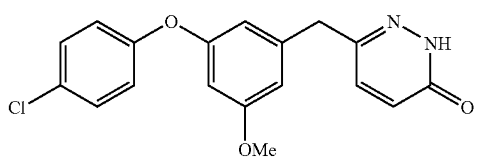 | 6-[3-(4-Chloro-phenoxy)-5-methoxy-benzyl]-2H-pyridazin-3-one | 342[1] (342.78) |
| I-17 | 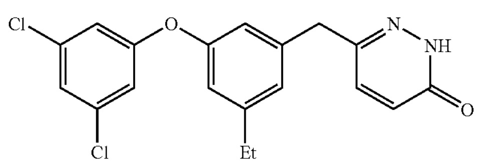 | 6-[3-(3,5-Dichloro-phenoxy)-5-ethyl-benzyl]-2H-pyridazin-3-one | 375[1] (375.25) |
| I-18 | 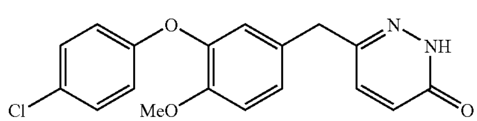 | 6-[3-(4-Chloro-phenoxy)-4-methyl-benzyl]-2H-pyridazin-3-one | 327 (326.78) |
| I-19 | 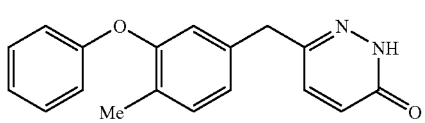 | 6-(4-Methyl-3-phenoxy-benzyl)-2H-pyridazin-3-one | 293 (292.33) 83–85 |
| I-20 | 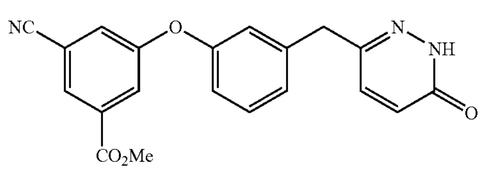 | 3-Cyano-5-[3-(6-oxo-1,6-dihydro-pyridazin-3-ylmethyl)-phenoxy]-benzoic acid methyl ester | 361[1] (361.35) |
| I-21 | 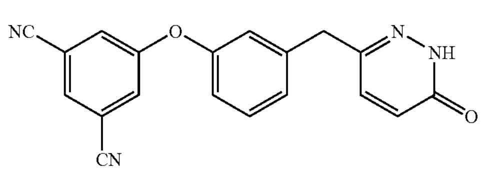 | 5-[3-(6-Oxo-1,6-dihydro-pyridazin-3-ylmethyl)-phenoxy]-isophthalonitrile | 328[1] (328.33) |

TABLE I-continued

| cpd # | Name | [M + H]+ (mw) mp |
|---|---|---|
| I-22 | 4-[2-Methoxy-5-(6-oxo-1,6-dihydro-pyridazin-3-ylmethyl)-phenoxy]-benzonitrile | 333[1] (333.35) |
| I-23 | 3-[2-Methoxy-5-(6-oxo-1,6-dihydro-pyridazin-3-ylmethyl)-phenoxy]-benzonitrile | 333[1] (333.35) |
| I-24 | 6-[3-(4-Chloro-phenoxy)-4-etbyl-benzyl]-2H-pyridazin-3-one | 341 (340.80) |
| I-25 | 6-[3-(3-Chloro-phenoxy)-5-methyl-benzyl]-2H-pyridazin-3-one | 326[1] (326.78) |
| I-26 | 6-[3-(4-Chloro-phenoxy)-5-methyl-benzyl]-2H-pyridazin-3-one | 326[1] (326.78) |
| I-27 | 6-[3-(3,5-Dichloro-phenoxy)-5-methyl-benzyl]-2H-pyridazin-3-one | 361[1] (361.22) |
| I-28 | 6-(4-Ethyl-3-phenoxy-benzyl)-2H-pyridazin-3-one | 307 (306.36) oil |
| I-29 | 6-[3-(3-Chloro-phenoxy)-4-ethyl-benzyl]-2H-pyridazin-3-one | 341 (340.80) oil |
| I-30 | 6-[3-(3-Chloro-phenoxy)-4-methyl-benzyl]-2H-pyridazin-3-one | 327 (326.78) oil |
| I-31 | 6-[4-Chloro-3-(3-chloro-phenoxy)-benzyl]-2H-pyridazin-3-one | 347 (347.2) oil |
| I-32 | 6-[3-(3-Chloro-phenoxy)-5-ethyl-benzyl]-2H-pyridazin-3-one | 340[1] 340.80 |

TABLE I-continued

| cpd # | Name | [M + H]+ (mw) mp |
|---|---|---|
| I-33 | 6-[3-(4-Chloro-phenoxy)-5-ethyl-benzyl]-2H-pyridazin-3-one | 340[1] (340.80) |
| I-34 | 6-[3-(2-Chloro-phenoxy)-4-methyl-benzyl]-2H-pyridazin-3-one | 327 (326.78) 116–118 |
| I-35 | 6-[3-(2-Chloro-phenoxy)-4-ethyl-benzyl]-2H-pyridazin-3-one | 341 (340.80) oil |
| I-36 | 6-[4-Chloro-3-(2-chloro-phenoxy)-benzyl]-2H-pyridazin-3-one | 347 (347.2) 132.1–133.7 |
| I-37 | 6-[3-(3-Metboxy-phenoxy)-4-methyl-benzyl]-2H-pyridazin-3-one | 323 (322.36) 66.5–70.7 |
| I-38 | 6-(4-Chloro-3-phenoxy-benzyl)-2H-pyridazin-3-one | 313 (312.75) |
| I-39 | 6-[4-Methyl-3-(3-trifluoromethyl-phenoxy)-benzyl]-2H-pyridazin-3-one | 361 (360.33) oil |
| I-40 | 6-[3-(3-Chloro-phenoxy)-4,5-dimethyl-benzyl]-2H-pyridazin-3-one | 341 340.80 121–123 |
| I-41 | 6-(4-Methyl-3-m-tolyloxy-benzyl)-2H-pyridazin-3-one | 307 (306.36) oil |
| I-42 | 6-[3-(3-Bromo-phenoxy)-4-methyl-benzyl]-2H-pyridazin-3-one | 371 (371.23) 96.6–101.3 |
| I-43 | 6-[3-(3-Chloro-phenoxy)-4-isopropyl-benzyl]-2H-pyridazin-3-one | 355 (354.83) 104–106 |

TABLE I-continued

| cpd # | Structure | Name | [M + H]+ (mw) mp |
|---|---|---|---|
| I-44 | 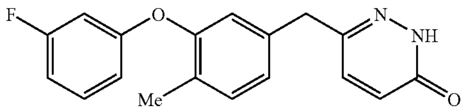 | 6-[3-(3-Fluoro-phenoxy)-4-methyl-benzyl]-2H-pyridazin-3-one | 311 (310.32) 119.2–121 |
| I-45 | 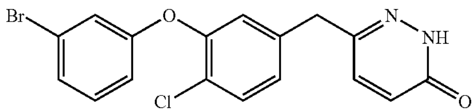 | 6-[3-(3-Bromo-phenoxy)-4-chloro-benzyl]-2H-pyridazin-3-one | 391 (391.65) 112.3 112.5 |
| I-46 | 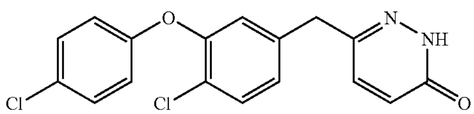 | 6-[4-Chloro-3-(4-chloro-phenoxy)-benzyl]-2H-pyridazin-3-one | 347 (347.2) 104.4–107.1 |
| I-47 | 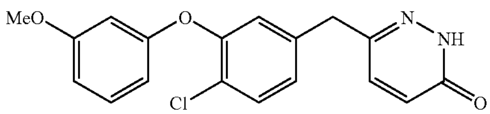 | 6-[4-Chloro-3-(3-methoxy-phenoxy)-benzyl]-2H-pyridazin-3-one | 343 (342.78) foam |
| I-48 | 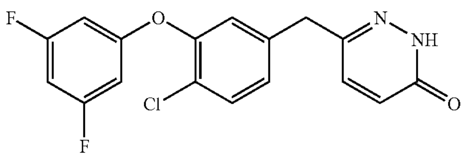 | 6-[4-Chloro-3-(3,5-difluoro-phenoxy)-benzyl]-2H-pyridazin-3-one | 349 (348.73) 91–93 |
| I-49 | 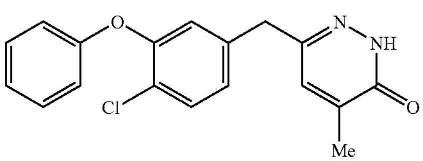 | 6-(4-Chloro-3-phenoxy-benzyl)-4-methyl-2H-pyridazin-3-one | 327 (326.78) |
| I-50 | 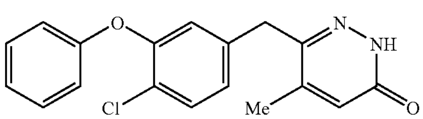 | 6-(4-Chloro-3-phenoxy-benzyl)-5-methyl-2H-pyridazin-3-one | 327 (326.78) |
| I-51 | 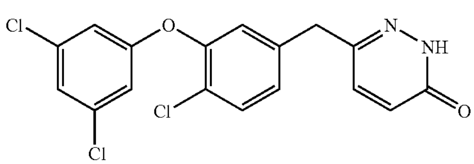 | 6-[4-Chloro-3-(3,5-dichloro-phenoxy)-benzyl]-2H-pyridazin-3-one | 381 (381.64) 160.9–163.0 |
| I-52 | 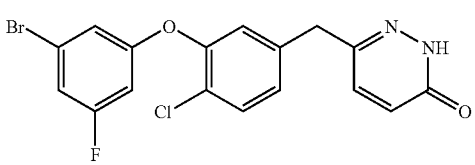 | 6-[3-(3-Bromo-5-fluoro-phenoxy)-4-chloro-benzyl]-2H-pyridazin-3-one | 409 (409.64) 98–101 |
| I-53 | 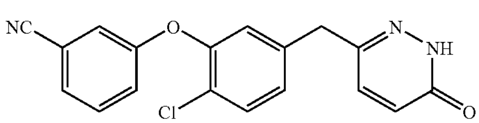 | 3-[2-Chloro-5-(6-oxo-1,6-dihydro-pyridazin-3-ylmethyl)-phenoxy]-benzonitrile | 338 (337.76) 114.5–119.8 |
| I-54 | 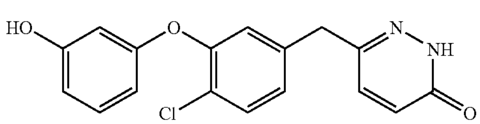 | 6-[4-Chloro-3-(3-hydroxy-phenoxy)-benzyl]-2H-pyridazin-3-one | 329 (328.75) 115–117 |

TABLE I-continued

| cpd # | Name | [M + H]+ (mw) mp |
|---|---|---|
| I-55 | 3-[2-Methyl-5-(6-oxo-1,6-dihydro-pyridazin-3-ylmethyl)-phenoxy]-benzonitrile | 318 (317.34) |
| I-56 | 6-[3-(4-Bromo-phenoxy)-4-chloro-benzyl]-2H-pyridazin-3-one | 391 (391.65) 139.2–142.8 |
| I-57 | 6-[4-Chloro-3-(3-fluoro-phenoxy)-benzyl]-2H-pyridazin-3-one | 331 (330.74) |
| I-58 | 6-[4-Chloro-3-(3-trifluoromethyl-phenoxy)-benzyl]-2H-pyridazin-3-one | 381 (380.75) 105–107 |
| I-59 | 6-[3-(3-Bromo-phenoxy)-4-chloro-benzyl]-4,5-dimethyl-2H-pyridazin-3-one | 419 (419.70) |
| I-60 | 6-[3-(3-Chloro-phenoxy)-4-fluoro-benzyl]-2H-pyridazin-3-one | 331 (330.74) 141–144 |
| I-61 | 6-[4-fluoro-3-(3-trifluoromethyl-phenoxy)-benzyl]-2H-pyridazin-3-one | 365 (364.29) 120–123 |
| I-62 | 6-[3-(3-Bromo-phenoxy)-4-fluoro-benzyl]-2H-pyridazin-3-one | 375 (375.19) 119–123 |
| I-63 | 6-[4-Chloro-3-(2-chloro-phenoxy)-benzyl]-4-isopropyl-2H-pyridazin-3-one | 389 (389.28) |
| I-64 | 6-[4-Chloro-3-(2-chloro-phenoxy)-benzyl]-4-ethyl-2H-pyridazin-3-one | 375 (375.25) |

TABLE I-continued

| cpd # | Structure | Name | [M + H]+ (mw) mp |
|---|---|---|---|
| I-65 | 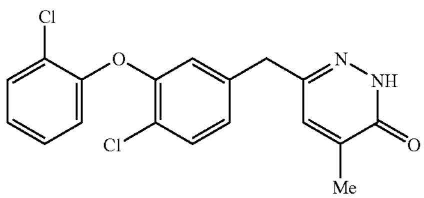 | 6-[4-Chloro-3-(2-chloro-phenoxy)-benzyl]-4-methyl-2H-pyridazin-3-one | 361 (361.22) |
| I-66 | 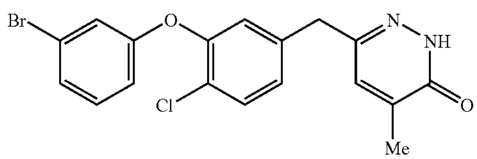 | 6-[3-(3-Bromo-phenoxy)-4-chloro-benzyl]-4-methyl-2H-pyridazin-3-one | 405 (405.67) |
| I-67 | 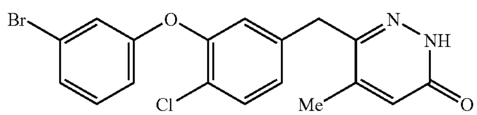 | 6-[3-(3-Bromo-phenoxy)-4-chloro-benzyl]-5-methyl-2H-pyridazin-3-one | 405 (405.67) |
| I-68 | 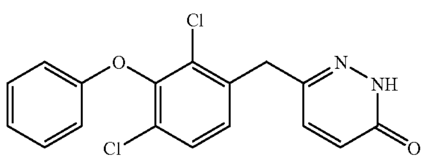 | 6-(2,4-Dichloro-3-phenoxy-benzyl)-2H-pyridazin-3-one | (347.2) |
| I-69 | 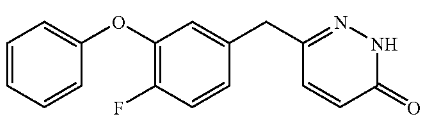 | 6-(4-Fluoro-3-phenoxy-benzyl)-2H-pyridazin-3-one | 297 (296.3) 130–132 |
| I-70 | 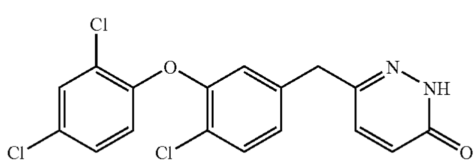 | 6-[4-Chloro-3-(2,4-dichloro-phenoxy)-benzyl]-2H-pyridazin-3-one | 381 (381.64) 88–92 |
| I-71 | 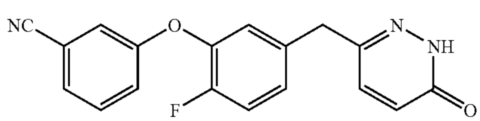 | 3-[2-fluoro-5-(6-oxo-1,6-dihydro-pyridazin-3-ylmethyl)-phenoxy]-benzonitrile | 322 (321.31) 169.2–171.3 |
| I-72 | 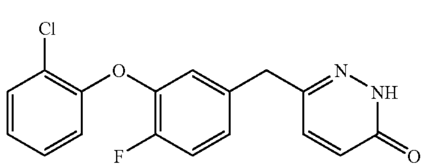 | 6-[3-(2-Chloro-phenoxy)-4-fluoro-benzyl]-2H-pyridazin-3-one | 331 (330.74) 137.5–139 |
| I-73 | 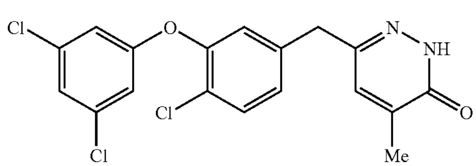 | 6-[4-Chloro-3-(3,5-dichloro-phenoxy)-benzyl]-4-methyl-2H-pyridazin-3-one | (395.67) |

TABLE I-continued

| cpd # | Name | [M + H]+ (mw) mp |
|---|---|---|
| I-74 | 6-[4-Chloro-3-(3,5-dichloro-phenoxy)-benzyl]-5-methyl-2H-pyridazin-3-one | (395.67) |
| I-75 | 3-[2-Chloro-5-(4,5-dimethyl-6-oxo-1,6-dihydro-pyridazin-3-ylmethyl)-phenoxy]-benzonitrile | 366 (365.81) |
| I-76 | 3-[2-Chloro-5-(4-methyl-6-oxo-1,6-dihydro-pyridazin-3-ylmethyl)-phenoxy]-benzonitrile | 352 (351.79) |
| I-77 | 6-[3-(2-Bromo-5-chloro-phenoxy)-4-chloro-benzyl]-2H-pyridazin-3-one | 425 (426.09) 152.7–155.1 |
| I-78 | 4-[2-Chloro-5-(6-oxo-1,6-dihydro-pyridazin-3-ylmethyl)-phenoxy]-benzonitrile | 338 (337.76) 193.4–201.4 |
| I-79 | 3-Chloro-4-[2-chloro-5-(6-oxo-1,6-dihydro-pyridazin-3-ylmethyl)-phenoxy]-benzonitrile | 372 (372.21) 180.7–182.1 |
| I-80 | 6-[3-(3,5-Dichloro-phenoxy)-4-fluoro-benzyl]-2H-pyridazin-3-one | 365 (365.19) 129.1–132.1 |
| I-81 | 6-[3-(3-Bromo-5-methyl-phenoxy)-4-chloro-benzyl]-2H-pyridazin-3-one | 405 (405.67) 155.1–157.4 |
| I-82 | 6-[3-(3-Bromo-phenoxy)-4-chloro-benzyl]-4-chloromethyl-2H-pyridazin-3-one | 441 (440.12) |

TABLE I-continued

| cpd # | Structure | Name | [M + H]+ (mw) mp |
|---|---|---|---|
| I-83 | 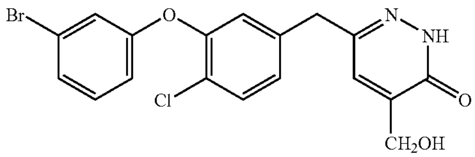 | 6-[3-(3-Bromo-phenoxy)-4-chloro-benzyl]-4-hydroxymethyl-2H-pyridazin-3-one | 423 (421.67) |
| I-84 | 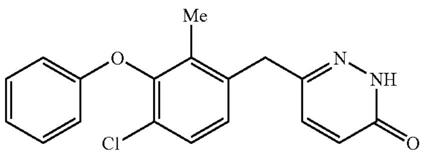 | 6-(4-Chloro-2-methyl-3-phenoxy-benzyl)-2H-pyridazin-3-one | 326 (326.78) |
| I-85 | 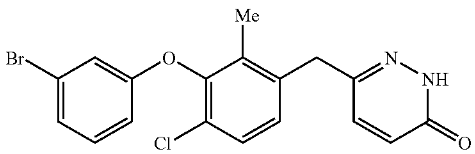 | 6-[3-(3-Bromo-phenoxy)-4-chloro-2-methyl-benzyl]-2H-pyridazin-3-one | 405 (405.67) |
| I-86 | 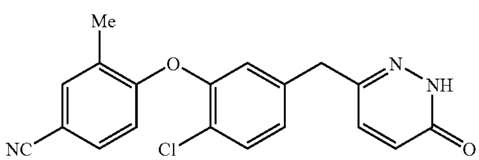 | 4-[2-Chloro-5-(6-oxo-1,6-dihydro-pyridazin-3-ylmethyl)-phenoxy]-3-methyl-benzonitrile | 352 (351.79) 146.1–150.2 |
| I-87 | 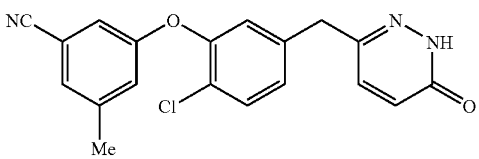 | 3-[2-Chloro-5-(6-oxo-1,6-dihydro-pyridazin-3-ylmethyl)-phenoxy]-5-methyl-benzonitrile | 352 (351.79) |
| I-88 | 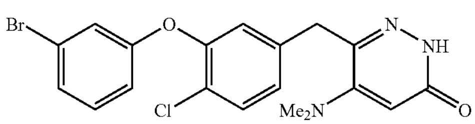 | 6-[3-(3-Bromo-phenoxy)-4-chloro-benzyl]-5-dimethylamino-2H-pyridazin-3-one | 436 (434.71) |
| I-89 | 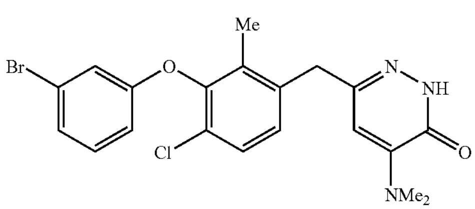 | 6-[3-(3-Bromo-phenoxy)-4-chloro-benzyl]-4-dimethylamino-2H-pyridazin-3-one | 436 (434.71) |
| I-90 | 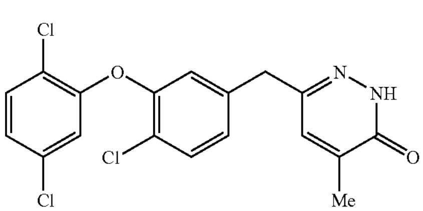 | 6-[4-Chloro-3-(2,5-dichloro-phenoxy)-benzyl]-4-methyl-2H-pyridazin-3-one | 395 (395.67) 195–198 |
| I-91 | 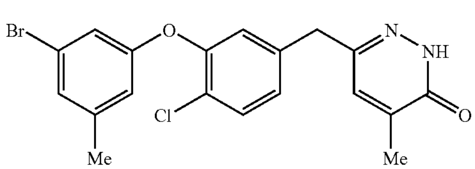 | 6-[3-(3-Bromo-5-methyl-phenoxy)-4-chloro-benzyl]-4-methyl-2H-pyridazin-3-one | 419 (419.70) 121.7–133 |

TABLE I-continued

| cpd # | Structure | Name | [M + H]+ (mw) mp |
|---|---|---|---|
| I-92 | 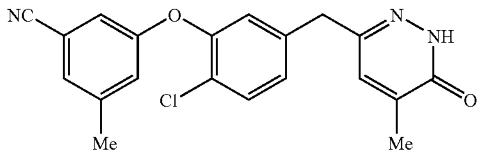 | | 366 (365.81) 177.5–180 |
| I-93 | 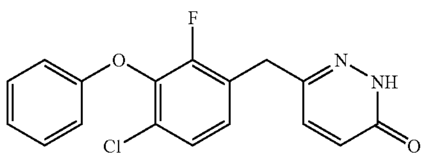 | 6-(4-Chloro-2-fluoro-3-phenoxy-benzyl)-2H-pyridazin-3-one | 330 (330.74) |
| I-94 | 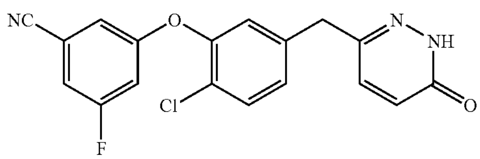 | 3-[2-Chloro-5-(6-oxo-1,6-dihydro-pyridazin-3-ylmethyl)-phenoxy]-5-fluoro-benzonitrile | (355.75) |
| I-95 | 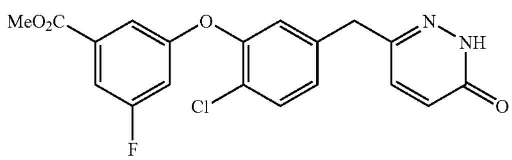 | 3-[2-Chloro-5-(6-oxo-1,6-dihydro-pyridazin-3-ylmethyl)-phenoxy]-5-fluoro-benzoic acid methyl ester | (388.78) |
| I-96 | 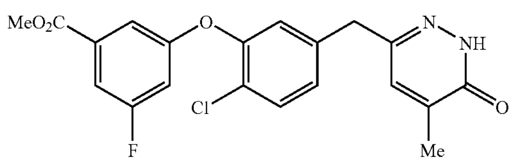 | 3-[2-Chloro-5-(5-methyl-6-oxo-1,6-dihydro-pyridazin-3-ylmethyl)-phenoxy]-5-fluoro-benzoic acid methyl ester | (402.81) |
| I-97 | 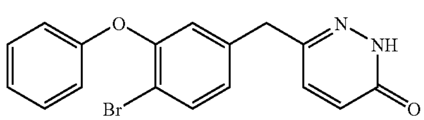 | 6-(4-Bromo-3-phenoxy-benzyl)-2H-pyridazin-3-one | 357 (357.20) |
| I-98 | 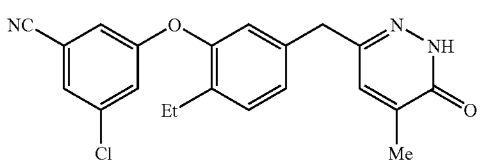 | 3-Chloro-5-[2-ethyl-5-(5-methyl-6-oxo-1,6-dihydro-pyridazin-3-ylmethyl)-phenoxy]-benzonitrile | (379.84) |
| I-99 | 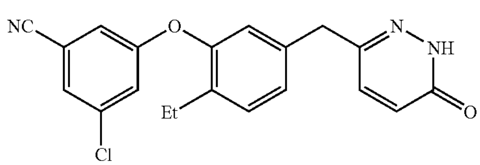 | 3-Chloro-5-[2-ethyl-5-(6-oxo-1,6-dihydro-pyridazin-3-ylmethyl)-phenoxy]-benzonitrile | (365.82) |
| I-100 | 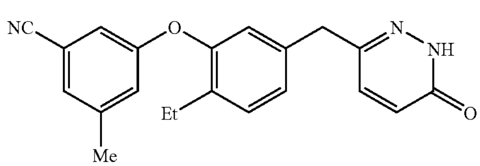 | 3-[2-Ethyl-5-(6-oxo-1,6-dihydro-ridazin-3-ylmethyl)-phenoxy]-5-methyl-nzonitrile | (345.40) |

TABLE I-continued

| cpd # | Structure | Name | [M + H]+ (mw) mp |
|---|---|---|---|
| I-101 | 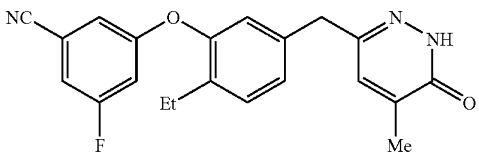 | 3-[2-Ethyl-5-(5-methyl-6-oxo-1,6-dihydro-pyridazin-3-ylmethyl)-phenoxy]-5-fluoro-benzonitrile | (363.39) |
| I-102 | 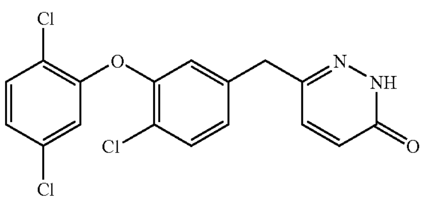 | 6-[4-Chloro-3-(2,5-dichloro-phenoxy)-benzyl]-2H-pyridazin-3-one | (381.64) |
| I-103 | 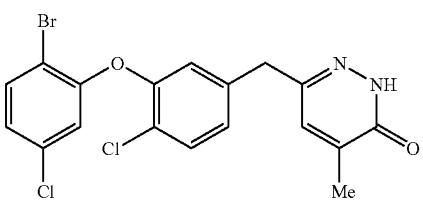 | 6-[3-(2-Bromo-5-chloro-phenoxy)-4-chloro-benzyl]-4-methyl-2H-pyridazin-3-one | (440.12) |
| I-104 | 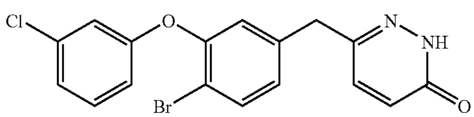 | 6-[4-Bromo-3-(3-chloro-phenoxy)-benzyl]-2H-pyridazin-3-one | 391 (391.65) |
| I-105 | 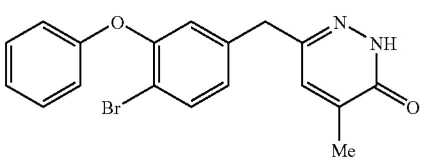 | 6-(4-Bromo-3-phenoxy-benzyl)-4-methyl-2H-pyridazin-3-one | 371 (371.23) |
| I-106 | 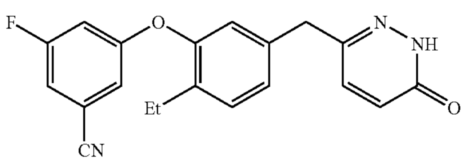 | 3-[2-Ethyl-5-(5-methyl-6-oxo-1,6-dihydro-pyridazin-3-ylmethyl)-phenoxy]-5-fluoro-benzonitrile | (349.36) |
| I-107 | 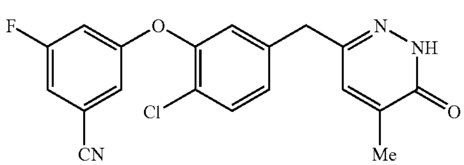 | 3-[2-Chloro-5-(5-methyl-6-oxo-1,6-dihydro-pyridazin-3-ylmethyl)-phenoxy]-5-fluoro-benzonitrile | (369.78) |
| I-108 | 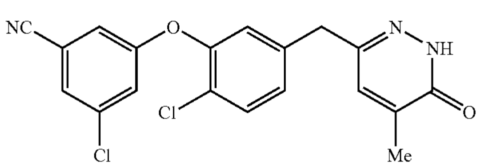 | 3-Chloro-5-[2-chloro-5-(5-methyl-6-oxo-1,6-dihydro-pyridazin-3-ylmethyl)-phenoxy]-benzonitrile | (386.24) |
| I-109 | 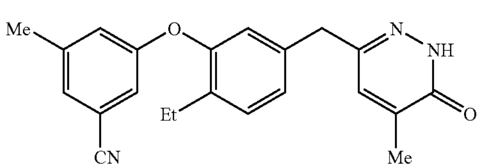 | 3-[2-Ethyl-5-(5-methyl-6-oxo-1,6-dihydro-yridazin-3-ylmethyl)-phenoxy]-5-methyl-benzonitrile | (359.43) |

TABLE I-continued

| cpd # | Name | [M + H]+ (mw) mp |
|---|---|---|
| I-110 | 6-[4-Chloro-3-(3-chloro-phenoxy)-benzyl]-5-methylamino-2H-pyridazin-3-one | 376 (376.24) |
| I-111 | 6-[4-Chloro-3-(3-chloro-phenoxy)-benzyl]-4-methylamino-2H-pyridazin-3-one | 376 (376.24) |
| I-112 | 6-[4-Chloro-3-(3-chloro-phenoxy)-benzyl]-4-morpholin-4-yl-2H-pyridazin-3-one | 432 (432.31) |
| I-113 | 2-[2-Chloro-5-(6-oxo-1,6-dihydro-pyridazin-3-ylmethyl)-phenoxy]-3-fluoro-benzonitrile | 355 (355.76) |
| I-114 | 3-Fluoro-5-[2-methyl-5-(6-oxo-1,6-dihydro-pyridazin-3-ylmethyl)-phenoxy]-benzonitrile | |
| I-115 | 3-Bromo-4-[2-chloro-5-(6-oxo-1,6-dihydro-pyridazin-3-ylmethyl)-phenoxy]-benzonitrile | 416 (466.66) |
| I-116 | 3-Chloro-2-[2-chloro-5-(6-oxo-1,6-dihydro-pyridazin-3-ylmethyl)-phenoxy]-benzonitrile | 372 (372.21) |
| I-117 | 6-[4-Chloro-3-(2,6-dichloro-phenoxy)-benzyl]-2H-pyridazin-3-one | 381 (381.65) |

TABLE I-continued

| cpd # | Structure | Name | [M + H]+ (mw) mp |
|---|---|---|---|
| I-118 | 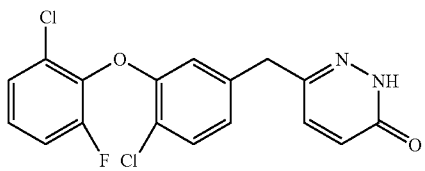 | 6-[4-Chloro-3-(2-chloro-6-fluoro-phenoxy)-benzyl]-2H-pyridazin-3-one | 365 (365.19) |
| I-119 | 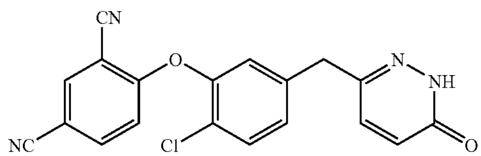 | 4-[2-Chloro-5-(6-oxo-1,6-dihydro-pyridazin-3-ylmethyl)-phenoxy]-isophthalonitrile | 363 (362.78) |
| I-120 | 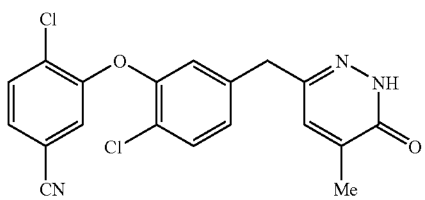 | 4-Chloro-3-[2-chloro-5-(5-methyl-6-oxo-1,6-dihydro-pyridazin-3-ylmethyl)-phenoxy]-benzonitrile | |
| I-121 | 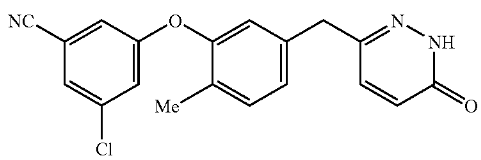 | 3-Chloro-5-[2-methyl-5-(6-oxo-1,6-dihydro-pyridazin-3-ylmethyl)-phenoxy]-benzonitrile | |
| I-122 | 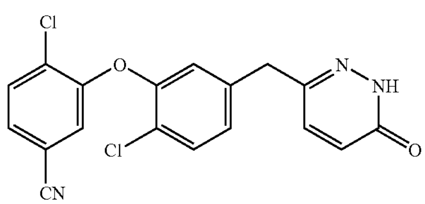 | 4-Chloro-3-[2-chloro-5-(6-oxo-1,6-dihydro-pyridazin-3-ylmethyl)-phenoxy]-benzonitrile | |
| I-123 | 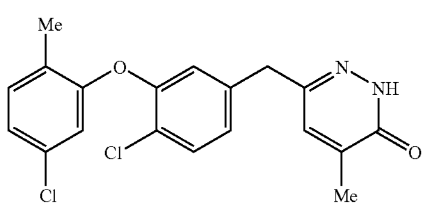 | 6-[4-Chloro-3-(5-chloro-2-methyl-phenoxy)-benzyl]-4-methyl-2H-pyridazin-3-one | |
| I-124 | 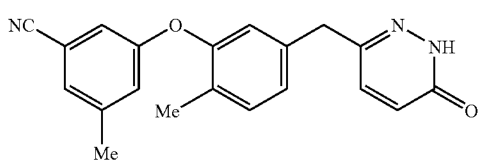 | 3-Methyl-5-[2-methyl-5-(6-oxo-1,6-dihydro-pyridazin-3-ylmethyl)-phenoxy]-benzonitrile | |
| I-125 | 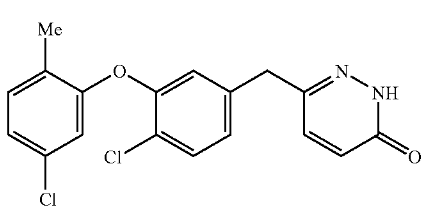 | 6-[4-Chloro-3-(5-chloro-2-methyl-phenoxy)-benzyl]-2H-pyridazin-3-one | |

TABLE I-continued

| cpd # | Structure | Name | [M + H]+ (mw) mp |
|---|---|---|---|
| I-126 | 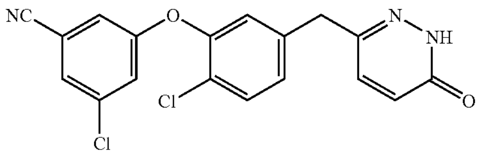 | 3-Chloro-5-[2-chloro-5-(6-oxo-1,6-dihydro-pyridazin-3-ylmethyl)-phenoxy]-benzonitrile | |
| I-127 | 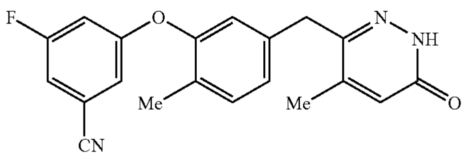 | 3-Fluoro-5-[2-methyl-5-(4-methyl-6-oxo-1,6-dihydro-pyridazin-3-ylmethyl)-phenoxy]-benzonitrile | |
| I-128 | 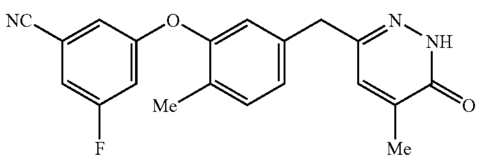 | 3-Fluoro-5-[2-methyl-5-(5-methyl-6-oxo-1,6-dihydro-pyridazin-3-ylmethyl)-phenoxy]-benzonitrile | |
| I-129 | 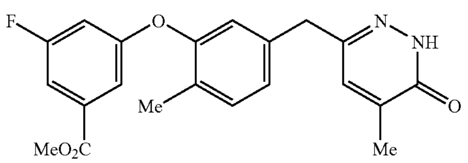 | 3-Fluoro-5-[2-methyl-5-(5-methyl-6-oxo-1,6-dihydro-pyridazin-3-ylmethyl)-phenoxy]-benzoic acid methyl ester | |
| I-130 | 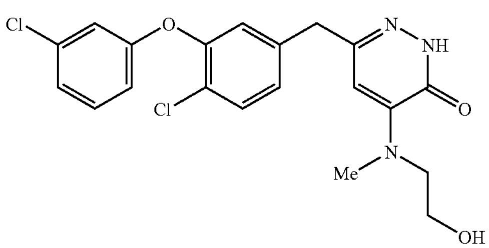 | 6-[4-Chloro-3-(3-chloro-phenoxy)-benzyl]-4-[(2-hydroxy-ethyl)-methyl-amino]-2H-pyridazin-3-one | 420 (420.30) |
| I-131 | 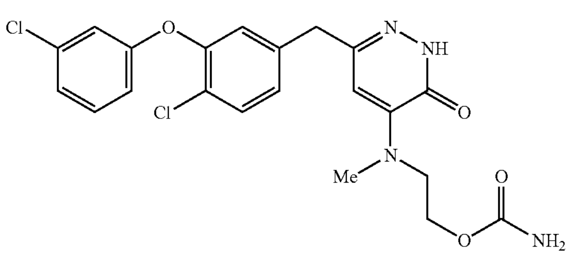 | Carbamic acid 2-({6-[4-chloro-3-(3-chloro-phenoxy)-benzyl]-3-oxo-2,3-dihydro-pyridazin-4-yl}-methyl-amino)-ethyl ester | 463 (463.32) |
| I-132 | 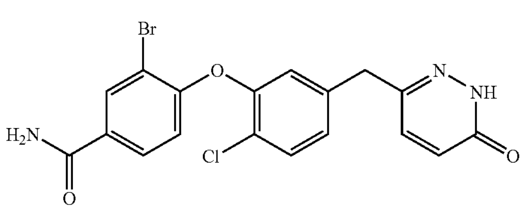 | 3-Bromo-4-[2-chloro-5-(6-oxo-1,6-dihydro-pyridazin-3-ylmethyl)-phenoxy]-benzamide | 436 (434.68) |

TABLE I-continued

| cpd # | Structure | Name | [M + H]+ (mw) mp |
|---|---|---|---|
| I-133 | 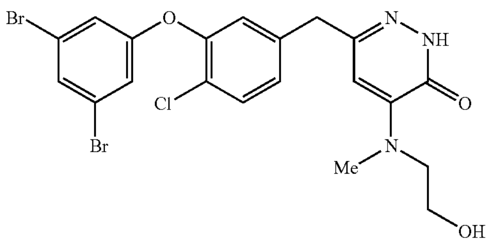 | 6-[4-Chloro-3-(3,5-dibromo-phenoxy)-benzyl]-2H-pyridazin-3-one | 471 (470.55) |
| I-134 | 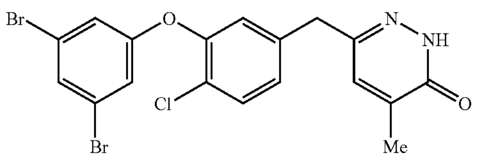 | 6-[4-Chloro-3-(3,5-dibromo-phenoxy)-benzyl]-4-methyl-2H-pyridazin-3-one | 485 (484.58) |
| I-135 | 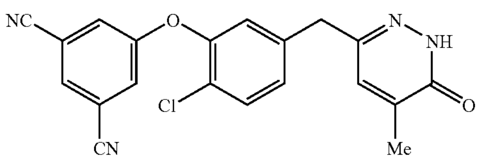 | 5-[2-Chloro-5-(5-methyl-6-oxo-1,6-dihydro-pyridazin-3-ylmethyl)-phenoxy]-isophthalonitrile | 377 (376.81) |
| I-136 | 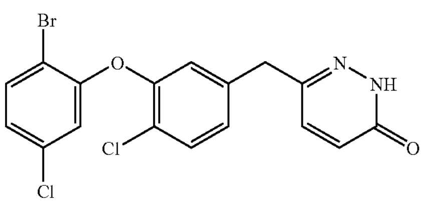 | 6-[3-(2-Bromo-5-chloro-phenoxy)-4-chloro-2-fluoro-benzyl]-2H-pyridazin-3-one | 445 (444.09) |
| I-137 | 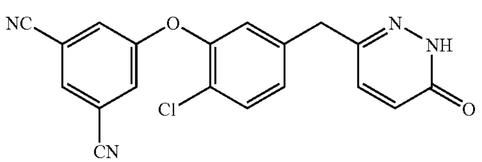 | 5-[2-Chloro-5-(6-oxo-1,6-dihydro-pyridazin-3-ylmethyl)-phenoxy]-isophthalonitrile | 363 (362.78) |
| I-138 | 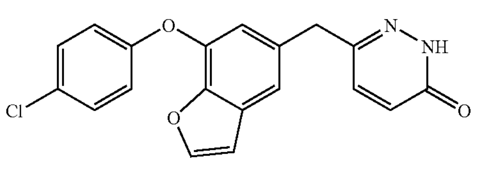 | 6-[7-(4-Chloro-phenoxy)-benzofuran-5-ylmethyl]-2H-pyridazin-3-one | 352 (352.7) 205–210 |
| I-139 | 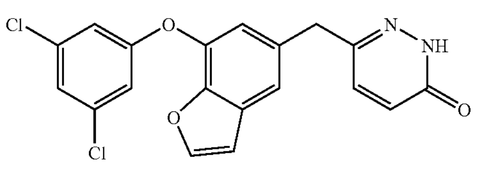 | 6-[7-(3,5-Dichloro-phenoxy)-benzofuran-5-ylmethyl]-2H-pyridazin-3-one | 386 (387.2) |
| I-140 | 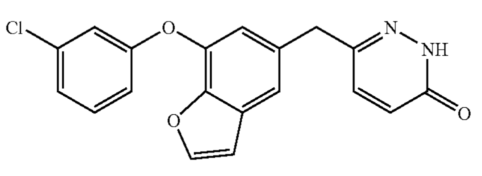 | 6-[7-(3-Chloro-phenoxy)-benzofuran-5-ylmethyl]-2H-pyridazin-3-one | 352[1] (352.8) |

TABLE I-continued

| cpd # | Structure | Name | [M + H]+ (mw) mp |
|---|---|---|---|
| I-141 | 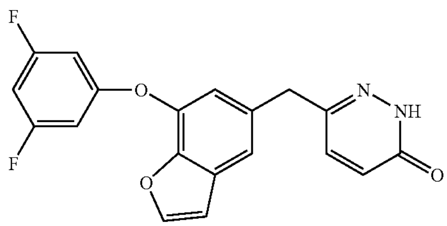 | 6-[7-(3,5-Difluoro-phenoxy)-benzofuran-5-ylmethyl]-2H-pyridazin-3-one | 355 (354.3) 213.4–215.5 |
| I-142 | 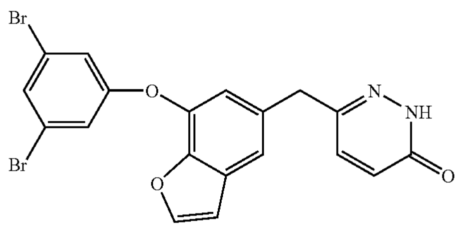 | 6-[7-(3,5-Dibromo-phenoxy)-benzofuran-5-ylmethyl]-2H-pyridazin-3-one | 477 (476.1) 183.9–185.3 |
| I-143 | 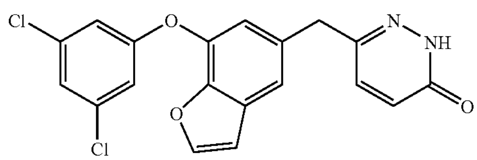 | 6-[7-(3,5-Dichloro-phenoxy)-2,3-dihydro-benzofuran-5-ylmethyl]-2H-pyridazin-3-one | 389 (389.2) 216.5–218.8 |
| I-144 | 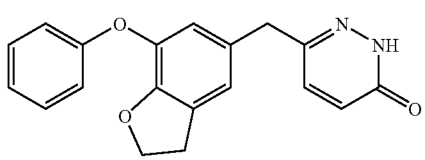 | 6-(7-Phenoxy-2,3-dihydro-benzofuran-5-ylmethyl)-2H-pyridazin-3-one | 321 (320.4) 133.7–135.8 |
| I-145 | 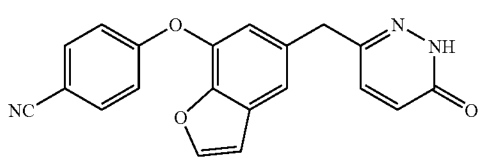 | 4-[5-(6-Oxo-1,6-dihydro-pyridazin-3-ylmethyl)-benzofuran-7-yloxy]-benzonitrile | 342² (343.3) 174–175 |
| I-146 | 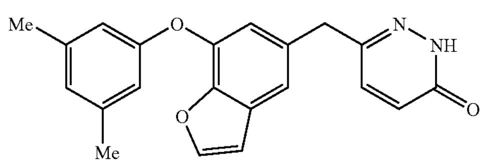 | 6-[7-(3,5-Dimethyl-phenoxy)-benzofuran-5-ylmethyl]-2H-pyridazin-3-one | 347 (346.4) 56–60 |
| I-147 | 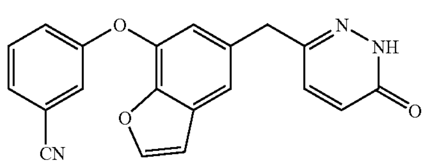 | 3-[5-(6-Oxo-1,6-dihydro-pyridazin-3-ylmethyl)-benzofuran-7-yloxy]-benzonitrile | 344 (343.3) 171.0–173.1 |
| I-148 | 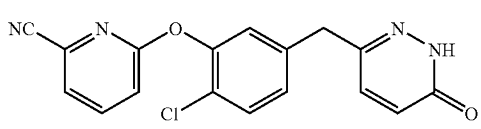 | 6-[2-Chloro-5-(6-oxo-1,6-dihydro-pyridazin-3-ylmethyl)-phenoxy]-pyridine-2-carbonitrile | (338.76) |

TABLE I-continued

| cpd # | Structure | Name | [M + H]+ (mw) mp |
|---|---|---|---|
| I-149 | 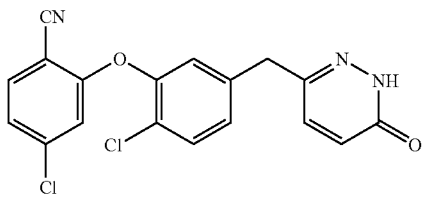 | 4-Chloro-2-[2-chloro-5-(6-oxo-1,6-dihydro-pyridazin-3-ylmethyl)-phenoxy]-benzonitrile | 372 (372.2) 228.0–229.6 |
| I-150 | 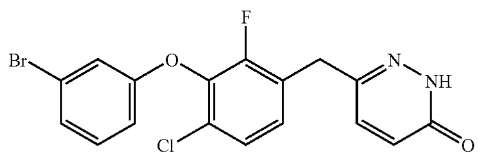 | 6-[3-(3-Bromo-phenoxy)-4-chloro-2-fluoro-benzyl]-2H-pyridazin-3-one | 411 (409.6) |
| I-151 | 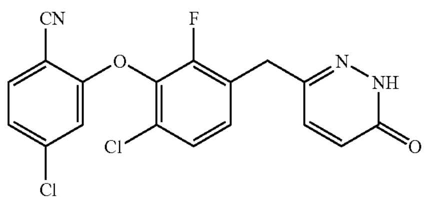 | 4-Chloro-2-[6-chloro-2-fluoro-3-(6-oxo-1,6-dihydro-pyridazin-3-ylmethyl)-phenoxy]-benzonitrile | 390 (390.2) |
| I-152 | 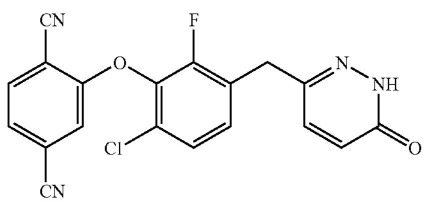 | 2-[6-Chloro-2-fluoro-3-(6-oxo-1,6-dihydro-pyridazin-3-ylmethyl)-phenoxy]-terephthalonitrile | 381 (380.77) |
| I-153 | 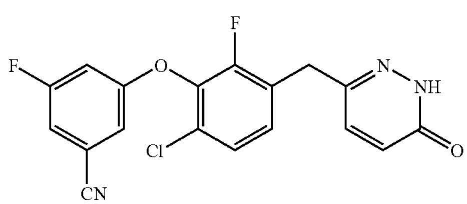 | 3-[6-Chloro-2-fluoro-3-(6-oxo-1,6-1,6-dihydro-pyridazin-3-ylmethyl)-phenoxy]-5-fluoro-benzonitrile | 374 (373.75) |
| I-154 | 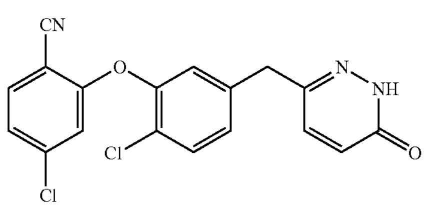 | 4-Chloro-2-[2-chloro-5-(5-methyl-6-oxo-1,6-dihydro-pyridazin-3-ylmethyl)-phenoxy]-benzonitrile | 386 (386.2) 215.1–215.9 |
| I-155 | 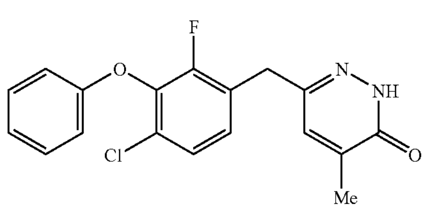 | 6-(4-Chloro-2-fluoro-3-phenoxy-benzyl)-4-methyl-2H-pyridazin-3-one | 345.16 (344.78) |

TABLE I-continued

| cpd # | Structure | Name | [M + H]+ (mw) mp |
|---|---|---|---|
| I-156 | 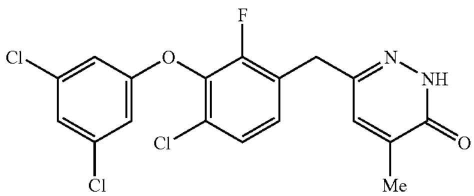 | 6-[4-Chloro-3-(3,5-dichloro-phenoxy)-2-fluoro-benzyl]-4-methyl-2H-pyridazin-3-one | 414.97 (413.67) |
| I-157 | 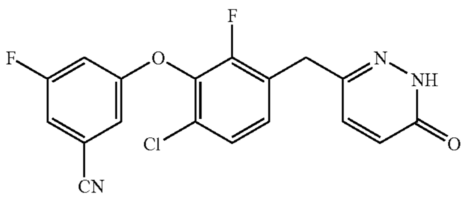 | 3-[6-Chloro-2-fluoro-3-(5-methyl-6-oxo-1,6-dihydro-pyridazin-3-ylmethyl)-phenoxy]-5-fluoro-benzonitrile | 388 (387.78) |
| I-158 | 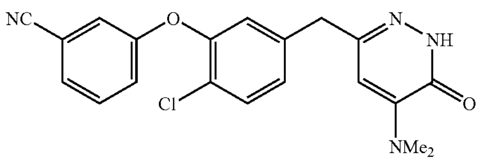 | 3-[2-Chloro-5-(5-dimethylamino-6-oxo-1,6-dihydro-pyridazin-3-ylmethyl)-phenoxy]-benzonitrile | 381 (380.84) |
| I-159 | 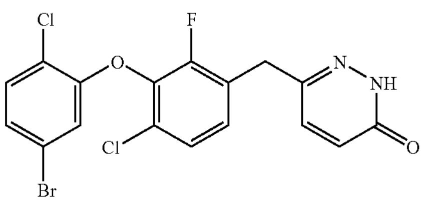 | 6-[3-(5-Bromo-2-chloro-phenoxy)-4-chloro-2-fluoro-benzyl]-2H-pyridazin-3-one | 445 (444.09) |
| I-160 | 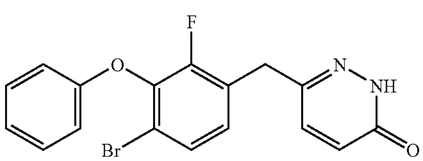 | 6-(4-Bromo-2-fluoro-3-phenoxy-benzyl)-2H-pyridazin-3-one | 375 (375.2) |
| I-161 | 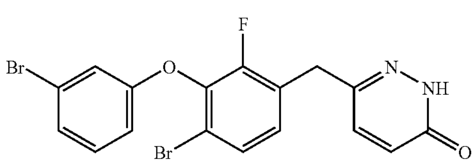 | 6-[4-Bromo-3-(3-bromo-phenoxy)-2-fluoro-benzyl]-2H-pyridazin-3-one | 455 (454.10) |
| I-162 | 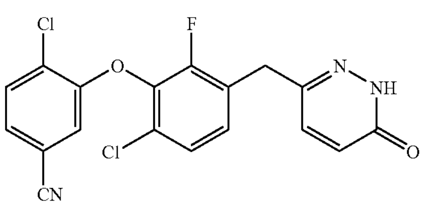 | 4-Chloro-3-[6-chloro-2-fluoro-3-(6-oxo-1,6-dihydro-pyridazin-3-ylmethyl)-phenoxy]-benzonitrile | 390 390.20 |
| I-163 | 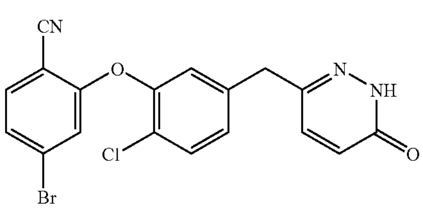 | 4-Bromo-2-[2-chloro-5-(6-oxo-1,6-dihydro-pyridazin-3-ylmethyl)-phenoxy]-benzonitrile | 418 416.66 |

TABLE I-continued

| cpd # | Structure | Name | [M + H]+ (mw) mp |
|---|---|---|---|
| I-164 | 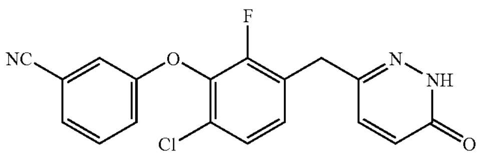 | 3-[6-Chloro-2-fluoro-3-(5-methyl-6-oxo-1,6-dihydro-pyridazin-3-ylmethyl)-phenoxy]-benzonitrile | 370 (369.79) |
| I-165 | 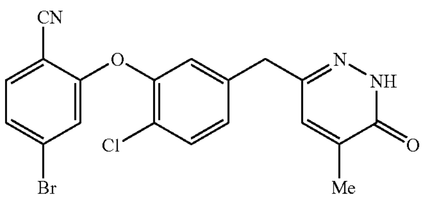 | 4-Bromo-2-[2-chloro-5-(5-methyl-6-oxo-1,6-dihydro-pyridazin-3-ylmethyl)-phenoxy]-benzonitrile | 432 (430.69) |
| I-166 | 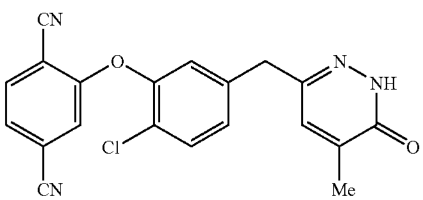 | 2-[2-Chloro-5-(5-methyl-6-oxo-1,6-dihydro-pyridazin-3-ylmethyl)-phenoxy]-terephthalonitrile | 377 (376.81) |
| I-167 | 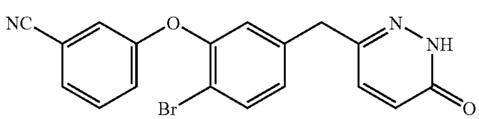 | 3-[2-Bromo-5-(6-oxo-1,6-dihydro-pyridazin-3-ylmethyl)-phenoxy]-benzonitrile | 382 (382.22) |
| I-168 | 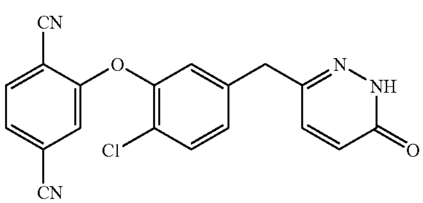 | 2-[2-Chloro-5-(6-oxo-1,6-dihydro-pyridazin-3-ylmethyl)-phenoxy]-terephthalonitrile | 363 (362.78) |
| I-169 | 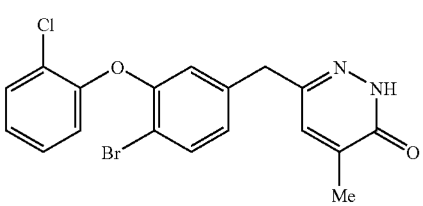 | 6-[4-Bromo-3-(2-chloro-phenoxy)-benzyl]-4-methyl-2H-pyridazin-3-one | 405 (405.68) foam |
| I-170 | 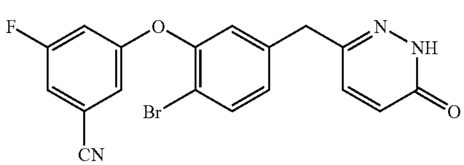 | 3-[6-Bromo-2-fluoro-3-(6-oxo-1,6-dihydro-pyridazin-3-ylmethyl)-phenoxy]-5-fluoro-benzonitrile | 418 (418.20) 185.2–186.7 |
| I-171 | 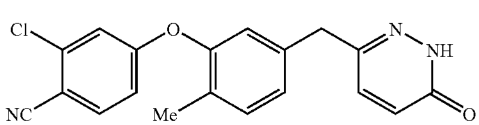 | 2-Chloro-4-[2-methyl-5-(6-oxo-1,6-dihydro-pyridazin-3-ylmethyl)-phenoxy]-benzonitrile | 352 (351.80) 184.0–184.8 |

TABLE I-continued

| cpd # | Structure | Name | [M + H]+ (mw) mp |
|---|---|---|---|
| I-172 | 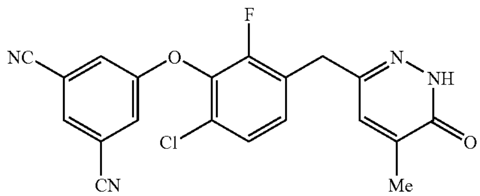 | 5-[6-Chloro-2-fluoro-3-(5-methyl-6-oxo-1,6-dihydro-pyridazin-3-ylmethyl)-phenoxy]-isophthalonitrile | 395 (394.80) 230.1–231.9 |
| I-173 | 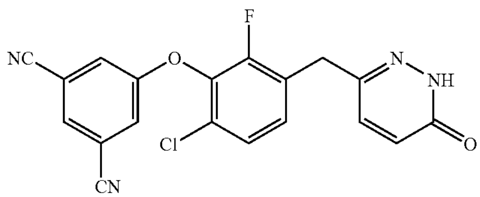 | 5-[6-Chloro-2-fluoro-3-(6-oxo-1,6-dihydro-pyridazin-3-ylmethyl)-phenoxy]-isophthalonitrile | 381 (380.77) |
| I-174 | 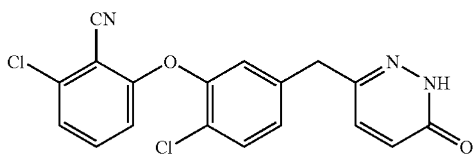 | 2-Chloro-6-[2-chloro-5-(6-oxo-1,6-dihydro-pyridazin-3-ylmethyl)-phenoxy]-benzonitrile | 372 (372.21) 213.9–215.5 |
| I-175 | 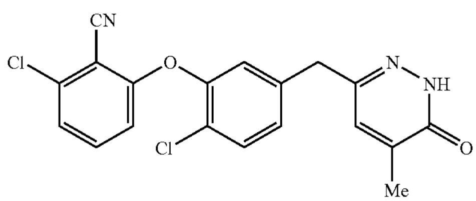 | 2-Chloro-6-[2-chloro-5-(5-methyl-6-oxo-1,6-dihydro-pyridazin-3-ylmethyl)-phenoxy]-benzonitrile | 386 (386.24) 220.2–221.9 |
| I-176 | 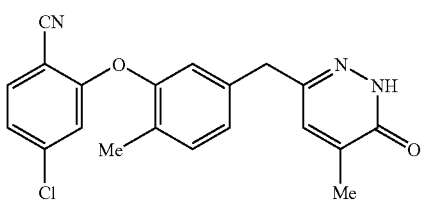 | 4-Chloro-2-[2-chloro-5-(5-methyl-6-oxo-1,6-dihydro-pyridazin-3-ylmethyl)-phenoxy]-benzonitrile | 366 (365.82) 201.2–202.3 |
| I-177 | 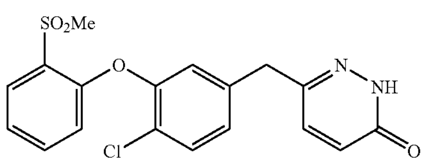 | 6-[4-Chloro-3-(2-methanesulfonyl-phenoxy)-benzyl]-2H-pyridazin-3-one | 391 (390.85) |
| I-178 | 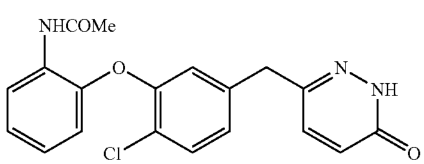 | N-{2-[2-Chloro-5-(6-oxo-1,6-dihydro-pyridazin-3-ylmethyl)-phenoxy]-phenyl}-acetamide | 370 (369.81) 190.0–190.4 |
| I-179 | 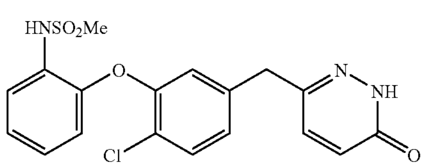 | N-{2-[2-Chloro-5-(6-oxo-1,6-dihydro-pyridazin-3-ylmethyl)-phenoxy]-phenyl}-methanesulfonamide | 406 (405.86) |

TABLE I-continued

| cpd # | Name | [M + H]+ (mw) mp |
|---|---|---|
| I-180 | 6-[4-Chloro-3-(2-nitro-phenoxy)-benzyl]-2H-pyridazin-3-one | 358 (357.76) |
| I-181 | 2-[2-Chloro-5-(6-oxo-1,6-dihydro-pyridazin-3-ylmethyl)-phenoxy]-benzonitrile | 338 (337.77) 173.0–174.5 |
| I-182 | 2-[2-Chloro-5-(5-methyl-6-oxo-1,6-dihydro-pyridazin-3-ylmethyl)-phenoxy]-terephthalonitrile | (394.80) |
| I-183 | 6-[3-(3-Chloro-phenoxy)-4-trifluoromethyl-benzyl]-2H-pyridazin-3-one | (380.76) |
| I-184 | 4-Chloro-3-[6-chloro-2-fluoro-3-(5-methyl-6-oxo-1,6-dihydro-pyridazin-3-ylmethyl)-phenoxy]-benzonitrile | 403 (404.23) 225.9–228.9 |
| I-185 | 6-[3-(3-Chloro-phenoxy)-4-trifluoromethyl-benzyl]-4-methyl-2H-pyridazin-3-one | (394.78) |
| I-186 | 6-[3-(2-Amino-phenoxy)-4-chloro-benzyl]-2H-pyridazin-3-one; compound with hydrochloric acid | 328 (364.23) 240.1 242.7 |
| I-187 | 4-Chloro-2-[2-chloro-5-(6-oxo-1,6-dihydro-pyridazin-3-ylmethyl)-phenoxy]-benzonitrile | 352 (351.80) 205.9–208.9 |

TABLE I-continued

| cpd # | Structure | Name | [M + H]+ (mw) mp |
|---|---|---|---|
| I-188 | 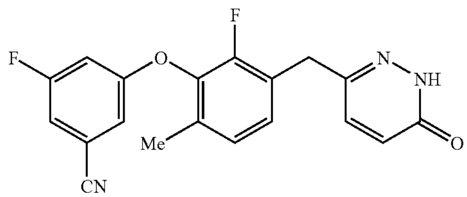 | 3-Fluoro-5-[2-fluoro-6-methyl-3-(6-oxo-1,6-dihydro-pyridazin-3-ylmethyl)-phenoxy]-benzonitrile | 354 (353.33) 170.1–172.0 |
| I-189 | 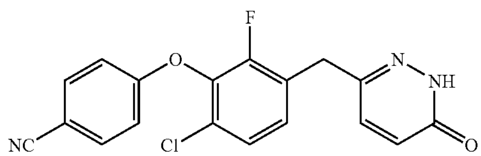 | 4-[6-Chloro-2-fluoro-3-(6-oxo-1,6-dihydro-pyridazin-3-ylmethyl)-phenoxy]-benzonitrile | 356 355.76 |
| I-190 | 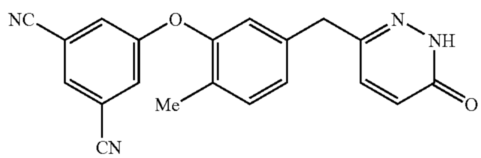 | 5-[6-Chloro-2-fluoro-3-(6-oxo-1,6-dihydro-pyridazin-3-ylmethyl)-phenoxy]-isophthalonitrile | 343 342.36 |
| I-191 | 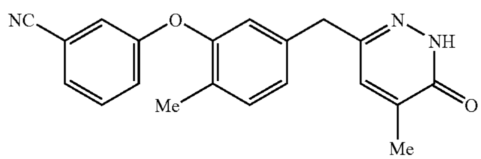 | 3-[2-Methyl-5-(5-methyl-6-oxo-1,6-dihydro-pyridazin-3-ylmethyl)-phenoxy]-benzonitrile | 332 331.38 |
| I-192 | 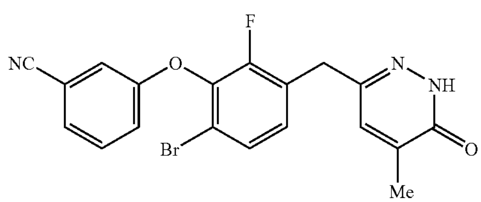 | 3-[6-Bromo-2-fluoro-3-(5-methyl-6-oxo-1,6-dihydro-pyridazin-3-ylmethyl)-phenoxy]-benzonitrile | 414 (414.24) |
| I-193 | 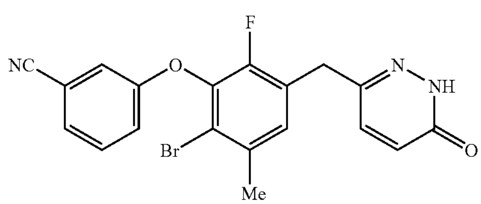 | 3-[2,3-Dibromo-6-fluoro-5-(6-oxo-1,6-dihydro-pyridazin-3-ylmethyl)-phenoxy]-benzonitrile | 480 (479.11) |
| I-194 | 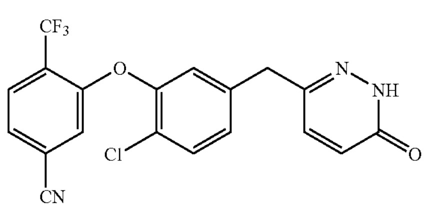 | 3-[2-Chloro-5-(6-oxo-1,6-dihydro-pyridazin-3-ylmethyl)-phenoxy]-4-trifluoromethyl-benzonitrile | 406 (405.77 195–196.8 |
| I-195 | 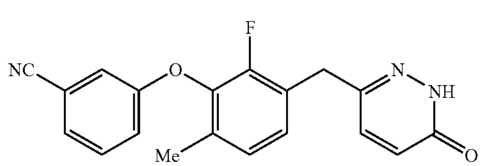 | 3-[2-Fluoro-6-methyl-3-(6-oxo-1,6-dihydro-pyridazin-3-ylmethyl)-phenoxy]-benzonitrile | 335 (335.34) 139.2–144.9 |

TABLE I-continued

| cpd # | Structure | Name | [M + H]+ (mw) mp |
|---|---|---|---|
| I-196 | 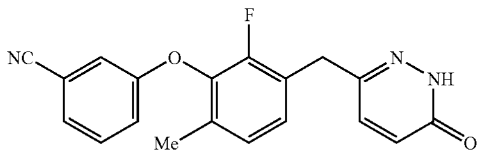 | 3-[2-Fluoro-6-methyl-3-(5-methyl-6-oxo-1,6-dihydro-pyridazin-3-ylmethyl)-phenoxy]-benzonitrile | 349 (349.37) 175.0–175.7 |
| I-197 | 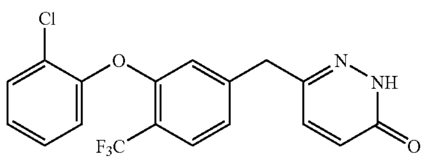 | 6-[3-(2-Chloro-phenoxy)-4-trifluoromethyl-benzyl]-2H-pyridazin-3-one | (380.76) |
| I-198 | 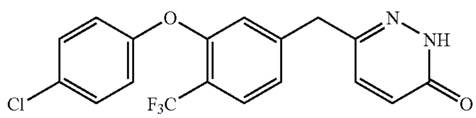 | 6-[3-(4-Chloro-phenoxy)-4-trifluoromethyl-benzyl]-2H-pyridazin-3-one | (380.76) |
| I-199 | 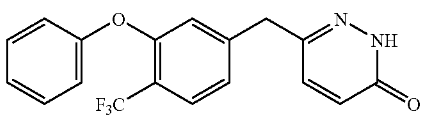 | 6-(3-Phenoxy-4-trifluoromethyl-benzyl)-2H-pyridazin-3-one | (346.31) |
| I-200 | 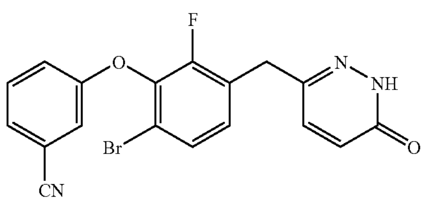 | 3-[6-Bromo-2-fluoro-3-(6-oxo-1,6-dihydro-pyridazin-3-ylmethyl)-phenoxy]-benzonitrile | 402 (400.21) |
| I-201 | 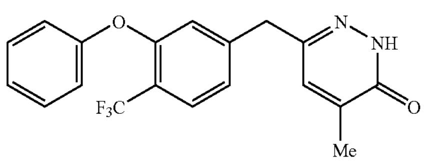 | 4-Methyl-6-(3-phenoxy-4-trifluoromethyl-benzyl)-2H-pyridazin-3-one | (360.34) |
| I-202 | 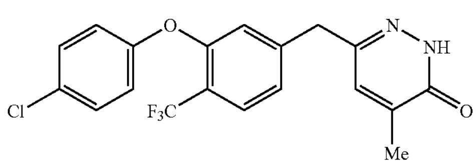 | 6-[3-(4-Chloro-phenoxy)-4-trifluoromethyl-benzyl]-4-methyl-2H-pyridazin-3-one | (394.78) |
| I-203 | 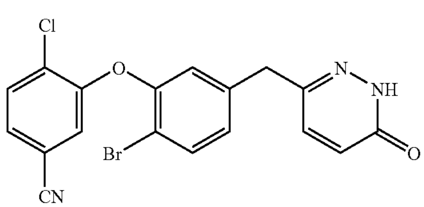 | 3-[2-Bromo-5-(6-oxo-1,6-dihydro-pyridazin-3-ylmethyl)-phenoxy]-4-chloro-benzonitrile | (416.66) 196.8–199.9 |
| I-204 | 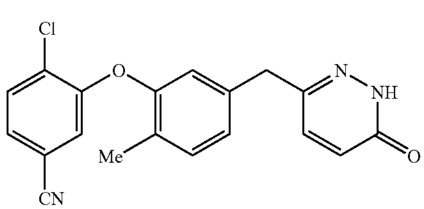 | 3-[2-Bromo-5-(6-oxo-1,6-dihydro-pyridazin-3-ylmethyl)-phenoxy]-4-chloro-benzonitrile | 352 (351.80) 189.9–191.0 |

TABLE I-continued

| cpd # | Structure | Name | [M + H]+ (mw) mp |
|---|---|---|---|
| I-205 | 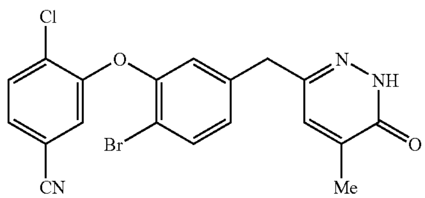 | 3-[2-Bromo-5-(5-methyl-6-oxo-1,6-dihydro-pyridazin-3-ylmethyl)-phenoxy]-4-chloro-benzonitrile | 432 (430.69) 179.5–197.7 |
| I-206 | 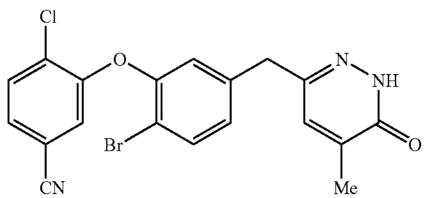 | 3-[2-Bromo-5-(5-methyl-6-oxo-1,6-dihydro-pyridazin-3-ylmethyl)-phenoxy]-4-cbloro-benzonitrile | 366 (365.82) 188.7–189.7 |
| I-207 | 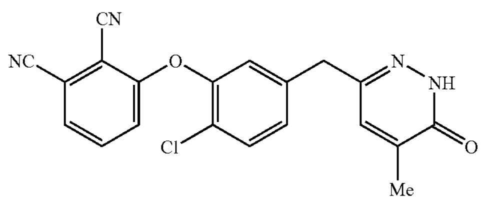 | 3-[2-Chloro-5-(5-metbyl-6-oxo-1,6-dihydro-pyridazin-3-ylmethyl)-phenoxy]-phthalonitrile | 377 (376.81) 201.2–204.1 |
| I-208 | 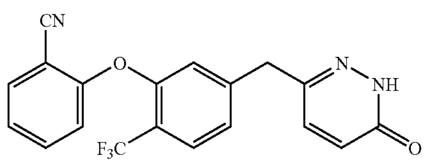 | 2-[5-(6-Oxo-1,6-dihydro-pyridazin-3-ylmethyl)-2-trifluoromethyl-phenoxy]-benzonitrile | 372 (371.32) 183.3–184.9 |
| I-209 | 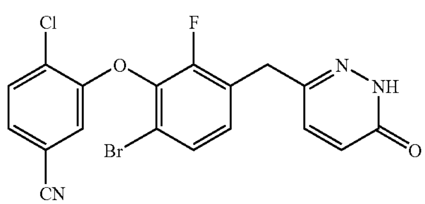 | 3-[6-Bromo-2-fluoro-3-(6-oxo-1,6-dihydro-pyridazin-3-ylmethyl)-phenoxy]-4-chloro-benzonitrile | 433 (464.65) 224.2–224.8 |
| I-210 | 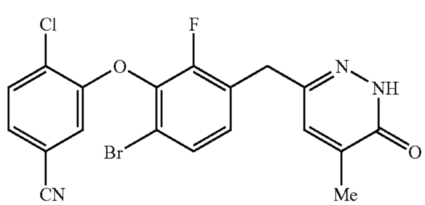 | 3-[6-Bromo-2-fluoro-3-(5-methyl-6-oxo-1,6-dihydro-pyridazin-3-ylmethyl)-phenoxy]-4-chloro-benzonitrile | 447 (448.68) 237.2–238.0 |
| I-211 | 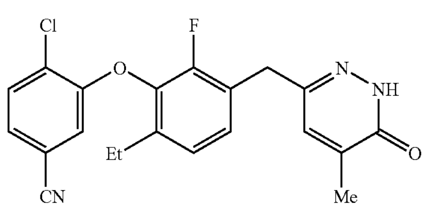 | 4-Chloro-3-[6-ethyl-2-fluoro-3-(5-methyl-6-oxo-1,6-dihydro-pyridazin-3-ylmethyl)-phenoxy]-benzonitrile | 397 (397.84) |

TABLE I-continued

| cpd # | Structure | Name | [M + H]+ (mw) mp |
|---|---|---|---|
| I-212 | 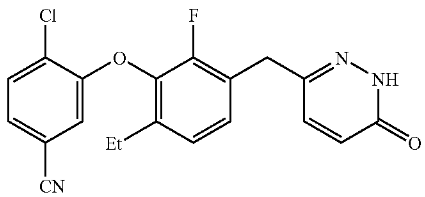 | 4-Chloro-3-[6-ethyl-2-fluoro-3-(6-oxo-1,6-dihydro-pyridazin-3-ylmethyl)-phenoxy]-benzonitrile | 384 (383.81) |
| I-213 | 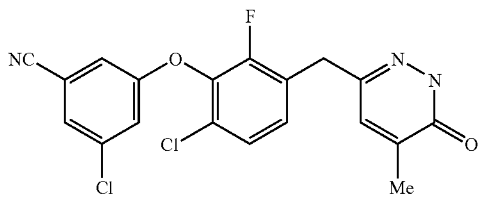 | 3-Chloro-5-[6-chloro-2-fluoro-3-(5-methyl-6-oxo-1,6-dihydro-pyridazin-3-ylmethyl)-phenoxy]-benzonitrile | 404.1 (404.23) 186.1–185.4 |
| I-214 | 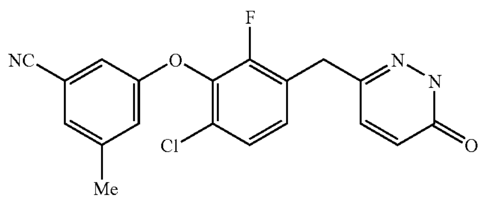 | 3-[6-Chloro-2-fluoro-3-(6-oxo-1,6-dihydro-pyridazin-3-ylmethyl)-phenoxy]-5-methyl-benzonitrile | 370 (369.79) 190–192.5 |
| I-215 | 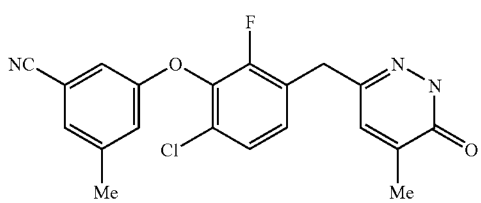 | 3-[6-Chloro-2-fluoro-3-(5-methyl-6-oxo-1,6-dihydro-pyridazin-3-ylmethyl)-phenoxy]-5-methyl-benzonitrile | 384 (383.81) 202.4–203.7 |
| I-216 | 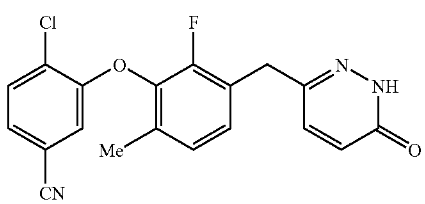 | 4-Chloro-3-[2-fluoro-6-methyl-3-(6-oxo-1,6-dihydro-pyridazin-3-ylmethyl)-phenoxy]-benzonitrile | 370 (369.79) 195.8–197.7 |
| I-217 | 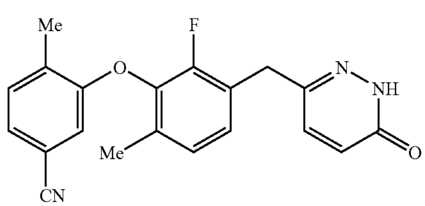 | 3-[2-Fluoro-6-methyl-3-(6-oxo-1,6-dihydro-pyridazin-3-ylmethyl)-phenoxy]-4-methyl-benzonitrile | 350 (349.37) 202.8–204.1 |
| I-218 | 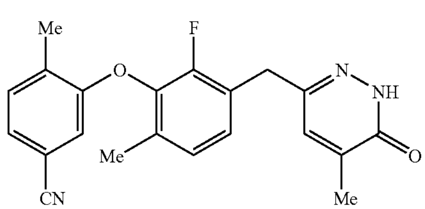 | 3-[2-Fluoro-6-methyl-3-(5-methyl-6-oxo-1,6-dihydro-pyridazin-3-ylmethyl)-phenoxy]-4-methyl-benzonitrile | 364 (363.39) 204–205.5 |

TABLE I-continued

| cpd # | Name | [M + H]+ (mw) mp |
|---|---|---|
| I-219 | 4-Chloro-3-[2-fluoro-6-methyl-3-(5-methyl-6-oxo-1,6-dihydro-pyridazin-3-ylmethyl)-phenoxy]-benzonitrile | 384 (383.81) 241.9–247.4 |
| I-220 | 3-[5-(6-Oxo-1,6-dihydro-pyridazin-3-ylmethyl)-2-trifluoromethyl-phenoxy]-benzonitrile | 372 (371.32) foam |
| I-221 | 3-[6-Bromo-3-(5-dimethylamino-6-oxo-1,6-dihydro-pyridazin-3-ylmethyl)-2-fluoro-phenoxy]-4-chloro-benzonitrile | 477 (477.72) 249.2–251.3 |
| I-222 | 6-[4-Chloro-2-fluoro-3-(1H-indol-4-yloxy)-benzyl]-2H-pyridazin-3-one | (369.79) |
| I-223 | 6-[4-Chloro-2-fluoro-3-(quinolin-5-yloxy)-benzyl]-4-methyl-2H-pyridazin-3-one | 370.1 (395.82) 194.5–196.3 |
| I-224 | 3-Chloro-5-[6-ethyl-2-fluoro-3-(6-oxo-1,6-dihydro-pyridazin-3-ylmethyl)-phenoxy]-benzonitrile | 384 (383.81) |
| I-225 | 3-[2-Fluoro-6-methyl-3-(6-oxo-1,6-dihydro-pyridazin-3-ylmethyl)-phenoxy]-5-methyl-benzonitrile | 350 (349.37) 180.1–181.9 |
| I-226 | 6-[4-Chloro-2-fluoro-3-(quinolin-8-yloxy)-benzyl]-4-methyl-2H-pyridazin-3-one | 396 (395.82) 239.7–242 |

TABLE I-continued

| cpd # | Structure | Name | [M + H]+ (mw) mp |
|---|---|---|---|
| I-227 | 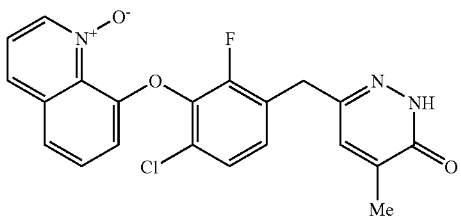 | 6-[4-Chloro-2-fluoro-3-(1-oxy-quinolin-8-yloxy)-benzyl]-4-methyl-2H-pyridazin-3-one | 412 (411.82) 118–120.9 |
| I-228 | 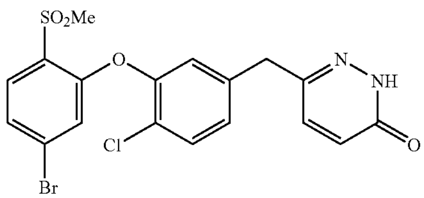 | 6-[3-(5-Bromo-2-methanesulfonyl-phenoxy)-4-chloro-benzyl]-2H-pyridazin-3-one | 469 (469.74) 242.0–243.8 |
| I-229 | 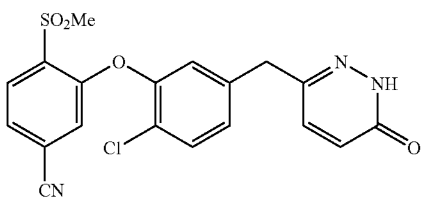 | 3-[2-Chloro-5-(6-oxo-1,6-dihydro-pyridazin-3-ylmethyl)-phenoxy]-4-methanesulfonyl-benzonitrile | 416 (415.86) 258.3–259.5 |
| I-230 | 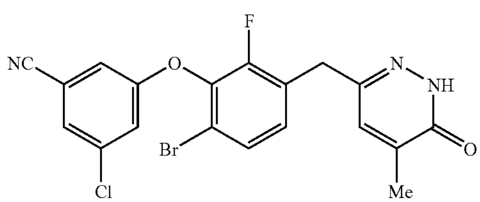 | 3-[6-Bromo-2-fluoro-3-(5-methyl-6-oxo-1,6-dihydro-pyridazin-3-ylmethyl)-phenoxy]-5-chloro-benzonitrile | 448 (448.68) 155–158.5 |
| I-231 | 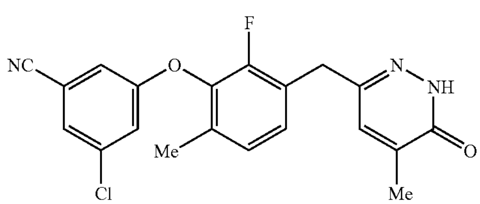 | 3-[6-Bromo-2-fluoro-3-(6-oxo-1,6-dihydro-pyridazin-3-ylmethyl)-phenoxy]-5-chloro-benzonitrile | 434 (434.65) 197.8–199.4 |
| I-232 | 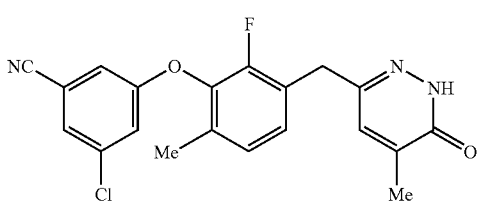 | 3-Chloro-5-[2-fluoro-6-methyl-3-(5-methyl-6-oxo-1,6-dihydro-pyridazin-3-ylmethyl)-phenoxy]-benzonitrile | 384 (383.81) 202.5–206.2 |
| I-233 | 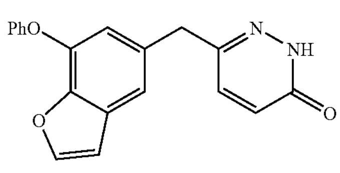 | 6-(7-Phenoxy-benzofuran-5-ylmethyl)-2H-pyridazin-3-one | 319 (318.3) 116.4–117.7 |

TABLE I-continued

| cpd # | Structure | Name | [M + H]+ (mw) mp |
|---|---|---|---|
| I-234 | 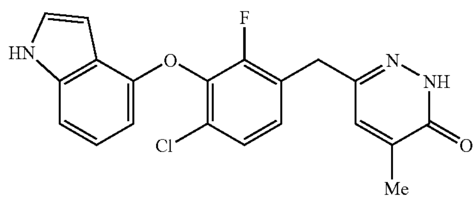 | 6-[4-Chloro-2-fluoro-3-(1H-indol-4-yloxy)-benzyl]-4-methyl-2H-pyridazin-3-one | 383 (383.81) 255.6–257.6 |
| I-235 | 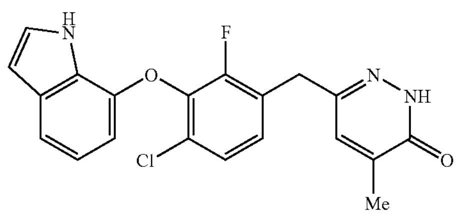 | 6-[4-Chloro-2-fluoro-3-(1H-indol-7-yloxy)-benzyl]-4-methyl-2H-pyridazin-3-one | 383 (383.81) 201.7–203.7 |
| I-236 | 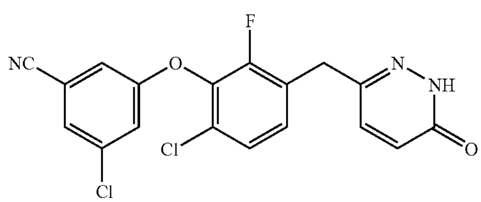 | 3-Chloro-5-[6-chloro-2-fluoro-3-(6-oxo-1,6-dihydro-pyridazin-3-ylmethyl)-phenoxy]-benzonitrile | 391 (390.20) 206–208 |
| I-237 | 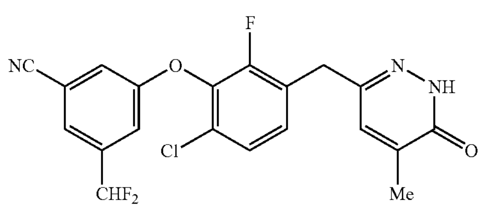 | 3-[6-Chloro-2-fluoro-3-(5-methyl-6-oxo-1,6-dihydro-pyridazin-3-ylmethyl)-phenoxy]-5-difluoromethyl-benzonitrile | 420 (419.79) 179.2–181.2 |
| I-238 | 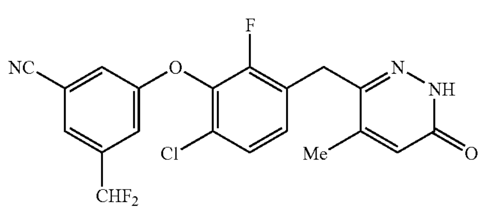 | 3-[6-Chloro-2-fluoro-3-(4-methyl-6-oxo-1,6-dihydro-pyridazin-3-ylmethyl)-phenoxy]-5-difluoromethyl-benzonitrile | (419.79) |
| I-239 | 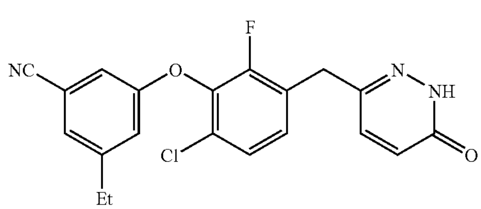 | 3-[6-Chloro-2-fluoro-3-(6-oxo-dihydro-pyridazin-3-ylmethyl)-phenoxy]-5-ethyl-benzonitrile | 383 ((383.81) 140–151 |
| I-240 | 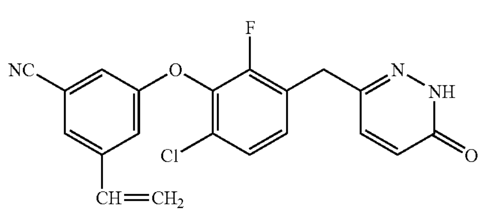 | 3-[6-Chloro-2-fluoro-3-(6-oxo-1,6-dihydro-pyridazin-3-ylmethyl)-phenoxy]-5-ethenyl-benzonitrile | 381 (381.79) 170.2–173.4 |

TABLE I-continued

| cpd # | Name | [M + H]+ (mw) mp |
|---|---|---|
| I-241 | 2-(3-Cyano-phenoxy)-3-fluoro-4-(5-methyl-6-oxo-1,6-dihydro-pyridazin-3-ylmethyl)-benzonitrile | 361 (360.35) 191.8–192.4 |
| I-242 | 6-[4-Chloro-3-(3-chloro-phenoxy)-2-fluoro-benzyl]-4-ethyl-2H-pyridazin-3-one | (375.23) |
| I-243 | 6-[4-Chloro-5-(3-chloro-phenoxy)-2-fluoro-benzyl]-4-methyl-2H-pyridazin-3-one | (379.22) |
| I-244 | 6-[4-Chloro-5-(3-chloro-phenoxy)-2-fluoro-benzyl]-2H-pyridazin-3-one | (365.19) |
| I-245 | 5-[6-Ethyl-2-fluoro-3-(5-methyl-6-oxo-1,6-dihydro-pyridazin-3-ylmethyl)-phenoxy]-isophthalonitrile | 389 (388.40) |
| I-246 | 2-[2-Chloro-5-(6-oxo-1,6-dihydro-pyridazin-3-ylmethyl)-phenoxy]-isonicotinonitrile | (338.76) |
| I-247 | 6-[3-(6-Chloro-pyridin-2-yloxy)-4-methyl-benzyl]-4-methyl-2H-pyridazin-3-one | 342 (341.80) |
| I-248 | 6-[3-(6-Chloro-pyridin-2-yloxy)-4-methyl-benzyl]-5-methyl-2H-pyridazin-3-one | 342 (341.80) 173.0–176.4 |
| I-249 | 6-[4-Chloro-3-(4-methyl-pyridin-2-yloxy)-benzyl]-4-methyl-2H-pyridazin-3-one | 342 (341.80) 188.0–188.9 |

TABLE I-continued

| cpd # | Structure | Name | [M + H]+ (mw) mp |
|---|---|---|---|
| I-250 | 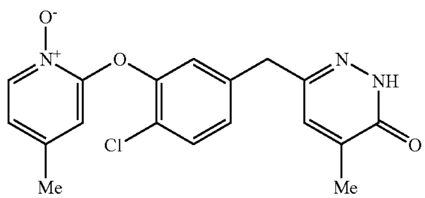 | 6-[4-Chloro-3-(4-methyl-1-oxy-pyridin-2-yloxy)-benzyl]-4-methyl-2H-pyridazin-3-one | 358 (357.80) 195.6–197.3 |
| I-251 | 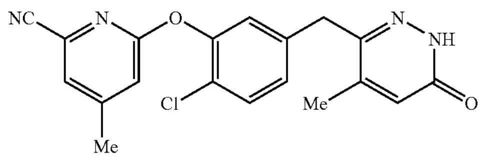 | 6-[2-Chloro-5-(4-methyl-6-oxo-1,6-dihydro-pyridazin-3-ylmethyl)-phenoxy]-4-methyl-pyridine-2-carbonitrile | 367 (366.81) 225–228.1 |
| I-252 | 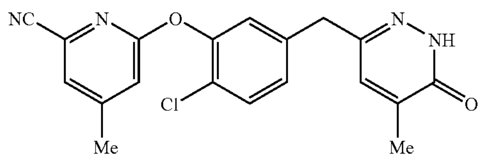 | 6-[2-Chloro-5-(5-methyl-6-oxo-1,6-dihydro-pyridazin-3-ylmethyl)-phenoxy]-4-methyl-pyridine-2-carbonitrile | (366.81) 249.9–253.6 |
| I-253 | 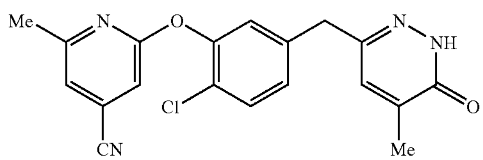 | 2-[2-Chloro-5-(5-methyl-6-oxo-1,6-dihydro-pyridazin-3-ylmethyl)-phenoxy]-6-methyl-isonicotinonitrile | 366 (366.81) 185–187.3 |
| I-254 | 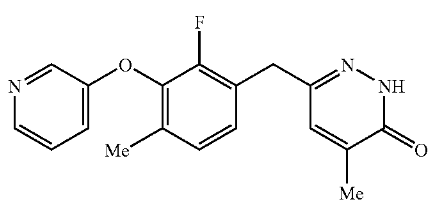 | 6-[2-Fluoro-4-methyl-3-(pyridin-3-yloxy)-benzyl]-4-methyl-2H-pyridazin-3-one | 326 (325.35) 16439–167.7 |
| I-255 | 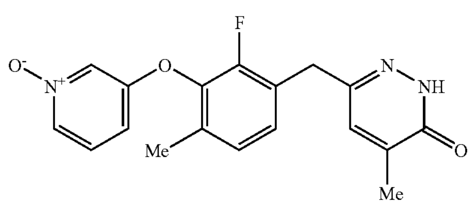 | 6-[2-Fluoro-4-methyl-3-(1-oxy-pyridin-3-yloxy)-benzyl]-4-methyl-2H-pyridazin-3-one | 342 (341.34) 207.8–212.7 |
| I-256 | 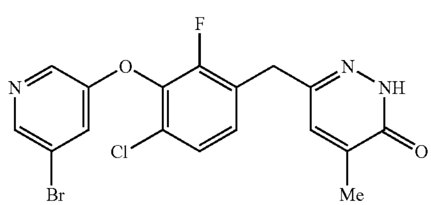 | 6-[3-(5-Bromo-pyridin-3-yloxy)-4-chloro-2-fluoro-benzyl]-4-methyl-2H-pyridazin-3-one | 424 (424.66) 184.9–188 |
| I-257 | 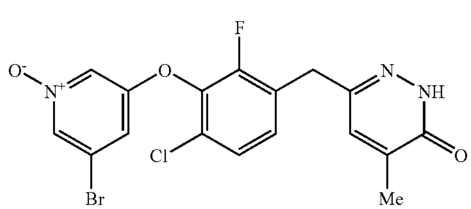 | 6-[3-(5-Bromo-1-oxy-pyridin-3-yloxy)-4-chloro-2-fluoro-benzyl]-4-methyl-2H-pyridazin-3-one | (440.66) 197.9–198.3 |

TABLE I-continued

| cpd # | Structure | Name | [M + H]+ (mw) mp |
|---|---|---|---|
| I-258 | 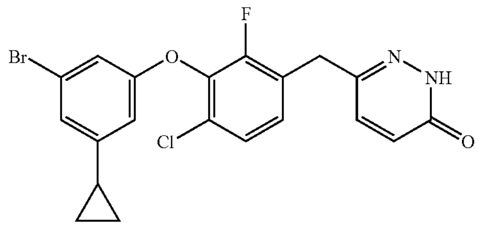 | 6-[3-(3-Bromo-5-cyclopropyl-phenoxy)-4-chloro-2-fluoro-benzyl]-2H-pyridazin-3-one | 449 (449.7) 16536–167.7 |
| I-259 | 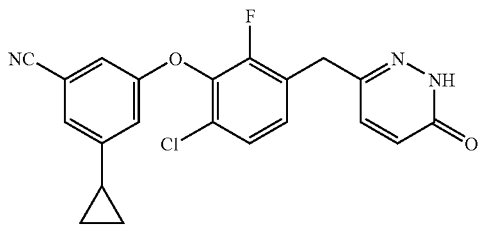 | 3-[6-Chloro-2-fluoro-3-(6-oxo-1,6-dihydro-pyridazin-3-ylmethyl)-phenoxy]-5-cyclopropyl-benzonitrile | 395 (395.8) 177.4–180.5 |
| I-260 | 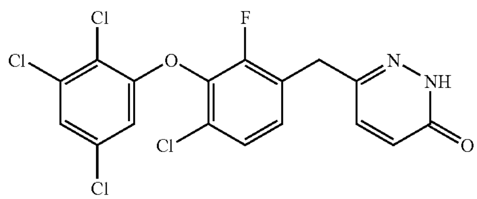 | 6-[4-Chloro-2-fluoro-3-(2,3,5-trichloro-phenoxy)-benzyl]-2H-pyridazin-3-one | (434) 187.5–189.5 |

[1] [M]+
[2] [M − H]+

TABLE II

| cpd # | Structure | Name | [M + H]+ (mw) mp |
|---|---|---|---|
| II-1 | 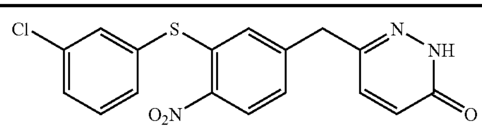 | 6-[3-(3-chloro-phenylsulfanyl)-4-nitro-benzyl]-2H-pyridazin-3-one | 373.82 |
| II-2 | 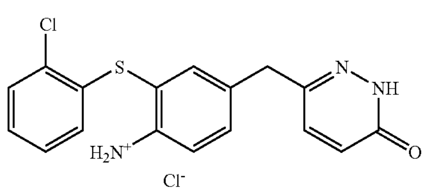 | 2-(2-Chloro-phenylsulfanyl)-4-(6-oxo-1,6-dihydro-pyridazin-3-ylmethyl)-phenyl-ammonium; chloride | 380.30 |
| II-3 | 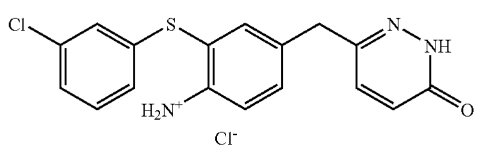 | 2-(3-Chloro-phenylsulfanyl)-4-(6-oxo-1,6-dihydro-pyridazin-3-ylmethyl)-phenyl-ammonium; chloride | 380.30 |
| II-4 | 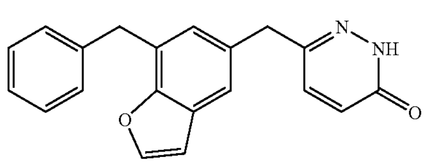 | 6-(7-Benzyl-benzofuran-5-ylmethyl)-2H-pyridazin-3-one | 317 (316.36) |

TABLE II-continued

| cpd # | Structure | Name | [M + H]+ (mw) mp |
|---|---|---|---|
| II-5 | 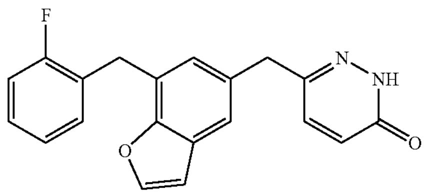 | 6-[7-(2-Fluoro-benzyl)-benzofuran-5-ylmethyl]-2H-pyridazin-3-one | 335<br>334.35 |
| II-6 | 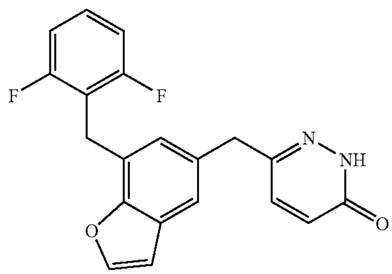 | 6-[7-(2,6-Difluoro-benzyl)-benzofuran-5-ylmethyl]-2H-pyridazin-3-one | [M]+ = 352<br>352.34 |
| II-7 | 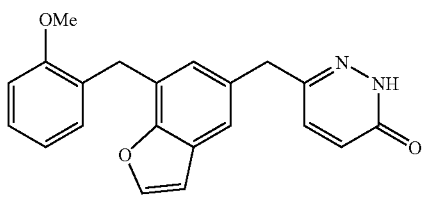 | 6-[7-(2-Methoxy-benzyl)-benzofuran-5-ylmethyl]-2H-pyridazin-3-one | 347<br>346.39 |
| II-8 | 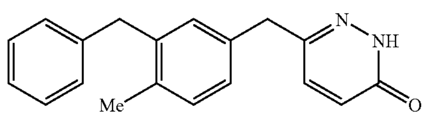 | 6-(3-Benzyl-4-methyl-benzyl)-2H-pyridazin-3-one | 291<br>290.37 |
| II-9 | 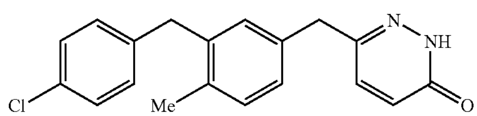 | 6-[3-(4-Chloro-benzyl)-4-methyl-benzyl]-2H-pyridazin-3-one | 325<br>324.81 |
| II-10 | 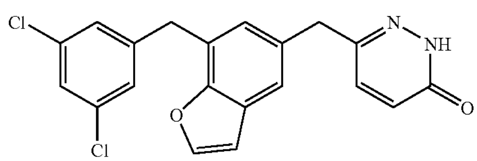 | 6-[7-(3,5-Dichloro-benzyl)-benzofuran-5-ylmethyl]-2H-pyridazin-3-one | [M]+ = 385<br>385.25 |
| II-11 | 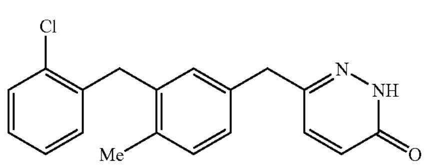 | 6-[3-(2-Chloro-benzyl)-4-methyl-benzyl]-2H-pyridazin-3-one | 325<br>324.81 |
| II-12 | 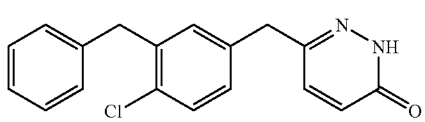 | 6-(3-Benzyl-4-chloro-benzyl)-2H-pyridazin-3-one | 311<br>310.79 |
| II-13 | 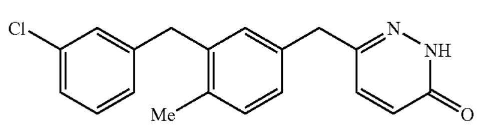 | 6-[3-(3-Chloro-benzyl)-4-methyl-benzyl]-2H-pyridazin-3-one | 325<br>324.81 |

TABLE II-continued

| cpd # | Structure | Name | [M + H]+ (mw) mp |
|---|---|---|---|
| II-14 | 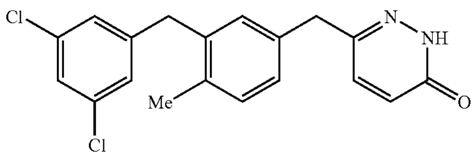 | 6-[3-(3,5-Dichloro-benzyl)-4-methyl-benzyl]-2H-pyridazin-3-one | [M]+ = 359 359.26 |
| II-15 | 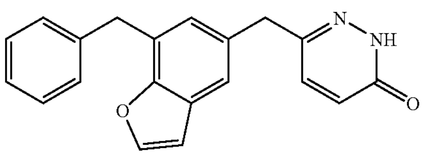 | 6-[7-(4-Bromo-benzyl)-benzofuran-5-ylmethyl]-2H-pyridazin-3-one | [M]+ = 395 395.26 |
| II-16 | 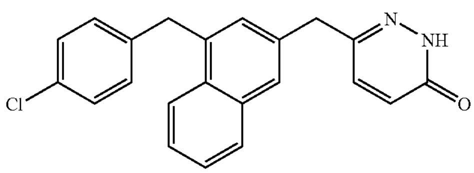 | 6-[4-(4-Chloro-benzyl)-naphthalen-2-ylmethyl]-2H-pyridazin-3-one | 361 360.85 |
| II-17 | 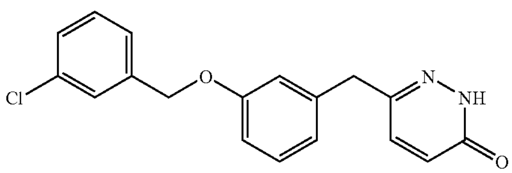 | 6-[3-(3-Chloro-benzyloxy)-benzyl]-2H-pyridazin-3-one | 326[1] (326.78) |
| II-18 | 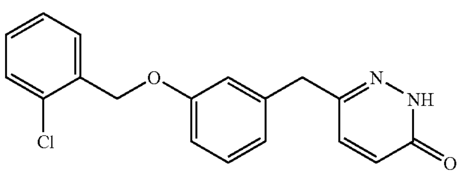 | 6-[3-(2-Chloro-benzyloxy)-benzyl]-2H-pyridazin-3-one | 326[1] (326.78) |
| II-19 | 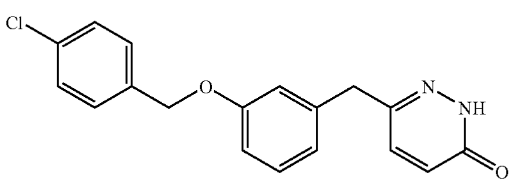 | 6-[3-(4-Chloro-benzyloxy)-benzyl]-2H-pyridazin-3-one | 326[1] (326.78) |
| II-20 | 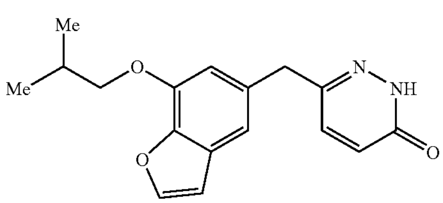 | 6-(7-Isobutoxy-benzofuran-5-ylmethyl)-2H-pyridazin-3-one | 299 (298.34) 99.7–100.9 |
| II-21 | 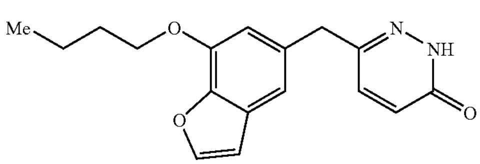 | 6-(7-Butoxy-benzofuran-5-ylmethyl)-2H-pyridazin-3-one | 299 (298.34) 78.5–82.5 |

TABLE II-continued

| cpd # | Structure | Name | [M + H]+ (mw) mp |
|---|---|---|---|
| II-22 | 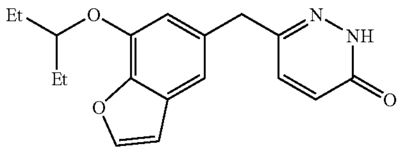 | 6-[7-(1-Ethyl-propoxy)-benzofuran-5-ylmethyl]-2H-pyridazin-3-one | 313 (312.36) |
| II-23 | 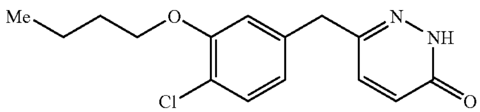 | 6-(3-Butoxy-4-chloro-benzyl)-2H-pyridazin-3-one | 293 (292.76) oil |
| II-24 | 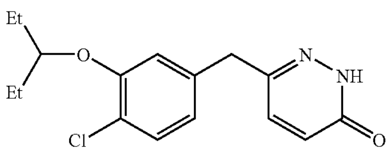 | 6-[4-Chloro-3-(1-ethyl-propoxy)-benzyl]-2H-pyridazin-3-one | 307 (306.79) 103.9–105.2 |
| II-25 | 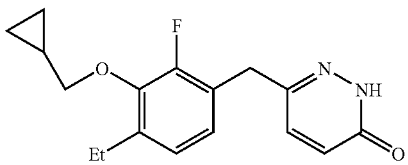 | 6-(3-Cyclopropylmethoxy-4-ethyl-2-fluoro-benzyl)-2H-pyridazin-3-one | 302 (302.34) |
| II-26 | 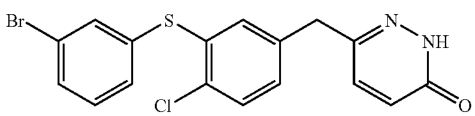 | 6-[3-(3-Bromo-phenylsulfanyl)-4-chloro-benzyl]-2H-pyridazin-3-one | 409 (407.72) |
| II-27 | 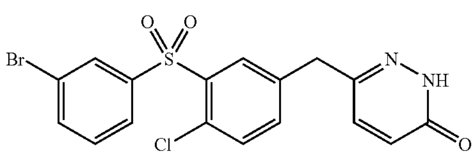 | 6-[3-(3-Bromo-benzenesulfonyl)-4-chloro-benzyl]-2H-pyridazin-3-one | 439 (439.72) |
| II-28 | 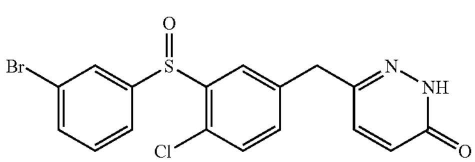 | 6-[3-(3-Bromo-benzenesulfinyl)-4-chloro-benzyl]-2H-pyridazin-3-one | 425 (423.72) |

TABLE III

| cpd# | Structure | Name | [M + H]+ (mw) mp |
|---|---|---|---|
| III-1 | 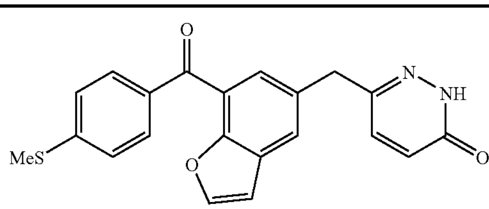 | 6-[7-(4-Methylsulfanyl-benzoyl)-benzofuran-5-ylmethyl]-2H-pyridazin-3-one | 376 (M)+ (376.44) 93–96° |

TABLE III-continued

| cpd# | Structure | Name | [M + H]+ (mw) mp |
|---|---|---|---|
| III-2 | 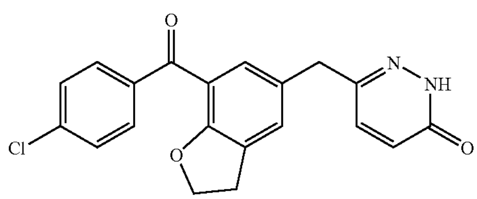 | 6-[7-(4-Chloro-benzoyl)-2,3-dihydro-benzofuran-5-ylmethyl]-2H-pyridazin-3-one | 366 (366.81) 196–200° |
| III-3 | 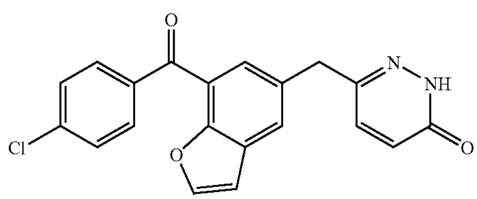 | 6-[7-(4-Chloro-benzoyl)-benzofuran-5-ylmethyl]-2H-pyridazin-3-one | 364 (M)+ (364.79) 197.5–148.7° |
| III-4 | 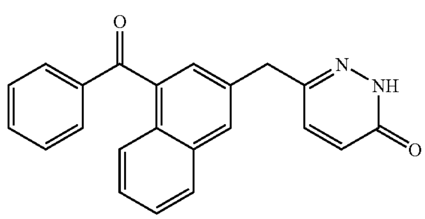 | 6-(4-Benzoyl-naphthalen-2-ylmethyl)-2H-pyridazin-3-one | (340.38) 175.6–175.9° |
| III-5 | 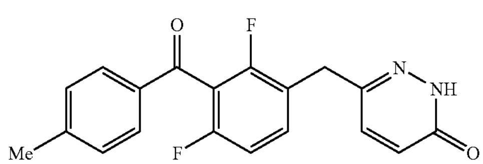 | 6-[2,4-Difluoro-3-(4-methyl-benzoyl)-benzyl]-2H-pyridazin-3-one | (340.33) |
| III-6 | 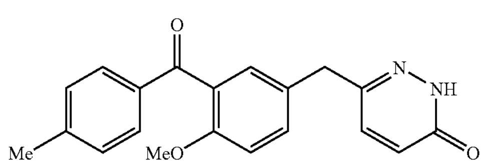 | 6-[4-Methoxy-3-(4-methyl-benzoyl)-benzyl]-2H-pyridazin-3-one | (334.38) |
| III-7 | 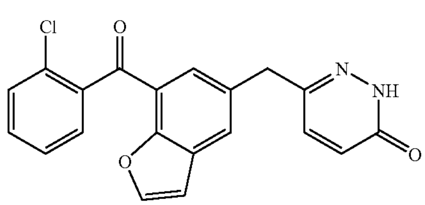 | 6-[7-(2-Chloro-benzoyl)-benzofuran-5-ylmethyl]-2H-pyridazin-3-one | 364 (M)+ (364.79) 196–198° |
| III-8 | 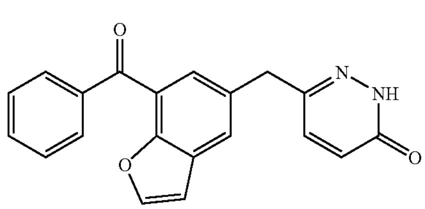 | 6-(7-Benzoyl-benzofuran-5-ylmethyl)-2H-pyridazin-3-one | 330 (M)+ (330.35) 177–181° |

TABLE III-continued

| cpd# | Name | [M + H]+ (mw) mp |
|---|---|---|
| III-9 | 6-[7-(2,4-Dichloro-benzoyl)-benzofuran-5-ylmethyl]-2H-pyridazin-3-one | 398 (M)+ (399.24) 208–214° |
| III-10 | 6-[5-(4-Chloro-benzoyl)-benzofuran-7-ylmethyl]-2H-pyridazin-3-one | 364.79 |
| III-11 | 6-[7-(3-Chloro-benzoyl)-benzofuran-5-ylmethyl]-2H-pyridazin-3-one | 364.79 |
| III-12 | 6-[7-(2-Fluoro-benzoyl)-benzofuran-5-ylmethyl]-2H-pyridazin-3-one | 348.34 |
| III-13 | 6-[7-(2,6-Difluoro-benzoyl)-benzofuran-5-ylmethyl]-2H-pyridazin-3-one | 366.33 |
| III-14 | 6-[7-(3-Methoxy-benzoyl)-benzofuran-5-ylmethyl]-2H-pyridazin-3-one | 360.373 |
| III-15 | 6-[7-(4-Chloro-benzoyl)-benzo[b]thiophen-5-ylmethyl]-2H-pyridazin-3-one | 380.86 |

TABLE III-continued

| cpd# | Structure | Name | [M + H]+ (mw) mp |
|---|---|---|---|
| III-16 | 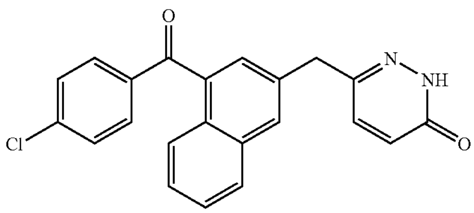 | 6-[4-(4-Chloro-benzoyl)-naphthalen-2-ylmethyl]-2H-pyridazin-3-one | 374.83 |
| III-17 | 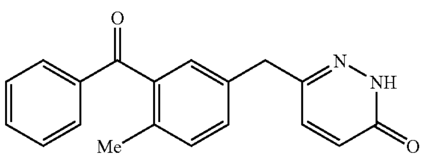 | 6-(3-Benzoyl-4-methyl-benzyl)-2H-pyridazin-3-one | 304.35 |
| III-18 | 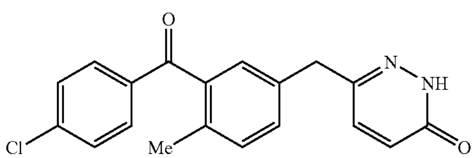 | 6-[3-(4-Chloro-benzoyl)-4-methyl-benzyl]-2H-pyridazin-3-one | 338.80 |
| III-19 | 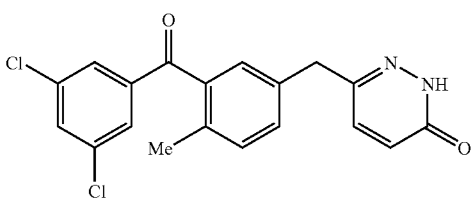 | 6-[3-(3,5-Dichloro-benzoyl)-4-methyl-benzyl]-2H-pyridazin-3-one | 373.24 |
| III-20 | 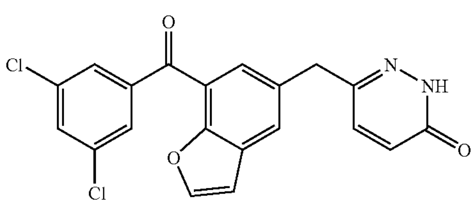 | 6-[7-(3,5-Dichloro-benzoyl)-benzofuran-5-ylmethyl]-2H-pyridazin-3-one | 399.24 |
| III-21 | 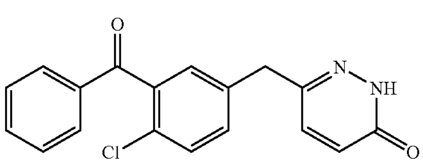 | 6-(3-Benzoyl-4-chloro-benzyl)-2H-pyridazin-3-one | 324.77 |
| III-22 | 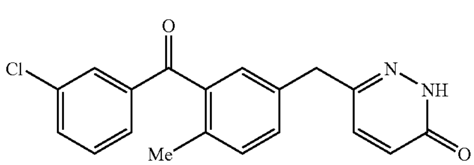 | 6-[3-(3-Chloro-benzoyl)-4-methyl-benzyl]-2H-pyridazin-3-one | 338.80 |
| III-23 | 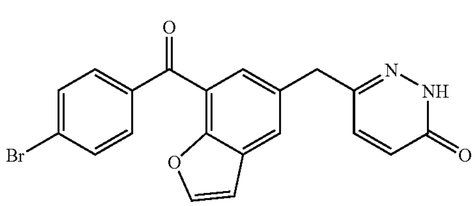 | 6-[7-(4-Bromo-benzoyl)-benzofuran-5-ylmethyl]-2H-pyridazin-3-one | 409.24 |

TABLE III-continued

| cpd# | Structure | Name | [M + H]+ (mw) mp |
|---|---|---|---|
| III-24 | (structure shown) | 4-[5-(6-Oxo-1,6-dihydro-pyridazin-3-ylmethyl)-benzofuran-7-carbonyl]-benzonitrile | 355.36 |

Preraration of Compounds of the Invention

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1–21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1–9 Pergamon, Oxford, 1991; *Comprehensive Heterocyclic Chemistry*, A. R. Katritzky and C. W. Rees (Eds) Pergamon, Oxford 1984, vol. 1–9; *Comprehensive Heterocyclic Chemistry II*, A. R. Katritzky and C. W. Rees (Eds) Pergamon, Oxford 1996, vol. 1–11; and *Organic Reactions*, Wiley & Sons: New York, 1991, Volumes 1–40. The following synthetic reaction schemes and examples are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. Moreover, the reaction conditions are exemplary and alternative conditions are well known. The reaction sequences in the following examples are not meant to limit the scope of the invention as set forth in the claims.

The heterocyclic compounds of the present invention are prepared by a two-stage process (Scheme 1) comprising construction of an appropriately substituted aryl ring 2 and subsequently introducing the heterocyclic ring to produce 3. Although stages can be accomplished in any order, the heterocyclic ring is generally introduced after the modifications of the aryl ring are completed. Substituted alkyl m-hydroxyphenylacetate 1a or m-hydroxyphenylacetonitrile 1b derivatives are convenient starting materials. They are often commercially available or readily prepared from commercially available precursors. Alternatively the aryl ring may be substituted with a methyl 1c or carboxylic acid ester Id substituent which is subsequently converted to 1b (for example, see schemes 4 and 5). One skilled in the art will also appreciate the substituents can altered after introduction of the heterocyclic ring.

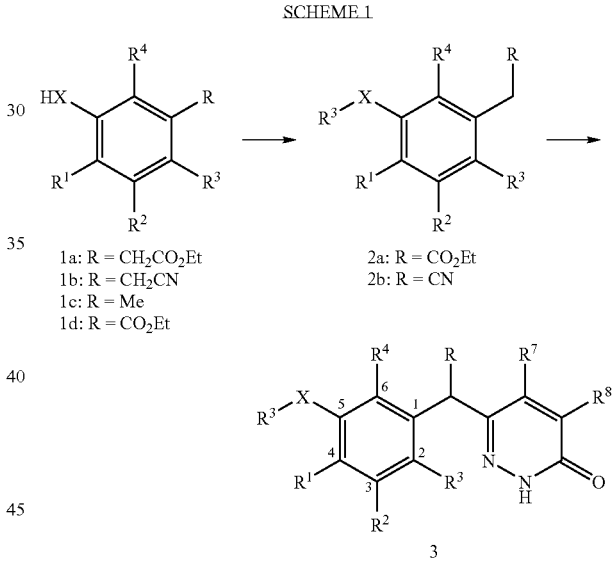

SCHEME 1

1a: R = CH$_2$CO$_2$Et
1b: R = CH$_2$CN
1c: R = Me
1d: R = CO$_2$Et

2a: R = CO$_2$Et
2b: R = CN

Preparation of Phenylacetic Acid and Phenylacetonitile Precursors (Scheme 1; 1)

Ethyl 3-hydroxy-4-methylphenylacetate (5a) was prepared from ethyl 3-methoxy-4-hydroxy-phenylacetate as shown in Scheme 2. The phenol was converted to the triflate ester 4b which was subjected to displacement with Me$_2$Zn, DIBAL-H and PdCl$_2$(dppf) (E.-i. Negishi in *Metal-catalyzed Cross-Coupling Reactions*, F. Diederich and P. J. Stang (eds.), Wiley-VCH, Mannheim 1998, chap. 1; E. Erdik, *Tetrahedron* 1992 48:9577–9648) to afford the 4c. Boron tribromide demethylation afforded 5a. Ethyl 3-hydroxy-4-ethylphenylacetate 5b was prepared by Friedel-Crafts acylation of 4d which afforded ethyl 4-acetyl-3-methoxyphenylacetate (4e). Reduction of the ketone with triethylsilane and TFA produced the corresponding 4-ethyl substituted derivative 4f which was demethylated with BBr$_3$ to afford 5b. Ethyl 3-hydroxy-4-iso-propylphenylacetate (5c) was prepared by Wittig olefination of 4e and subsequent catalytic hydrogenation of the 2-propenyl substituent to yield 4h. Demethylation with boron tribromide produced 5c.

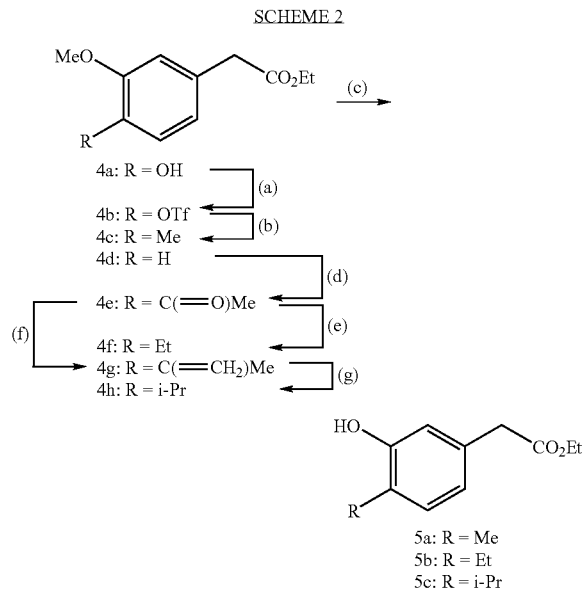

SCHEME 2

4a: R = OH
4b: R = OTf
4c: R = Me
4d: R = H
4e: R = C(=O)Me
4f: R = Et
4g: R = C(=CH₂)Me
4h: R = i-Pr

5a: R = Me
5b: R = Et
5c: R = i-Pr (a) (CF₃SO₂)₂O, Pyr, CH₂Cl₂; (b) ZnMe₂, PdCl₂ (dppf), DIBAL-H, 0° to Δ; (c) BBr₃, CH₂Cl₂, -78° C.; (d) MeCOCl, SnCl₄, CH₂Cl₂; (e) Et₃SiH, TFA; (f) MePPh3⁺Cl⁻, n-BuLi, THF; (e) H₂, Pd/C, EtOH Ethyl 3,4-dimethyl-5-hydroxyphenylacetate (8) was prepared by formylation of 6a and esterification of the resulting carboxylic acid 6b to produce ethyl 3-formyl-4-hydroxy-5-methoxyphenyl acetate (7a). Reduction of the aldehyde and hydrogenolysis the resulting benzyl alcohol afforded 7b. The second methyl substituent was introduced by sequential treatment of 7b with triflic anhydride which yielded 7c and displacement with Me₂Zn, PdCl₂(dppf) and DIBAL-H (supra) to produce 7d. Boron tribromide mediated demethylation afforded 8. (Scheme 3)

SCHEME 3

6a: R = H
6b: R = CHO

7a: R = CHO; R¹ = OH
7b: R = Me; R¹ = OH
7c: R = Me; R¹ = OTf
7d: R = R¹ = Me

8

(a) hexamethylene, tetraamine, TFA; (b) EtOH, H₂SO₄; (c) H₂, Pd/C, HOAc; (d) Tf₂O, pyr, CH₂Cl₂; (e) MeZn, PdCl₂(prof), DIBAL-H; (f) BBr₃, CH₂Cl₂, -78° C.

Ethyl 4-chloro-3-hydroxyphenyl acetate (10) was prepared from 4-chloro-3-methoxytoluene by sequential free radical bromination (9b), nucleophilic displacement of the bromine atom with cyanide (9c) and a two-step hydrolysis of the nitrile to the amidine hydrochloride 9d and subsequently to the ethyl ester 9e. Boron tribromide mediated demethylation as described previously afforded 10. (Scheme 4)

9a: R = H
9b: R = Br
9c: R = CN
9d: R = C(=NH)OEt•HCl
9e: R = CO₂Et

10

(a) NBS, benzoyl peroxide, CCl₄; (b) NaCN, 90% EtOH; (c) HCl, EtOH, Et₂O; (d) H₂O, 40° C.; (e) BBr₃, CH₂Cl₂, -78° C.

6-Methyl derivatives were prepared from 3-hydroxy-2-methylbenzoic acid (11) which was chlorinated (NaOCl/NaOH) and esterified to afford 13. Cupric acetate mediated coupling (infra) of benzeneboronic acid provided the diaryl ether 14. The nitrile was introduced by sequential reduction, mesylation and cyanide displacement to afford 17. The mesylate underwent an in situ displacement by chloride during the mesylation reaction.

SCHEME 5

11: R = H
12: R = Cl

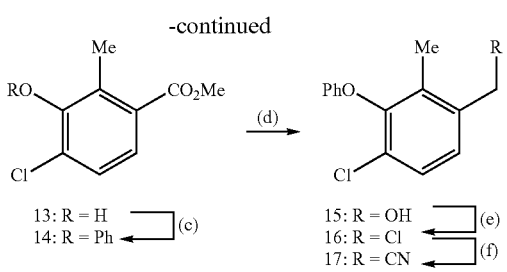

(a) NaOH, NaOCl, H₂O; (b) H₂SO₄, MeOH; (c) benzeneboronic acid, Cu(OAc)₂, TEA, molecular sieves, CH₂Cl₂; (d) DIBAL-H; (e) MsCl, TEA; (f) NaCN, EtOH.

6-fluoro- and chloro-derivatives were available from 6-chloro-2-fluoro-3-methylphenol (18) and 3-bromo-2,4-dichlorotoluene (19), respectively (Scheme 6). The base-catalyzed reaction of 18 and p-fluoro-nitrobenzene yielded dairyl ether 20. Conversion of the nitro substiuent to the corresponding amine followed by diazotization and reduction produced 4-chloro-2-fluoro-3-phenoxytoluene (22). One skilled in the art will appreciate that the availability of amino-substituted aryl groups affords the possibility to replace the amino substiuent with a variety of other substituents utilizing the Sandmeyer reaction. Cupric chloride-mediated coupling (see infra) of 19 afforded the corresponding 2,4-dichloro-3-phenoxytoluene (23). Elaboration of the acetonitrile sidechain in 24 and 25 was accomplished by benzylic bromination and displacement.

SCHEME 6

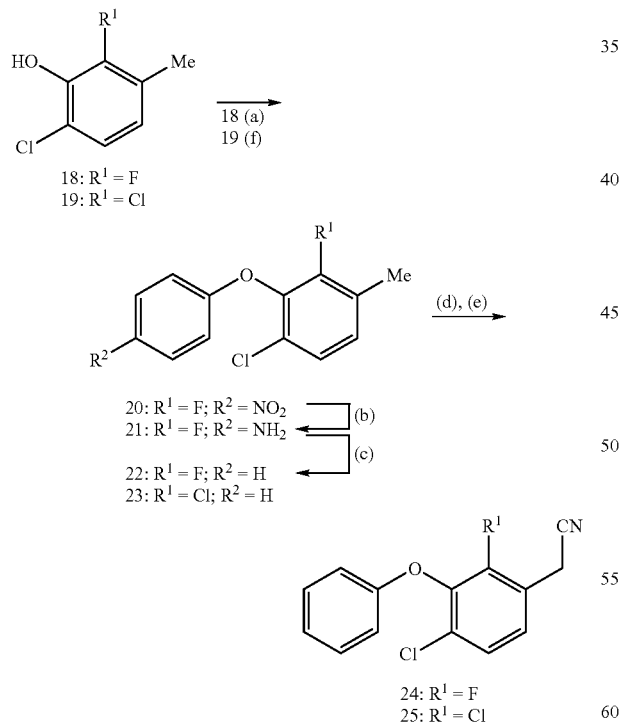

(a) K₂CO₃; (b) SnCl₂; (c)(i) NaNO₂, HOAc, HCl, H₂O (ii) FeSO₄•7H₂O, DMF; (d)(i) NBS, benzoyl peroxide, CCl₄ (ii) NaCN, EtOH; (f) Cs₂CO₃, CuCl, NMP.

Benzofuran 31 and dihydrobenzofuran 29 derivatives (Scheme 7) were prepared from dihydrobenzofuran (26). Acylation with ethyl chloro oxalate produced the α-ketoester 27 which was reduced to the corresponding phenylacetic acid derivative 28a under Wolff-Kischner conditions. The preparation of 29 by a Wilgerodt reaction also has been reported (J. Dunn et al. *J. Med Chem* 1986 29:2326). Freidel-Crafts acylation with acetyl chloride afforded the acetyl derivative 28b which was converted to the acetate 28c under Baeyer-Villiger conditions and subsequently hydrolyzed to 29. The corresponding benzofuran analogs were prepared by benzylic bromination and concomitant dehydrohalogention to yield 31.

SCHEME 7

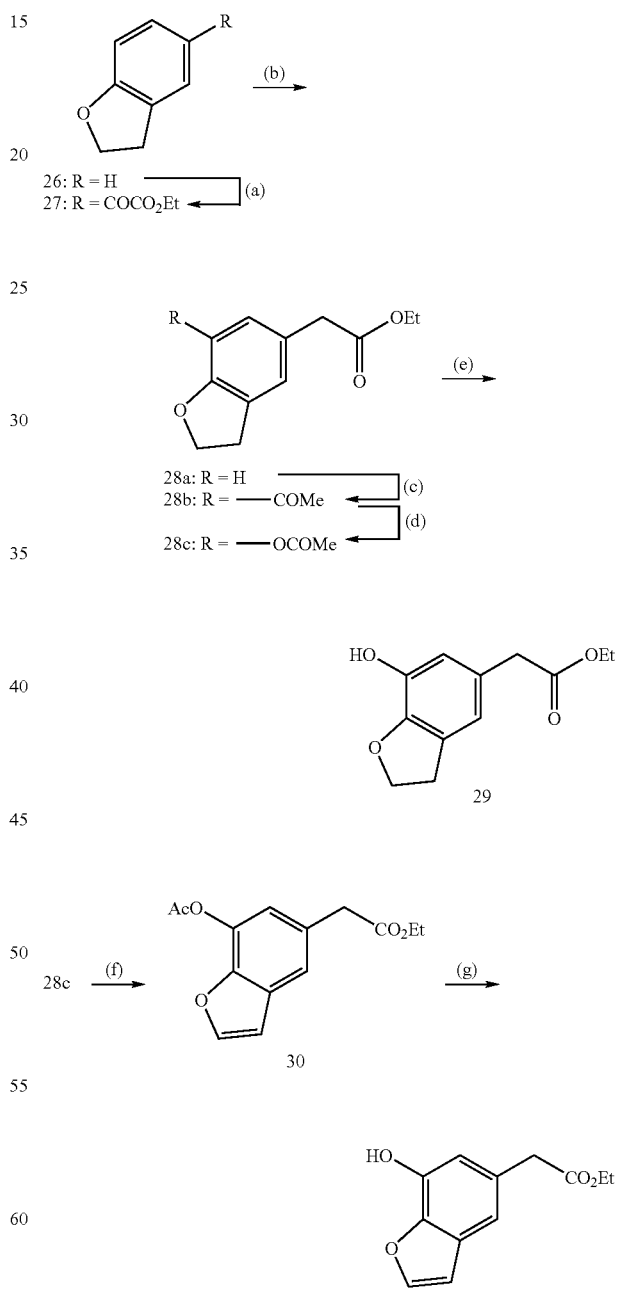

(a) ClC(=O)CO₂Et, AlCl₃, solvent; (b) NH₂NH₂, KOH, ethylene glycol; (c) CH₃COCl, AlCl₃, solvent; (d) H₂O₂, solvent; (e) hydrolysis conditions; (f) NBS; (g) NaHCO₃, H₂O, EtOH.

Preparation of Aryl Ether Intermediates (Scheme 1; 2; X=O or S)

The preparation of diaryl ethers has been reviewed (J. S. Sawyer, *Recent Advances in Diaryl Ether Synthesis, Tetrahedron* 2000 56:5045–5065). The diaryl ethers required herein were prepared by three different methods (Scheme 8): (i) $Cu(OAc)_2$ catalyzed condensation of substituted benzene boronic acids and phenols (D. A. Evans et al., *Synthesis of Diaryl Ethers through the Copper-Promoted Arylation of Phenols with Aryl Boronic Acids. An Expedient Synthesis of Thyroxine, Tetrahedron Lett.*, 1998 39:2937–2940 and D. M. T. Chan et al., *New N- and O-Arylations with Phenylboronic Acids and Cupric Acetate, Tetrahedron Lett.* 1998 39:2933–2936; Scheme 1, conditions (a), (b), (e), (f), (i); (ii) by variations of the Ullmann diaryl ether synthesis with Cu(I) salts (J.-F. Marcoux et al., *A General Copper-Catalyzed Synthesis of Diaryl Ethers, J. Am. Chem. Soc.* 1997 119:10539–540; E. Buck et al, *Ullmann Diaryl Ether Synthesis:Rate Acceleration by 2,2,6,6-tetramethylheptane-3,5-dione, Org. Lett.* 2002 4(9):1623–1626); conditions (c), (d) and (h); or by nucleophilic aromatic displacement reactions (Sawyer supra pp 5047–5059; conditions Scheme 1(g) and ()). An alternative process utilizing palladium-catalyzed coupling procedures also has been reported (G. Mann et al., *Palladium-Catalyzed Coupling Involving Unactivated Aryl Halides. Sterically Induced Reductive Elimination to Form the C—O Bond in Diaryl Ethers, J. Am. Chem. Soc.*, 1999 121:3224–3225). The preparation of aryl ethers 33a–g from the appropriate phenol 32a–e, and 35a–d from 34a and 34b, as described exemplifies these transformations. One skilled in the art will appreciate that optimal procedure will vary depending on the nature and position of substituents on the aryl rings.

SCHEME 8

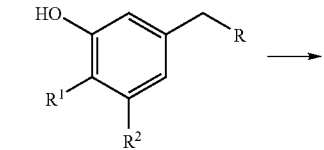

32a: $R = CN, R^1 = Me, R^2 = H$
32b: $R = CO_2Et, R^1 = Me, R^2 = H$
32c: $R = CO_2Et, R^1 = Et, R^2 = H$
32d: $R = CO_2Et, R^1 = i\text{-Pr}, R^2 = H$
32e: $R = CO_2Et, R^1 = R^2 = Me$

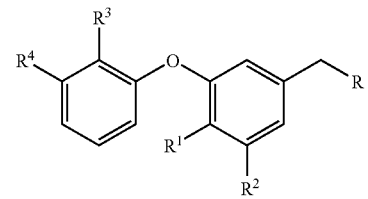

33a: $R = CN, R^1 = Me, R^2 = R^4 = H, R^3 = Br$ (a)
33b: $R = CO_2Et, R^1 = Me, R^2 = R^4 = H, R^3 = Cl$ (b)
33c: $R = CO_2Et, R^1 = Me, R^2 = R^3 = H, R^4 = F$ (c)
33d: $R = CO_2Et, R^1 = Et, R^2 = R^4 = H, R^3 = Cl$ (d)
33e: $R = CO_2Et, R^1 = Et, R^2 = R^3 = H, R^4 = Cl$ (e)
33f: $R = CO_2Et, R^1 = i\text{-Pr}, R^2 = R^3 = H, R^4 = Cl$ (f)
33g: $R = CO_2Et, R^1 = R^2 = Me, R^3 = H, R^4 = Cl$ (f)

(a) 2-bromobenzeneboronic acid, $Cu(OAc)_2$, pyridine, 4Å molecular sieves, $CH_2Cl_2$;
(b) 2-chlorobenzeneboronic acid, $Cu(OAc)_2$, pyridine, 4Å molecular sieves, $CH_2Cl_2$;
(c) m-fluorobromobenzene, CuCl $Cs_2CO_3$, TMHD, NMP; (d) 2-iodochlorobenzene; CuCl $Cs_2CO_3$, TMHD, NMP; (e) 3-chlorobenzeneboronic acid; $Cu(OAc)_2$, TEA, 4Å molecular sieves, $CH_2Cl_2$; (f) 3-chlorobenzeneboronic acid, $Cu(OAc)_2$, TEA, 4Å molecular sieves, $CH_2Cl_2$.

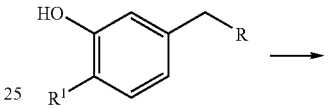

34a: $R = CO_2Et, R^1 = Cl$
34b: $R = H, R^1 = Cl$

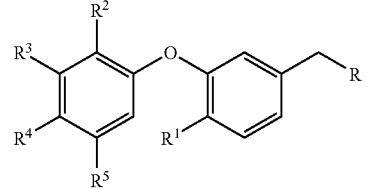

35a: $R = CO_2Et, R^1 = Cl, R^2 = R^4 = H, R^3 = F, R^5 = CN$ (g)
35b: $R = CO_2Et, R^1 = R^2 = R^5 = Cl, R^3 = R^4 = H$ (h)
35c: $R = CO_2Et, R^1 = Cl, R^2 = R^3 = R^5 = H, R^4 = Br$ (i)
35d: $R = H, R^1 = Cl, R^3 = Br, R^5 = F, R^2 = R^4 = H$ (j)

(g) 3,5-difluorobenzonitrile, $K_2CO_3$, NMP, 120° C.; (h) 2,5-dichloroboromobenzene, CuCl, $Cs_2CO_3$, TMHP, NMP 120° C.; (i) 4-bromobenzeneboronic acid, $Cu(OAc)_2$, TEA, 4Å molecular sieves, $CH_2Cl_2$; (j) 3,5-dibromofluorobenzene, $Cs_2CO_3$, TMHD, NMP.

Substituted m-cresol derivatives are also suitable substrates for coupling using these procedures. After introduction of the meta substituent the intermediate can be converted to the corresponding phenylacetonitrile derivative by bromination and cyanide displacement (Scheme 9).

SCHEME 9

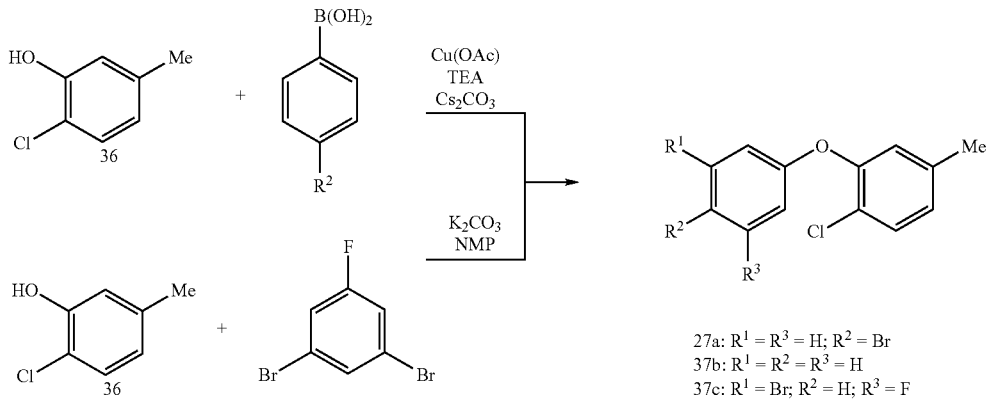

27a: $R^1 = R^3 = H; R^2 = Br$
37b: $R^1 = R^2 = R^3 = H$
37c: $R^1 = Br; R^2 = H; R^3 = F$ coupling of compounds with a fused aryl, heteroaryl or heterocyclic ring to produce diaryl ethers, alkylaryl ethers or arylaralkylethers can be carried out by the same procedures. The preparation of alkyl aryloxybenzofuranacetate and aryloxydihydrobenzofuranylacetate derivatives is exemplified in Scheme 10. Alkoxybenzofurans are prepared by Mitsunobu coupling of the alcohol and the hydroxybenzofuranacetic acid.

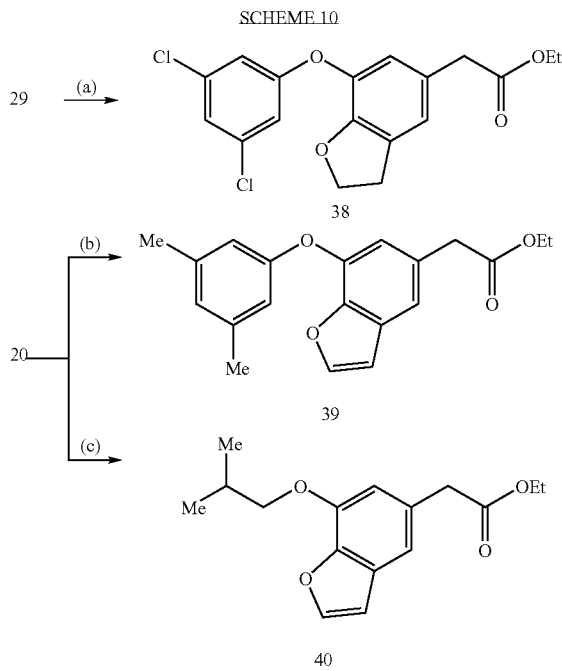

(a) 3,5-dichlorobenzeneboronic acid, Cu(OAc)$_2$, TEA, molecular sieves, CH$_2$Cl$_2$;
(b) 3,5-dimethylbenzeneboronic acid, Cu(OAc)$_2$, TEA, molecular sieves, CH$_2$Cl$_2$;
(c) Me$_2$CHCH$_2$OH, DIAD, PPh$_3$.

Alkyl aryl and aralkyl aryl ethers were prepared using Mitsunobu conditions (Scheme 11; O. Mitsunobu, *Synthesis* 1981 1–28). Alternatively alkyl and aralkyl ethers can be prepared via a classical Williamson ether synthesis (J. March, *Advanced Organic Chemistry*; 4$^{th}$ Edition; Wiley & Sons: New York, 1992;pp. 386–87) or utilizing palladium-catalyzed coupling (M. Palucki et al., *Palladium-catalyzed Intermolecular Carbon-Oxygen Bond Formation: A New Synthesis of Aryl Ethers, J. Am. Chem. Soc.* 1997 119: 3395–96).

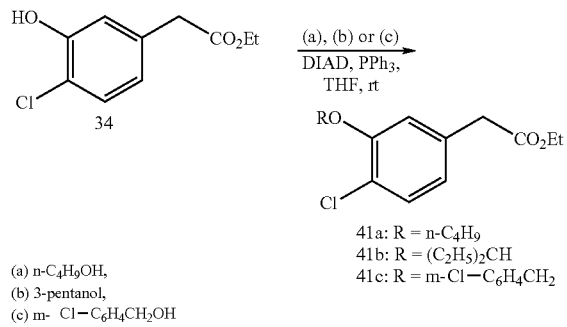

(a) n-C$_4$H$_9$OH,
(b) 3-pentanol,
(c) m- Cl—C$_6$H$_4$CH$_2$OH

Preparation of Diphenylamine Intermediates (Scheme 1: X=NR$^6$)

Diphenylamine compounds with in the scope of the present invention can be prepared by palladium-catalyzed coupling reactions as described by Hartwig (*Transition Metal Catalyzed Synthesis of Aryl Amines and Aryl Ethers from Aryl Halides and Triflates: Scope and Mechanism, Angew. Chem. Int. Ed. Eng.* 1998 37:2046–67)

Preparation of Diphenyl Methane Intermediates (Scheme 1: 2: X=CH$_2$ or C=O)

Diphenylmethane compounds of the present invention can be prepared by reduction of the corresponding benzoyl derivatives 42. While reductions are conveniently carried out with triethylsilylhydride and trifluoroacetic acid, a variety of other procedures to effect this transformation are well known within the art.

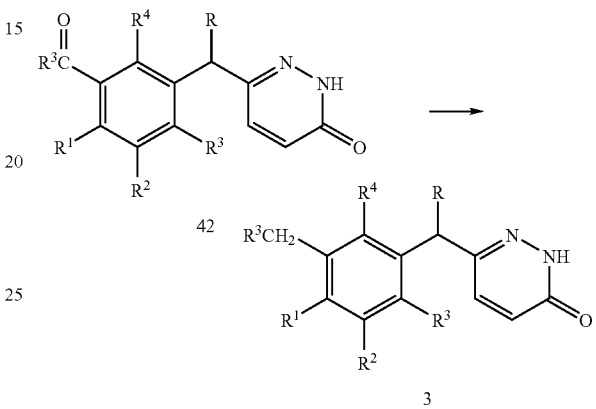

The preparation of the requisite benzoyl derivatives has been described in U.S. Pat. No. 5,886,178 (D. A. Allen et al.). The synthesis of benzoyl substituted benzofuran derivatives have also been reported in U.S. Pat. No. 4,780,480 (J. P. Dunn) and the scientific literature (J. P. Dunn et al. *Analgetic and Antiinflammatory 7-Aroylbenzofuran-5-ylacetic acids and 7-Aroylbenzothiophene-5-ylacetic Acids, J. Med. Chem.* 1986 29:2326) These references are hereby incorporated by reference in its entirety.

Introduction of the Pyridazinone Ring (Scheme 1; 3)

Introduction of a pyridazinone is accomplished by base-catalyzed condensation of the appropriately substituted phenylacetate 43b or phenylacetonitrile 43a and 3,6-dichloropyrazine (Scheme 12). The condensation is accomplished efficiently with NaH and DMF. Hydrolysis of nitrile 44a under acidic conditions with aqueous hydrochloric acid and acetic acid resulted in hydrolysis, decarboxylation and concomitant hydrolysis of the pyrazine to produce pyridazinone 45a. Saponification of 44b under basic conditions resulted in hydrolysis, acidification, and decarboxylation of the of the carboxylic acid to produce chloropyridazine 44c which was converted to pyridazinone 45a by exposure to sodium acetate and acetic acid or the more stringent acetic acid, water and hydrochloric acid.

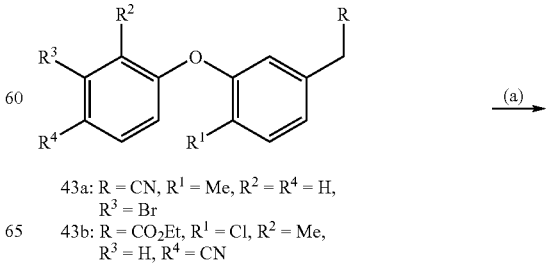

43a: R = CN, R$^1$ = Me, R$^2$ = R$^4$ = H, R$^3$ = Br
43b: R = CO$_2$Et, R$^1$ = Cl, R$^2$ = Me, R$^3$ = H, R$^4$ = CN

-continued

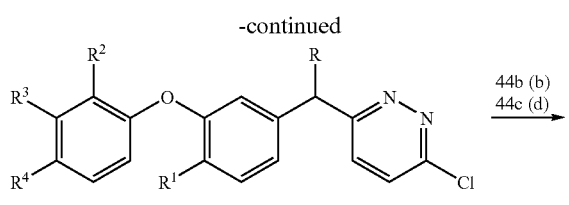

44a: R = CN, R¹ = Me, R² = R⁴ = H, R³ = Br;
44b: R = CO₂Et, R¹ = Cl, R² = Me, R³ = H, R⁴ = CN;
44c: R = R³ = H, R¹ = Cl, R² = Me, R⁴ = CN

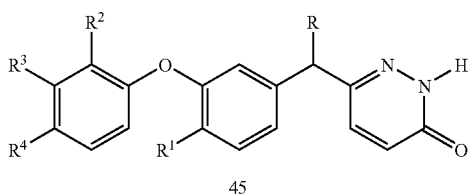

45

45a: R = R² = R⁴ = H, R¹ = Me, R³ = Br
45b: R = R H, R¹ = Cl, R² = Me, R⁴ = CN (a) 3,6-dichloropyrazine, NaH, DMF;
(b) HOAc, HCl, H₂O;
(c) LiOH, MeOH, H₂O;
(d) NaOAc, HOAc While the conditions exemplified utilized 3,6-dichloropyrazine, other pyrazine derivatives, e.g. 3-alkoxy-6-halopyridazines, may also be utilized in the preparation of compounds of the present invention (T. L. Drapier and T. R. Bailey, J. Org. Chem. 1995 60(3):748–50; Druey et al. *Helv. Chim. Acta* 1954 37:121). Substituted 3,6-dichloropyrazine derivatives can also be utilized. 5-Ethyl-, 5-iso-propyl and 5-hydroxymethyl-1,4-dichloropyrazines have been prepared J. G. Samaritoni *Org. Prep. & Procedures Int.* 1988 20(2): 117–121). (3,6-Dichloro-pyridazin-4-yl)-dimethyl-amine can be prepared by literature methods (Tsujimoto et al. *Chem. Pharm. Bull.* 1979 27:1169; Fenton et al. *J. Chem. Soc.* C, 1971 1536). (3,6-Dichloro-pyridazin-4-yl)-methylamine was prepared as described in Example 22. 4-(3,6-Dichloro-pyridazin-4-yl)-morpholine was prepared by the method of Fenton et al. (*J. Chem. Soc. Perkin Trans. I* 1972 2323). While the pyrazine coupling is conveniently accomplished with phenylacetic acid and phenyl acetonitrile derivatives, other carbon nucleophiles can also be used. For example, deprotonation of an aromatic methyl substituent with strong bases, e.g. n-BuLi or lithium di-iso-propylamide propylamide affords a benzylic organometallic intermediate, ArO—C₆H₄CH₂⁻M⁺, which can react with electrophiles including (see, e.g., R. B. Bates et al. *J. Org. Chem.* 1989 54:311–17). Transmetallation of halomethylethers, ArO—C₆H₄CH₂X (March, supra pp. 454–456 and 920–931) provides an alternative method to produce benzylic organometallic intermediates capable of reacting with 3,6-dichlorpyrazine or equivalents.

SCHEME 13

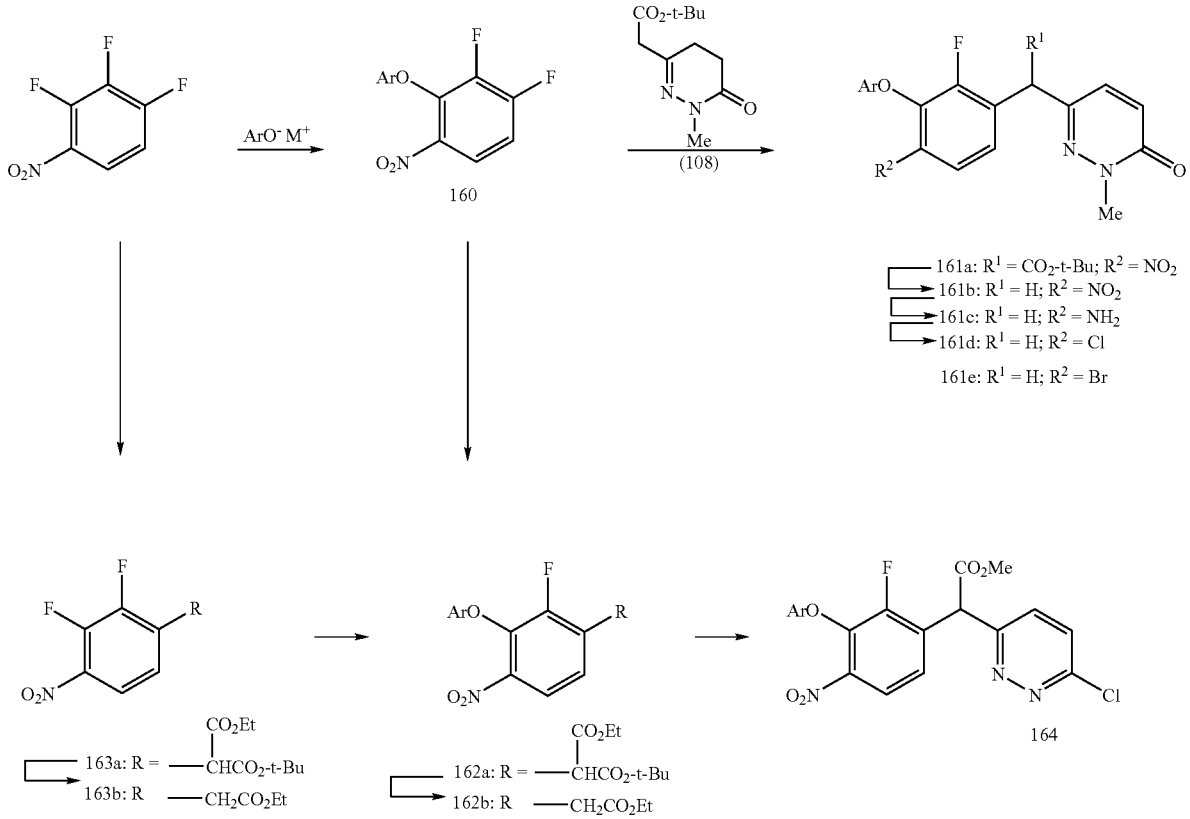

161a: R¹ = CO₂-t-Bu; R² = NO₂
161b: R¹ = H; R² = NO₂
161c: R¹ = H; R² = NH₂
161d: R¹ = H; R² = Cl
161e: R¹ = H; R² = Br

163a: R = CHCO₂-t-Bu / CO₂Et
163b: R = CH₂CO₂Et

162a: R = CHCO₂-t-Bu / CO₂Et
162b: R = CH₂CO₂Et

Alternatively the pyridazinone can be introduced prior to final elaboration of the aromatic substituents by taking advantage of the propensity for fluoro nitrobenzene compounds to undergo nucleophilic aromatic substitution. Thus 2,3,4-trifluoronitrobenzene can be reacted with a phenoxide salt resulting in the displacement of the 3-fluoro radical to yield the daryl ether 160. Deprotonation of the side chain of 108 and reaction with 160 results in displacement of the 4-fluoro radical to afford 161b which can be saponified and decarboxylated as illustrated previously to yield 161b. The remaining nitro radical allows for convenient introduction of a variety of substituents. Halogens can be introduced by a variant of the classical reduction, diazotization and displacement sequence (i.e., the Sandmeyer reaction). While the reaction is exemplified in Scheme 13 with a chloride substituent, it would be readily apparent that other halogens could be introduced in similar manner. Further one skilled in the art will immediately recognize that 161e is a versatile substrate for palladium-catalyzed reactions allowing the introduction of a wide variety of other functional groups at the 4-position into the aromatic ring. The sequence of steps can be altered to incorporate an acetic acid side chain which can be used to introduce the pyridazinone by alkylation of 3,6-pyrazine. Alkylation of 2,3,4-trifluoronitrobenzene with methyl t-butyl malonate affords 163a which can be hydrolyzed and decarboxylated to afford 163b. Alkylation with a phenoxide affords 162b. Alternatively the diaryl ether 160 can be subjected to displacement with a malonate ester to afford 162a which can be hydrolyzed and decarboxylated in an analogous manner.

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another nonnucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions, and that the treatment of animals includes the treatment of humans as well as other animals. Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The pharmaceutical compositions in Example 46 are given to enable those skilled in the art to more clearly understand and to practice the present invention. They should not be considered as limiting the scope of the invention, but merely as being illustrative and representative thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds of formula I may be prepared by various methods known in the art of organic chemistry. The starting materials for the syntheses are either readily available from commercial sources or are known or may themselves be prepared by techniques known in the art. The following examples (infra) are given to enable those skilled in the art to more clearly understand and to practice the present invention. They should not be considered as limiting the scope of the invention, but merely as being illustrative and representative thereof.

Example 1

Ethyl 4-Chloro-3-methoxyphenylacetate

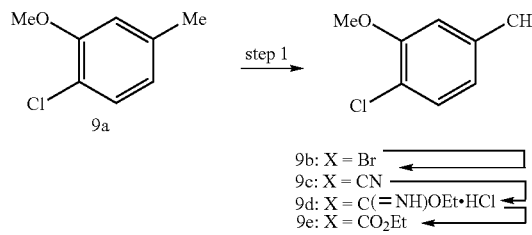

Step 1

A solution of 4-chloro-3-methoxytoluene (9a; 0.5 g; 3.2 mmol), NBS (0.57 g; 3.2 mmol) and benzoyl peroxide (0.031 g; 0.13 mmol) and 32 mL of DCE were heated at reflux for 3 h. The reaction mixture was cooled, diluted with $CH_2Cl_2$ and washed with water and brine. The organic extract was dried filtered and evaporated to yield the bromomethyl compound 9b which was used without further purification.

Step 2

The 28 g (0.166 mmol) of 9b from the previous step, NaCN (28 g; 0.58 mmol; 3.5 equiv.) and 500 mL of 90% aqueous EtOH were stirred at room temperature overnight. The crude residue was partitioned between EtOAc/H2O (359 mL of each), washed with brine, dried, filtered and evaporated. Silica gel chromatography and elution with a gradient (100% hexane→90:10 hexane:EtOAc) yielded 21 g of 9c.

Step 3

Gaseous HCl was slowly bubbled into a cooled solution of 4-chloro-3-methoxyacetonitrile (9b) in toluene (10 mL), ether (10 mL) and EtOH (1 mL) for about 10 min. The reaction was stoppered and stored at −30° C. for one week. TLC failed to detect any remaining starting material. The solvent was evaporated and the yellow solid was stirred with $Et_2O$, filtered and washed with $Et_2O$ and dried in a vacuum oven to yield 0.57 g (90%) of ethyl 4-chloro-3-methoxyphenylmethylimidate (9d).

Step 4

A solution of 0.57 g of 9d and 10 mL of $H_2O$ was heated at 40° C. for 3 h. The reaction was cooled to rt and extracted with EtOAc. The reaction was dried (MgSO4), filtered and evaporated and the resulting product 9e was used without further purification.

Example 2

6-[3-(2-chloro-phenoxy)-4-methylbenzyl]-2H-pyridazin-3one

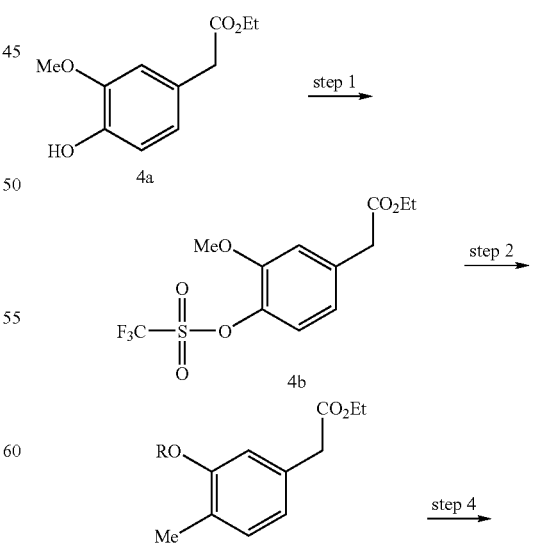

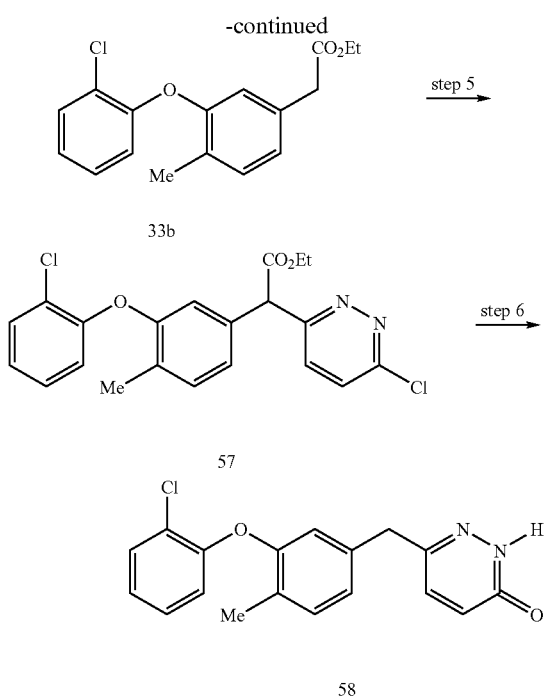

Step 1

To a cooled solution of ethyl 4-hydroxy-3-methoxyphenylacetate (4a; 13.7 g; 65.2 mmol) and 260 mL of $CH_2Cl_2$ under $N_2$ atmosphere was added dropwise triflic anhydride (16 mL; 97.9 mmol) followed by dropwise addition of pyridine (8.9 mL; 8.8 mmol). The reaction was stirred in an ice-water bath for 3 h. The solution was transferred to a separatory funnel and washed with water and brine, dried ($Na_2SO_4$), filtered and evaporated to yield 21 g (90%) of 4b.

Step 2

To a solution of ethyl 3-methoxy-4-trifluorosulfonyloxyphenylacetate (4b) in 4 mL of THF cooled in an ice-water bath was added slowly a solution of Pd(dppf)$Cl_2$ (0.024 g; 0.029 mmol) and DIBAL-H (6 mL; 0.058 mmol; 1.0M in PhMe)and a small quantity of THF followed by dimethylzinc (0.29 mL; 0.58 mmol; 2.0 M in PhMe). After addition was completed the ice bath was removed and the reaction allowed to warm to rt and then heated to reflux for 1 h. The reaction was carefully quenched with a small quantity of water, filtered through a pad of CELITE® and the solids washed thoroughly with EtOAc. The combined organic extracts were washed with water and brine, dried (MgSO$_4$) and the solvent evaporated to afford 0.240 g (85%) of ethyl 3-methoxy-4-methylphenylacetate (4c).

Step 3

To a solution of 4c (2.2 g; 8.0 mmol) and 250 mL $CH_2Cl_2$ cooled to −78° C. was added dropwise via syringe $BBr_3$ (9.8 mL; 0.104 mol). After 1 h at −78° C. the reaction was stirred for 4 h in an ice-water bath. The reaction mixture was recooled to −78° C. and the reaction quenched aqueous $NaHCO_3$ then warmed to rt and the organic phase washed with water, saturated $NaHCO_3$ and brine. The organic phase was dried (MgSO$_4$) and the solvent evaporated to afford 1.4 g of ethyl 3-hydroxy-4-methylphenylacetate (5a).

Step 4

To a suspension of 5a (4.8 g; 25 mmol), 2-chlorobenzeneboronic acid (7.8 g; 50 mmol), Cu(OAc)$_2$ (5 g; 27.5 mmol), powdered 4 Å molecular sieves (15 g) and 250 mL of $CH_2Cl_2$. After 4 days starting material was still evident by tlc and an addition 5.0 g of the boronic acid was added. The reaction was stirred for an additional day and the suspension filtered through a pad of CELITE® and silica gel. The solids were washed well with $CH_2Cl_2$. The combined filtrates were washed sequentially with 2N HCl (2×25 mL), NaHCO$_3$ (25 mL), water and brine. The extracts were dried (MgSO$_4$), filtered and evaporated. The crude product was purified by silica gel chromatogaphy and eluted with 25% EtOAc:hexane to yield 2.2 g (28%) of 33b Step 5

To an ice-cold solution of 33b (0.7 g; 7.2 mmol), 3,6-dichloropyrazine (2.1 g; 14.4 mmol) and 72 mL of dry DMF was added portionwise NaH (0.4 g; 15.2 mmol; 60% in mineral oil). The reaction was stirred at 0° C. for 15 min and allowed to warm to rt overnight. The reaction mixture and poured into 100 mL of $H_2O$ containing about 1 g of NaHSO$_4$. The organic phase was washed with EtOAc and the combined organic extracts washed with 5% LiCl dried (Na$_2$SO$_4$), filtered and evaporated. The product was purified by silica gel chromatography and eluted with 20% EtOAc:hexane to yield 0.72 g (37%) of 57.

Step 6

A mixture of 0.72 g (2.6 mmol) of 57, HOAc (3.5 mL), HCl (7 mL) and $H_2O$ (3.5 mL) were heated at reflux for 6 h, cooled to rt, diluted with water and extracted with EtOAc. The combined extracts were washed sequentially with water, sat'd NaHCO$_3$, and brine, dried (Na$_2$SO$_4$), filtered and concentrated. The crude product was purified by chromatography on silica gel. The eluted product, which still contained the 3-chloropyridazine was dissolved in HOAc (20 mL) and NaOAc (0.2 g) and reisolated to yield 0.4 g (50%) of 58 as a white solid; m.p. 116–118.

Example 3

3-(2-Chloro-phenoxy)-4-ethyl-phenyl]-acetic acid ethyl ester

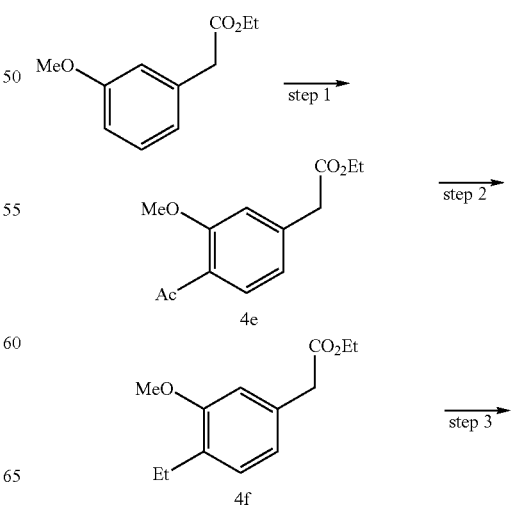

115

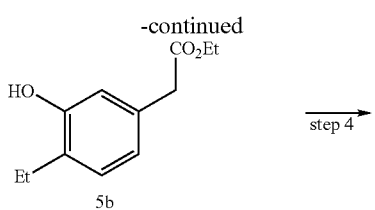

33d

Step 1

To a stirred solution of ethyl 3-methoxyphenylacetate (16.0 g; 82.38 mmol) in CH$_2$Cl$_2$ (200 mL) at rt was added dropwise AcCl (9.88 mL; 138.9 mmol) followed by stannic chloride (16.9 mL; 169 mmol; 1.0 M solution in CH$_2$Cl$_2$). The reaction mixture was stirred at rt for 6 h and poured into an ice-water mixture. The aqueous phase was extracted with CH$_2$Cl$_2$ and the combined extracts were washed with water, dried (Na$_2$SO$_4$) and the solvent removed in vacuo. The crude product 4e was purified by chromatography on silica gel and eluted with CH$_2$Cl$_2$:EtOAc (20:1) to yield 13.96 g (69.5%) of a white solid.

Step 2

To a solution of 4e (19 g; 80.42 mmol) and 200 mL of TFA cooled to 0° C. was added an excess of Et$_3$SiH and the reaction allowed to warm to rt for 3 h. Excess TFA was removed in vacuo and the residue partitioned between water and CH$_2$Cl$_2$. The crude product was purified by chromatography on silica gel and eluted with CH$_2$Cl$_2$:hexane (3:1) to yield 3.0 g (16%) of 4f.

Step 3

A solution of ethyl 4-ethyl-3-methoxyphenylacetate (4f; 3.0 g; 13.50 mmol) and CH$_2$Cl$_2$ (80 mL) cooled to −78° C. and a solution of BBr$_3$ (5.10 mL; 53.94 mmol; 1.0 M in CH$_2$Cl$_2$) over 30 min. After 1 h at −78° C. the reaction was allowed to warm to rt and stirred for 12 h. The reaction was cooled in an ice-water bath and the reaction quenched with 20 mL of water. The aqueous phase was extracted with CH$_2$Cl$_2$:EtOAc (4:1 v/v), dried (Na$_2$SO$_4$), filtered and evaporated. The crude product was purified by silica gel chromatography and eluted with a CH$_2$Cl$_2$:EtOAc gradient (100:1→100:4) to yield 5b (2.0 g; 71%): m.s. 209.2 (M+H)$^+$.

Step 4

A solution of ethyl 4-ethyl-3-hydroxyphenylacetate (5b; 0.20 g; 0.96 mmol), 2-iodo-chlorobenzene (0.18 mL; 1.44 mmol), Cs$_2$CO$_3$ (0.469 g; 1.44 mmol), TMHD (0.020 mL; 0.096 mmol) and NMP (15 mL) was degassed with a stream of nitrogen for 15 m. Cuprous chloride (0.48 g; 4.8 mmol) was added and the solution was degassed. The reaction mixture was heated to 120° C. for 11 h then cooled to rt. The suspension was filtered through a pad of CELITE® and the solid washed thoroughly with EtOAc. The combined filtrate was washed with 2N HCl dried (Na$_2$SO$_4$) and the solvent evaporated. The product was purified by chromatography on silica gel and eluted with EtOAc:hexane (1:10) to yield 0.31 g (39%) of 33d.

116

Example 4

6-[3-(3-Chloro-phenoxy)-4-isopropyl-benzyl]-2H-pyridazin-3-one

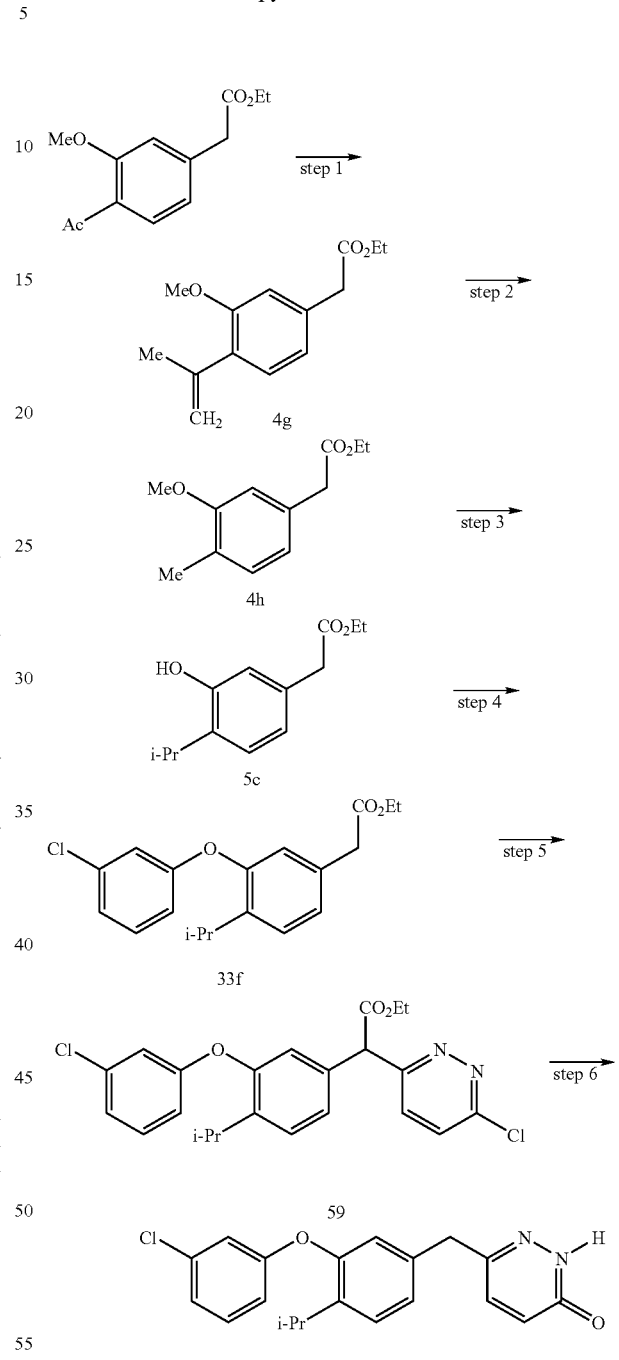

Step 1

To a suspension of PPh$_3$CH$_3$$^+$Br$^-$ (36.29 g; 101.6 mmol) in THF (150 mL) cooled to −40° C. was added dropwise n-BuLi (40.6 mL; 1.6M in hexanes) and the resulting solution was allowed to warm to −10° C. for 10 m and re-cooled to −40° C. To the resulting solution was added in one portion ethyl 4-acetyl-3-methoxyphenylacetate (see Example 4; step 1) and the reaction mixture was stirred at 0°

C. for 30 m and warmed to rt and stirred for an additional 2 h. The reaction mixture was diluted with hexane filtered through a pad of CELITE® and the solids washed with hexane:Et$_2$O (5:1 v/v; 60 mL). The combined organic layers were washed with water (50 mL) and brine (50 mL), dried (Na$_2$SO$_4$), filtered and evaporated to yield a yellow oil. The product was purified by silica gel chromatography and eluted with CH$_2$Cl$_2$:hexane(1:1→2:1) to yield 9.1 g of 4g.

Step 2

A suspension of 4g (9.0 g; 38.41 mmol), 5% Pd/C (380 mg) in 50 mL HOAc and 50 mL EtOH was shaken under a hydrogen atmosphere (50 psi) for 7 h. The mixture was filtered through a pad of CELITE® and the filtered catalyst was washed with EtOAc. The solvents were evaporated under reduced pressure and the residue dissolved in MTBE and carefully washed with sat'd HaHCO$_3$, water and brine. The resulting solution was dried (Na$_2$SO$_4$), filtered and evaporated to yield ethyl 4-iso-propyl-3-methoxyphenylacetate (4h; 9.0 g) as a yellow oil.

Step 3

A solution of 4h (3.38 g; 14.30 mmol) and CH$_2$Cl$_2$ (150 mL) were cooled to −78° C. and a solution of BBr$_3$ (5.41 mL; 57.22 mmol) in 130 mL of CH$_2$Cl$_2$ were added dropwise over a 30 m period. The reaction mixture was stirred at −78° C. for 1 h, allowed to warm to rt for 4 h and re-cooled to −78° C. and carefully quenched with sat'd. NaHCO$_3$ (80 mL). The aqueous layer was extracted with CH$_2$Cl$_2$ (1×100 mL), EtOAc (50 mL) and the combined aqueous layers washed with water and brine, dried (Na$_2$SO$_4$) and evaporated to yield a light brown oil. The phenol was purified by silica gel chromatography and eluted with CH$_2$Cl$_2$:hexane (3:1)→CH$_2$Cl$_2$→CH$_2$Cl$_2$:EtOAc (100:4) to yield ethyl 4-iso-propyl-3-hydroxyphenylacetate (5c; 3.0 g; 94%)

Step 4

To a solution of 5c (1.0 g; 4.5 mmol), 3-chlorobenzeneboronic acid (0.844 g; 5.4 mmol), cupric acetate (0.899 g; 4.95 mmol), 4 Å molecular sieves (5.0 g) and CH$_2$Cl$_2$ (50 mL) was added TEA (3.14 mL; 22.53 mmol) and the reaction was stirred for 3 days. The reaction mixture was filtered through a pad of CELITE®. The top layer containing the molecular sieves was removed and stirred with CH$_2$Cl$_2$ and refiltered. The combined organic filtrates were washed with 2N HCl brine, dried (Na$_2$SO$_4$), filtered and evaporated. The crude product was chromatographed with silica gel and eluted with a gradient of hexane/EtOAc (90% hexane/EtOAc) to yield 33f (1.0 g; 66%).

Step 5

To a ice-cold solution of 33f (1.0 g; 3.00 mmol), of 3,6-dichloropyrazine (0.895 g; 7.50 mmol) in 15 mL dry DMF was added portionwise 0.300 g NaH(7.50 mmol; 60% in oil). The reaction was allowed to warm to ambient temperature and stirred 6 h. The reaction was poured onto a mixture of ice, water and sodium bisulfate. The mixture was extracted thoroughly with EtOAc and the combined extracts were washed 6 times with water and brine. The extract was dried (MgSO$_4$), filtered and evaporated and the residue chromatographed on silica gel and eluted with a hexane:EtOAc gradient (15:1→8:1) to yield 0.80 g of 59 (purity ca. 80%)

Step 6

A mixture of 0.64 g (1.44 mmol) of 59, HOAc (12 mL), HCl (24 mL) and H$_2$O (12 mL) were heated at reflux for 16 h, cooled to rt and extracted with EtOAc. The combined extracts were washed with H$_2$O, dried (Na$_2$SO$_4$), filtered and concentrated in vacuo to afford a brown solid. The crude product was purified by chromatography on silica gel and eluted with a gradient of CH$_2$Cl$_2$:EtOAc (15:1→8:1) to yield 0.10 g (20%) of 60.

Example 5

Ethyl 4-methyl-3-(3-fluorophenoxy)phenylacetate

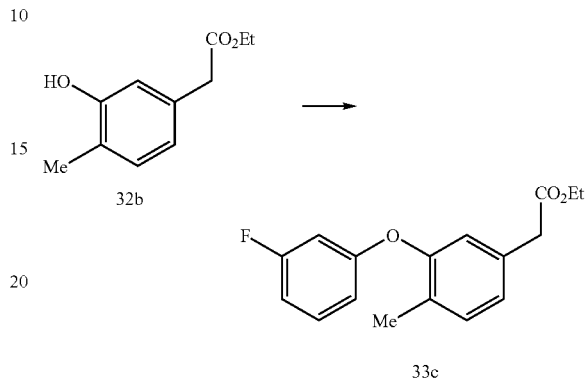

To a stirred solution of 32b (0.80 g; 4.12 mmol) and 7 mL NMP under a N$_2$ atmosphere was added 1-bromo-3-fluorobenzene (0.69 mL; 6.18 mmol), TMHD (0.086 mL; 0.41 mmol), Cs$_2$CO$_3$ (2.68 g; 8.24 mmol) and Cu(I)Cl (0.204 g; 2.06 mmol). The reaction was heated to 120° C. for 3 h. The reaction mixture was cooled to ambient temperature, and quenched with a mixture of 2 N HCl and EtOAc. The aqueous layer was thrice extracted with EtOAc and the combined organic layers were washed with water and brine, dried (MgSO$_4$), filtered and evaporated to dryness. The crude product was chromatographed on silica gel and eluted with hexane:Et$_2$O (9:1) which yielded 33c (0.60 g; 50%).

Example 6

6-[3-(3-chloro-phenoxy)-4,5-dimethyl-benzyl]-2H-pyridazin-3-one

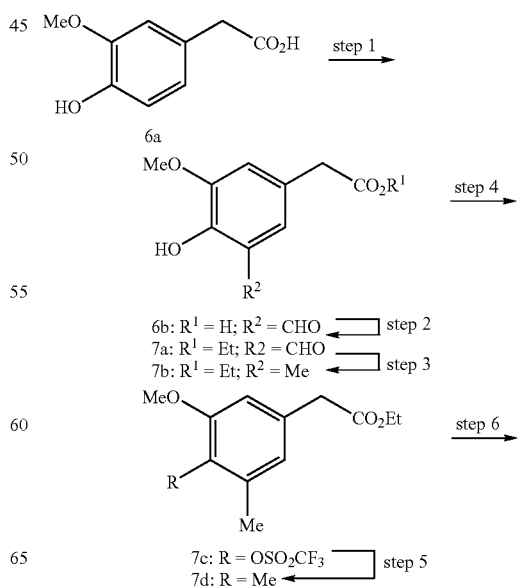

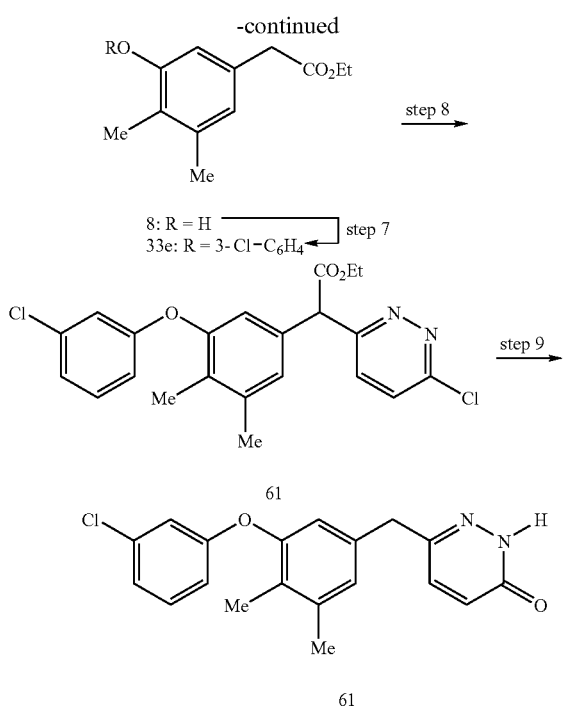

Step 1

A mixture of 4-hydroxy-3-methoxyphenylacetic acid (6a; 1.0 g; 5.49 mmol) and hexamethylenetetramine (0.808 g; 5.76 mmol) and TFA (7 mL) were stirred and heated at 90° C. for 4 h. The reaction was cooled and excess TFA removed in vacuo and 35 mL of ice and water was added to the residue. The resulting dark brown solution was stirred at rt for 20 m. The aqueous solution was extracted with $Et_2O$ (40 mL) and the extract was dried ($Na_2SO_4$), filtered and evaporated to afford 0.70 g of 6b (61%; m.s. (M+H)$^+$=211.13; mw=210).

Step 2

To a solution of 6b (4.0 g; 19.03 mmol) in EtOH (80 mL) was added con $H_2SO_4$ (1 mL). The reaction was heated at reflux for 6 h. Approximately 80% of the EtOH was removed in vacuo and the residue partitioned between EtOAc/$H_2O$ (1:1) the organic phase residue washed with 10% NaHCO$_3$, water (100 mL), dried ($Na_2SO_4$), filtered and evaporated to afford a brown oil 7a (88%; m.s. (M+H)$^+$ = 239.19; mw=238.3).

Step 3

A mixture of 7a (3.70 g; 15.53 mmol), 5% Pd/C (0.350 g), HOAc (45 mL) were shaken under a $H_2$ atmosphere (40 psi) for 8 h. TLC showed product and the corresponding benyl alcohol. An additional 300 mg of Pd/C in 25 mL HOAc was added and hydrogenation continued for another 8 h. A second portion of 0.15 g of Pd/C in HOAc (15 mL) was added and reaction continued for another 12 h. The mixture was diluted with EtOAc and filtered through a pad of CELITE®. The catalyst was washed with EtOAc and the combined organic extracts dried ($Na_2SO_4$) and evaporated. The product was purified by silica gel chromatography and eluted with $CH_2Cl_2$:hexane (4:1) to afford 2.64 g of 7b (75.8%).

Step 4

To a solution of 7b (5.87 g; 26.175 mmol) in $CH_2Cl_2$ cooled to 0° C. was added pyridine (3.60 mL; 44.51 mmol) followed by dropwise addition of triflic anhydride (6.605 mL; 39.26 mmol) over about 20 min. The reaction was stirred at 0° C. for 3.5 h. The reaction mixture was extracted with dilute HCl and half-saturated NaHCO$_3$, dried ($Na_2SO_4$) and evaporated to yield 9.41 g of 7c as a brown oil (100%).

Step 5

To a suspension of PdCl$_2$(dppf) (0.650 g; 0.785 mmol) in THF (40 mL) cooled to 0° C. was added dropwise a solution of DIBAL-H (1.0 M in PhMe; 1.57 mL; 1.57 mmol). The resulting mixture was stirred at 0° C. for 5 minutes and a solution of 7c in 5 mL of THF was added followed by Me$_2$Zn (23 mL; 46.0 mmol; 1.0 M in PhMe). The mixture was stirred at 0° C. for 5 m and heated at reflux for 2.5 h then cooled to rt for 30 m. The reaction was poured into dilute HCl and extracted with EtOAc (2×100 mL), dried ($Na_2SO_4$), and evaporated. The crude product was purified by silica gel chromatography and eluted with $CH_2Cl_2$:hexane (1:2→1: 1→2:1 v/v) to yield 5.1 g (87.6%) of 8.

Step 6

A solution of ethyl 3,4-dimethyl-5-methoxyphenylacetate (8; 0.560 g; 2.519 mmol) and $CH_2Cl_2$ (40 mL) was cooled to −78° C. and a solution of BBr$_3$ (10.1 mL; 10.1 mmol; 1.0 M in $CH_2Cl_2$) dropwise over 10 min. After 1 h at −78° C. the reaction was allowed to warm to rt and stirred for 12 h. The reaction was cooled in an ice-water bath and the reaction quenched with 15 mL of ice/water. The aqueous phase was extracted with $CH_2Cl_2$:EtOAc (3:1 v/v), dried ($Na_2SO_4$), filtered and evaporated to yield 8 (0.52 g; 99%; m.s. 209.21 (M+H)$^+$).

Step 7

To a suspension of ethyl 3,4-dimethyl-5-hydroxyphenylacetate (8, 1.0 g; 4.8 mmol), 3-chloro-benzeneboronic acid (0.901 g; 5.762 mmol), Cu(OAc)$_2$ (0.959 g; 5.28 mmol), powdered 4 Å molecular sieves (5 g) and 40 mL of $CH_2Cl_2$. After 40 h starting material was still evident by tlc and an addition 0.35 g of the boronic acid was added. The reaction was stirred for an additional 72 h. The reaction mixture was filtered through a pad of CELITE® and silica gel. The solids were washed well with $CH_2Cl_2$. The combined filtrates were washed sequentially with 2N HCl (2×25 mL), NaHCO$_3$ (25 mL), water and brine. The extracts were dried ($Na_2SO_4$), filtered and evaporated. The crude product was purified by silica gel chromatogaphy and eluted with EtOAc:hexane (1:15→1:10) to yield 33e (1.0 g; 65%; m.s. (M+H)$^+$=319.34, mw=318).

Step 8

To a solution of 1.0 g of 33e (3.14 mmol), 0.935 g (6.276 mmol) of 3,6-dichloropyrazine in 10 mL dry DMF cooled in an ice-water bath was added portionwise 0.313 g NaH (7.825 mmol; 60% in oil). The reaction stirred at 0° C. for 5 m then was allowed to warm to ambient temperature and stirred for 14 hour. The reaction was poured onto a mixture of ice, water and sodium bisulfate. The mixture was extracted thoroughly with EtOAc and the combined extracts were washed with 5% LiCl, water and brine. The extract was dried (MgSO$_4$), filtered and evaporated and the residue chromatographed on silica gel and eluted with hexane: EtOAc (10:1→8:1) to yield 1.0 g (73.9%) of 61: m.s. (M+H)$^+$=431.29)

Step 9

A mixture of 1.0 g (2.318 mmol) of 61, HOAc (12 mL), HCl (24 mL) and H$_2$O (12 mL) were heated at reflux for 16 h, cooled to rt and extracted with EtOAc. The combined extracts were washed with H$_2$O, dried ($Na_2SO_4$), filtered and concentrated in vacuo to afford a brown solid. The crude product was purified by chromatography on silica gel and eluted with a gradient of $CH_2Cl_2$:EtOAc (8:1) to yield 0.150 g (18%) of 62 as a brown solid: m.s. $(M+H)^+=341.27$; mw=340.8.

Example 7

(4-chloro-2-methyl-3-phenoxy-phenyl)-acetonitrile

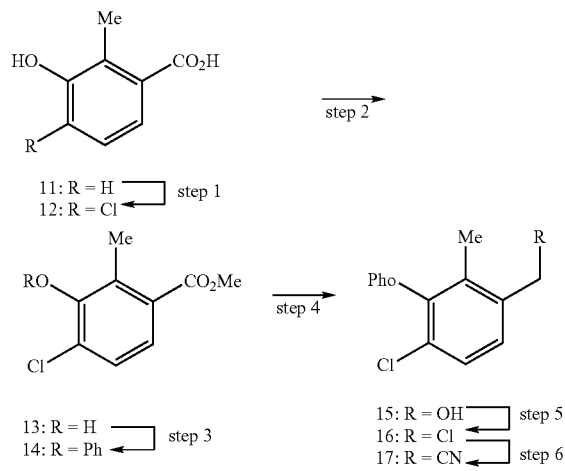

Step 1

To a suspension of 3-hydroxy-2-methylbenzoic acid (11; 22.8 g; 0.15 mol) and water (300 mL) cooled in an ice-water bath was added 3 M NaOH to adjust pH to about 10 (ca. 60 mL). NaOCl (208 mL; 5.35% aqueous solution; 0.15 mol) was added dropwise over about 30 m while maintaining the temperature between 2–6° C. After the addition was completed, 90 mL of 3 M HCl was added in one portion. The resulting precipitate was collected and dried on a sintered glass filter. The crude product was recrystallized from $Et_2O$: hexane (ca. 3:1) to yield a yellow solid 12 (12.24 g; 44%).

Step 2

A solution of 12 (12.24 g; 65.6 mmol), MeOH (200 mL) and con $H_2SO_4$ (3.85 mL) was stirred overnight at rt then heated to reflux for 6 h. The solution was cooled, concentrated to approximately 10% of the original volume and the residue redissolved in EtOAc. The organic phase was washed with sat'd. $NaHCO_3$ and brine, dried, filtered and evaporated. The crude product was purified by silica gel chromatography and eluted with a EtOAc:hexane gradient (1:9→4:6). The combined fractions were evaporated to yield 13 (8.32 g; 63.2%).

Step 3

To a solution of methyl 4-chloro-3-hydroxy-2-methylbenzoate (13; 1.0 g; 4.98 mmol), benzeneboronic acid (1.52 g; 12.5 mmol), cupric acetate (1.00 g; 5.48 mmol), 4 Å molecular sieves (1 g), and $CH_2Cl_2$ (25 mL) was added TEA (3.47 mL; 24.9 mmol) and the reaction was stirred overnight. Starting material was still detected by tlc and an additional 0.62 g of benzeneboronic acid was added and stirred for another 24 h. The reaction mixture was filtered through a pad of CELITE®. The top layer containing the molecular sieves was washed with $CHCl_3$. The combined organic filtrates were evaporated. The crude product was chromatographed with silica gel and eluted with hexane/EtOAc gradient (100:0→85:15) to yield 14 (0.82 g; 60%).

Step 4

To a solution of methyl 4-chloro-2-methyl-3-phenoxy-benzoate (14; 0.780 g; 2.81 mmol) dissolved in PhMe (20 mL) cooled in an ice-water bath was added dropwise DIBAL-H (7.41 mL; 7.41 mmol; 1.0 M in PhMe) The reaction was quenched by sequentially adding MeOH, $H_2O$, and con HCl. The organic phase was extracted with $Et_2O$. The combined organic extracts were washed with sat'd. $NaHCO_3$, water and brine, dried $(Na_2SO_4)$, filter and evaporated to yield 15 as a colorless oil which was used in the next step without further purification.

Step 5

To a solution of 15 (0.736 g; 2.96 mmol) dissolved in pyridine (10 mL) was added dropwise methanesulfonyl chloride (0.252 μL; 5.92 mmol) over 5 min. After 30 min a small quantity of starting material was evident and an addition 25 μL of methanesulfonyl chloride was added. The reaction was partitioned between $Et_2O$ and 5% HCl. The organic phase was twice washed with 5% HCl water, sat'd. NaHCO3 and brine. The organic extract was dried $(MgSO_4)$, filtered and evaporated. The crude product was chromatographed on silica gel eluting with 10% EtOAc:hexane to yield the benzylic chloride 16 (0.220 g) as a colorless oil.

Step 6

The benzyl chloride 16 (0.220 g; 0.82 mmol) was dissolved in EtOH (1 mL) and KCN (0.107 g; 1.64 mmol and 1 mL of water. The mixture was heated to reflux and $CH_3CN$ (0.3 mL) was added to produce a homogenous solution which was allow to reflux overnight. The reaction mixture was concentrated in vacuo and partitioned between water and $CH_2Cl_2$. The organic phase was washed twice with brine, dried $(MgSO_4)$, filtered and evaporated to yield 17 (0.210 g) sufficiently pure for further processing.

Example 8

Ethyl 4-chloro-3-(3-cyano-5-fluorophenoxy)phenylacetate

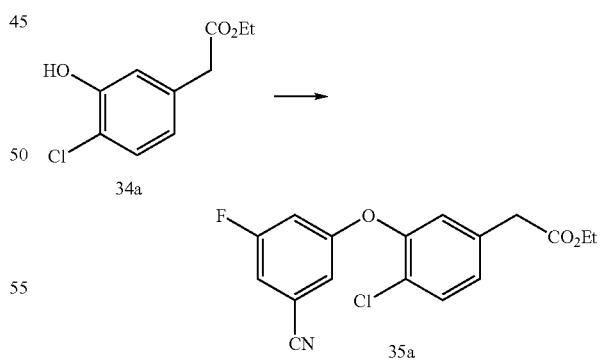

To a solution of ethyl 4-chloro-3-hydroxyphenylacetate (34a; 1.4 g; 6.5 mmol) and NMP (13 mL) was added potassium carbonate (2.7 g; 19.6 mmol) and 1.2 g of 3,5-difluorobenzonitrile (1.2 g; 8.5 mmol). The reaction mixture was heated to 120° C. and monitored by TLC. After 3.5 h an additional 0.9 g of $K_2CO_3$ was added and at 5.5 h an additional 0.9 g of $K_2CO_3$ and 0.3 g of 3,5-difluorobenzonitrile was added. After 8 h of heating the reaction was cooled to rt and the reaction mixture was filtered through a pad of CELITE® and the solid cake was washed well with EtOAc. The filtrate was washed with 2 portions of 2N HCl 1N NaOH, water and brine. The organic extract was dried (MgSO₄), filtered and evaporated to yield 1.3 g of the ether 35a.

Example 9

Ethyl 4-chloro-3-(2,5-dichlorophenoxy)phenylacetate

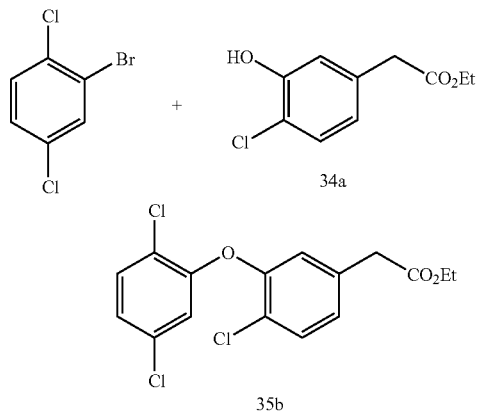

A solution of ethyl 4-chloro-3-hydroxyphenylacetate (34a; 2.0 g; 9.3 mmol), 2,5-dichloro-bromobenzene, Cs₂CO₃ (6.0 g; 18.6 mmol), TMHD (0.38 mL; 1.9 mmol) and NMP (15 mL) was degassed with a stream of nitrogen for 15 m. Cuprous chloride (0.5 g; 4.7 mmol) was added and the solution again was degassed. The reaction mixture was heated to 120° C. for 18 h then cooled to rt. The suspension was filtered through a pad of CELITE® and the solid washed thoroughly with EtOAc. The combined filtrate was washed with 2N HCl dried (Na₂SO₄) and the solvent evaporated. The product was purified by chromatography on silica gel and eluted with EtOAc:hexane (1:10) to yield 35b (0.554 g; 16%).

Example 10

4-Chloro-3-(4-bromophenoxy)toluene

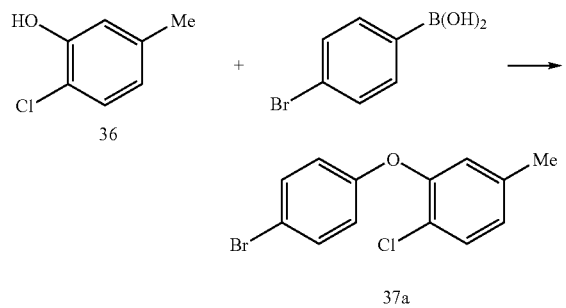

A solution of 2-chloro-4-methylphenol (36; 3.0 g; 21 mmol), 4-bromobenzeneboronic acid (5.0 g; 24 mmol), cupric acetate (4.2 g; 23.1 mmol), 4 Å molecular sieves and CH₂Cl₂ (210 mL) was added TEA (9.8 mL; 70 mmol) and the reaction was stirred for 3 days. The reaction mixture was filtered through a pad of CELITE®. The top layer containing the molecular sieves was removed and stirred with CH₂Cl₂ and refiltered. The combined organic filtrates were washed with 2N HCl brine, dried (Na₂SO₄), filtered and evaporated. The crude product was chromatographed with silica gel and eluted with a gradient of hexane/EtOAc (100:0→90:10) to yield 37a.

Example 11

4-chloro-3-phenoxytoluene

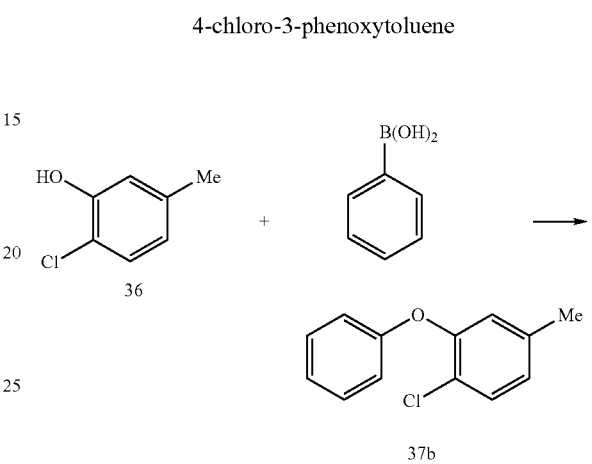

To a solution of benzeneboronic acid (1.9 g; 15.8 mmol) dissolved in CH₂Cl₂ (250 mL) was added 2-chloro-5-methylphenol (36; 2.5 g; 17.5 mmol), cupric acetate (3.5 g; 19.3 mmol), TEA ((12.3 mL; 87.7 mmol) and 12.5 g of 4 Å molecular sieves. The reaction was stirred for 24 h and an additional aliquot of benzeneboronic (2.4 g; 19.3 mmol) was added and stirring continued for an additional 48 hr. The reaction mixture was filtered through a bed of CELITE® and the filtered solids were washed thoroughly with CH₂Cl₂. The combined organic extracts were washed with 2N HCl H₂O, sat'd NaHCO₃, H₂O and brine, dried (MgSO₄) filtered and evaporated. The crude product was purified by silica gel chromatography and eluted with hexane:EtOAc (9:1) to yield 37b (1.6 g; 47.1%) as a clear oil.

Example 12

4-Chloro-2-fluoro-3-phenoxytoluene

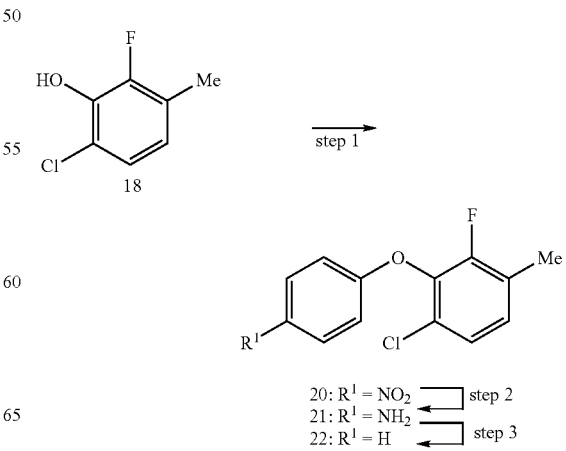

Step 1

A solution of 4-chloro-2-fluoro-3-hydroxytoluene (18; 0.161 g; 1.0 mmol; N. Imazaki et al., WO 2002100833), p-fluoronitro-benzene (0.141 g; 1.0 mmol), $K_2CO_3$ (0.276 g; 2 mmol) and DMF (4 mL) was heated to reflux for 4 h under a $N_2$ atmosphere. The reaction was cooled to rt and poured into water and stirred for several minutes. The aqueous solution was extracted twice with $CH_2Cl_2$ and the combined organic extracts washed with brine, dried ($MgSO_4$), filtered and evaporated to yield 20.

Step 2

A solution of 20 (1.58 g; 5.3 mmol), stannous chloride dihydrate (6.0 g; 26.6 mmol) and EtOH (5 mL) were heated to 70° C. stirred overnight. The reaction mixture was added to a small quantity of ice and made basic with 10% $Na_2CO_3$. The aqueous phase was extracted with EtOAc (5 mL) which resulted in an emulsion. About 7 mL of ethylenediamine was added to chelate remaining tin which resulted in a blue aqueous solution. The EtOAc was washed with water and brine, dried ($NaHCO_3$), filtered and evaporated to yield 1.35 g of 21 which was carried on to the next step.

Step 3

A solution of 21 (0.830 g; 3.3 mmol) was dissolved in HOAc (2.25 mL) and added to a solution of ice-water (7.5 mL) and HCl (1.2 mL). A solution of $NaNO_2$ (0.254 g; 5.6 mmol) and $H_2O$ (1.5 mL) was added over a 10–15 m period. The resulting solution was stirred for several minutes then added dropwise over 15 m to a suspension of $FeSO_4\cdot7H_2O$ (0.917 g; 3.3 mmol) and DMF (10.5 mL). The reaction was stirred for 0.5 h and a mixture of hexanes:EtOAc (1:1; 30 mL) was added. The organic phase was washed thrice with water, dried ($MgSO_4$), filtered and concentrated in vacuo. The dark oil was purified by chromatography on silica gel and eluted with an EtOAc:hexane gradient (0:100→20:80) which yielded 22 as a clear oil (0.450 g; 58%).

Example 13

[3-(3-Bromo-5-fluoro-phenoxy)-4-chloro-phenyl]-(6-oxo-1,6-dihydro-pyridazin-3-yl)-acetonitrile, (64a) and 6-[3-(3-Bromo-5-fluoro-phenoxy)-4-chloro-benzyl]-2H-pyridazin-3-one), (64b)

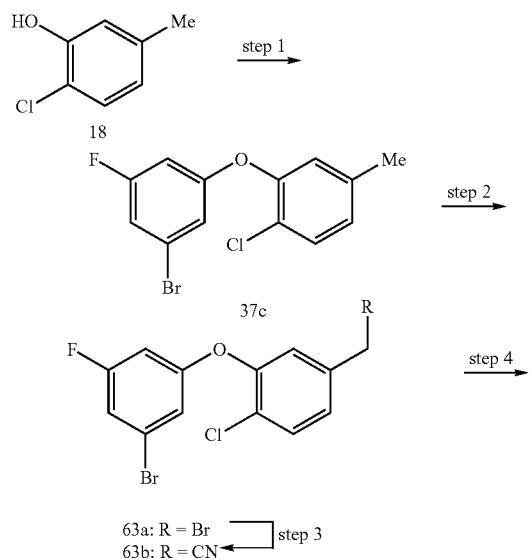

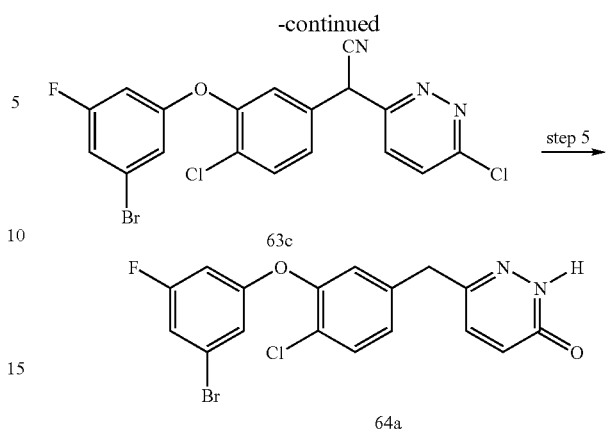

Step 1

Cesium carbonate (11.4 g; 8.79 mmol) was added to a solution of 2-chloro-5-methylphenol (18; 2.5 g; 17.53 mmol) and NMP (16 mL). The resulting slurry was degassed and the flask alternately purged and refilled with nitrogen. 1,3-Dibromo-fluorobenzene (3.54 g; 28.13 mmol), TMHD (0.92 mL; 0.81 g; 4.41 mmol) and Cu(I)Cl (0.87 g; 8.79 mmol) were added sequentially and the reaction mixture was heated to 110° C. for 6 h. The reaction mixture was cooled to ambient temperature, filtered through a bed of CELITE® and the filter cake washed thoroughly with EtOAc. The filtrate was washed sequentially with dilute HCl dilute NaOH, water and brine. The organic extract was dried ($Na_2SO_4$), filtered and evaporated. The residue was chromatographed on silica gel and eluted with hexane:$Et_2O$ which yielded 1.8 g (32%) of 37c as a colorless oil.

Step 2

A mixture of 37c (1.8 g; 5.704 mmol), NBS (1.066 g; 5.989 mmol), benzoyl peroxide (0.069 g; 0.28 mmol) and $CCl_4$ (20 mL) was heated to 90° C. for 2.5 h. The reaction mixture was cooled to room temperature and poured into 100 mL of $H_2O$. The mixture was extracted with $CH_2Cl_2$ (2×80 mL), dried ($Na_2SO_4$) and evaporated to yield 63a (2.25 g) as a colorless oil.

Step 3

A solution of 63a (2.25 g; 5.704 mmol), NaCN (0.839 g; 17.12 mmol) and 20 mL of 90% aqueous EtOH was stirred at room temperature for 24 h. The solvent was evaporated and the residue partitioned between EtOAc (100 mL) and $H_2O$ (100 mL). The EtOAc phase was washed with $H_2O$ and saturated brine. The organic extracts were dried ($Na_2SO_4$) and evaporated. The crude product was purified by silica gel chromatography and eluted with a hexane/EtOAc gradient (10:1→6:1) to yield 1.10 g (56.6%) of 63b as a colorless oil.

Step 4

To a mixture of 1.00 g of 63b (1.0 g; 2.936 mmol) 3,6-dichloropyridazine (0.96 g; 6.5 mmol) and 16 mL of DMF cooled to 0° C. was added portionwise 0.30 g of NaH (7.5 mmol; 60% in mineral oil). The reaction mixture was stirred at 0° C. for 2 h and allowed to warm to room temperature for 12 h. The reaction was poured into aqueous 10% $NaHSO_4$ and extracted with EtOAc (2×120 mL). The combined organic extracts were washed six times with $H_2O$, dried ($Na_2SO_4$), filtered and evaporated. The crude product was purified by silica gel chromatography and eluted with a hexane/EtOAc gradient (15:1→8:1) to provide 63c as an orange oil (0.93 g; 70%).

Step 5

A mixture of 0.93 g of 63c, HOAc (10 mL), HCl (20 mL) and H20 (10 mL) were heated at reflux for 8 h, cooled to rt and extracted with EtOAc. The combined extracts were dried (Na$_2$SO$_4$), filtered and concentrated. The crude product was purified by chromatography on silica gel and eluted with a gradient of CH$_2$Cl$_2$:EtOAc (8:1→4:1) to yield 40.56 g (67%) of 64a as a white solid.

Example 14

6-[3-chloro-phenoxy)-4-ethyl-benzyl]-2H-pyridazin-3-one

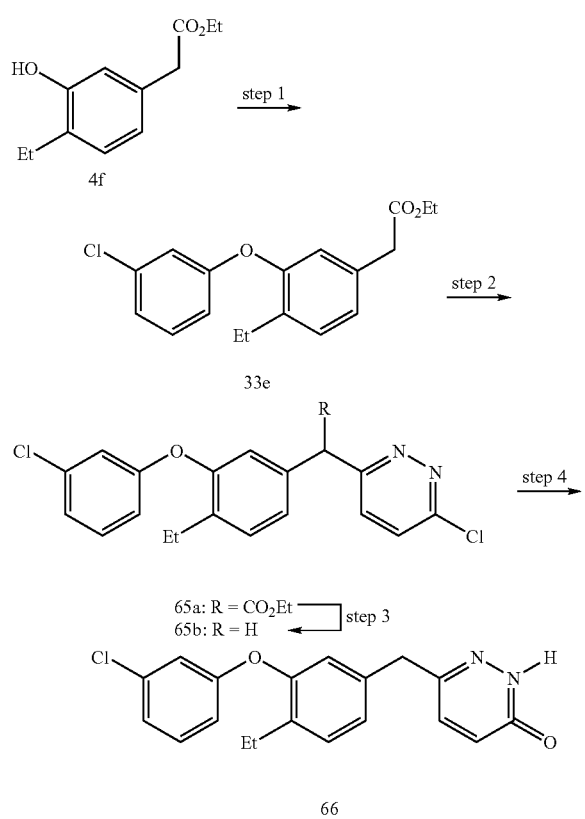

Step 1

To a solution of ethyl 4-ethyl-3-hydroxyphenylacetate (4f; 1.0 g; 4.81 mmol), 3-chlorobenzeneboronic acid (1.56 g; 10.1 mmol), cupric acetate (0.96 g; 5.29 mmol), 4A molecular sieves (5 g), and CH$_2$Cl$_2$ (48 mL) was added TEA (3.34 mL; 24.05 mmol) and the reaction was stirred for 4 days. The reaction mixture was filtered through a pad of CELITE®. The top layer containing the molecular sieves was removed and stirred with CH$_2$Cl$_2$ and refiltered. The combined organic filtrates were washed with 2N HCl brine, dried (Na$_2$SO$_4$), filtered and evaporated. The crude product was chromatographed with silica gel and eluted with hexane/EtOAc (90% hexane/EtOAc) to yield 33e (0.38 g; 25%).

Step 2

To a solution of 0.34 g (1.07 mmol) of 33e, 3,6-dichloropyrazine (0.30 g; 2.03 mmol) in 15 mL dry DMF cooled in an ice-water bath was added portionwise 0.107 g NaH (2.6 mmol; 60% in oil). The reaction was allowed to warm to ambient temperature and 2 h. The reaction was poured onto a mixture of ice, water and 10% sodium bisulfate. The mixture was extracted thoroughly with EtOAc and the combined extracts were washed with six times with water and then brine. The extract was dried (MgSO$_4$), filtered and evaporated and the residue chromatographed on silica gel and eluted with hexane:EtOAc (85:15) to yield 65a (0.40 g; 87%).

Step 3

A mixture of 65a (0.55 g; 1.27 mmol), HOAc (3 mL), HCl (6 mL) and H$_2$O (3 mL) were heated at reflux for 3 h, cooled to rt and thrice extracted with EtOAc. The combined extracts were washed with brine, dried (MgSO$_4$), filtered and concentrated in vacuo. The crude product was purified by chromatography on silica gel and eluted with a gradient of CH$_2$Cl$_2$:EtOAc (7:3→3:7) to yield 65b (0.28 g).

Step 4

A mixture of 65b (0.35 g; 0.97 mmol), HOAc (8 mL) and NaOAc (110 mg) was heated at reflux for 2 h, cooled to rt and thrice extracted with EtOAc. The combined extracts were thrice washed with dilute NaHCO$_3$ and brine, dried (MgSO$_4$), filtered and concentrated in vacuo. The crude product was purified by chromatography on silica gel and eluted with a gradient of hexane:EtOAc (6:4) to yield 66 (0.0511 g).

Example 15

6-(3-Butoxy-4-chloro-benzyl)-2H-pyridazin-3-one

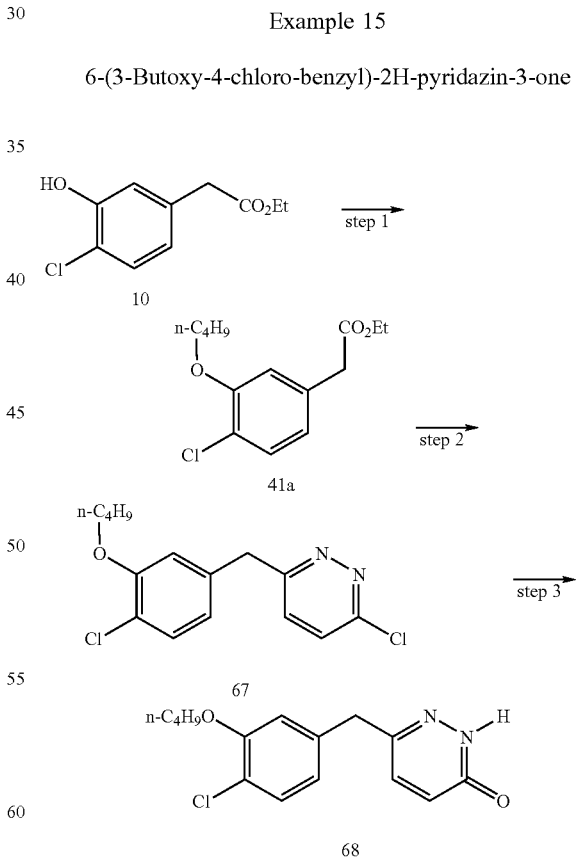

Step 1

Ethyl 4-chloro-3-hydroxyphenylacetate (10; 0.5 g; 2.33 mmol), n-butanol (0.43 mL; 4.66 mmol) and PPh$_3$ (0.92 g;

3.5 mmol) were dissolved in THF (8 mL) and cooled in an ice bath. DIAD was added dropwise to the cooled solution and the reaction mixture then allowed to warm to rt under N₂ atmosphere for 30 m. The THF was evaporated and the viscous yellow oil adsorbed onto silica gel and eluted with a hexane:EtOAc gradient (9:1→8:2) to yield 41a (0.472 g; 75%).

Step 2

To a solution of 41a (0.472 g; 1.75 mmol), 3,6-dichloropyrazine (0.7 g; 3.28 mmol) in 8 mL dry DMF cooled in an ice-water bath was added portionwise 0.160 g NaH (4.1 mmol; 60% in oil). The reaction was allowed to warm to ambient temperature and stirred overnight. The reaction was poured onto a mixture of ice, water and sodium bisulfate. The mixture was extracted thoroughly with EtOAc and the combined extracts were washed with water (six times) and brine. The extract was dried (MgSO₄), filtered and evaporated and the residue chromatographed on silica gel and eluted with hexane:EtOAc (8:2) to yield 67 (0.463 g).

Step 3

A mixture of 67 (0.465 g), HOAc (5 mL), HCl (10 mL) and H₂O (50 mL) were heated at reflux for 1 h, cooled to rt and extracted with EtOAc. The combined extracts were washed with H₂O, dried (Na₂SO₄), filtered and concentrated in vacuo. The crude product was purified by chromatography on silica gel and eluted with a gradient of CH₂Cl₂:EtOAc (7:3→3:7) to yield 68 (0.28 g).

Example 16

[4-chloro-3-(3-cyano-5-fluoro-phenoxy)-phenyl]-(6-chloro-5-methyl-pyridazin-3-yl)-acetic acid ethyl ester

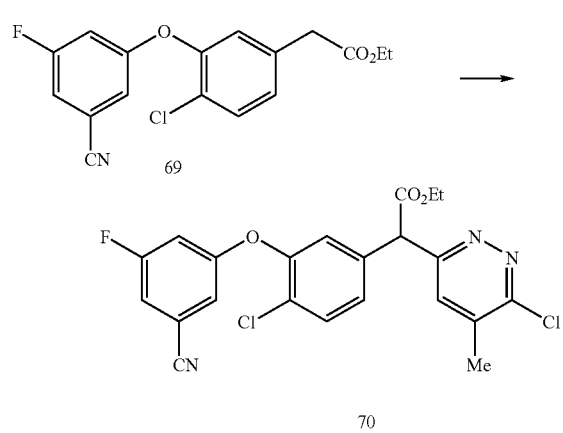

To a solution of 69 (3.9 g), 0.7 g of 3,6-dichloro-4-methylpyrazine in 40 mL dry DMF cooled in an ice-water bath was added portionwise 0.33 g NaH (60% in oil). The reaction was allowed to warm to ambient temperature and stirred for one hour. The reaction was poured onto a mixture of ice, water and sodium bisulfate. The mixture was extracted thoroughly with EtOAc and the combined extracts were washed with 5% LiCl, water (six times) and brine. The extract was dried (MgSO₄), filtered and evaporated and the residue chromatographed on silica gel and eluted with hexane:EtOAc (7:3) to yield 70 (0.65 g)

Hydrolysis to the pyridazinone was carried out as described in step 2 of Example 18.

Example 17

6-[4-chloro-3-(1-ethyl-propoxy)-benzyl]-2H-pyridazin-3-one

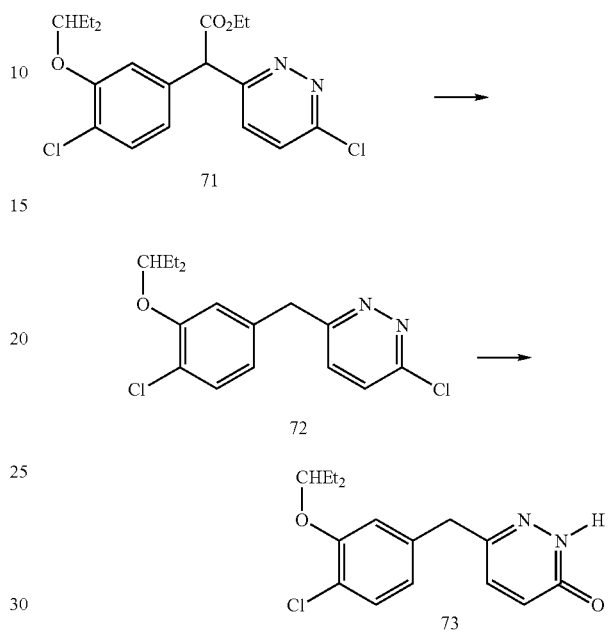

Step 1

To a solution of 71 (1.2 g; 3.02 mmol) in MeOH (5 mL) and water (1.5 mL) was added LiOH.H₂O (0.178 g; 4.23 mmol) and stirred for 30 m. The reaction mixture was diluted with EtOAc, and washed with 2N HCl water and brine. The organic extract was dried (Na₂SO₄), filtered and evaporated to yield 72 which as used in the next step without additional purification.

Step 2

To a solution of crude 72 (0.80 g) from the previous step and HOAc (15 mL) was added NaOAc (0.40 g) and the reaction heated to reflux for 1 h. The reaction mixture was cooled to rt and diluted with EtOAc, The organic phase was washed with water and brine, dried (Na₂SO₄) and evaporated. The crude product was purified by silica gel chromatography and eluted with a hexane:EtOAc gradient (7:3→6:4) to yield pyridazinone 73 (0.350 g).

Example 18

3-Chloro-5-[2-chloro-5-(5-methyl-6-oxo-1,6-dihydro-pyridazin-3-ylmethyl)-phenoxy]-benzonitrile

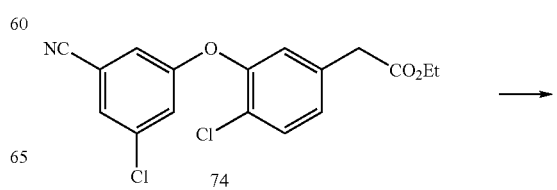

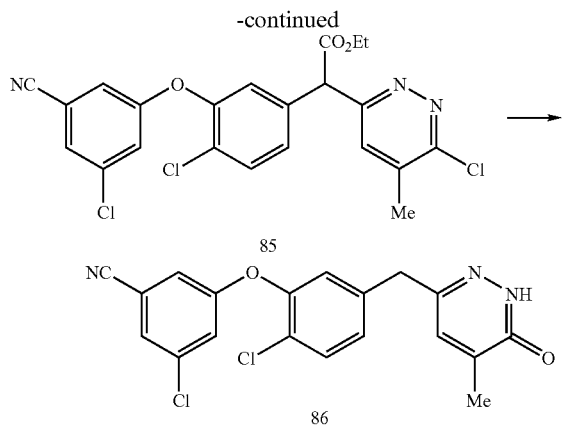

Step 1

To a ice-cold solution of 74 (1.30 g; 3.712 mmol), 5-methyl-1,4-dichloropyrazine (1.21 g; 7.42 mmol) and DMF (16 mL) under an nitrogen atmosphere was added in one portion NaH (0.297 g; 7.43 mmol; 60% in mineral oil). The reaction mixture was stirred at 0° C. for 10 minutes and then allowed to warm to room temperature and stir for 6 h. The mixture was diluted with 75 mL EtOAc and poured into about 100 mL of ice-water containing a small quantity of $NaHSO_4$. The aqueous layer was separated and washed with 50 mL of EtOAc. The combined organic phases were dried ($Na_2SO_4$), filtered and evaporated. The residue was purified by silica gel chromatography and eluted with a hexane:EtOAc gradient (12:1→8:1) to yield 85 as a yellow oil which partially solidified (350 mg; 20%). A small quantity of the isomeric compound was isolated after elution of the major product.

Step 2

A mixture of 85, LiOH (1.47 mL; 0.734 mmol; 0.5M in MeOH/$H_2O$) and degassed MeOH/$H_2O$ (4:1 v/v; 8 mL) was stirred at 0° C. for 5 minutes then allowed to stir 12 h at room temperature under an $N_2$ atmosphere. The reaction mixture was carefully acidified with 1 N HCl and partitioned between 25 mL of EtOAc and 50 mL of water. The EtOAc layer was dried ($Na_2SO_4$), filter and evaporated. The crude residue was dissolved in 18 mL of HOAc and 900 mg of NaOAc and refluxed for 3 h under an $N_2$ atmosphere. The reaction mixture was cooled, diluted with 50 mL of EtOAc and poured into $H_2O$. The organic layer was dried ($Na_2SO_4$), filtered and evaporated and the crude product was purified by silica gel chromatography and eluted with Ch2Cl2/EtOAc to yield a yellow solid 86 (0.120 g; 42%)

Example 19

6-[3-Bromo-phenoxy)-4-chloro-benzyl]-2H-pyridazin-3-one

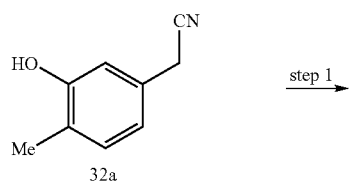

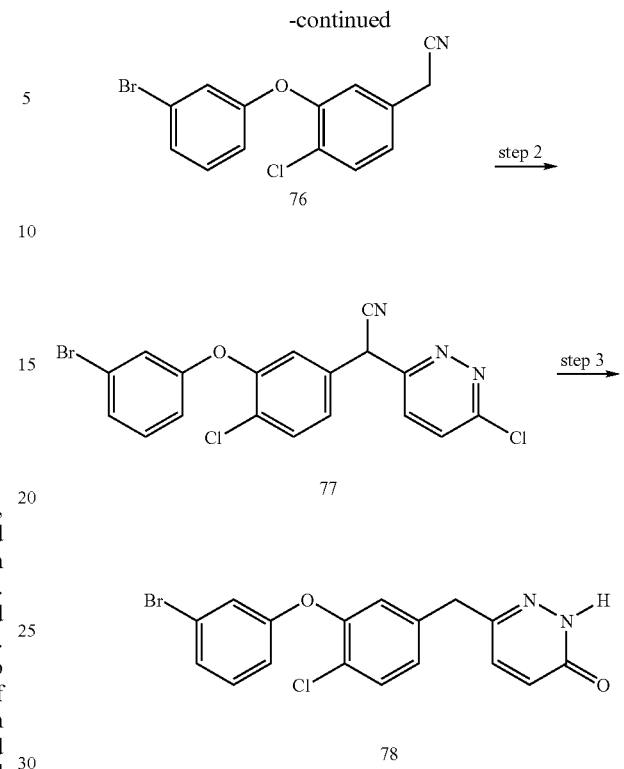

To a flask was charged with 3-hydroxy-4-methylphenylacetonitrile (32a; 0.92 g; 6.2 mmol), $Cu(OAc)_2$ (1.3 g; 6.9 mmol), 3-bromobenzeneboronic acid (1.1 g; 5.5 mmol) and powdered 4 Å molecular sieves, was added $CH_2Cl_2$ (62 mL) followed by pyridine (2.5 mL; 31 mmol). The reaction was stirred at rt for 3 days. The suspension was filtered through a bed of CELITE®/silica gel and the solid washed with $CH_2Cl_2$. The combined filtrates were washed sequentially with 2N HCl (2×25 mL), $NaHCO_3$ (25 mL), water and brine. The extracts were dried ($MgSO_4$), filtered and evaporated. The crude product 76 was sufficiently pure to use in the next step.

Step 2

To an ice-cold solution of 76 (0.8028 g; 3.6 mmol), 3,6-dichloropyrazine (0.54 g; 3.6 mmol) and 17 mL of dry DMF was added portionwise NaH (0.3 g; 7.6 mmol; 60% in mineral oil). The reaction was stirred at rt for 2 h and poured into 75 mL of $H_2O$ containing about 1 g of $NaHSO_4$. The aqueous solution as thoroughly extracted with EtOAc and the combined EtOAc extracts washed with six times with water, then with brine, dried ($Na_2SO_4$), filtered and evaporated. Nitrile 77 was purified by silica gel chromatography and eluted with 25% EtOAc:hexane.

Step 3

A solution of 77 (1.0 g; 2.4 mmol), HOAc (4 mL), HCl (8 mL) and water (4 mL) was heated at 100° C. for 12 h. The reaction mixture was cooled and diluted wit EtOAc and washed three time with water and once with brine. The organic phase was dried ($MgSO_4$), filtered and evaporated. The crude product was purified by chromatography on silica and eluted with an EtOAc:hexane gradient (25:75→75:25) to yield 78 (62 mg).

Example 20

3-[2-Fluoro-5-(6-oxo-1,6-dihydro-pyridazin-3-ylmethyl)-phenoxy]-benzonitrile

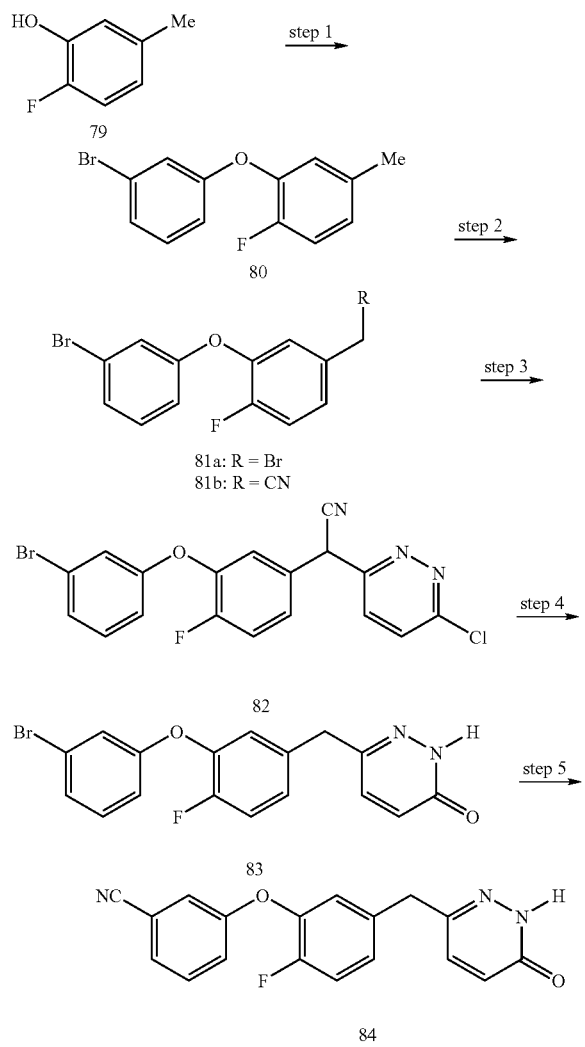

Step 1

To a solution of 2-fluoro-4-methylphenol (79; 3.0 g; 24 mmol), 3-bromobenzeneboronic acid (5.3 g; 24 mmol), cupric acetate (4.8 g; 23.1 mmol), 4 Å molecular sieves (15 g) and $CH_2Cl_2$ (240 mL) was added TEA (17 mL; 120 mmol) and the reaction was stirred for 4 days. The molecular sieves were filtered and washed well with $CH_2Cl_2$. The combined organic filtrates were washed with 2N HCl brine, 2N NaOH, water and brine, dried ($Na_2SO_4$), filtered and evaporated. The crude product was chromatographed with silica gel and eluted with hexane:EtOAc (90% hexane:EtOAc) to yield 80 (5.7 g; estimated purity 72%).

Step 2

A solution of 80 (4.1 g; 14.6 mmol), NBS (2.6 g; 14.6 mmol), AIBN (0.25 g; 1.50 mmol) and 146 mL of $CCl_4$ was heated at reflux for 5.0 h, cooled to rt and the precipitated succinimide filtered through a pad of CELITE®. The filtrate was evaporated and the crude product 81a was sufficiently pure to use in the next step.

The crude bromomethyl compound 81a from the previous step was dissolved in 73 mL of 90% aq. EtOH and 2.5 g of NaCN (49.01 mmol) was added. The reaction mixture was stirred overnight at rt. The solid material was filtered through a pad of CELITE® and the filtrate was evaporated. The crude product purified by silica gel chromatography and eluted with 30% EtOAc:hexane to yield the nitrile 81b (2.4 g; 54%).

Step 3

To a ice-cold solution of 81b (2.4 g; 7.4 mmol), 3,6-dichloropyrazine (2.2 g; 14.4 mmol) and 74 mL of dry DMF was added portionwise NaH (0.62 g; 15.5 mmol; 60% in mineral oil). The reaction was stirred at 0° C. for 15 min and allowed to stir at rt for 2 h and poured into 75 mL of $H_2O$ containing about 1 g of $NaHSO_4$. The aqueous solution as thoroughly extracted with EtOAc and the combined EtOAc extracts washed with six times with water, once with 5% LiCl dried ($Na_2SO_4$), filtered and evaporated. The product was purified by silica gel chromatography to yield 82 (2.9 g; 94%).

Step 4

A mixture of 82 (0.209 g; 2.6 mmol), HOAc (10 mL), HCl (20 mL) and $H_2O$ (10 mL) were heated at reflux for overnight, cooled to rt, diluted with water and EtOAc. The aqueous phase was washed with EtOAc and the combined extracts were washed sequentially with water and sat'd $NaHCO_3$, dried ($Na_2SO_4$), filtered and evaporated to yield 83 (2.0 g; 77%).

Step 5

A solution of 83 (0.750 g; 0.20 mmol) and $CH_3CN$ (10 mL) was degassed for 10 m with a stream of $N_2$ and $Zn(CN)_2$ (0.14 g; 1.2 mmol) and $Pd(PPh_3)_4$ (0.35 g; 0.30 mmol) and CuI (0.039 g; 0.2 mmol) were added. The reaction mixture was heated to 120° C. for 12 h, cooled to rt and diluted with EtOAc. The resulting suspension was filtered through a bed of CELITE®, the solids washed with EtOAc and the combined organic filtrates evaporated. The crude product was purified by silica gel chromatography to yield nitrile 84 (0.060 g).

Example 21

6-[4-Chloro-3-(3-chloro-phenoxy)-benzyl]-4-methylamino-2H-pyridazin-3-one (92) and 6-[4-Chloro-3-(3-chloro-phenoxy)-benzyl]-5-methylamino-2H-pyridazin-3-one (93)

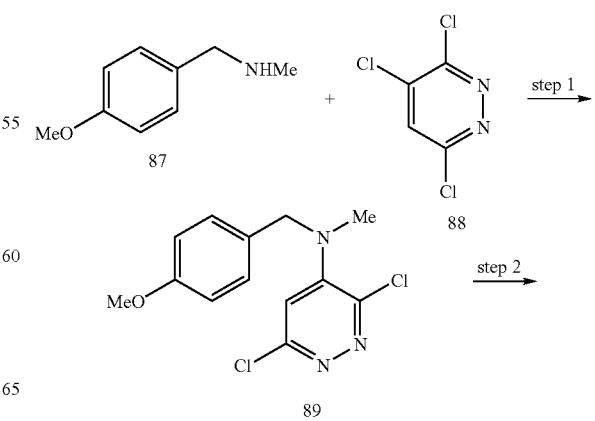

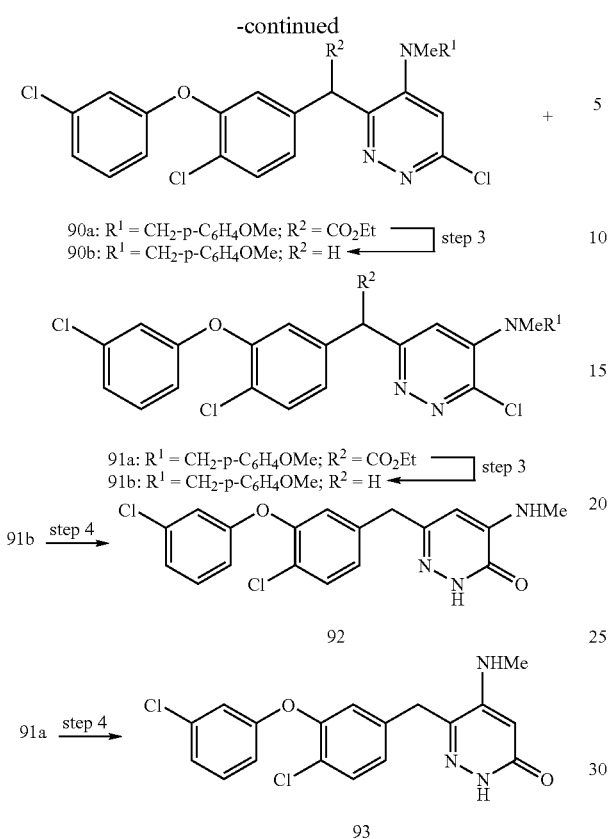

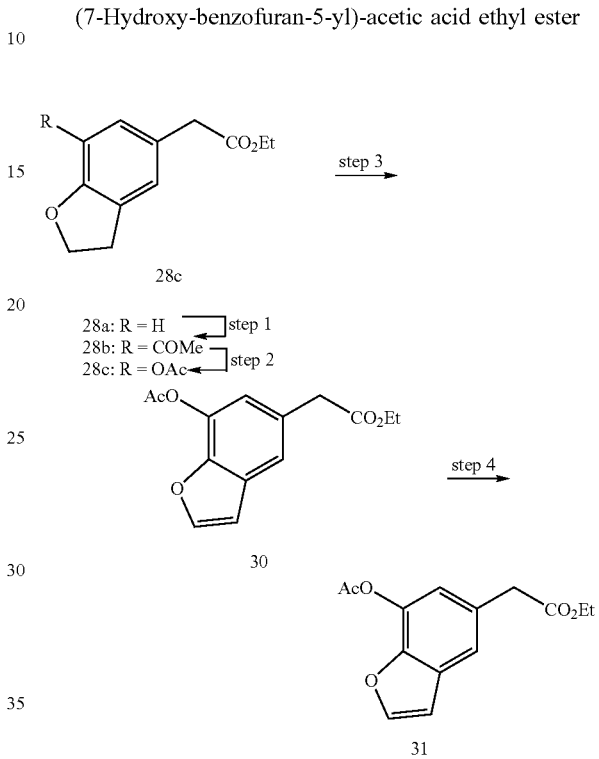

Step 1

A solution of p-methoxybenzylmethylamine (1.11 g; 7.34 mmol) and EtOH (10 mL) was added to a solution of 3,4,6-trichloropyrazine (1.28 g; 6.99 mmol), TEA (0.983 mL; 6.99 mmol) and anhydrous EtOH (20 mL) and the reaction stirred overnight at room temperature. The solvent was evaporated and the residue partitioned between EtOAc and $H_2O$. The phases were separated, the water washed with EtOAc, and the combined EtOAc solutions washed with water and brine. The solution was dried ($MgSO_4$), filtered and evaporated. The product was purified by silica gel chromatography and eluted with an EtOAc:hexane mixture (5:95→30:70) to yield 89 as a white solid (1.3 g; 62%).

Step 2 and Step 3

The condensation of 89 and [4-Chloro-3-(3-chloro-phenoxy)-phenyl]-acetic acid ethyl ester to yield 90a and 91a was carried out as described in step 4 of Example 14 and the subsequent saponification and decarboxylation step to yield 90b and 91b was carried out as described in step 1 of Example 18. The product was a mixture of isomers. The isomers were separated by silica gel chromatography and eluted with an EtOAc:hexane gradient (10:90→50:50). The first isomer to elute was 90b.

Step 4

A solution of 90b, NaOAc (0.25 g) and HOAc (5 mL) was heated for 8 h. The solution was cooled and the solvent removed in vacuo. The residue was partitioned between EtOAc and $H_2O$. The phases were separated and the $H_2O$ phase washed with EtOAc. The combined organic layers were washed with brine, dried and evaporated. The residue was purified by silica gel chromatography and eluted with a MeOH:$CH_2Cl_2$ gradient (1:99→10:90) to yield 16 mg of 93.

The other isomer was prepared in identical manner except the product was purified by silica gel chromatography and eluted with a EtOAc:hexane gradient (30:70→70:30) to yield 64 mg of 92.

The overall yield of steps 2–4 was 28%.

Example 22

(7-Hydroxy-benzofuran-5-yl)-acetic acid ethyl ester

Step 1

To a solution of 28a (5.0 g; 24.2 mmol) and anhydrous $CH_2Cl_2$ (75 mL) was added sequentially acetyl chloride ((2.42 mL; 33.9 mmol) and SnCl4 (5.39 mL; 46.1 mmol; 1 M solution in $CH_2Cl_2$). The reaction was stirred at room temperature for 50 minutes and poured into a mixture of ice and 2 N HCl (200 mL). The organic phase was separated and diluted with about 50 mL of $CH_2Cl_2$ and thrice washed with water (100 mL) and once with brine (100 mL). The organic phase was dried ($MgSO_4$), filtered and evaporated to yield 28b (6.0 g) which contained about 10% of 28a. The crude product was used without further purification.

Step 2

To an ice-cold solution of 28b (6.01 g; 24.2 mmol) and $CH_2Cl_2$ (100 mL) under a nitrogen atmosphere was added sequentially a solution of MCPBA (11.9 g; 48.4 mmol) and $CH_2Cl_2$ (12 mL) followed by TFA (2.14 mL; 27.8 mmol). The reaction mixture was stirred at rt overnight. The reaction mixture was cooled to 0° C. and a 5% aqueous $Na_2SO_3$ solution (150 mL) was added slowly with stirring. The mixture was stirred for 5 minutes after addition was completed and precipitated m-chlorobenzoic acid was filtered. The solid was with $CH_2Cl_2$ and the combined filtrates were washed with 10% NaOH (2×250 mL), 2 N HCl (200 mL), water and brine. The resulting solution was dried ($MgSO_4$), filtered through a pad of CELITE® and concentrated in vacuo to yield 28c (4.1 g).

Step 3

To a solution of dihydrofuran derivative 28c (14.6 g; 0.0553 mol) and CCl₄ (500 mL) was added NBS (10.3 g; 0.0580 mol) and AIBN (1.4 g). The reaction was heated to reflux for 30 minutes under a nitrogen atmosphere. The reaction was cooled, the solid succinimide filtered, and the organic phase was washed with 0.5 M NaHSO₄ (150 mL) and brine. The product was dried (Na2SO4), filtered and evaporated to yield 15.2 g of a yellow syrup. The crude product was purified by silica gel chromatography and eluted with a EtOAc:hexane gradient (3:97→10:90) to yield 10.3 g (78.1%) of 30.

Step 4

A solution of 30 (10.3 g; 39.3 mmol), EtOH (250 mL) and saturated NaHCO₃ (100 mL) were heated to reflux for 1 h. The reaction mixture was cooled to room temperature and the EtOH removed in vacuo. Ice was added to the residue aqueous solution and the reaction carefully acidified to about pH 2 with 2 N HCl. The resulting mixture was extracted with EtOAc (2×300 mL) and the combined organic phase washed with brine, dried (NaSO₄), filtered and evaporated to yield a brown oil (8.8 g). The crude product was run through a silica gel column with 15% EtOAc:hexane to yield 31 (5.44 g; 62.9%) as a white solid.

Example 23

6-(3-Benzyl-4-chloro-benzyl)-2H-pyridazin-3-one

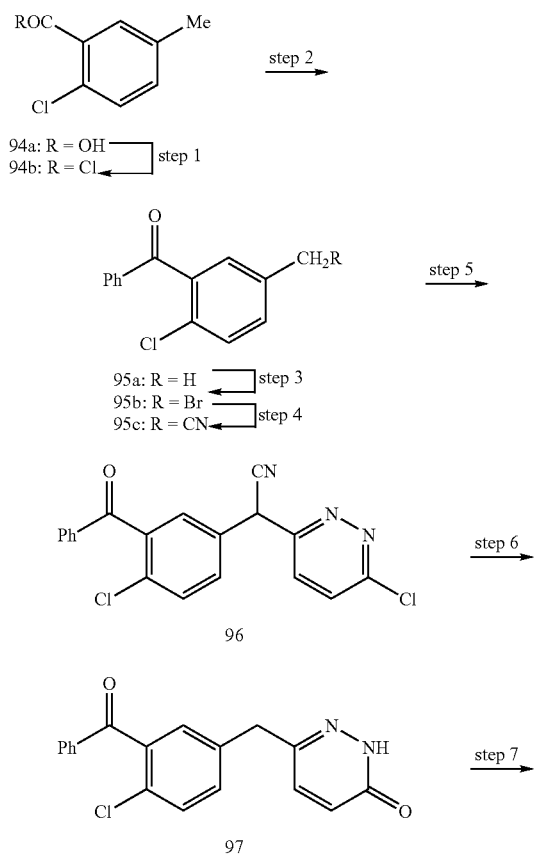

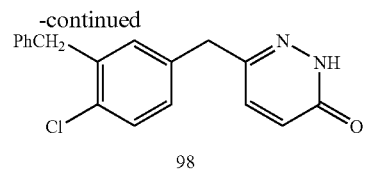

Step 1

To a ice-cold solution of 94a (4.0 g; 23.44 mmol) and CH₂Cl₂ (60 mL) was added oxalyl chloride (10.26 mL; 0.117 mol) and one drop of DMF. The reaction mixture was allowed to warm to rt and stirred overnight. The volatile solvents were removed in vacuo and oxalyl chloride removed by thrice adding CH₂Cl₂ (30 mL) and re-evaporating the solvent to yield 94b (4.4 g) as a yellow oil which was used directly in step 2.

Step 2

The acid chloride 94b from step 1 (4.4 g; 23.27 mmol) was dissolved in benzene (80 mL) and the solution cooled to 0° C. Solid AlCl₃ was added in portions to the solution and after the addition was complete the reaction was warmed to room temperature and stirred for two days. The reaction mixture was poured into ice containing a small quantity of con HCl and the aqueous mixture extracted with CH₂Cl₂ which was washed sequentially with water, 2N HCl and brine. The resulting solution was dried (MgSO₄) filtered and evaporated to yield an orange oil which was purified by silica gel chromatography and eluted with a EtOAc:hexane (1:20) to yield 3.46 g (64%) of 95a as an orange oil.

Step 3

A solution of 95a (3.46g; 0.15 mol), NBS (2.67 g; 0.015 mol), AIBN (0.27 g; 0.0015 mol) and 60 mL of CCl₄ (60 mL) was heated at reflux overnight. The reaction was cooled to room temperature and filtered. The filtrate was diluted with 50 mL of CH₂Cl₂, washed with H₂O (100 mL) and brine (100 mL), dried (Na₂SO₄), filtered and evaporated. The crude product was purified by silica gel chromatography and eluted with a EtOAc:hexane (1:20) to yield 1.23 g (29%) of 95b as an oil.

Step 4

A solution of 95b (1.23 g; 3.98 mmol), NaCN (0.293 g; 5.97 mmol) and 8 mL of DMSO was stirred at room temperature for two days. The reaction mixture was diluted with EtOAc (100 mL), washed with water and brine, dried (Na₂SO₄), filtered and evaporated to yield 95c (0.93 g) sufficiently pure to carry onto the next step.

Step 5

To a ice-cold solution of 95c (0.930 g; 3.63 mmol), 3,6-dichloropyrazine (1.08 g; 7.266 mmol) and 8 mL of dry DMF was added portionwise NaH (0.303 g; 9.082 mmol; 60% in mineral oil). The reaction was stirred at 0° C. for 15 min and allowed to stir at rt for 24 h and poured into an ice cold solution of 144 mL of H₂O containing about 9 g of NaHSO₄. The aqueous solution as thrice extracted with EtOAc (50 mL). The combined extracts were with three times with water, twice with brine, dried (Na₂SO₄), filtered and evaporated to yield 2.48 g of a brown oil which was chromatographed on silica gel and eluted with EtOAc:hexane (3:1) to yield 96 (0.744 g; 56%).

Step 6

A mixture of 96 (0.744 g; 2.02 mmol), HOAc (8 mL), HCl (16 mL) and H₂O (8 mL) was heated at reflux for 14 h, cooled to rt partitioned between water and EtOAc. The aqueous phase was thrice extracted with EtOAc and the combined extracts were washed with water, dried (Na$_2$SO$_4$), filtered and evaporated to yield 97 (0.356 g; 55%).

Step 7

To an ice-cold solution of 97 (0.529 g; 1.633 mmol) and TFA (8 mL) was added triethylsilane (0.8 mL; 4.898 mmol) and the resulting mixture was stirred at 0° C. for 2 h then at room temperature overnight. The TFA was remove in vacuo and the residue diluted with EtOAc, washed with water and brine, dried (MgSO$_4$), filtered and evaporated. The crude product was purified by silica gel chromatography and eluted with a CH$_2$Cl$_2$:EtOAc (2:1→1:1) to yield 98 (0.250 g; 49%) as a yellow oil. The product was maintained at 35° C. in a vacuum oven for final drying.

Example 24

[3-(6-Methyl-4-cyano-pyridin-2-yloxy)-4-chloro-phenyl]-acetic acid ethyl ester (99)

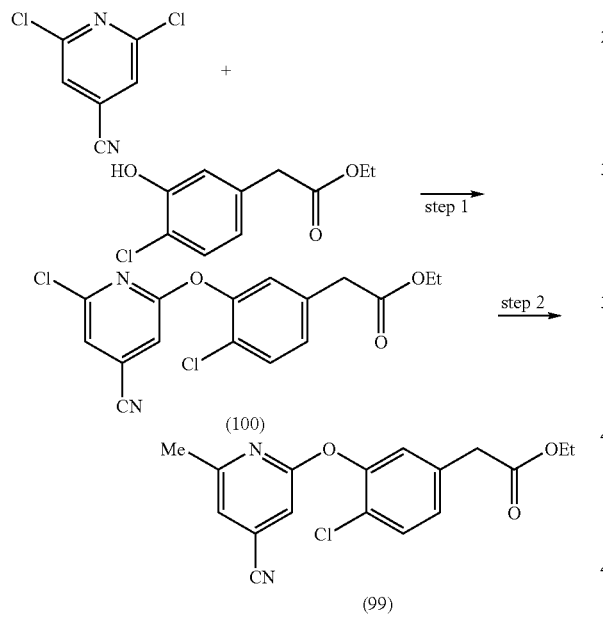

Step 1

A 100 mL round bottom flask was charged with 2,6-dichloro-4-cyanopyridine (2.50 g, 14.45 mmol), ethyl (4-chloro-3-hydroxy-phenyl)-acetate (3.10 g, 14.45 mmol), and anhydrous K$_2$CO$_3$ (2.10 g, 15.20 mmol) under nitrogen. DMA (50 mL) was added via syringe, and the heterogeneous mixture was heated to 100° C. for 2 h. The solution was cooled to RT, poured into 2M NH$_4$Cl (150 mL), and extracted with EtOAc (3×50 mL). The combined organics were washed with brine (50 mL), dried with MgSO$_4$, and the volatile materials were evaporated. The crude product was purified by flash chromatography (SiO$_2$, 0% to 35% EtOAc/Hexanes) to afford 2.30 g (45% yield) of 100

Step 2

To a stirred solution of 100 (2.12 g, 6.05 mmol), dichlorobis(triphenylphosphine) palladium(II) (425 mg, 0.61 mmol), and 2-dimethylaminoethanol (122 µL, 1.21 mmol) cooled to 0° C. was added dimethylzinc (6.05 mL of a 2.0 M solution in toluene, 12.10 mmol). The mixture was warmed to RT, heated to 85° C. for 1.5 h, and then cooled to RT. This solution was then slowly added to 2 M NH$_4$Cl (100 mL) cooled to 0° C. The resulting mixture was extracted with EtOAc (3×50 mL), and the combined organics were washed with brine (50 mL), dried with MgSO$_4$, and evaporated. The crude oil was purified by flash chromatography (SiO$_2$, 0% to 20% EtOAc/hexanes) to afford 1.25 g (62%) of [3-(6-chloro-4-cyano-pyridin-2-yloxy)-4-ethyl-phenyl]-acetic acid ethyl ester (99) as an oil that slowly crystallized.

The introduction of the pyridazinone ring and saponification and decarboxylation of the ester was accomplished utilizing the procedure described in steps 2–4 of Example 14.

Example 25

[3-(6-Cyano-4-methyl-pyridin-2-yloxy)-4-ethyl-phenyl]-acetic acid ethyl ester (101)

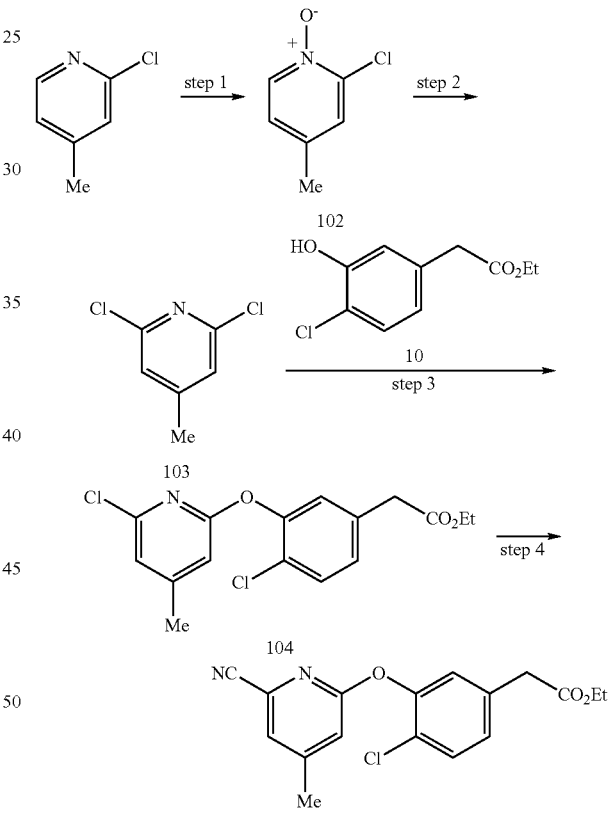

Step 1

A solution of 2-chloro-4-methylpyridine (5.00 g, 39.2 mmol), MCPBA (9.02 g; assay 75% pure, 39.2 mmol), and chloroform (80 mL) was heated to reflux for 5 h. The reaction mixture was cooled to RT, and approximately 20 mL of the solvent was evaporated (without heating). The benzoic acid that precipitated from the solution was removed by filtration. The remaining filtrate was washed with saturated aqueous K$_2$CO$_3$ (50 mL), 1 M NaOH (50 mL), brine (25 mL), and dried with anhydrous Na$_2$SO$_4$. The solvent was evaporated, and the remaining material was purified by flash chromatography on silica gel (0% to 5% MeOH/CHCl₃) to provide 3.60 g (64%) of 102

Step 2

A 50 mL round bottom flask was charged with 2-chloro-4-methylpyridine-N-oxide, and 20 mL of POCl₃ was slowly added. (WARNING!) A sudden exotherm occurred (the N-oxide should be added slowly to the POCl₃). An additional 10 mL of POCl₃ was added to the brown reaction mixture, and the solution was heated to 95° C. for 5 h. The reaction mixture was cooled to RT, and the volatile materials were evaporated. The remaining mixture was slowly added to a saturated aqueous solution of NaHCO₃ (150 mL), and extracted with EtOAc (3×50 mL). The combined organic fractions were washed with brine (50 mL) and dried over MgSO₄. The solvent was evaporated, and the remaining brown solid was purified by flash chromatography on silica gel (0% to 7% EtOAc/hexanes) to provide 1.56 g (43%) of 103.

Step 3

A solution of 2,6-dichloro-4-methylpyridine (1.04 g, 6.42 mmol), ethyl (4-chloro-3-hydroxy-phenyl)-acetate (1.38 g, 6.42 mmol), and anhydrous CS₂CO₃ (2.20 g, 6.74 mmol) in DMA (15 mL) under nitrogen was heated to 120° C. for 15 h. The solution was cooled to RT, and poured into a saturated aqueous solution of NH₄Cl (50 mL). The resulting mixture was extracted with 1:1 EtOAc/hexanes (3×50 mL). The combined organic fractions were washed with water (3×30 mL), brine (30 mL), and dried with anhydrous MgSO₄. The volatile materials were evaporated and the remaining oil was purified by flash chromatography on silica gel (0% to 10% EtOAc/hexanes to provide 975 mg (45%) of 104.

Step 4

A mixture of 104 (1.01 g, 2.97 mmol), zinc cyanide (209 mg, 1.78 mmol), zinc dust (116 mg, 1.78 mmol), bis (diphenylphosphino)ferrocene (329 mg, 0.59 mmol), Pd(dba)₂—CHCl₃ (307 mg, 0.30 mmol) and in DMA (7 mL) under nitrogen was heated to 120° C. for 4 h. The mixture was cooled to RT, and diluted with 1:1 EtOAc/hexanes (150 mL). This solution was washed with saturated aqueous NH₄Cl (2×25 mL), water (25 mL), brine (25 mL), and dried with anhydrous MgSO₄. The solvents were evaporated, and the remaining material was purified by flash chromatography on silica gel (0% to 25% EtOAc/hexanes) to provide 730 mg of 101 (74%).

The introduction of the pyridazinone ring and saponification and decarboxylation of the ester was accomplished utilizing the procedure described in steps 2–4 of Example 14.

Example 26

4-(6-Chloro-3-ethoxycarbonylmethyl-2-fluoro-phenoxy)-indole-1-carboxylic acid tert-butyl ester

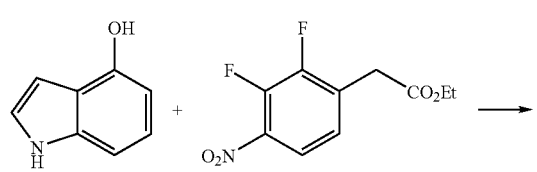

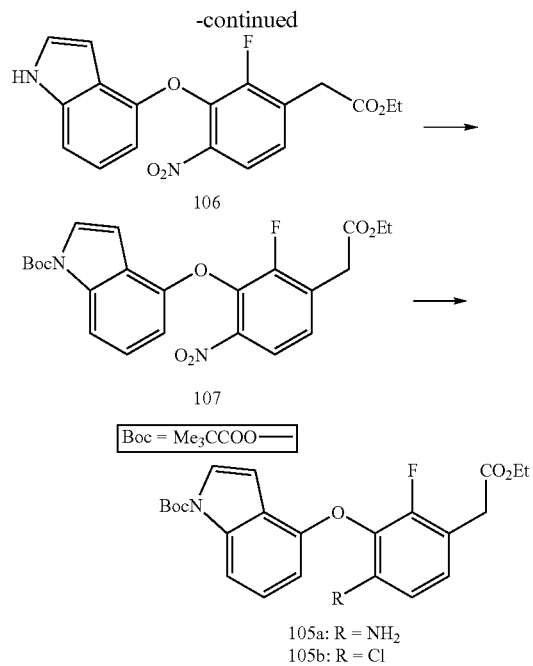

105a: R = NH₂
105b: R = Cl

Step 1

Solid sodium tert-butoxide (400 mg, 4.16 mmol) was added to a solution of 7-hydroxyindole (610 mg, 4.58 mmol) in THF (5 mL) under a nitrogen atmosphere, and the mixture was stirred for 10 m. A solution of ethyl 2,3-difluoro-4-nitrophenylacetate (1.02 g, 4.16 mmol in 5 mL of anhydrous THF) was added to the solution of the phenoxide via syringe. The resulting purple mixture was stirred overnight at RT, and then poured into a mixture of H₂O (30 mL) and brine (30 mL). The mixture was extracted with 2:1 EtOAc/hexanes (3×40 mL), and the combined organics were washed with H₂O (3×30 mL), brine (20 mL), and dried over anhydrous MgSO₄. The solvents were evaporated, and the remaining material was purified by flash chromatography on silica gel (0% to 40% EtOAc/hexanes) to afford 106 in 82% yield.

Step 2 tert-Butoxycarbonylanhydride (533 mg, 2.44 mmol) was added to a solution of 106 (878 mg, 2.44 mmol) in anhydrous THF (12 mL) under a nitrogen atmosphere. The solution was cooled to 0° C., and 4-dimethylaminopyridine (30 mg, 0.24 mmol) was added. After 0.5 h, the solution was warmed to RT and stirred for an additional 2 h. The mixture was poured into H₂O (25 mL) and extracted with EtOAc (3×30 mL). The combined organic fractions were washed with brine (20 mL), and dried over anhydrous MgSO₄. The volatile materials were evaporated, and the remaining oil was purified by flash chromatography on silica gel (0% to 25% EtOAc/hexanes) to provide 560 mg (50%) of the protected indole 107 and 260 mg (30%) of recovered starting material.

Step 3

Protected indole 107 (790 mg, 1.72 mmol), 5% palladium on carbon (79 mg), and EtOH (15 mL) were added to a thick-walled bottle. The bottle was evacuated and pressurized with 50 psi of H₂ gas. After 4 hrs, the pressure was released, and the mixture was filtered through CELITE®. The EtOH was evaporated, and the remaining oil was purified by flash chromatography on silica gel (0% to 25% EtOAc/hexanes) to afford 105a 609 mg (83%).

Conversion of the amine 105a to the corresponding chloride 105b was effected with CuCl₂ and tert-butyl nitrite as described in step 3 of Example 27 (for the one step preparation of aryl chlorides and bromides from aryl amines see Doyle et a., *J. Org Chem.* 1977 42:2426). The introduction of the pyridazinone ring and saponification and decarboxylation of the ester was accomplished utilizing the procedure described in steps 2–4 of Example 14. Deprotection of the Boc protecting group occurred spontaneously during the pyridazine hydrolysis.

Example 27

6-[4-Chloro-2-fluoro-3-(1-indol-7-yloxy)-benzyl]-4-methyl-2H-pyridazin-3-one (I-235)

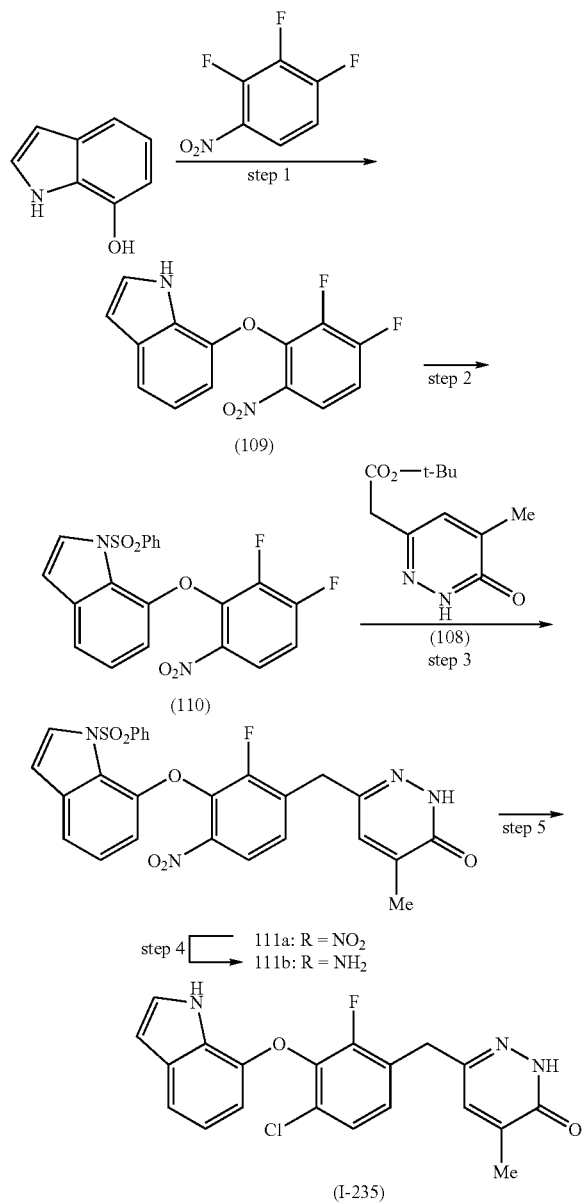

Step 1

Solid sodium tert-butoxide was added to a ice cold solution of 4-hydroxyindole (1.23 g, 9.24 mmol; *Synthetic Communications* 2003 33:507) in anhydrous THF (145 mL) under a nitrogen atmosphere. The mixture was stirred for 10 m, and 2,3,4-trifluoronitrobenzene (1.06 mL, 9.24 mmol) was added dropwise. The brown solution was stirred for 2 h, and then added to a saturated aqueous solution of NH₄Cl (150 mL). The aqueous layer was extracted with EtOAc (3×100 mL), and the combined organic fractions were washed with H₂O (100 mL), brine (75 mL), and dried over anhydrous MgSO₄. The solvents were evaporated, and the remaining oil was purified by flash chromatography on silica gel (0% to 30% EtOAc/hexanes) to afford 2.26 g (84%) of 109.

Step 2

Phenyl sulfonyl chloride (1.05 mL, 8.18 mmol), powdered NaOH (4 g), and Bu₄NHSO₄ (400 mg) were added sequentially to a solution of 109 (2.26 g, 7.79 mmol) in anhydrous CH₂Cl₂ (25 mL). The mixture was stirred for 3 h, and then filtered through CELITE®. The filtrate was washed with H₂O (25 mL), and dried over anhydrous MgSO₄. The solvents were evaporated, and the remaining material was recrystallized from EtOAc. The impure filtrate was purified by column chromatography on silica gel (25% to 40% EtOAc/hexanes), and combined with the crystallized material to afford 2.08 g (62%) of 110.

Step 3

A solution of sodium hexamethyldisilazane (15.5 mL of a 1 M solution in THF, 15.5 mmol) was added slowly to a solution of 110 (2.08 g, 4.83 mmol) and 108 (1.14 g, 5.07 mmol) in anhydrous THF (25 mL) under nitrogen at 0° C. The reaction mixture was stirred for 3 h, and then added to a saturated aqueous solution of NH₄Cl (200 mL). The aqueous mixture was extracted with EtOAc (3×70 mL). The combined organic fractions were then washed with brine (50 mL), and dried over anhydrous MgSO₄. Evaporation of the solvents afforded a red oil which was dissolved in acetic acid (100 mL) and heated to reflux for 5 h. The solvent was removed, and the remaining material was dissolved in EtOAc (100 mL). The organic layer was washed with H₂O (40 mL), brine (25 mL), and dried over anhydrous MgSO₄. The solvents were evaporated and the crude product purified by flash chromatography on silica gel (20% to 100% EtOAc/hexanes) to afford 111a (1.79 g, 69%) as a solid that was only slightly soluble in EtOAc.

Step 4

A mixture of pyridazinone 111a (1.79 g, 3.36 mmol), Fe powder (845 mg, 15.12 mmol), and NH₄Cl (809 mg, 15.12 mmol) in EtOH (60 mL) and H₂O (15 mL) was heated to reflux for 3 h. The reaction mixture was cooled to RT and filtered through CELITE®. The filter cake was washed with EtOAc (150 mL), and the combined organic fractions were washed with brine (75 mL), and dried over anhydrous MgSO₄. The solvents were evaporated to provide an oil. The oil was dissolved in CH₂Cl₂ (100 mL), and the organic layer was washed with brine (50 mL), and dried over anhydrous MgSO₄. Evaporation of the solvent provided 111b (1.50 g; 88% theory).

Step 5

The aniline 111b (700 mg, 1.39 mmol) and CuCl₂ (381 mg, 2.77 mmol) were suspended in anhydrous CH₃CN (14 mL) under a nitrogen atmosphere. tert-Butylnitrite (0.33 mL, 2.77 mmol) was added dropwise, and the reaction mixture was warmed to 60° C. for 1 h. The solution was cooled to RT, and a 5% aqueous HCl solution (20 mL) was added. The layers were separated, and the aqueous layer was extracted with EtOAc (3×30 mL). The combined organic fractions were washed with brine (30 mL) and dried over anhydrous $MgSO_4$. The solvents were evaporated, and the remaining solid was purified by flash chromatography over silica gel (20% to 100% EtOAc/Hexanes) to provide 500 mg of a solid. The solid was dissolved in anhydrous THF (10 mL) under nitrogen, and TBAF was added dropwise (5.73 mL of a 1.0 M solution, 5.73 mmol). The solution was heated to reflux for 1 h and then cooled to RT. The mixture was quenched with saturated aqueous $NaHCO_3$, and the aqueous solution was extracted with $CH_2Cl_2$ (3×30 mL). The combined organic fractions were washed with $H_2O$ (30 mL), brine (30 mL), and dried over anhydrous $MgSO_4$. The solvents were evaporated, and the remaining solid was purified by repeated flash chromatography on silica gel(1% to 3% $MeOH/CH_2Cl_2$) to afford I-235 (135 mg; 25% theory).

Example 28

[4-Chloro-3-(6-cyano-4-methyl-pyridin-2-yloxy)-phenyl]-acetic acid ethyl ester

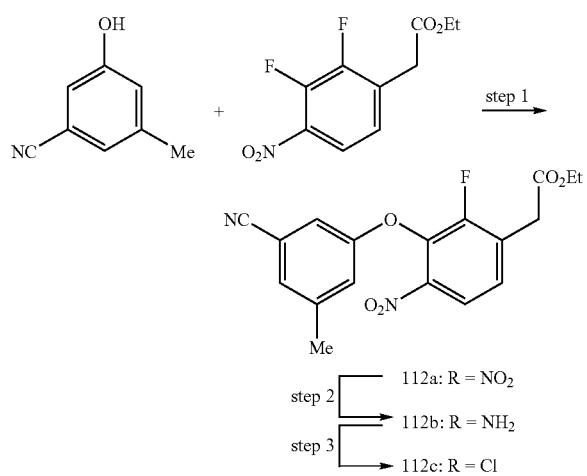

Synthesis of ethyl 2,3-difluoro-4-nitrophenylacetate

To an ice-cold solution of tert-butyl ethylmalonate (Alfa Aesar) (31.2 g, 166 mmole) in NMP (300 mL) cooled to 0° C. under a nitrogen atmosphere was added NaH (60% oil dispersion, 13.1 g, 218 mmole) while maintaining the temperature below 20°. After addition complete, the solution was allowed to age for 20 minutes. To this solution was added dropwise 2,3,4-trifluoronitrobenzene (Oakwood Products Inc.) (26.6 g, 163 mmole) in NMP (50 ml), while maintaining the temperature below 20° (highly exothermic). Upon completion of addition the reaction aged at room temperature for 2 hours. The solution was added to an aqueous solution of $NH_4Cl$ (1.5 L), extracted with ethyl acetate (3×200 mL), and washed 5 times with water (400 mL), dried ($MgSO_4$) and evaporated. The crude product was used without further purification.

The substituted malonic ester was dissolved in dichloromethane (400 mL) and TFA was added (100 mL), this solution heated at 40° for 16 hours. The reaction mixture was cooled to RT, and the solvents evaporated. The crude product dissolved in EtOAc (400 mL), washed sequentially with aqueous $NaHCO_3$, water, and brine, dried ($MgSO_4$) and evaporated. The remaining oil was purified by flash chromatography on silica gel (5% EtOAc/hexane) to give the product as a golden oil (11.9 g) (30%) which crystallizes upon sitting.

Step 1

Solid sodium tert-butoxide (1.32 g, 13.71 mmol) was added in 3 portions to a solution of 3-cyano-5-methylphenol (2.01 g, 15.08 mmol, prepared as described in WO 2002085860) in anhydrous THF (50 mL) under a nitrogen atmosphere. The resulting heterogeneous solution was stirred at RT for 15 m and then cooled to 0° C. A solution of the ethyl 2,3-difluoro-4-nitrophenylacetate (3.36 g, 13.71 mmol) in THF was added dropwise over 1 h. The purple mixture was warmed to RT, stirred for 16 h, and then added to a saturated aqueous solution of $NH_4Cl$ (150 mL). The mixture was extracted with ethyl ether (3×100 mL), and the combined organics were washed with brine (1×100 mL), and dried over anhydrous $MgSO_4$. The solvents were evaporated, and the remaining oil was purified by flash chromatography on silica gel (0% to 50% EtOAc/hexanes) to provide 4.28 g (90%) of 112a.

Step 2

A mixture of 112a (4.28 g, 12.31 mmol), Fe powder (2.89 g, 51.69 mmol), and $NH_4Cl$ (2.76 g, 51.69 mmol) in EtOH (40 mL) and $H_2O$ (40 mL) was heated to reflux for 3 h. The solution was cooled to RT, and filtered through CELITE®. The filter cake was washed with EtOAc (200 mL), the aqueous and organic layers were separated, and the organic layer was washed with brine (2×60 mL). The solution was dried over anhydrous $MgSO_4$ and evaporated to provide 3.81 g (100%) of the aniline 112b.

Step 3

A solution of 112b (3.81 g, 12.28 mmol) in anhydrous $CH_3CN$ (40 mL) under a nitrogen atmosphere was added slowly to a mixture of tert-butyl nitrite (2.63 mL, 22.10 mmol) and $CuCl_2$ (2.48 g, 18.42 mmol) that had been prepared under a nitrogen atmosphere and was warmed to 60° C. The reaction temperature was maintained at 60° C. for 1 h then aged at RT for an additional 2 h. The solution was cooled to 0° C., and an aqueous 5% HCl solution (80 mL) was added. The mixture was extracted with 1:1 EtOAc/hexanes (3×75 mL) and the combined organics were washed with brine (75 mL), dried over anhydrous $MgSO_4$, and evaporated. The remaining oil was purified by flash chromatography on silica gel (0% to 30% EtOAc/hexanes) to provide 2.20 g (52%) of 112c.

The introduction of the pyridazinone ring and saponification and decarboxylation of the ester were accomplished utilizing the procedure described in steps 2–4 of Example 14.

Example 29

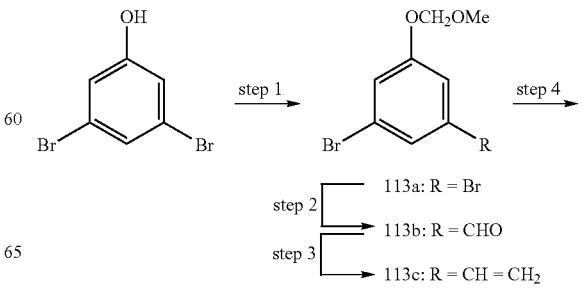

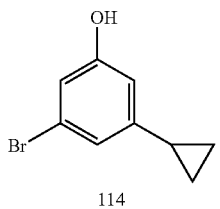

114

Step 1

Chloromethylmethyl ether (1.45 mL, 19.13 mmol) was added dropwise to a solution of 3,5-dibromophenol (4.38 g, 17.39 mmol) and diisopropylethylamine (3.63 mL, 20.90 mmol) in $CH_2Cl_2$ (40 mL) at 0° C. The mixture was warmed to RT, stirred for 16 h, and added to $H_2O$ (50 mL). The layers were separated, and the aqueous fraction was extracted with $CH_2Cl_2$ (2×50 mL). The combined organic fractions were washed with brine (25 mL), dried over anhydrous $MgSO_4$, and the solvent was evaporated to provide 5.20 g (100%) of 1,3-dibromo-5-methoxymethoxy-benzene (113a).

Step 2 n-BuLi (8.34 mL of a 1.6 M solution in $Et_2O$, 13.34 mmol) was added dropwise to a solution cooled to −78° C. of 1,3-dibromo-5-methoxymethoxy-benzene (3.59 g, 12.13 mmol) in anhydrous $Et_2O$ (40 mL) under a nitrogen atmosphere. The solution was aged at −78° C. for 45 m, anhydrous DMF (1.03 mL, 13.34 mmol) was added, and the reaction mixture was slowly warmed to RT. The mixture was poured into $H_2O$ (50 mL), and the aqueous phase was extracted with $Et_2O$ (2×75 mL). The combined organic fractions were washed with brine (50 mL) and dried over anhydrous $MgSO_4$. The solvents were evaporated, and the remaining oil was purified by flash chromatography over silica gel (0% to 10% EtOAc/hexanes) to afford 2.18 g (74%) of 3-bromo-5-methoxymethoxy-benzaldehyde (113b).

Step 3

A solution of n-BuLi (5.65 mL of a 1.6 M solution in $Et_2O$, 9.04 mmol) was added dropwise to a solution of methyltriphenylphosphonium bromide (3.23 g, 9.05 mmol) in THF (15 mL) that was cooled to 0° C. The resulting yellow solution was stirred for 30 m, cooled to −78° C., and a solution of 3-bromo-5-methoxymethoxy-benzaldehyde (1.58 g, 6.46 mmol) in anhydrous THF (15 mL) was added dropwise. The mixture was slowly warmed to RT, stirred for 16 h, and then added to a saturated aqueous solution of $NaHCO_3$ (60 mL). The layers were separated, and the aqueous layer was extracted with $Et_2O$ (2×50 mL). The combined organic layers were washed with brine (30 mL), and dried with anhydrous $MgSO_4$. The volatile materials were evaporated, and the remaining oil was purified by flash chromatography on silica gel (0% to 3% EtOAc/hexanes) to provide 600 mg (76%) of 1-bromo-3-methoxymethoxy-5-vinyl-benzene (113c).

Step 4

To anhydrous $CH_2Cl_2$ (10 mL) was added $ZnEt_2$ (12.34 of a 1.0 M in heptane, 12.34 mmol) under nitrogen. The solution was cooled to 0° C., and a solution of trifluoroacetic acid (0.95 mL, 12.34 mmol) in anhydrous $CH_2Cl_2$ (4 mL) was added very slowly. After stirring the reaction mixture for 20 m, a solution of $CH_2I_2$ (0.99 mL, 12.34 mmol) in $CH_2Cl_2$ (4 mL) was added. After an additional 20 m stirring, a solution of the 1-bromo-3-methoxymethoxy-5-vinyl-benzene (1.20 g, 4.94 mmol) in $CH_2Cl_2$ (6 mL) was added, and the reaction was allowed to warm to RT. After 1.5 h, the reaction was quenched with saturated aqueous $NH_4Cl$ (30 mL) and hexanes (50 mL), and the layers were separated. The aqueous layer was extracted with $Et_2O$ (2×40 mL), and the combined organic layers were washed with $H_2O$ (30 mL), brine (30 mL), and dried with anhydrous $MgSO_4$. The solvents were evaporated, and the remaining oil was partially purified by flash chromatography on silica gel (0% to 5% EtOAc/hexanes). The partially purified material was placed in i-PrOH (10 mL), and 2 mL of 1.0 M HCl was added. The mixture was aged at 50° C. for 14 h, cooled to RT, and added to $H_2O$ (25 mL). The aqueous mixture was extracted with $Et_2O$ (3×40 mL), and the combined organics were washed with brine (30 mL), and dried over anhydrous $MgSO_4$. The solvents were evaporated, and the remaining oil was purified by flash chromatography on silica gel (0% to 10% EtOAc/hexanes) to afford 325 mg (31%) of 3-bromo-5-cyclopropyl-phenol (114).

Phenols 113c and 114 were condensed with ethyl 2,3-difluoro-4-nitrophenyl acetate as described in Example 28. Substitution of the bromo radical with a cyano radical was accomplished by palladium-mediated displacement by $Zn(CN)_2$ as described in step 5 of Example 20.

Example 30

[4-Chloro-3-(3-cyano-5-vinyl-phenoxy)-2-fluoro-phenyl]-acetic acid ethyl ester

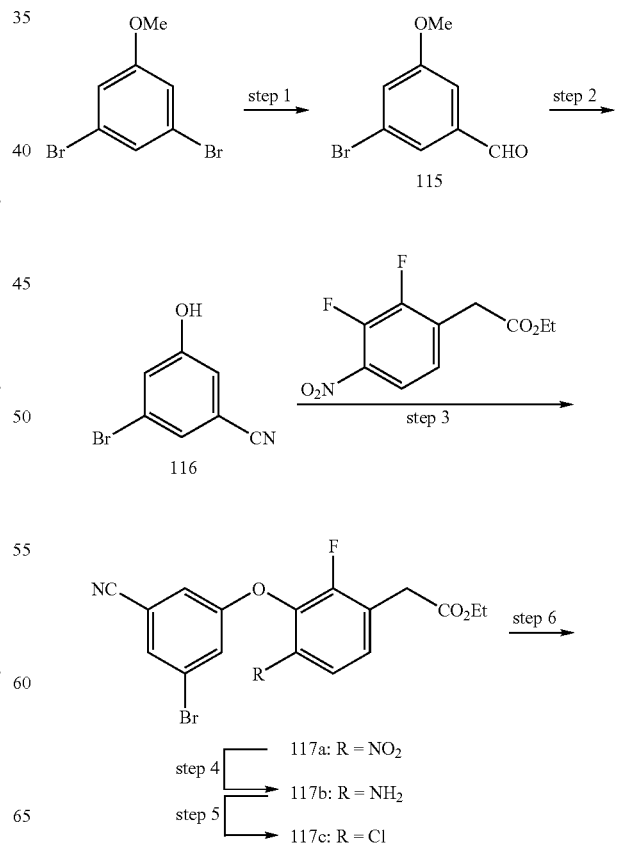

-continued

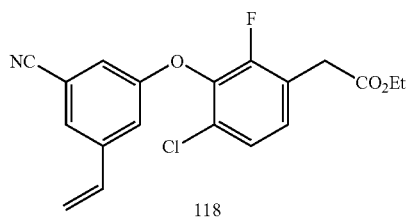

118

Step 1

A solution of 1,3-dibromo-5-methoxybenzene (15 g, 56.40 mmol) in anhydrous Et$_2$O (200 mL) under nitrogen was cooled to −78° C. n-BuLi (38.80 mL of a 1.6 M solution in Et$_2$O, 62.00 mmol) was added dropwise, and the solution was aged at −78° C. for 45 m. To the resulting heterogeneous mixture was added anhydrous DMF (4.78 mL, 62.00 mmol), and the solution was slowly warmed to RT. The mixture was poured into H$_2$O (200 mL), and the aqueous phase was extracted with Et$_2$O (3×125 mL). The combined organic fractions were washed with brine (100 mL) and dried over anhydrous MgSO$_4$. Evaporation of the solvent provided 11.70 g (96%) of 3-bromo-5-methoxybenzaldehyde (115).

Step 2

A solution of 3-bromo-5-methoxybenzaldehyde (4.02 g, 18.7 mmol) and hydroxylamine hydrochloride (6.50 g, 93.5 mmol) in pyridine (50 mL) and EtOH (50 mL) was heated to 65° C. for 16 h. The solvent was removed, and the remaining materials were partitioned between 1:1 EtOAc/hexanes (150 mL) and H$_2$O (75 mL). The organic layer was washed with brine (60 mL), and the solvents were evaporated. The remaining oil was dissolved in anhydrous dioxane (50 mL), and trifluoroacetic anhydride (5.1 mL, 37.4 mmol) and pyridine (9.07 mL, 112.2 mmol) were added. The mixture was heated to 60° C. for 3 h and then cooled to RT. CHCl$_3$ (100 mL) was added, and the organic layer was washed with H$_2$O (2×50 mL), 5% aqueous HCl solution (30 mL), brine (30 mL), and dried with anhydrous MgSO$_4$. The solvents were removed to provide a white solid. This solid was placed in a 150 mL flask that was flushed with nitrogen. Collidine (40 mL) and LiI (7.92 g, 59.10 mmol) were added, and the mixture was heated to 180° C. for 5 h. The reaction mixture was cooled to RT, and partitioned between H$_2$O (400 mL) and EtOAc (100 mL). The layers were separated, and the aqueous layer was acidified with 10% aqueous HCl solution, and extracted with 2:1 EtOAc/hexanes (3×125 mL). The combined organic layers were washed with H$_2$O (100 mL), 10% aqueous HCl solution (2×50 mL), brine (75 mL), and dried with anhydrous MgSO$_4$. The solvents were evaporated and the resulting solid was purified by flash chromatography on silica gel (10% to 40% EtOAc/hexanes) to provide 3.40 g (92%) of 3-bromo-5-hydroxybenzonitrile (116).

Step 3

Solid sodium tert-butoxide (1.67 g, 16.50 mmol) was added in three portions to a solution of 3-bromo-5-hydroxybenzonitrile (3.27 g, 16.50 mmol) in anhydrous THF (40 mL) under nitrogen. The resulting heterogeneous solution was aged at RT for 15 m. The solution was cooled to 0 C, and a solution of the ester (4.04 g, 13.71 mmol) was added dropwise over 30 m. The purple mixture was warmed to RT, stirred for 16 h, and then added to a saturated aqueous solution of NH$_4$Cl (100 mL). The mixture was extracted with ethyl ether (3×100 mL), and the combined organics were washed with brine (1×100 mL) and dried over anhydrous MgSO$_4$. The solvents were evaporated, and the remaining solid was purified by crystallization from 1:1 EtOAc/hexanes to provide 4.34 g (62%) of [3-(3-bromo-5-cyano-phenoxy)-2-fluoro-4-nitro-phenyl]-acetic acid ethyl ester (117a).

Step 4

A solution of ester (117a, 4.34 g, 10.26 mmol), Fe powder (2.40 g, 43.07 mmol), and NH$_4$Cl (2.30 g, 43.07 mmol) in EtOH (80 mL) and H$_2$O (40 mL) was heated to reflux for 2 h. The solution was cooled to RT and filtered through CELITE®. The filter cake was washed with EtOAc (200 mL), the aqueous and organic layers were separated, and the organic layer was washed with brine (2×60 mL). The solution was dried with anhydrous MgSO$_4$, and evaporated to provide 3.98 g (98%) of the [4-amino-3-(3-bromo-5-cyano-phenoxy)-2-fluoro-phenyl]-acetic acid ethyl ester (117b).

Step 5

The aniline 117b (3.98 g, 10.10 mmol) was dissolved in anhydrous CH$_3$CN (35 mL) under nitrogen. This solution was then added dropwise to a mixture of tert-butylnitrite (2.40 mL, 20.20 mmol) and CuCl$_2$ (2.72 g, 20.20 mmol) that had been prepared under nitrogen and warmed to 60° C. The reaction temperature was maintained at 60° C. for 2 h, then cooled to 0° C. A 5% aqueous HCl solution (80 mL) was added, and the mixture was extracted with 1:1 EtOAc/hexanes (3×75 mL). The combined organics were washed with brine (75 mL), dried over anhydrous MgSO$_4$, and evaporated. The remaining oil was purified by flash chromatography on silica gel (0% to 30% EtOAc/Hexanes) to provide 2.67 g (64%) of the [4-chloro-3-(3-bromo-5-cyano-phenoxy)-2-fluoro-phenyl]-acetic acid ethyl ester (117c).

Step 6

A 2-necked flask was equipped with a reflux condenser and charged with 117c (1.14 g, 2.78 mmol) and tetrakis (triphenylphosphine)palladium (308 mg, 0.28 mmol). Anhydrous toluene (15 mL) and tributylvinyltin (0.85 mL, 2.91 mmol) were added, and the reaction was heated to reflux under nitrogen for 16 h. The solution was cooled to RT and EtOAc (50 mL) was added. The mixture was washed with H$_2$O (25 mL) and brine (25 mL), and dried over anhydrous MgSO$_4$. The solvents were evaporated, and the resulting oil purified by flash chromatography over silica gel(0% to 25% EtOAc/hexanes) to provide 770 mg (78%) of [4-chloro-3-(3-cyano-5-vinyl-phenoxy)-2-fluoro-phenyl]-acetic acid ethyl ester (118).

The introduction of the pyridazinone ring into 118 and saponification and decarboxylation of the ester were accomplished utilizing the procedure described in steps 2–4 of Example 14. Introduction of other alkyl, alkenyl or alkynyl is accomplished as described in step 6 with the appropriate tributyltin derivative.

Example 31

3-[6-Chloro-2-fluoro-3-(6-oxo-1,6-dihydro-pyridazin-3-ylmethyl)-phenoxy]-5-ethyl-benzonitrile

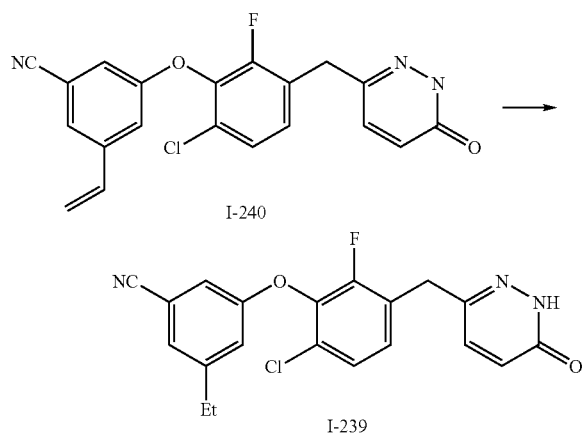

A round-bottom flask was charged with I-240 (100 mg, 0.26 mmol) and 5% palladium on carbon (20 mg) and EtOAc (5 mL) was added. The flask was evacuated, backfilled with $H_2$ (balloon pressure), and the solution was stirred for 3 h. The solution was filtered through CELITE®, and the filter cake was washed with EtOAc (20 mL). Removal of the solvent provided 90 mg (90%) of 3-[6-chloro-2-fluoro-3-(6-oxo-1,6-dihydro-pyridazin-3-ylmethyl)-phenoxy]-5-ethyl-benzonitrile (I-239).

Example 32

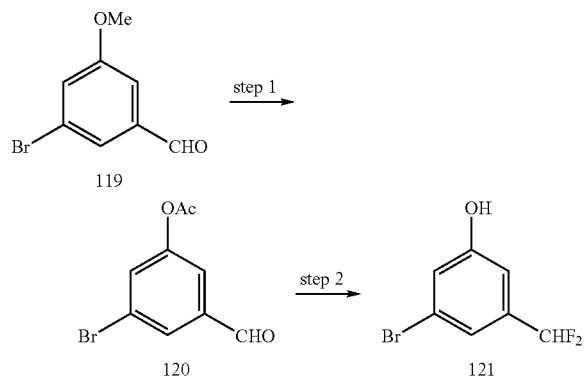

Step 1

A solution of $BBr_3$ (29.1 mL of a 1.0 M solution in $CH_2Cl_2$, 29.1 mmol) was added slowly to a solution of 119 (2.5 g, 11.62 mmol) in anhydrous $CH_2Cl_2$ (25 mL) under nitrogen at −78° C. The orange solution was warmed to RT, stirred for 2 h, and poured onto ice. The mixture was extracted with $CH_2Cl_2$ (100 mL), and the organic layer was washed with $H_2O$ (50 mL) and brine (50 mL). The solvents were evaporated, and the remaining oil was purified by flash chromatography on silica gel (0% to 20% EtOAc/hexanes) to provide the desired phenol. To a solution of this phenol in pyridine (10 mL) under argon was slowly added acetic anhydride (0.6 mL, 6.33 mmol). After 2 h, the volatile materials were removed to provide 3-bromo-5-formyl-phenyl acetate (120, 1.02 g, 40%).

Step 2

Diethylaminosulfur trifluoride (1.02 mL, 7.69 mmol) was added to a solution of the 3-bromo-5-formyl-phenyl acetate (120, 1.1 g, 4.52 mmol) in $CH_2Cl_2$ (5 mL) under nitrogen contained in a NALGENE® bottle. EtOH (0.013 mL, 0.23 mmol) was added, and the mixture was stirred for 16 h. The reaction mixture was then added slowly to an aqueous solution of saturated $NaHCO_3$. After the bubbling was finished, $CH_2Cl_2$ (50 mL) was added and the layers were separated. The organic layer was washed with brine (30 mL) and dried with anhydrous $MgSO_4$. The solvent was removed to provide a yellow oil that was placed in a mixture of THF (15 mL) and $H_2O$ (4 mL). LiOH monohydrate (474 mg, 11.3 mmol) was added, and the reaction mixture was stirred at RT for 2 h. The solution was then added dropwise to 5% aqueous HCl (50 mL), and the mixture was extracted with EtOAc (3×30 mL). The combined organic fractions were washed with brine (30 mL), and dried with anhydrous $MgSO_4$. Evaporation of the volatile materials gave an oil that was purified by flash chromatography on silica gel (0% to 25% EtOAc/hexanes) to provide 800 mg (79%) of 3-bromo-5-difluoromethylphenol (121).

The phenol 121 was condensed with ethyl 2,3-difluoro-4-nitro-phenyl acetate as described in step 1 of Example 28. Reduction of the nitro group and diazotization and displacement of the diazonium salt by chloride were carried out as described in steps 2 and 3 of Example 28 to afford 122.

Step 3

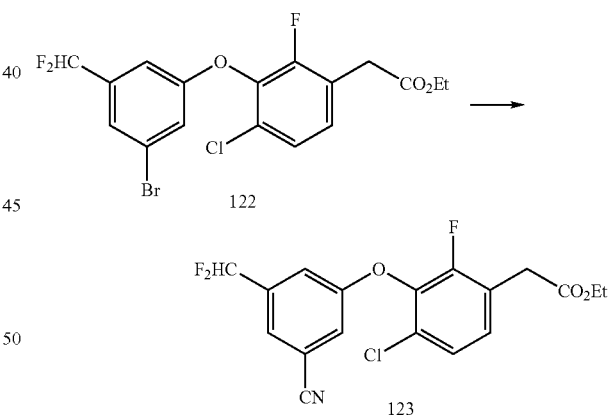

A solution of 122 (757 mg, 1.73 mmol), $Pd[P(Ph)_3]_4(0)$ (300 mg, 0.26 mmol), and zinc cyaninide (122 mg, 1.04 mmol) in DMF (8 mL) under nitrogen was heated to 80° C. for 4 h. The reaction mixture was cooled to RT and added to 2 M aqueous $NH_4OH$. The solution was extracted with 1:1 EtOAc/hexanes (3×30 mL), and the combined organic fractions were washed with $H_2O$ (3×20 mL) and dried over anhydrous $MgSO_4$. The solvent was evaporated, and the remaining oil was purified by flash chromatography on silica gel (0% to 25% EtOAc/hexanes) to provide 580 mg (87%) of [4-chloro-3-(3-cyano-5-difluoromethyl-phenoxy)-2-fluoro-phenyl]-acetic acid ethyl ester (123).

Example 33

6-[3-(2-Chloro-phenoxy)-4-trifluoromethyl-benzyl]-2H-pyridazin-3-one

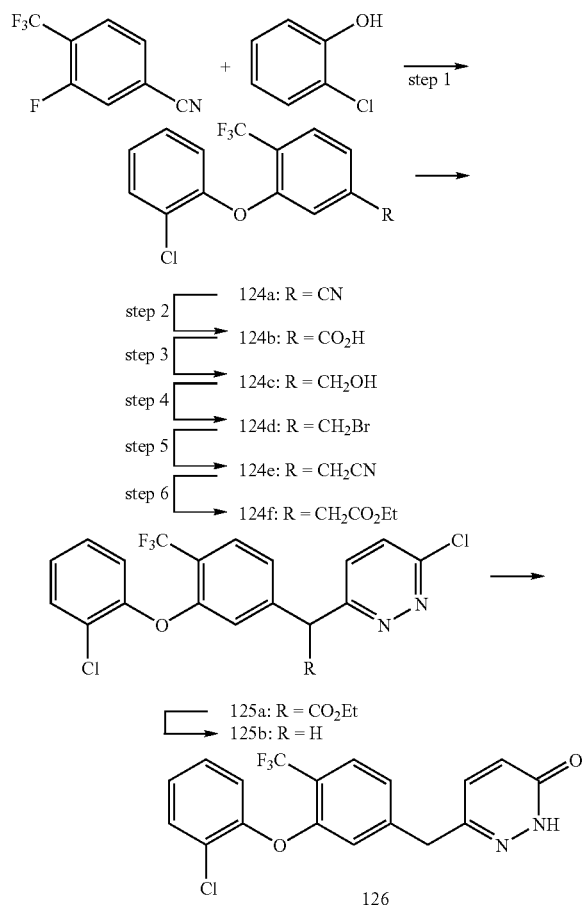

Step 1
A round-bottom flask was charged with sodium hydride (254 mg, 6.35 mmol; 60% in mineral oil) and a solution of 2-chlorophenol (658 μL, 6.35 mmol) in 20 mL of NMP. After stirring for 30 m, a solution of 3-fluoro-4-trifluoromethylbenzonitrile in 5 mL of NMP was added and the reaction was heated at 120° C. for 17 h. The reaction mixture was cooled and petitioned between dichloromethane and water.

The aqueous phase was twice extracted with DCM and the combined organic phases were washed with water and brine, dried (MgSO$_4$), filtered and evaporated. The crude product was purified by flash chromatography on silica gel (EtOAc:hexane 1:30) to afford 1.64 g of 3-(2-chlorophenoxy)-4-trifluoromethylbenzonitrile (124a).

Step 2
To a solution of 3-(2-chlorophenoxy)-4-trifluoromethylbenzonitrile (124a, 1.64 g, 5.51 mmol) in MeOH (25 mL) was added a solution of NaOH (450 mg) in water (5 mL). The reaction mixture was heated at reflux for 16 h. The mixture was cooled to RT and partitioned between water and EtOAc. The EtOAc was removed and the aqueous phase was acidified with 1N HCl and thrice extracted with EtOAc (25 mL). The combined organic extracts were sequentially washed with water and brine, dried over MgSO$_4$, filter and evaporated to yield a white solid which was washed with hexane and dried to afford 1.44 g of carboxylic acid 124b.

Step 3
To an ice-cold solution of 124b (1.44 g, 4.55 mmol) and anhydrous THF (25 mL) was added dropwise BH$_3$-THF (31.8 mL of a 1.0 M solution in THF) and the solution then heated at reflux for 1.5 f. The reaction was cooled to RT and methanol was added very slowly. The reaction mixture was diluted with EtOAc and washed sequentially with 1N HCl saturated NaHCO$_3$ and water. The organic phase was dried MgSO$_4$, filtered and evaporated. The crude product was purified by flash chromatography on silica gel (EtOAc:hexane 1:4) to afford 1.23 g of 124c.

Step 4
To a solution of the alcohol 124c (1.37 g, 4.53 mmol) was dissolved 25 mL of THF was added sequentially CBr$_4$ (3.09 g, 9.05 mmol) and triphenylphosphine (2.37 g, 9.05 mmol). After 30 m the reaction was diluted with 30 mL EtOAc, washed with brine, dried (MgSO$_4$), filtered and evaporated. The crude product was purified by flash chromatography over silica gel (hexane) to afford 1.69 g 124d.

Step 5
To a solution of 124d (1.69 g, 4.62 mL) in 25 mL of EtOH was added a solution of KCN (793 mg, 16.2 mmol) in 3 mL of water. The reaction mixture was stirred for 6 h at RT and the volatile solvents removed in vacuo. The crude product was partition between EtOAc and saturated aqueous NaHCO3. The organic phase was washed with brine, dried (MgSO$_4$), filtered and evaporated. The crude product was purified by flash chromatography on silica gel to afford the nitrile 124e (790 mg)

Step 6
A solution of 124 e (0.790 g, 2.53 mmol), 48% HBr (4 mL) and glacial HOAc (4 mL) was heated at 110° C. for 4 h. The reaction was cooled and diluted with EtOAc and washed twice with brine. The organic phase was evaporated in vacuo and the resulting oil was dissolved in 10 mL of EtOH and 1 mL of con H$_2$SO$_4$ was added and the resulting solution heated at 75° C. for 15 h. The reaction mixture was cooled and partitioned between water and Et$_2$O. The Et$_2$O was washed sequentially with saturated NaHCO$_3$, water and brine, dried MgSO$_4$, filtered and evaporated to afford 124f (578 mg, 1.61 mmol).

Step 7
To a solution of 124f (250 mg, 0.7 mmol) and 3,6-dichloropyridazine (261 mg, 1.4 mmol) in 10 mL of DMF was added NaH (56 mg, 1.4 mmol, 60% in mineral oil) The reaction mixture was stirred for 1 h. The workup that afforded 125a and subsequent conversion to the pyridazinone is carried out as described in steps 1 and 2 of Example 18.

Example 34

3-(2-Chloro-5-cyano-phenoxy)-4-nitro-benzoic acid methyl ester

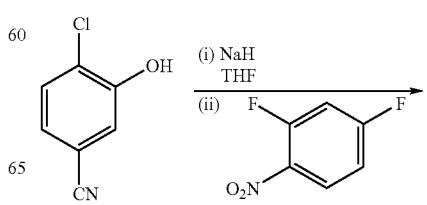

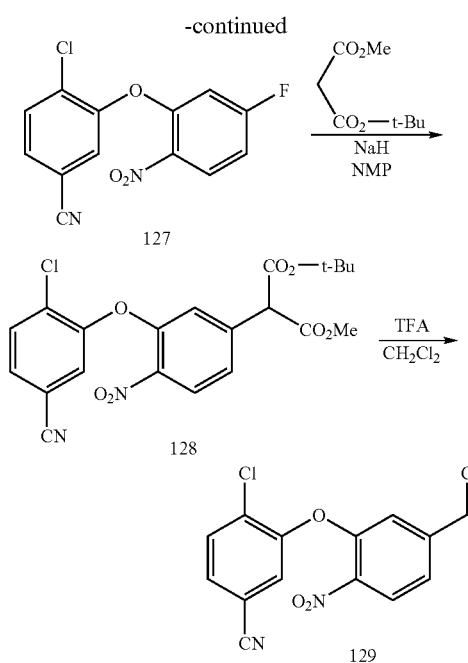

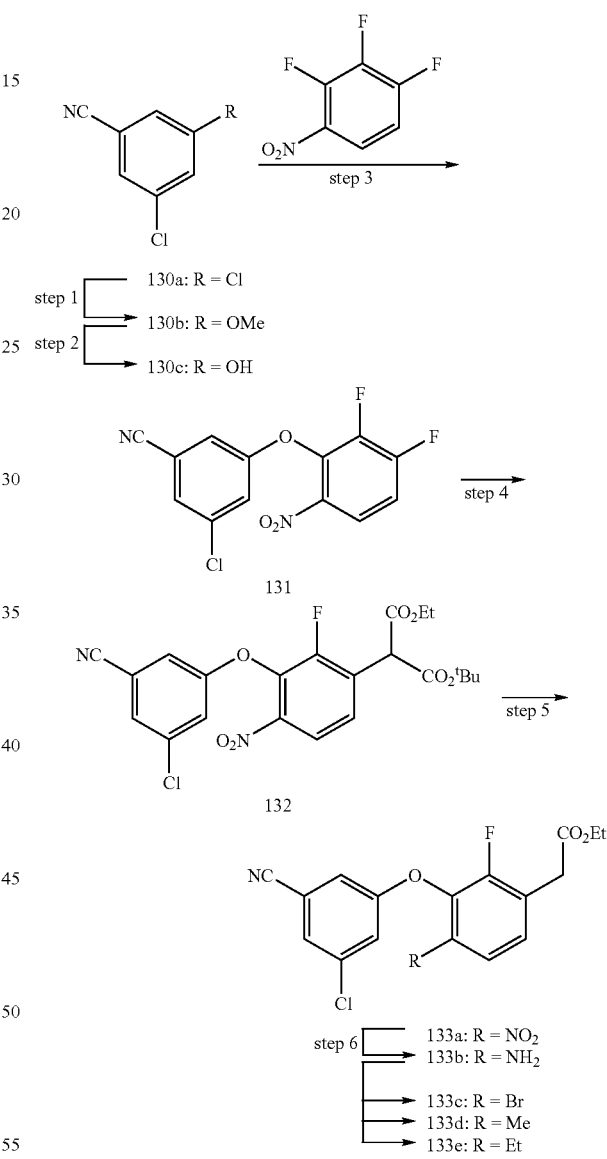

Step 1

To an ice-cold solution under argon atmosphere of 2-chloro-5-cyanophenol (7.36 g, 48.10 mmol) in anhydrous THF (100 mL) was added potassium tert-butoxide (52.92 mL of 1 M solution in THF, 52.92 mmol) with stirring over 30 m. The cooling bath was then removed and the resulting mixture was stirred for 40 m at RT. The reaction mixture was cooled down to 0° C. A solution of 2,4-difluoronitrobenzene (8.41 g, 52.92 mmol) in THF (10 mL) was then added to the potassium phenoxide at 0° C. over a 20 m period. The resulting yellow slurry was then heated at 50° C. for 16 h. The final reaction mixture was poured into ice-water (500 mL) and the mixture was extracted with EtOAc (4×100 mL). Organic layer was washed with water (100 mL), dried (MgSO$_4$), and purified by flash chromatography on silica gel (hexane:EtOAc 9:1) to afford 127 (13.3 g; 94.6% theory )as pale yellow oil.

Step 2

To a well stirred solution at 0° C. under argon atmosphere of tert-butyl methyl malonate (8.18 g, 46.98 mmol) in anhydrous NMP (120 mL) was added carefully NaH (3.76 g, 94 mmol; 60% on mineral oil) over 40 m. The resulting mixture was then stirred at 0° C. for 30 m and a solution of 127 (12.5 g, 42.71 mmol) in anhydrous NMP (50 mL) was added dropwise over 1.5 h with stirring while maintaining the temperature at 0° C. under argon atmosphere. The cooling bath was removed and the reaction mixture was stirred at RT for 2.5 h. The reaction mixture was poured into 10% NaHSO$_4$ (400 mL) and the mixture was extracted with EtOAc (4×200 mL). The combined organic layers were washed with water (3×100 mL) and brine (1×100 mL) and dried (MgSO$_4$). After filtration of the MgSO$_4$ the solvent was evaporated in vacuo to afford 128 as yellow residue.

Step 3

The crude product was dissolved in DCM (30 mL) and TFA (80 mL) was added with stirring. The resulting mixture was refluxed for 2 hours. TFA and DCM were removed in vacuo and the residue was mixed with water (100 mL). The mixture was adjusted to a pH between 7 and 8 with 10% NaHCO$_3$ and the resulting mixture was extracted with EtOAc (4×100 mL). The combined organic layers were washed with water (2×100 mL), dried (MgSO$_4$) and purified by flash chromatography on silica gel (hexane:EtOAc 3:1) to yield 12.42 g (84.3%) of 3-(2-chloro-5-cyano-phenoxy)-4-nitro-benzoic acid methyl ester (129) as yellow oil.

Example 35

Step 1

To a 250 mL round bottom flask charged with 3,5-dichlorobenzonitrile (130a, 7.31 g; 34.90 mmol) and maintained under an argon atmosphere was added DMF (70 mL). The flask was cooled to 0° C. and powdered sodium methoxide (1.88 g; 34.90 mmol) was added in two portions 15 m apart. The homogeneous mixture was allowed to warm to room temperature and stirred for 24 h. The solution was cooled to 0° C. and aqueous 10% HCl (20 mL) was added dropwise via an addition funnel after which the reaction was warmed to RT. The mixture was extracted with EtOAc and the combined extracts washed sequentially with water and brine. The organic phase was dried (Na₂SO₄), filtered, and volatile solvents were removed in vacuo. The resulting solid was recrystallized from hexanes to afford 3-chloro-5-methoxybenzonitrile (130b, 4.2 g; 72%).

Step 2

A 250 mL round bottom flask was charged 3-chloro-5-methoxybenzonitrile (4.2 g; 25.05 mmol) and 2,4,6-collidine (60 mL) was added. The mixture was stirred under an argon atmosphere until the solution was homogeneous. Anhydrous lithium iodide (10.06 g; 75.18 mmol) was added and the mixture was heated to 175° C. for 3 h. The reaction mixture was cooled to RT and partitioned between 10% HCl and EtOAc. The EtOAc phase was washed sequentially with 10% HCl and brine, dried (Na₂SO₄), filtered and evaporated in vacuo to afford a oil which was crystallized from hexanes to afford 3-chloro-5-hydroxybenzonitrile (130c, 3.5 g, 91% theory).

Step 3

To an ice-cold solution of 3-chloro-5-hydroxybenzonitrile (130c, 3.5 g; 22.80 mmol) and dry THF (50 mL) maintained under an argon atmosphere was sodium tert-butoxide (2.2 g; 22.80 mmol) in two portions 15 m apart. The reaction mixture was stirred until the mixture was homogeneous. To the ice-cold solution was added dropwise 2,3,4-trifluoronitrobenzene (4.0 g; 22.80 mmol),over 30 m. The reaction was stirred at 0° C. for 3 h and then allowed to warm to RT. The reaction was cooled to 0° C. and quenched by addition of 10% HCl via addition funnel. The resulting mixture was extracted with EtOAc and the combined organic phases washed sequentially with 10% HCl and brine. The EtOAc was dried (Na₂SO₄), filtered and the volatile solvent removed in vacuo to yield a yellow oil which was crystallized from hexanes to yield 131 (6.3 g, 89% theory)

Step 4

To an ice-cold solution of tert -butyl ethyl malonate (3.8 g; 20.28 mmol) and dry NMP maintained under an argon atmosphere was added NaH (1.2 g, 48.67 mmol, 60% in mineral oil) over a 45 m interval. The reaction was stirred for an additional 30 m after which 131 (6.3 g, 20.28 mmol) was added dropwise and the resulting solution stirred for 4 h. The reaction mixture was cooled to 0° C. and quenched by dropwise addition of a saturated NaHSO₄ solution. The mixture was EtOAc and the combined organic extracts washed sequentially with water and brine. The EtOAc solution was dried (Na₂SO₄), filtered and the volatile solvents removed in vacuo to afford 132 as a purple oil that was used without further purification.

Step 5

The crude mixed ester 132 from the previous step (8.9 g; 18.60 mmol) was dissolved in DCM (100 mL) and 50 mL of TFA was added and the solution was to heated to 60° C. for 24 h. The reaction mixture was cooled to 0° C. and saturated NaHCO₃ was added dropwise to the stirred reaction mixture. The resulting solution was extracted with EtOAc and washed sequentially with saturated NaHCO₃, water and brine. The organic phase was dried (Na₂SO₄), filter and the volatile solvents removed in vacuo. The resulting dark oil was recrystallized from hexanes to afford 133a (6.5 g, 92% theory).

Step 6

To a solution of 133a (6.5 g; 17.20 mmol) and absolute EtOH (100 mL) was added NH₄Cl (1.84 g, 34.39 mmol) dissolved in water (20 mL). The resulting mixture was heated at 60° C. until the reaction was homogeneous. Fe(0) (1.44 g, 25.80 mmol) was then added and the mixture stirred vigorously at 60° C. for 6 h. When reduction was complete the hot reaction mixture was filtered through a pad of CELITE® which subsequently was washed with hot EtOAc. The resulting filtrated was cooled and extracted with EtOAc and the combined extracts washed sequentially with water and brine. The EtOAc extract was dried (Na₂SO₄), filtered and the volatile solvent was removed in vacuo to afford a pale orange oil which was recrystallized from hexanes to yield 133b (5.0 g, 83% theory).

Introduction of 5-bromo Substituent

A 150 mL three-neck round bottom flask was charged with MeCN (50 mL), CuBr (2.8 g, 12.61 mmol) and t-butyl nitrite (1.4 g, 13.76 mmol), degassed and maintained under an Ar atmosphere and heated to 70° C. To the mixture was added dropwise a solution of 133b (4.0 g, 11.47 mmol) dissolved MeCN (20 mL). The reaction mixture was stirred at 70° C. for 4 h and then cooled to 0° C. The reaction was quenched by addition of 10% HCl (30 mL) and extracted with EtOAc. The combined extracts were sequentially washed with 10% HCl and brine. The organic extract was dried (Na₂SO₄), filtered and the volatile solvents removed in vacuo to yield a black oil which was purified by flash chromatography on silica gel (hexanes:EtOAc 95:5) to afford 133c (2.5 g, 52.8% theory).

Introduction of 5-methyl Substituent

To a degassed ice-cold solution of THF (15 mL), Pd(dppf)Cl₂ (0.09 g, 0.121 mmol) was added DIBAL-H (0.012 mmol; 1M in toluene). The reaction mixture was allowed to warm to RT. A solution of 133b (1.0 g, 2.42 mmol) was added followed by dimethyl zinc (1M in THF, 4.240 mmol). The reaction was heated to 65° C. for 4 h, cooled to RT and quenched with aqueous NH₄Cl. The resulting mixture was extracted with EtOAc and washed sequentially with NH₄Cl and brine. The EtOAc extract was dried (Na₂SO₄), filtered and the volatile solvent removed in vacuo to yield a dark brown oil that was purified by flash chromatography on silica gel (hexanes:EtOAc 95:5) to yield 133d (0.50 g, 59% theory).

Introduction of 5-ethyl Substituent 133e was prepared in by an identical procedure except diethylzinc was substituted for dimethyl zinc. The product was purified by flash chromatography on silica gel (hexanes: EtOAc 95:5) to yield 133e (0.65 g, 74% theory).

Example 36

(5-Methyl-6-oxo-1,6-dihydro-pyridazin-3-yl)-acetic acid tert-butyl ester (108)

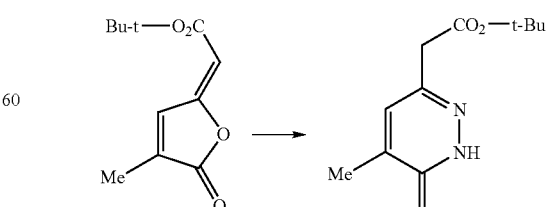

(108)

The alkylidene lactone was synthesized from citraconic anhydride via a Wittig reaction using the procedure previously described in the literature (Massy-Westropp, R. A. and Price, M. F., *Aust. J. Chem.* 1980, 33, 333–341). To a solution of the lactone (9.02 g, 42.9 mmol) in 100 mL of ethanol was added 4.5 mL (144 mmol) of hydrazine hydrate. The reaction mixture was refluxed for 6 h, cooled and concentrated. Successive crystallizations of the crude reaction mixture from hexanes yielded 108 as a clear crystalline solid (8.02 g, 83%): mp=113.0–113.9° C., ms: [M+H]$^+$=225.

Example 37

6-[3-(5-bromo-1-oxy-pyridin-3-yloxy)-4-chloro-2-fluoro-benzyl]-4-methyl-2H-pyridazin-3-one

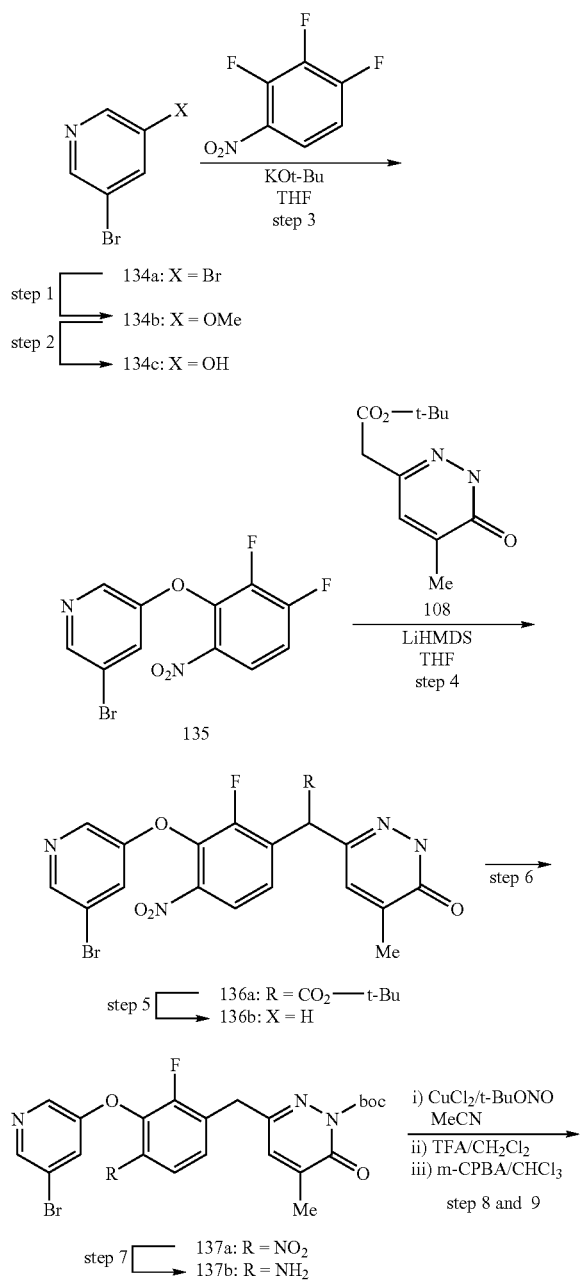

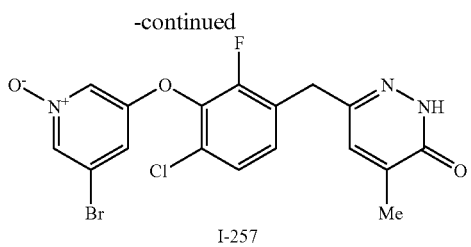

I-257

Step 1

A solution of 3,5-dibromopyridine (134a, 20 g, 84.4 mmol) in DMF (200 mL) was stirred at RT under nitrogen atmosphere and then 21.3 mL of sodium methoxide (25% by wt. in methanol (92.8 mmol) was added slowly. The reaction mixture was stirred overnight at 70° C. under $N_2$. The reaction was cooled to RT and quenched with water (200 mL) and extracted with $Et_2O$ (2×200 mL). The combined organic extracts was washed with brine, dried ($MgSO_4$) and concentrated in vacuo. The crude 3-bromo-5-methoxypyridine (134b 14.8 g, 93% theory) afforded a colorless oil after purification by flash chromatography on silica gel (EtOAc:hexane 1:10).

Step 2

A solution of 3-bromo-5-methoxy-pyridine (134b 18.8 g, 0.1 mol ), HBr (80 mL, 48%) and glacial HOAc (60 mL) was stirred overnight at 120° C. The reaction mixture was cooled to RT and then poured into the ice. The pH was adjusted to about 6 by adding 6N NaOH and then extracted with EtOAc (2×200 mL). The organic layer was dried over $Na_2SO_4$ and concentrated in vacuo. The crude product was stirred in $CH_2Cl_2$ (150 mL) and the resulting precipitate was filtered. The product was washed with $CH_2Cl_2$ to afford 3-bromo-5-hydroxypyridine (134c 15.2 g, 87.4% theory) as a white solid.

Step 3

A solution of 3-bromo-5-hydoxypyridine (134c 7.4 g, 42.5 mmol) in anhydrous THF (40 mL) was stirred at 0° C. under Ar atmosphere and potassium tert-butoxide (46.8 mL, 1M solution in THF) was added slowly. After 1 h at 0° C., 2,3,4-trifluoronitrobenzene (7.91 g, 44.6 mmol) in 15 mL of THF was added very slowly. The reaction mixture was stirred at RT for 2 h, quenched with water (80 mL) and extracted with EtOAc (2×80 mL). The combined organic extracts were dried ($MgSO_4$) and concentrated in vacuo. The crude product was purified by flash chromatography on silica gel (EtOAc:hexane 1:15) to afford 135 (11 g, 78%) as a light orange oil.

Step 4

A solution of (5-methyl-6-oxo-1,6-dihydro-pyridazin-3-yl)-acetic acid tert-butyl ester (108, 7.1 g, 31.7 mmol) and 135 (11 g, 33.3 mmol) in anhydrous THF (30 mL) was stirred at −78° C. under an Ar atmosphere and 112 mL of LiHMDS (1.0M solution in THF) was added very slowly. The reaction mixture was stirred in the cold bath (dry-ice/IPA) for 3 h then in an ice bath for 2 h. The reaction was quenched with a solution of $NaHSO_4 \cdot H_2O$ (5% by wt) and extracted with EtOAc (2×100 mL). The combined organic extracts were dried ($MgSO_4$) and concentrated in vacuo. The product was isolated by a flash chromatography on silica gel (EtOAc:hexane 1:2 to 2:1) to afford 136a as a yellow solid (10.2 g, 60% yield).

Step 5

A solution of 136a (10.2 g, 19.1 mmol) in HOAc (120 mL) under a nitrogen atmosphere was heated to reflux overnight. It was cooled to RT and the HOAc was evaporated in vacuo. A saturated NaHCO$_3$ solution (70 mL) was added and the aqueous mixture extracted with EtOAc (2×80 mL). The combined organic fractions were dried (MgSO$_4$) and concentrated in vacuo. The crude product was isolated by a flash chromatography on silica gel (EtOAc:hexane 1:2 to 2:1) to afford 136b as a light yellow solid (4.6 g, 55.3% theory ): ms (M+H)$^+$=436.

Step 6

A solution of the 136a starting material(1.8 g, 4.4 mmol), di-tert-butyl dicarbonate (1.16 g, 5.3 mmol), and 4-dimethylaminopyridine (0.2 g) in anhydrous THF (30 mL) was maintained under an Ar atmosphere and stirred at RT overnight. The reaction mixture was quenched with water and extracted with EtOAc (2×30 mL). The combined organic fractions were dried (MgSO$_4$) and concentrated in vacuo. The product was isolated by a flash chromatography on silica gel (1:10 to 2:1 EtOAc:hexane) to afford 137a as a white solid compound (0.85 g; 38% theory).

Step 7

The reduction was carried out as described in step 6 of Example 35. From 137a (4 g, 9.19 mmol) there was obtained 1.8 g (4.44 mmol) of 137b as an off-white solid (48.3% yield).

Step 8

Reduction of the nitro group and diazotization and displacement of the diazonium salt by chloride were carried out as described in step 3 of example 26. The Boc group was removed with trifluoroacetic acid and DME. From 0.85 g (1.69 mmol) of 137a there was obtained 290 mg of the aryl chloride (49.9% theory for the two steps) as a white solid: mp 184.9–188° C., ms [M+H]$^+$=424.

Step 9

A solution of the pyridinyl compound (0.2 g, 0.47 mmol) and MCPBA (0.09 g, 0.52 mmol) in anhydrous chloroform (10 mL) was heated at reflux for 6 hours. The reaction mixture was cooled to RT, and diluted with 0.05N NaOH (5 mL) and extracted with chloroform (2×10 mL). The combined organic fractions were dried (MgSO$_4$) and concentrated in vacuo. The crude product was purified by a flash chromatography on silica gel (MeOH:CH$_2$Cl$_2$ 0.1 to 1:10) to afford 6-[3-(5-bromo-1-oxy-pyridin-3-yloxy)-4-chloro-2-fluoro-benzyl]-4-methyl-2H-pyridazin-3-one (I-257, 60 mg; 32% theory) as a white solid: mp 197.9–198.9° C., ms (M+H)$^+$=440.

Example 38

[4-Chloro-3-(3,5-dicyano-phenoxy)-2-fluoro-phenyl]-acetic acid ethyl ester

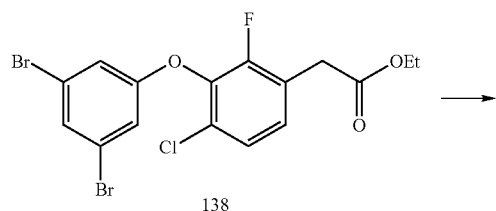
138

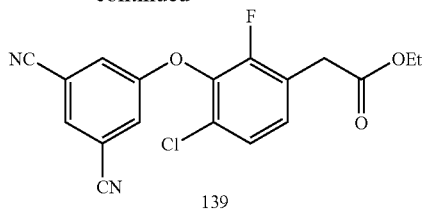
139

A mixture of ethyl 4-chloro-3-(3,5-dibromo-phenoxy)-2-fluoro-phenyl-acetate (138, 41.45 g, 88.8 mmol), zinc cyanide (12.5 g, 106 mmol), Pd(PPh$_3$)$_4$(0) (10.26 g, 8.88 mmol) and anhydrous DMF (500 mL) was evacuated under house vacuum and purged with argon three times. The mixture was stirred at 80° C. under an argon atmosphere. After 4 h the mixture was cooled to RT and filtered through a pad of silica gel. The filtrate was extracted with 1:1 EtOAc-hexanes (3×200 mL). The combined organic phases were sequentially washed with water and brine and dried (MgSO$_4$). The product (37.4 g) was purified by flash chromatography on 500 g of silica gel (EtOAc-hexanes 1:10 to 2:10). The resulting material was recrystallized from isopropanol to afford 139 (28.3 g, 89% theory).

Example 39

2-(3-Cyano-phenoxy)-3-fluoro-4-(5-methyl-6-oxo-1,6-dihydro-pyridazin-3-ylmethyl)-benzonitrile

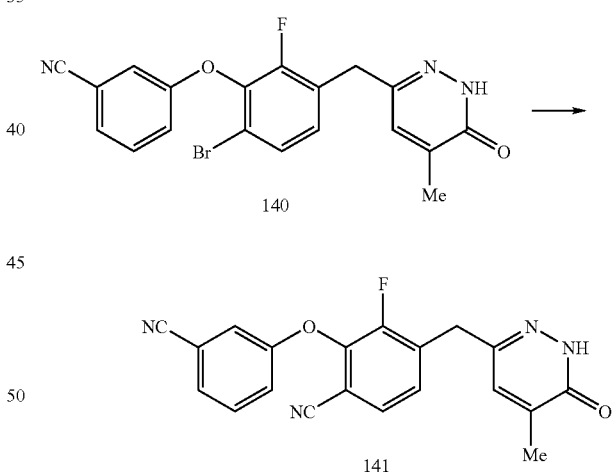
140

141

Pyridazinone 140 (100 mg, 0.24 mmol), ZnCl$_2$ (22 mg, 0.19 mmol), and Pd(PPh$_3$)$_4$ (62 mg, 0.05 mmol) were combined in a dry round bottom flask, purged of atmospheric oxygen with argon and subsequently charged with dry DMF (2.7 mL). The mixture was heated to 80° C. and allowed to stir for two h. The mixture was allowed to cool to room temperature, diluted with 1:1 EtOAc/hexanes (50 mL) and washed with water (4×50 mL). The organic phase was dried (MgSO$_4$) and concentrated in vacuo. The crude oil was purified by flash chromatography on silica gel (5% methanol/dichloromethane) followed by preparative HPLC to afford 141 (36 mg, 39%) as a white solid.

Example 40

6-[4-Chloro-5-(3-chloro-phenoxy)-2-fluoro-benzyl]-2H-pyridazin-3-one (144a) and 6-[4-Chloro-5-(3-chloro-phenoxy)-2-fluoro-benzyl]-4-methyl-2H-pyridazin-3-one (144b)

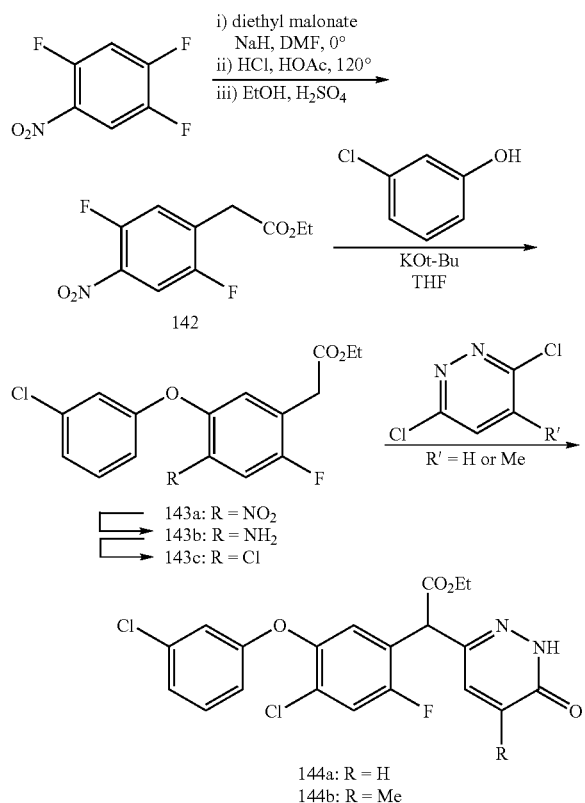

Step 1

An ice-cooled slurry of NaH (2.2 g, 54.9 mmol, 60% in mineral oil) in dry DMF (60 mL) was prepared under an $N_2$ atmosphere in a septum-equipped flask. Diethyl malonate (4.2 mL, 27.5 mmol) was added dropwise by syringe over 10 m, and stirring at 0° C. was continued for another 30 m. Trifluoronitrobenzene (Aldrich, 3.0 mL, 26.2 mmol) was then added dropwise over 20 m and the mixture was stored at −6° C. for 16 h. The mixture was diluted with water and extracted with a 3:2 mixture of EtOAc and hexane. The organic extracts were washed with $H_2O$, dried ($Na_2SO_4$) and the solvents evaporated to afford the crude product which was purified by flash chromatography on silica gel (acetone: hexane 1:10) to afford the diethyl malonate adduct (7.9 g, 95% theory) as a yellow oil. A mixture of substituted malonate ester (7.8 g, 24.6 mM) with glacial HOAc (80 mL) and HCl (6N, 80 mL) was heated under nitrogen at 120° for 2.5 h and then allowed to cool and stirred for 16 h. Most of the solvent was removed by evaporation and then water was added to the residue which produced a precipitate. The slurry was cooled in ice and the precipitate collected by filtration, further washed with water and dried under vacuum to afford 2,5-difluoro-4-nitrophenylacetic acid (4.37 g, 82% theory) as a pale yellow solid.

To a solution of the carboxylic acid (4.26 g, 19.6 mM) in absolute EtOH (40 mL) was added conc. $H_2SO_4$ (4 mL) and the mixture was heated at reflux for 5 h. The mixture was then diluted with water and extracted with EtOAc affording ester 142 as an oil (4.75 g, 98.5% theory) which crystallized on standing

Step 2

To a ice-cooled solution of 3-chlorophenol (2.8 mL, 26.5 mM) in dry THF (25 mL) under $N_2$ was added a solution of potassium tert-butoxide (1M in THF, 5.2 mL, 5.2 mM). After 30 m stirring at 0° C. a solution of 142 (1.23 g, 5.0 mM) in THF (5 mL) was added dropwise over 3m. The mixture was then heated at reflux for 1 h, after which the reaction was complete. The reaction mixture was partitioned between EtOAc and aqueous $NH_4Cl$ and the EtOAc phase was dried and the crude product was purified by flash chromatography on silica gel (5% EtOAc-35% hexane-60% toluene) to afford 143a (1.28 g, 72% theory) as a yellow oil.

Step 3

To a solution of 143a (945 mg, 2.67 mM) in absolute EtOH (50 mL) was added ammonium chloride (850 mg, 16 mM) iron powder (900 mg, 16 mM) and water (20 mL), and the mixture was stirred vigorously while heating at 80° C. for 8 h. The mixture was cooled and filtered through CELITE®, the filter cake was washed with EtOH, and most of the solvent was then removed by evaporation. The residue was diluted with EtOAc, washed with water and dried ($Na_2SO_4$). The organic solution was evaporated to give a crude product that was purified by flash chromatography on silica gel (8% EtOAc-25% methylene chloride-67% hexane) to afford 143b (776 mg, 90% theory) as a violet colored oil.

Step 4

To a solution of 143b (776 mg, 2.41 mmol) in dry MeCN (18 mL) was added $CuCl_2$ (390 mg, 2.89 mmol) followed by tert-butyl nitrite (0.35 mL, 2.65 mM). The mixture was stirred under an argon atmosphere for 2.5 hrs, and was then stored at −60° C. for 16 h. The mixture was diluted with EtOAc, washed sequentially with dilute aqueous HCl twice with water and dried ($Na_2SO_4$). The solvent was evaporated and the crude product purified by flash chromatography on silica gel (EtOAc:hexane 7:93) to afford 143c (530 mg, 64% theory) as a colorless oil.

Using the procedure in steps 5 and 6 of example 2 there was prepared pyridazinone 144a as an amorphous foam: ms [M+H]$^+$=365: anal; calc'd for $C_{17}H_{11}C_{12}FN_2O_2$: C, 55.91; H, 3.04; N, 7.67; found: C, 55.67; H, 3.06; N, 7.63. Using the procedure in example 16 there was prepared pyridazinone 144b as an amorphous foam: ms [M+H]$^]$=379: anal; calc'd for $C_{17}H_{11}C_{12}FN_2O_2$:

Example 41

6-[4-Chloro-3-(2-nitro-phenoxy)-benzyl]-2H-pyridazin-3-one

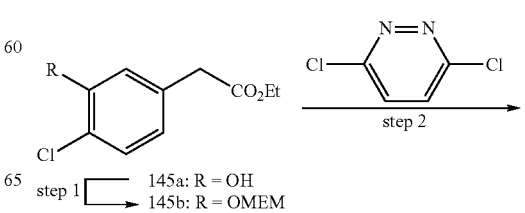

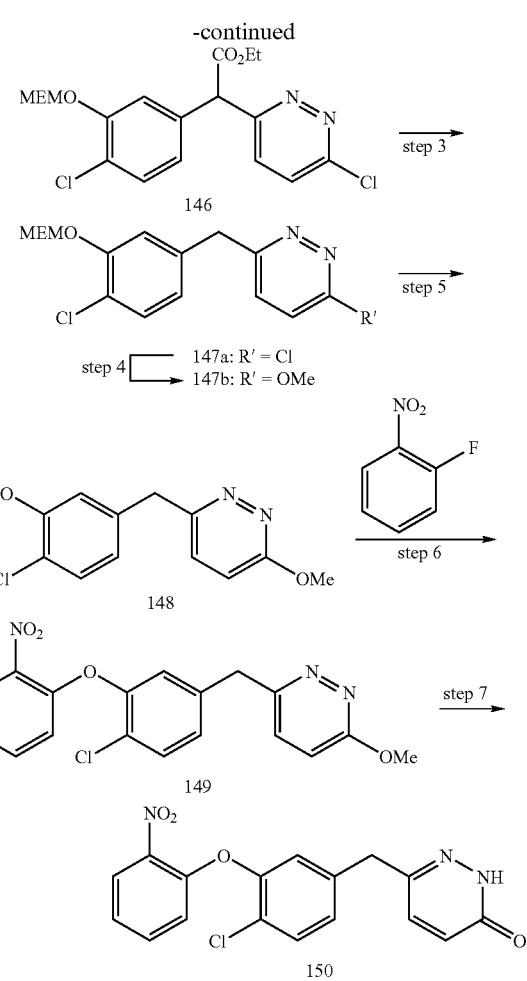

Step 1

To a solution of ethyl 4-chloro-3-hydroxyphenylacetate (145a, 12.66 g; 59.0 mmol), N,N-diisopropylethylamine (12.3 ml; 70.8 mmol) and $CH_2Cl_2$ (170 ml) at 0° C. was added MEMCl (7.4 ml; 64.9 mmol) dropwise. The reaction mixture was allowed to warm to room temperature and stirred overnight. The reaction was poured into $H_2O$ and extracted with $CH_2Cl_2$. The combined organic extracts were dried ($Na_2SO_4$), filtered and evaporated to yield of 145b (13.5 g; 76%).

Step 2

A solution of 145b (10.00 g; 33.0 mmol) and 3,6-dichloropyridazine (10.33 g; 69.4 mmol) in DMF (100 mL) was degassed and the flask alternately purged and refilled with $N_2$. NaH (3.3 g, 82.6 mmol; 60% in mineral oil) was added portionwise at 0° C. and the reaction was allowed to warm to room temperature and stirred for 1.5 h. The reaction was poured into aqueous 10% $NaHSO_4$ and extracted with EtOAc. The combined organic extracts were washed six times with $H_2O$ and brine, dried ($Na_2SO_4$), filtered and evaporated. The crude product was purified by flash chromatography on silica gel (hexane/EtOAc 85:15 to 75:25) to afford 146 (9.3 g, 68%).

Step 3

A solution of 146 (9.27 g; 22.3 mmol) in THF (70 mL) and $H_2O$ (18 mL) was degassed and the flask alternately purged and refilled with nitrogen. LiOH (1.07 g; 44.6 mmol) was added. The reddish-orange reaction mixture was stirred for 3 h and them acidified with HCl (10%) to pH 2. The aqueous solution was thrice extracted with $CH_2Cl_2$, and the combined extracts washed with $H_2O$ and brine, dried, filtered and evaporated to yield 147a (7.6 g, 99%).

Step 4

To a solution of 147a (7.58 g; 22.1 mmol) and MeOH (180 mL), was added NaOMe (5.97 g; 110.5 mmol) and the solution heated to reflux for 3 h under a $N_2$ atmosphere. The reaction mixture was concentrated and $CH_2Cl_2$ was added. The mixture was washed with $H_2O$ (3×) and brine, dried ($Na_2SO_4$), filtered and concentrated. The crude product was then purified by flash chromatography on silica gel (hexane:EtOAc 90:10 to 60:40) to yield 147b (7.1 g, 95%).

Step 5

A mixture of 147b (7.10 g; 21 mmol), 15.9 mL of 10% HCl and MeOH (80 mL) was heated at 50° C. overnight. The reaction was cooled to room temperature and saturated $NaHCO_3$ was added. The mixture was extracted with EtOAc, washed with brine, dried ($MgSO_4$) and concentrated to yield 148 (5.20 g, 99%).

Step 6

To a solution of 148 (0.20 g; 0.8 mmol), $K_2CO_3$ (0.33 g; 2.4 mmol) and DMF (2 mL) was added 2-fluoronitrobenzene (0.11 ml; 1.04 mmol) and the reaction mixture was heated to 40° C. overnight. The reaction was cooled to RT and 10% $NaHSO_4$ was added. The aqueous phase was extracted with EtOAc. The combined organic extracts were washed with $H_2O$ and brine, dried ($Na_2SO_4$), filtered and evaporated. The crude product was purified by flash chromatography on silica gel (hexane/EtOAc 90:10 to 60:40) to yield 149 (0.285 g, 96%).

Step 7

A mixture of HBr (1 mL) and HOAc (1 mL) was added to 1 g of 149 (0.140 g; 0.376 mmol). The reaction mixture was heated for 3 h at 100° C. them cooled to rt and extracted with EtOAc. The organic layer was washed with $H_2O$ and brine, dried ($Na_2SO_4$), filtered and evaporated to yield 150 (0.125 g, 93 %).

Example 42

N-{2-[2-Chloro-5-(6-oxo-1,6-dihydro-pyridazin-3-ylmethyl)-phenoxy]-phenyl}-methanesulfonamide (152a) and N-{2-[2-Chloro-5-(6-oxo-1,6-dihydro-pyridazin-3-ylmethyl)-phenoxy]-phenyl}-acetamide (152b)

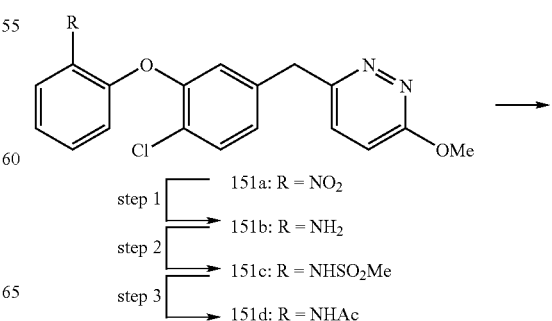

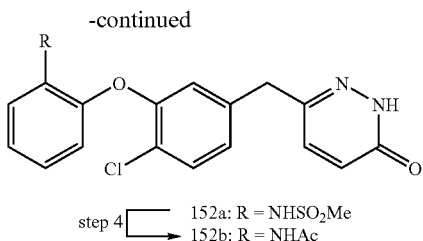

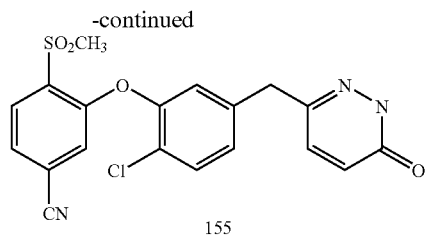

Reduction of the nitro group of 151a was carried out as described in step 3 of example 43 to afford 151b Sulfonylation and acetylation of the aryl amine to afford 151c and 151d respectively was carried out by treating 151b with methanesulfonyl choride/TEA or acetyl/TEA using standard protocols.

To a solution of 151c (0.115 g; 0.274 mmol) in collidine (2 mL) was added LiI (0.110 g; 0.822 mmol). The mixture was heated at 180° C. for 1 h and then cooled to RT. The reaction mixture was diluted with 10% HCl and extracted with EtOAc. The organic extract was washed with H$_2$O and brine, dried (Na$_2$SO$_4$), filtered and evaporated to afford 152a (0.062 g, 56%).

The acetamide 151d was demethylated under similar conditions to afford 152b.

Example 43

3-[2-Chloro-5-(6-oxo-1,6-dihydro-pyridazin-3-ylmethyl)-phenoxy]-4-methanesulfonyl-benzonitrile (155)

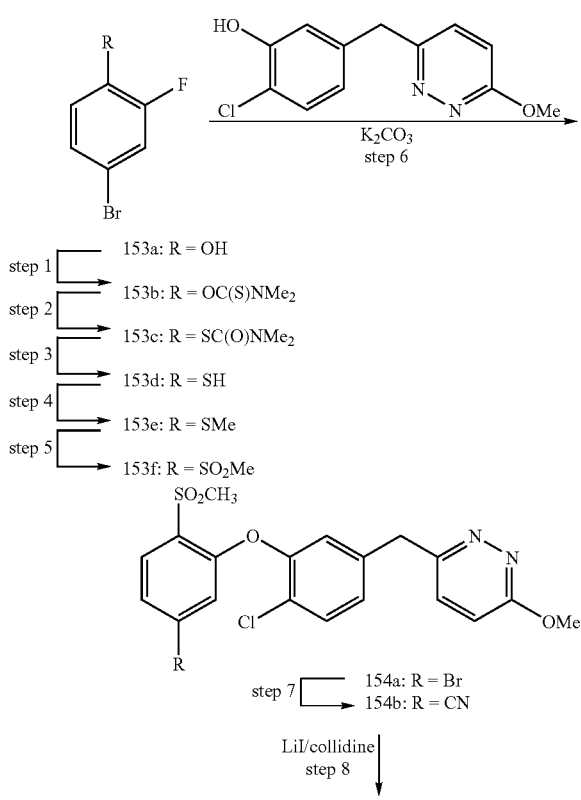

Step 1

To a solution of 4-bromo-2-fluorophenol (5.73 ml; 52.4 mmol ) in DMF (100 mL) was added DABCO (11.75 g; 104.7 mmol) and N,N-dimethylthiocarbamoyl chloride (9.71 g; 78.5 mmol). The reaction mixture was heated at 75° C. for 1 h. The reaction was cooled to RT and H$_2$O was added. The suspension was filtered and the solid washed with H$_2$O, dried and used in step 2.

Step 2

A solution of 153b dissolved in sulfolane was heated at 220° C. for 14 h under an N$_2$ atmosphere. The solvent was removed under high vacuum and the product was purified by flash chromatography on silica gel to yield 153c (4.90 g, 34% for steps 1 & 2).

Step 3

To a solution of 153c (4.88 g; 17.5 mmol) in MeOH (50 mL), was added NaOH (1.40 g, 35.1 mmol in 14 mL of H$_2$O). The reaction mixture was heated to reflux under N$_2$ atmosphere for 5 h. The reaction was cooled to RT and aqueous 10% NaHSO$_4$ was added. The aqueous solution was extracted with EtOAc and the combined organic extracts were washed with H$_2$O and brine, dried (Na$_2$SO$_4$), filtered and evaporated to yield 153d (3.34 g, 92%).

Step 4

To a solution of 153d (0.90 g; 4.3 mmol), K$_2$CO$_3$ (1.50 g; 10.9 mmol), in NMP (10 mL) was added MeI (0.54 ml; 8.7 mmol). The reaction was heated at 85° C. in an oil bath for 1 h and then allowed to cool to RT. A saturated solution of NaHCO$_3$ was added and the mixture was extracted with EtOAc, washed with saturated NaHCO$_3$ and brine, dried (Na$_2$SO$_4$) and concentrated to yield 153e (0.95 g, 99%).

The thiomethyl ether was oxidized to the corresponding sulfone 152f with MCPBA (procedure). Substitution of the bromo radical with a cyano radical was accomplished by palladium-mediated displacement by Zn(CN)$_2$ as described in step 5 of Example 20. Displacement of the bromide with Zn(CN)2 was achieved as described in example 44. demethylated with lithium chloride and collidine as describe in step 2 of example 30.

A similar series of reactions start from 2-fluorophenol was used to prepare 6-[4-chloro-3-(2-methanesulfonyl-phenoxy)-benzyl]-2H-pyridazin-3-one Example 44

6-[3-(3-Bromo-benzenesulfinyl)-4-chloro-benzyl]-2H-pyridazin-3-one (157a); 6-[3-(3-Bromo-benzenesulfinyl)-4-chloro-benzyl]-2H-pyridazin-3-one (157b); 6-[3-(3-Bromo-benzenesulfonyl)-4-chlorobenzyl]-2H-pyridazin-3-one (157c)

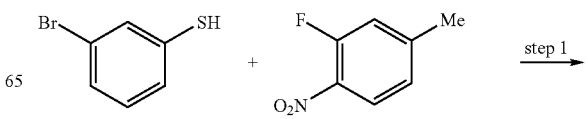

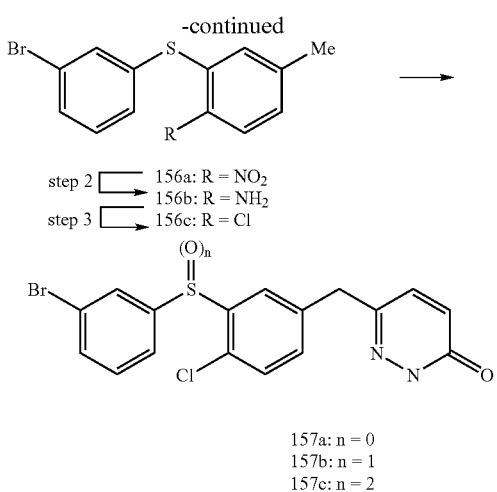

157a: n = 0
157b: n = 1
157c: n = 2

Step 1

To a suspension of m-fluoro-p-nitrotoluene (4.1 g,. 26.4 mmol) and $K_2CO_3$ (11 g, 79.5 mmol) in dry DMF (75 mL) under a nitrogen atmosphere was added p-bromothiophenol (5 g, 26.4 mmol) in single portion. The suspension was heated to reflux at 160° C. for 4 h then allowed to cool to RT. The mixture was then filtered through silica gel. The filtrated was concentrated and purified by flash chromatography on silica gel (ethyl acetate/hexanes 10% to 50%) to yield 156a (6.8 g, 79%) an orange oil.

Step 2

A round bottom flask was charged with 156a (6.8 g, 20.97 mmol) and $SnCl_2H_2 2H_2O$ (18.93 g, 83.9 mmol). The mixture was suspended in EtOH (50 mL) and refluxed at 70° C. for 4.5 h. The suspension was allowed to cool to RT and the pH was adjusted to pH 8 with 2 M NaOH. To this was added ethyl acetate (100 mL) and the mixture was filtered through CELITE®. The filtrate was washed with water (100 mL), brine (50 mL), and dried ($MgSO_4$). The solvents were evaporated in vacuo to afford 156b (5.6 g, 90%) as an orange oil and that used without any further purification.

Step 3

A dry round bottom flask was charged with $CuCl_2$ (1.65 g, 12.2 mmol), purged with nitrogen and MeCN (25 mL) was added. The suspension was heated to 65° C. To the suspension was added t-butyl nitrite (1.82 mL, 15.3 mmol) and the solution was stirred for 5 m and a solution of the 156b (3 g, 10.2 mmol) in MeCN (15 mL) was added dropwise over 15 m. The reaction was stirred for another 75 m before cooling in an ice bath. The reaction mixture was diluted with 5% HCl (10 mL) and stirred for a few minutes before extracting with ethyl acetate (3×50 mL). The combined organic extracts were combined, sequentially washed with water (100 mL) and brine (50 mL) and dried ($MgSO_4$). The crude was purified by flash chromatography on silica gel (hexanes) to afford Preparation of 6-[3-(3-Bromo-benzenesulfinyl)-4-chlorobenzyl]-2H-pyridazin-3-one A solution of 157a (55 mg, 0.135 mmol), MCPBA (32 mg, 0.18 mmol) and dry dichloromethane was stirred under nitrogen for 24 h at RT. The reaction was diluted with EtOAc and washed sequentially with saturated sodium bisulfite, 1M NaOH (aq, 10 mL), water (10 mL), brine (10 mL), and dried over anhydrous $MgSO_4$. The crude material was purified by prep TLC ($SiO_2$, ethyl acetate) to yield 157b (29 mg, 57%).

Preparation of 6-[3-(3-Bromo-benzenesulfonyl)-4-chlorobenzyl]-2H-pyridazin-3-one (157c)

A solution of 157a (55 mg, 0.135 mmol), MCPBA (64 mg, 0.37 mmol) and dry dichloromethane was stirred under nitrogen for 24 h at RT. The reaction was diluted with EtOAc and washed sequentially with saturated sodium bisulfite, 1M NaOH (10 mL), water (10 mL), brine (10 mL), and dried over anhydrous $MgSO_4$. The crude material was purified by prep TLC ($SiO_2$, ethyl acetate) to yield 157c (34 mg, 64%).

Example 45

HIV Reverse Transcriptase Assay: Inhibitor $IC_{50}$ Determination

HIV-1 RT assay was carried out in 96-well Millipore MultiScreen MADVNOB50 plates using purified recombinant enzyme and a poly(rA)/oligo(dT)$_{16}$ template-primer in a total volume of 50 μL. The assay constituents were 50 mM Tris/HCl 50 mM NaCl, 1 mM EDTA, 6 mM $MgCl_2$, 5 μM dTTP, 0.15 μCi [$^3$H] dTTP, 5 μg/ml poly (rA) pre annealed to 2.5 μg/ml oligo (dT)$_{16}$ and a range of inhibitor concentrations in a final concentration of 10% DMSO. Reactions were initiated by adding 4 nM HIV-1 RT and after incubation at 37° C. for 30 min, they were stopped by the addition of 50 μl ice cold 20% TCA and allowed to precipitate at 4° C. for 30 min. The precipitates were collected by applying vacuum to the plate and sequentially washing with 3×200 μl of 10% TCA and 2×200 μl 70% ethanol. Finally, the plates were dried and radioactivity counted in a Packard Top-Counter after the addition of 25 μl scintillation fluid per well. $IC_{50}$'s, were calculated by plotting % inhibition versus $\log_{10}$ inhibitor concentrations.

TABLE 3

| Compound # | RT inhibition $IC_{50}$ (μM) |
|---|---|
| I-136 | 0.008 |
| I-103 | 0.00935 |
| I-108 | 0.01115 |
| I-135 | 0.0125 |
| I-142 | 0.015 |
| I-98 | 0.0194 |
| I-102 | 0.02063 |
| I-109 | 0.0216 |
| I-123 | 0.0231 |
| I-100 | 0.02415 |
| I-77 | 0.02425 |
| I-76 | 0.059 |
| I-224 | 0.018 |
| I-237 | 0.0128 |

Example 46

Pharmaceutical Compositions

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (IV)

| Ingredient | % wt./wt. |
|---|---|
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula I

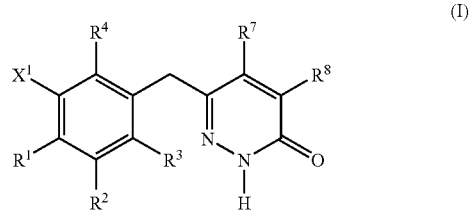

(I)

wherein;
   $X^1$ is selected from the group consisting of $R^5O$, $R^5S(O)_n$, $R^5CH_2$, $R^5CH_2O$, $R^5CH_2S(O)_n$, $R^5OCH_2$, $R^5S(O)_nCH_2$ and $NR^5R^6$;
   $R^1$ and $R^2$ are
      (i) each independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, amino, alkylamino, dialkylamino, aminoacyl, nitro and cyano; or,
      (ii) taken together are —CH=CH—CH=CH—, or
      (iii) taken together along with the carbons to which they are attached form a five- or six-membered heteroaromatic or heterocyclic ring with a one or two heteroatoms independently selected from the group consisting of O, S and NH;
   $R^3$ is selected from the group consisting of hydrogen, $C_{1-6}$ alkyl, $C_{1-6}$ haloalkyl, $C_{3-8}$ cycloalkyl, $C_{1-6}$ alkylthio, $C_{1-6}$ haloalkylthio, halogen, amino, alkylamino, dialkylamino, aminoacyl, nitro and cyano;
   $R^4$ is selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ haloalkoxy, $C_{1-6}$ haloalkylthio, halogen, amino, alkylamino, dialkylamino, aminoacyl, nitro and cyano;
   $R^5$ is selected from the group consisting of alkyl, haloalkyl, cycloalkyl, phenyl, naphthyl, pyridinyl, pyridine N-oxide, pyridine N-oxide, indole, indole N-oxide, quinoline, quinoline N-oxide, pyrimidinyl, pyrazinyl and pyrrolyl; wherein,
      said alkyl and said cycloalkyl are optionally substituted with one or two substituents independently selected from the group consisting of alkyl, hydroxy, alkoxy, thiol, alkylthio, halogen, amino, alkylamino, dialkylamino, aminoalkyl, alkylaminoalkyl, and dialkylamino; and,
      said phenyl, said naphthyl, said pyridinyl, said pyridine N-oxide, said indole, said indole N-oxide, said quinoline, said quinoline N-oxide, said pyrimidinyl, said pyrazinyl and said pyrrolyl groups are optionally substituted with one to three substituents independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, hydroxy, halogen, amino, $C_{1-6}$ alkylamino, $C_{1-6}$ dialkylamino, aminoacyl, acyl, $C_{1-6}$ alkoxycarbonyl, carbamoyl, $C_{1-6}$ N-alkylcarbamoyl, $C_{1-6}$N,N-dialkylcarbamoyl, nitro and cyano;
   $R^6$ is hydrogen, $C_{1-6}$ alkyl, or acyl;
   $R^7$ and $R^8$ taken independently are selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl or $C_{1-6}$ alkyl optionally substituted with one or two substituents independently selected from the group consisting of hydroxy, alkoxy, thiol, alkylthio, $C_{1-6}$ alkylsulfinyl, $C_{1-6}$ sulfonyl and halogen, N-morpholinyl;
   n is an integer from 0 to 2;
   or an acid addition salts thereof.

2. A compound according to claim 1 wherein $R^5$ is selected from the group consisting of $C_{2-6}$ alkyl, haloalkyl, cycloalkyl, phenyl, naphthyl, pyridinyl, pyrimidinyl, pyrazinyl and pyrrolyl; and,
   said alkyl and said cycloalkyl are optionally substituted with one or two substituents independently selected from the group consisting of alkyl, hydroxy, alkoxy, thiol, alkylthio, halogen, amino, alkylamino, dialkylamino, aminoalkyl, alkylaminoalkyl, and dialkylamino; and,
   said phenyl, said naphthyl, said pyridinyl, said pyrimidinyl, said pyrazinyl and said pyrrolyl groups are optionally substituted with one to three substituents independently selected from the group consisting of $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, alkylamino, dialkylamino, aminoacyl, cyano, and acyl.

3. A compound according to claim 2 wherein:
   $X^1$ is $OR^5$ or $SR^5$;
   $R^3$ is hydrogen or fluoro;
   $R^4$ is selected from the group consisting of hydrogen, chloro, fluoro and methyl;
   $R^5$ is optionally substituted phenyl; and,
   $R^7$ and $R^8$ are selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio, halogen.

4. A compound according to claim 3 wherein $R^1$ is methyl, ethyl, trifluoromethyl or halogen.

5. A compound according to claim 4 wherein $R^5$ is monosubstituted phenyl.

6. A compound according to claim 4 wherein $R^5$ is 2,5-disubstituted phenyl.

7. A compound according to claim 4 wherein $R^5$ is 3,5-disubstituted phenyl.

8. A compound according to claim 4 wherein $R^5$ is 2,4-disubstituted phenyl.

9. A compound according to claim 4 wherein $R^5$ is 2,6-disubstituted phenyl.

10. A compound according to claim 2 wherein:
    $X^1$ is —$OR^5$ or —$SR^5$;
    $R^3$ and $R^2$ are independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, amino, alkylamino, dialkylamino, aminoacyl, nitro and cyano; and
    $R^3$ is hydrogen or fluorine.

11. A compound according to claim 10 wherein:
    $X^1$ is $OR^5$;
    $R^1$ is methyl, ethyl, trifluoromethyl or halogen;
    $R^2$ and $R^4$ are hydrogen, fluoro, chloro, methyl or ethyl;
    $R^3$ is hydrogen or fluoro;
    $R^7$ is hydrogen, methyl or ethyl; and,
    $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio, halogen.

12. A compound according to claim 11 wherein $R^5$ is monosubstituted phenyl.

13. A compound according to claim 12 wherein $R^5$ is a monosubstituted phenyl and the substituent is selected from the group consisting of halogen, cyano, $C_{1-6}$ alkyl, $C_{1-6}$ alkenyl, $C_{3-8}$ cycloalkyl, $C_{1-6}$ haloalkyl, $C_{1-6}$ alkoxy, $C_{1-6}$ alkylthio and $C_{1-6}$ haloalkoxy.

14. A compound according to claim 13 wherein $R^1$ is selected from the group consisting of halogen, methyl, ethyl, $R^3$ and $R^7$ are hydrogen, $R^5$ is a monosubstituted phenyl and the substituent is selected from the group consisting of halogen, cyano, $C_{1-6}$ alkyl and $C_{1-6}$ haloalkyl and $R^8$ is selected from the group consisting of hydrogen, methyl and ethyl.

15. A compound according to claim 11 wherein $R^5$ is 2,5-disubstituted phenyl.

16. A compound according to claim 15 wherein $R^5$ is a 2,5-disubstituted phenyl and the substituents are independently selected from the group consisting of halogen, cyano, $C_{1-6}$ alkyl, $C_{1-6}$ alkenyl, $C_{3-8}$ cycloalkyl, $C_{1-6}$ haloalkyl, $C_{1-6}$ alkoxy, $C_{1-6}$ alkylthio and $C_{1-6}$ haloalkoxy.

17. A compound according to claim 16 wherein $R^1$ is selected from the group consisting of halogen, methyl, ethyl, $R^3$ and $R^7$ are hydrogen, $R^5$ is a 2,5-disubstituted phenyl and the substituent is selected from the group consisting of halogen, cyano, $C_{1-6}$ alkyl and $C_{1-6}$ haloalkyl and $R^8$ is selected from the group consisting of hydrogen, methyl and ethyl.

18. A compound according to claim 11 wherein $R^5$ is 3,5-disubstituted phenyl.

19. A compound according to claim 18 wherein $R^5$ is a 3,5-disubstituted phenyl and the substituents are independently selected from the group consisting of halogen, cyano, $C_{1-6}$ alkyl, $C_{1-6}$ alkenyl, $C_{3-8}$ cycloalkyl, $C_{1-6}$ haloalkyl, $C_{1-6}$ alkoxy, $C_{1-6}$ alkylthio and $C_{1-6}$ haloalkoxy.

20. A compound according to claim 19 wherein $R^1$ is selected from the group consisting of halogen, methyl, ethyl, $R^3$ and $R^7$ are hydrogen, $R^5$ is a 3,5-disubstituted phenyl and the substituent is selected from the group consisting of halogen, cyano, $C_{1-6}$ alkyl and $C_{1-6}$ haloalkyl and $R^8$ is selected from the group consisting of hydrogen, methyl and ethyl.

21. A compound according to claim 20 with formula Ia wherein:

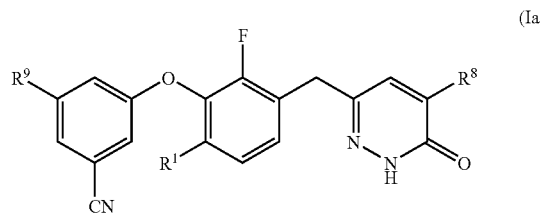

(Ia)

$R^1$ is selected from the group consisting of fluoro, chloro, bromo and methyl;
$R^8$ is selected from the group consisting of hydrogen, methyl and ethyl;
$R^9$ is selected from the group consisting of $C_{1-6}$ alkyl, $C_{3-8}$ cycloalkyl, $C_{1-6}$ haloalkyl, halogen and cyano.

22. A compound according to claim 11 wherein $R^5$ is 2,4-disubstituted phenyl.

23. A compound according to claim 22 wherein $R^5$ is a 2,4-disubstituted phenyl and the substituents are independently selected from the group consisting of halogen, cyano, $C_{1-6}$ alkyl, $C_{1-6}$ alkenyl, $C_{3-8}$ cycloalkyl, $C_{1-6}$ haloalkyl, $C_{1-6}$ alkoxy, $C_{1-6}$ alkylthio and $C_{1-6}$ haloalkoxy.

24. A compound according to claim 23 wherein $R^1$ is selected from the group consisting of halogen, methyl, ethyl, $R^3$ and $R^7$ are hydrogen, $R^5$ is a 2,4-disubstituted phenyl and the substituent is selected from the group consisting of halogen, cyano, $C_{1-6}$ alkyl and $C_{1-6}$ haloalkyl and $R^8$ is selected from the group consisting of hydrogen, methyl and ethyl.

25. A compound according to claim 11 wherein $R^5$ is 2,6-disubstituted phenyl.

26. A compound according to claim 25 wherein $R^5$ is a 2,6-disubstituted phenyl and the substituents are independently selected from the group consisting of halogen, cyano, $C_{1-6}$ alkyl, $C_{1-6}$ alkenyl, $C_{3-8}$ cycloalkyl, $C_{1-6}$ haloalkyl, $C_{1-6}$ alkoxy, $C_{1-6}$ alkylthio and $C_{1-6}$ haloalkoxy.

27. A compound according to claim 26 wherein $R^1$ is selected from the group consisting of halogen, methyl, ethyl, $R^3$ and $R^7$ are hydrogen, $R^5$ is a 2,6-disubstituted phenyl and the substituent is selected from the group consisting of halogen, cyano, $C_{1-6}$ alkyl and $C_{1-6}$ haloalkyl and $R^8$ is selected from the group consisting of hydrogen, methyl and ethyl.

28. A compound according to claim 11 wherein $R^5$ is 2,3,5-trisubstituted phenyl.

29. A compound according to claim 1 wherein:
$X^1$ is $OR^5$ or $SR^5$;
$R^3$ and $R^4$ are selected from the group consisting of hydrogen, chloro, fluoro, and methyl;
$R^5$ is optionally substituted pyridinyl, pyridine N-oxide, indole, indole N-oxide, quinoline, quinoline N-oxide, pyrimidinyl, pyrazinyl and pyrrolyl.

30. A compound according to claim 1 wherein $R^1$ and $R^2$ along with the carbon atoms to which they are attached form a phenyl, dihydropyran, dihydrofuran or furan ring.

31. A compound according to claim 30 wherein:
$X^1$ is $OR^5$ or $SR^5$;
$R^3$, and $R^7$ are hydrogen;
$R^4$ is hydrogen or fluoro;
$R^8$ is hydrogen or methyl; and,
$R^5$ is optionally substituted phenyl.

32. A method for treating an HIV-1 infection comprising administering to a host in need thereof a therapeutically effective amount of a compound of formula I

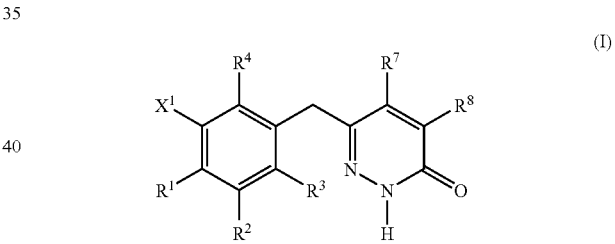

(I)

wherein,
$X^1$ is selected from the group consisting of $R^5O$, $R^5S$, $R^5CH_2$, $R^5CH_2O$, $R^5CH_2S(O)_n$, $R^5OCH_2$, $R^5S(O)_nCH_2$, $NR^5R^6$ and $R^5C(=O)$;
$R^1$ and $R^2$ are
(i) each independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, amino, alkylamino, dialkylamino, aminoacyl, nitro and cyano; or,
(ii) taken together are —CH=CH—CH=CH—, or
(iii) taken together along with the carbons to which they are attached form a five- or six-membered heteroaromatic or heterocyclic ring with a one or two heteroatoms independently selected from the group consisting of O, S and NH;
$R^3$ and $R^4$ are each independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ haloalkoxy, $C_{1-6}$ haloalkylthio, halogen, amino, alkylamino, dialkylamino, aminoacyl, nitro and cyano;

R⁵ is selected from the group consisting of alkyl, haloalkyl, cycloalkyl, phenyl, naphthyl, pyridinyl, pyrimidinyl, pyrazinyl and pyrrolyl; wherein,
  said alkyl and said cycloalkyl are optionally substituted with one or two substituents independently selected from the group consisting of alkyl, hydroxy, alkoxy, thiol, alkylthio, halogen, amino, alkylamino, dialkylamino, aminoalkyl, alkylaminoalkyl, and dialkylamino; and,
  said phenyl, said naphthyl, said pyridinyl, said pyrimidinyl, said pyrazinyl and said pyrrolyl groups are optionally substituted with one to three substituents independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, hydroxy, halogen, amino, alkylamino, dialkylamino, aminoacyl, acyl, alkoxycarbonyl, carbamoyl, N-alkylcarbamoyl, N,N-dialkylcarbamoyl, nitro and cyano;
R⁶ is hydrogen, $C_{1-6}$ alkyl, or acyl;
R⁷ and R⁸ taken independently are selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl or $C_{1-6}$ alkyl optionally substituted with one or two substituents independently selected from the group consisting of hydroxy, alkoxy, thiol, alkylthio, $C_{1-6}$ alkylsulfinyl, $C_{1-6}$ sulfonyl and halogen, N-morpholinyl;
n is an integer from 0 to 2;
or an acid addition salts thereof.

33. A method according to claim 32 wherein:
X¹ is OR⁵;
R¹ is methyl, ethyl, trifluoromethyl or halogen;
R² and R⁴ are independently hydrogen, fluoro, chloro, methyl or ethyl;
R³ is hydrogen or fluoro; and,
R⁵ is optionally substituted phenyl;
R⁷ is hydrogen, methyl or ethyl.

34. A method according to claim 33 comprising administering a compound of formula Ia wherein

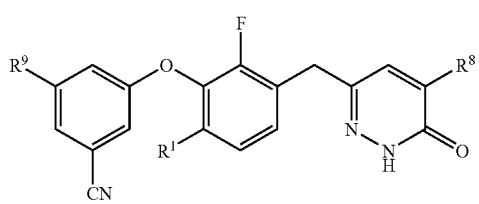

(Ia)

R¹ is selected from the group consisting of fluoro, chloro, bromo and methyl;
R⁸ is selected from the group consisting of hydrogen, methyl and ethyl;
R⁹ is selected from the group consisting of alkyl, cycloalkyl, haloalkyl, halogen and cyano.

35. A method for treating HIV-1 infection according to claim 32 further comprising co-administering at least one compound selected from the group consisting of HIV protease inhibitors, nucleoside reverse transcriptase inhibitors, non-nucleoside reverse transcriptase inhibitors, CCR5 inhibitors and viral fusion inhibitors.

36. A method according to claim 35 wherein the reverse transcriptase inhibitor is selected from the group consisting of zidovudine, lamivudine, didanosine, zalcitabine, stavudine, rescriptor, sustiva and viramune, efavirenz, nevirapine or delavirdine and/or the protease inhibitor is selected from the group consisting of saquinavir, ritonavir, nelfinavir, indinavir, amprenavir, lopinavir.

37. A method for inhibiting a HIV-1 reverse transcriptase comprising administering a compound according to claim 1.

38. A method according to claim 37 wherein the HIV-1 reverse transcriptase contains at least one mutation compared to wild type virus.

39. A method according to claim 32 wherein said strain of HIV-1 exhibits reduced susceptibility to efavirenz, nevirapine or delavirdine.

40. A pharmaceutical composition comprising a therapeutically effective quantity of a compound of formula I

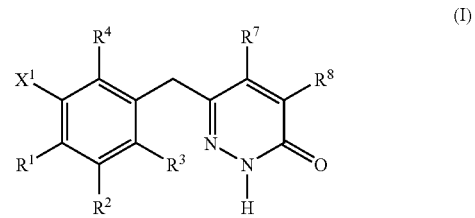

(I)

wherein:
X¹ is selected from the group consisting of $R^5O$, $R^5S(O)_n$, $R^5CH_2$, $R^5CH_2O$, $R^5CH_2S(O)_n$, $R^5OCH_2$, $R_5S(O)_nCH_2$ and $NR^5R^6$;
R¹ and R² are
  (i) each independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, halogen, amino, alkylamino, dialkylamino, aminoacyl, nitro and cyano; or,
  (ii) taken together are —CH=CH—CH=CH—, or
  (iii) taken together along with the carbons to which they are attached form a five- or six-membered heteroaromatic or heterocyclic ring with a one or two heteroatoms independently selected from the group consisting of O, S and NH;
R³ is selected from the group consisting of hydrogen, $C_{1-6}$ alkyl, $C_{1-6}$ haloalkyl, $C_{3-8}$ cycloalkyl, $C_{1-6}$ alkylthio, $C_{1-6}$ haloalkylthio, halogen, amino, alkylamino, dialkylamino, aminoacyl, nitro and cyano;
R⁴ is selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ haloalkoxy, $C_{1-6}$ haloalkylthio, halogen, amino, alkylamino, dialkylamino, aminoacyl, nitro and cyano;
R⁵ is selected from the group consisting of alkyl, haloalkyl, cycloalkyl, phenyl, naphthyl, pyridinyl, pyrimidinyl, pyrazinyl and pyrrolyl; wherein,
  said alkyl and said cycloalkyl are optionally substituted with one or two substituents independently selected from the group consisting of alkyl, hydroxy, alkoxy, thiol, alkylthio, halogen, amino, alkylamino, dialkylamino, aminoalkyl, alkylaminoalkyl, and dialkylamino; and,
  said phenyl, said naphthyl, said pyridinyl, said pyrimidinyl, said pyrazinyl and said pyrrolyl groups are optionally substituted with one to three substituents independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, hydroxy, halogen, amino, alkylamino, dialkylamino, aminoacyl, acyl, alkoxycarbonyl, carbamoyl, N-alkylcarbamoyl, N,N-dialkylcarbamoyl, nitro and cyano;

$R^6$ is hydrogen, $C_{1-6}$ alkyl, or acyl;

$R^7$ and $R^8$ taken independently are selected from the group consisting of hydrogen amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl or $C_{1-6}$ alkyl optionally substituted with one or two substituents independently selected from the group consisting of hydroxy, alkoxy, thiol, alkylthio, $C_{1-6}$ alkylsulfinyl, $C_{1-6}$ sulfonyl and halogen, N-morpholinyl; n is an integer from 0 to 2;

or an acid addition salts thereof, in admixture with at least one pharmaceutically acceptable carrier or diluent.

* * * * *